US011345693B2

(12) United States Patent
Burstein et al.

(10) Patent No.: US 11,345,693 B2
(45) Date of Patent: May 31, 2022

(54) COMPOUNDS, SALTS THEREOF AND METHODS FOR TREATMENT OF DISEASES

(71) Applicant: ACADIA PHARMACEUTICALS INC., San Diego, CA (US)

(72) Inventors: Ethan S. Burstein, San Diego, CA (US); Roger Olsson, Bunkeflostrand (SE); Björn Gustav Borgström, Lund (SE); Karl Erik Jansson, Dalby (SE); Niklas Patrik Sköld, Lund (SE); Henrik Von Wachenfeldt, Malmö (SE); Larisa Yudina Wahlström, Eslöv (SE)

(73) Assignee: ACADIA PHARMACEUTICALS INC., San Diego, CA (US)

( * ) Notice: Subject to any disclaimer, the term of this patent is extended or adjusted under 35 U.S.C. 154(b) by 0 days.

(21) Appl. No.: 16/797,611

(22) Filed: Feb. 21, 2020

(65) Prior Publication Data

US 2020/0270239 A1 Aug. 27, 2020

Related U.S. Application Data

(63) Continuation-in-part of application No. PCT/US2018/000354, filed on Aug. 20, 2018.

(60) Provisional application No. 62/548,301, filed on Aug. 21, 2017.

(30) Foreign Application Priority Data

Aug. 24, 2017 (SE) .................................. 1730225-8

(51) Int. Cl.
| | | |
|---|---|---|
| *C07D 413/12* | (2006.01) | |
| *C07D 211/58* | (2006.01) | |
| *C07D 401/12* | (2006.01) | |
| *C07D 405/12* | (2006.01) | |
| *C07D 409/12* | (2006.01) | |
| *C07D 417/12* | (2006.01) | |

(52) U.S. Cl.
CPC .......... *C07D 413/12* (2013.01); *C07D 211/58* (2013.01); *C07D 401/12* (2013.01); *C07D 405/12* (2013.01); *C07D 409/12* (2013.01); *C07D 417/12* (2013.01)

(58) Field of Classification Search
CPC .. C07D 413/12; C07D 211/58; C07D 401/12; C07D 405/12; C07D 409/13; C07D 417/12
See application file for complete search history.

(56) References Cited

U.S. PATENT DOCUMENTS

| | | | |
|---|---|---|---|
| 5,707,798 A | 1/1998 | Brann | |
| 7,115,634 B2 * | 10/2006 | Thurieau | A61P 15/00 514/320 |
| 2004/0106600 A1 | 6/2004 | Andersson et al. | |
| 2005/0239796 A1 | 10/2005 | Thurieau et al. | |
| 2007/0260064 A1 | 11/2007 | Tolf et al. | |
| 2008/0280886 A1 | 11/2008 | Gant et al. | |
| 2021/0122713 A1 | 4/2021 | Burstein et al. | |

FOREIGN PATENT DOCUMENTS

| | | |
|---|---|---|
| CN | 104844502 A | 8/2015 |
| CN | 105481757 A | 4/2016 |
| WO | WO-0144191 A1 | 6/2001 |
| WO | WO-0166521 A1 | 9/2001 |
| WO | WO-2004000808 A2 | 12/2003 |
| WO | WO-2004064738 A2 | 8/2004 |
| WO | WO-2006036874 A1 | 4/2006 |
| WO | WO-2006086705 A1 | 8/2006 |
| WO | WO-2008-071961 A1 | 6/2008 |
| WO | WO-2008141057 A1 | 11/2008 |
| WO | WO-2008-150089 A1 | 12/2008 |
| WO | WO-2009039461 A2 | 3/2009 |
| WO | WO-2010111353 A1 | 9/2010 |
| WO | WO-2012116176 A2 | 8/2012 |
| WO | WO-2015-095701 A1 | 6/2015 |
| WO | WO-2017015272 A1 | 1/2017 |
| WO | WO-2019-040104 A2 | 2/2019 |
| WO | WO-2019040107 A1 | 2/2019 |

OTHER PUBLICATIONS

International Search Report and Written Opinion for International Application No. PCT/US2018/000354, European Patent Office, Germany, dated Jan. 22, 2019, 6 pages.

Barnes, N.M., and Sharp T., "A review of central 5-HT receptors and their function," Neuropharmacology 38(8):1083-1152, Pergamon Press, England (Aug. 1999).

Glennon, R.A., "Serotonin receptors: Clinical implications," Neuroscience and Biobehavioral Reviews 14(1):35-47, Pergamon Press, United States, (1990).

Saltzman, A.G., et al., "Cloning of the human serotonin 5-HT2 and 5-HT1C receptor subtypes," Biochemical and Biophysical Research Communications 181(3):1469-1478, Elsevier, United States, (Dec. 1991).

IUPAC-IUB Comm. Biochem. Nomenclature. IUPAC-IUB [International Union of Pure and Applied Chemistry—International Union of Biochemistry] Commission of Biochemical Nomenclature. Abbreviated nomenclature of synthetic polypeptides (polymerized amino acids). Revised recommendations (1971). Biochemistry 11(5): 942-944, (1972).

Meltzer, H.Y., "The role of serotonin in antipsychotic drug action," Neuropsychopharmacology 21(2 Suppl):106S-115S, Elsevier Science Group, United States (Aug. 1999).

Prabhakaran, J., et al., "Synthesis and in vivo evaluation of [O-methyl-11C] 2-(4-methoxyphenyl)-N-(4-methylbenzyl)-N-( 1-methylpiperidin-4-yl)acetamide as an imaging probe for 5-HT2A receptors," Journal of Labelled Compounds and Radiopharmaceuticals 49(12):1069-1077, John Wiley & Sons, United States (Oct. 2006).

(Continued)

*Primary Examiner* — Rebecca L Anderson
(74) *Attorney, Agent, or Firm* — Sterne, Kessler, Goldstesn & Fox P.L.L.C.

(57) ABSTRACT

The present disclosure relates to compounds according to Formula (I), useful for treating diseases.

38 Claims, No Drawings

(56) References Cited

OTHER PUBLICATIONS

Cheng, Y., el al., "Relationship between the inhibition constant (K1) and the concentration of inhibitor which causes 50 per cent inhibition (I50) of an enzymatic reaction," *Biochemical Pharmacology* 22(23):3099-3108, Pergamon Press, Great Britain (1973).

Fuller, R.W., "Drags acting on serotonergic neuronal systems," in *Biology of Serotonergic Transmission*, N. N. Osborne, ed., Chapter 9, pp. 221-247, Wiley, New York, United States (1982).

Nogrady, T., "Principles of Drug Design," in *Medicinal Chemistry: A Biochemical Approach*, Chapter 8, pp. 375-394. Oxford University Press, New York United States (1985).

Office Action dated Dec. 16, 2021, in U.S. Appl. No. 16/640,994, Burstein, E.S., et al., 371 filed Feb. 21, 2020, 13 pages.

Office Action dated Jul. 6, 2021, in U.S. Appl. No. 16/640.994, Burstein, E.S., et al., 371 filed Feb. 21, 2020, 10 pages.

Saxena, P.R., et al., "Cardiovascular effects of serotonin agonists and antagonists," *Journal of Cardiovascular Pharmacology and Therapeutics 15* Suppl 7:S17-S34, Raven Press, Ltd., New York (1990).

Silverman, R. B. "The Organic Chemistry of Drug Design and Drug Action." p. 19, Academic Press, United States (1992).

Shah, P. and Westwell, A. D.; "The role of fluorine in medicinal chemistry," *Journal of Enzyme Inhibition and Medicinal Chemistry*, 22(5): 527-540 Informa UK Ltd. (Oct. 2007).

Bhatia, R., et al. "A Review on Bioisosterism: A Rational Approach for Drug Design and Molecular Modification," *Pharmacologyonline* 1: 272-299 (2011).

* cited by examiner

COMPOUNDS, SALTS THEREOF AND METHODS FOR TREATMENT OF DISEASES

CROSS REFERENCE

This application is a continuation-in-part of PCT/US2018/000354, filed Aug. 20, 2018, and claims the benefit of priority of U.S. Provisional Patent Application No. 62/548,301, filed Aug. 21, 2017, and Swedish Application No. 1730225-8, filed Aug. 24, 2017, the content of each of which is incorporated herein by reference in its entirety.

FIELD

Provided herein are compounds and their pharmaceutically acceptable salts for treatment of diseases and conditions associated with the serotonin receptor 5-HT.

BACKGROUND

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, *Rev. Neurol.* 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, Biology of Serotonergic Transmission, 1982; Boullin, *Serotonin In Mental Abnormalities* 1:316 (1978); Barchas, et al., *Serotonin and Behavior*, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., *The Peripheral Actions of 5-Hydroxytryptamine*, 246 (1989); Saxena, et al., *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 14 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology*, 21:106S-115S (1999); Barnes & Sharp, Neuropharmacology, 38:1083-1152 (1999); Glennon, *Neurosci. Biobehavioral Rev.*, 14:35 (1990)).

Given the broad distribution of serotonin within the body and its role in a wide range of physiological and pathological processes, it is understandable that there is tremendous interest in drugs that affect serotonergic systems (Gershon, et al., *The Peripheral Actions of 5-Hydroxytryptamine*, 246 (1989); Saxena, et al., *J. Cardiovascular Pharmacol.* 15: Supp. 7 (1990)).

The effects of serotonin are mediated by at least 14 genetically distinct 5-HT receptor subtypes have been identified and assigned to one of seven families (5-HT1-7). Each subtype displays a unique distribution, preference for various ligands, and functional correlate(s). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects as well as some additional undesired effects of antipsychotic therapies such as a worsening of depression symptoms, anhedonia and impairment of cognitive processes. Antagonism of 5-HT2A receptors is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects or other undesired effects associated with blockade of dopamine D2 receptors.

Traditionally, GPCRs such as the 5-HT2A receptor have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

Consequently there is a need of new compounds for making antipsychotic drugs that target serotonin receptors.

SUMMARY

Provided herein are compounds according to Formula (I),

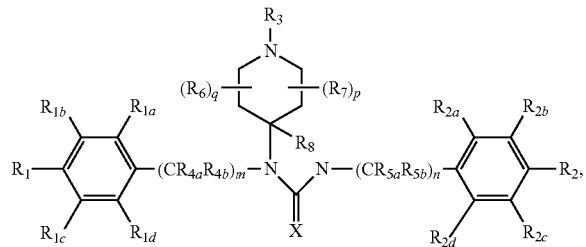

(I)

or a pharmaceutically acceptable salt, hydrate, solvate, polymorph, prodrug, stereoisomer, and deuterated analogue thereof, wherein:

m, and n are independently an integer selected from the group consisting of 0, 1, 2, and 3;

p, and q are independently an integer selected from the group consisting of 0, 1, 2, 3, and 4;

$R_1$, $R_{1a}$, $R_{1b}$, $R_{1c}$ and $R_{1d}$ are independently selected from the group consisting of hydrogen, deuterium, hydroxyl, —OD, halogen, cyano, amino, —SO$_2$R$_{10}$, —OC(=O)R$_{11}$, —C(=O)OR$_{11}$, —NR$_{10}$C(=O)R$_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein at least one of $R_1$, $R_{1a}$, $R_{1b}$, $R_{1c}$ and $R_{1d}$ is not hydrogen, wherein $R_{10}$ and $R_{11}$, independently are selected from the group consisting of hydrogen, amino, unsubstituted or substituted $C_{1-6}$ alkyl;

$R_2$, $R_{2a}$, $R_{2b}$, $R_{2c}$ and $R_{2d}$ are independently selected from the group consisting of hydrogen, deuterium, amino, hydroxyl, —OD, halogen, cyano, nitro, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{2-6}$ alkenyloxy, unsubstituted or substituted $C_{2-6}$ alkynyl, unsubstituted or substituted $C_{2-6}$ alkynyloxy, unsubstituted or substituted $C_{1-8}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein $R_2$ is not hydrogen, hydroxy or benzyloxy; or $R_2$ and $R_{2b}$ or $R_{2c}$, taken together with the atoms to which they are attached form a ring system;

$R_3$ is selected from hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

$R_{4a}$, $R_{4b}$, $R_{5a}$, and $R_{5b}$, are independently selected from the group consisting of hydrogen, deuterium, and unsubstituted or substituted $C_{1-6}$ alkyl; wherein when m and n are 1 then $R_{4a}$, $R_{4b}$, $R_{5a}$, $R_{5b}$ are hydrogen.

$R_6$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl;

$R_7$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;

$R_8$ is absent, or selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

X is selected from O or S;

Some embodiments disclosed herein relate to a method for treating a disease in a patient comprising administering to the patient an effective amount of a compound, pharmaceutically acceptable salt, polymorph or stereoisomer of a compound according to Formula (I), wherein the disease is selected from the group consisting of Abnormal hormonal activity, Alzheimer's disease, Alzheimer's disease dementia, Alzheimer's disease psychosis, Addiction (alcohol, cocaine, methamphetamine, nicotine and opioid), Addison's disease, ADHD, Alzheimer's disease psychosis, Affective disorders, Aggressiveness, Agitation, Akathisia, Alcohol addiction, Alcohol withdrawal, Amenorrhea, Amyotrophic lateral sclerosis, Anhedonia, Anorexia, Anti-NMDAR encephalitis, Anxiety, Appetite disorders, Asthma, Autism, Behavioral disorders, Behavioral disturbances associated with dementia, Binge eating disorder associated with impulse control disorder (ICD), Bipolar disorder, Blindness, Borderline disorder, Borderline personality disorder, Bradykinesia, Bulimia, Buying associated with ICD, Cardiac arrhythmia, Cerebral vascular accidents, Charles Bonnet disease, Chemotherapy-induced emesis, Childhood autism, Chronic pain, Chronic insomnia, cocaine addiction, Cognitive disorders, craniofacial pain, temporomandibular joint (TMJ)/temporomandibular disorder (TMD), Cushing's disease, Delusion, Dementia, Dementia with Lewy Body or Lewy Body dementia, dementia and psychosis associated with Creutzfeld-Jakob disease (CJD), Gerstmann-Strausser-Schenker disease (GSSD) and fatal familiar insomnia (FFI), Depression, Diabetes mellitus (non-insulin dependent), Diabetic peripheral neuropathy, Drug addiction, Double vision, Down's syndrome, Dyskinesia, Dysthymia, Dystonia, Ejaculatory problem, Emphysema, Epilepsy, Extrapyramidal disorder, Fibromyalgia, Frailty, Friedrich's Ataxia, Frontotemperal Dementia, Gambling associated with ICD, Galactorrhea, General anxiety disorder, Glaucoma, Hair loss or thinning, Hallucination, Headache, Hemorrhoids, Huntington's disease, Hyperprolactinemia, Hypertension, Hypersexuality associated with ICD, Hypotension, Hypoglutamateriga disorders, Impulse control disorder, Idiopathic thrombocytopenic purpura, Impotence, Incontinence, Increased intraocular pressure, Infertility, Inflammatory pain, Insomnia, Ischemia, Ischemic stroke, Lewy body disease (LBD), Learning disorders, Libido (decreased), Loss of libido, Low male fertility, Low sperm mobility, Lupus, Machado-Joseph disease, Major depression, Mania, Menopausal symptoms, Metabolic syndrome, methamphetamine addiction, Migraine, mild cognitive impairment (MCI), Motor tics, Multi-infarct dementia, Multiple sclerosis, Multiplex development disorder, Myocardial infarction, Myoclonus, Neuropathic pain, Neurodegenerative disorder, Neuropsychiatric disease, Nicotine addiction, Non motor symptoms of Parkinson's disease selected from dementia, depression, apathy, hallucinations, dribbling saliva (sialorrhea), constipation, pain, genitourinary problems and sleep disorders, Obsessive compulsive disorder, On/off phenomena, Opioid addiction, Osteoporosis, Pancreatis, Panic attacks, Parkinson's disease, Parkinson's disease dementia, Parkinson's disease psychosis, Periodic limb movement during sleep (PLMS), Peripheral vascular disease, Pituitary tumor, Postherpetic neuralgia, Progressive Supranucelar Palsy, Prion disease including Creutzfeld-Jakob disease (CID), Gerstmann-Strausser-Schenker disease (GSSD) and fatal familiar insomnia (FFI), Prolactinoma, Pseudobulbar affect (PBA), Psychomotor slowing, Psychosis, Psychoses secondary to neurodegenerative disorders, Psychosomatic disorders, Psychotic depression, post-traumatic stress disorder (PTSD), Raynaud's disease, Reflex sympathetic dystrophy, Restless legs syndrome, Retinal disease, Schizoaffective disorders, Schizophrenia, negative symptoms of schizophrenia, cognitive impairment associated with schizophrenia, Sepsis, Serotonin syndrome, Sexual dysfunction, Sexual dysfunction associated with antidepressant use, Sleep apnea, Sleep disorders, Sleep maintenance insomnia, social anxiety disorder, Spinal injury, Spinocerebellar Atrophy, Suicidal tendency, Thrombosis, Thrombotic stroke, Thrombotic thrombocytopenic purpura, Tinnitus, Tiredness, Tourette's syndrome, Transient insomnia, Traumatic brain injury, Treatment-resistant depression, Treatment-resistant schizophrenia, Tremor, Vaginal dryness, Vasospasm Wakefulness, vascular dementia, Hallucinations associated with Parkinson's disease, Delusions associated with Parkinson's disease; cancer, brain cancer, glioma, Pancreatic cancer, Hypoactive sexual desire disorder, adult type 2 diabetes mellitus with Parkinson's disease or dementia and Liver fibrosis.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

As used herein, any "R" group(s) such as, without limitation, $R_1$, $R_2$, $R_3$, $R_4$, $R_8$, $R_6$, $R_7$, $R_8$, $R_9$, and $R_{10}$, represent substituents that can be attached to the indicated atom. A non-limiting list of R groups includes but is not limited to hydrogen, alkyl, alkenyl, alkynyl, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined" as defined herein to form a cycloalkyl, aryl, heteroaryl or heteroalicyclyl group. For example, without limitation, if $R_a$ and $R_b$ of an $NR_aR_b$ group are indicated to be "taken together" or "combined", it means that they are covalently bonded to one another at their terminal atoms to form a ring that includes the nitrogen:

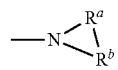

As readily recognized by the skilled person, any given atom with unsatisfied valences disclosed in the text, formulas, schemes, examples and figures herein is assumed to have a sufficient number of hydrogen atoms to satisfy the valency.

Whenever a group is described as being "unsubstituted or substituted," if substituted, the substituent(s) (which may be present one or more times, such as 1, 2, 3 or 4 times) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

Whenever a group, such as an "unsubstituted or substituted" alkyl group, is described without the use of "unsubstituted or substituted", e.g. "alkyl" it is understood as an "unsubstituted alkyl", unless the group is separately defined herein to be able to carry substituents. For example $C_{1-6}$ alkyl means an unsubstituted alkyl comprising 1 to 6 carbon atoms.

When a substituent on a group is deemed to be "substituted," the substituent itself is substituted with one or more of the indicated substituents. When the referenced substituent is substituted, it is meant that one or more hydrogen atoms on the referenced substituent may be replaced with a group(s) individually and independently selected from deuterium, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, 3$^{rd}$ Ed., John Wiley & Sons, New York, N.Y., 1999, which is hereby incorporated by reference in its entirety.

As used herein, "$C_m$ to $C_n$," "$C_m$-$C_n$" or "$C_{m-n}$" in which "m" and "n" are integers refers to the number of carbon atoms in the relevant group. That is, the group can contain from "m" to "n", inclusive, carbon atoms. Thus, for example, a "$C_1$ to $C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH)_3CH_2$—, $CH_3CH(CH)_3CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms, such as "$C_{1-6}$". The alkyl group could also be a lower alkyl having 1 to 4 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, the term "optionally", for example "optionally deuterated" means that group may be unsubstituted or substituted with one or more of the indicated substituents, e.g. one or more hydrogen(s) may be replaced by one or more deuterium(s).

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atoms, 3 carbon atoms, 4 carbon atoms, etc., up to and including 20 carbon atoms, although the present definition also covers the occurrence of the term "alkenyl" where no numerical range is designated). When substituted, the substituent group(s) is(are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, nitro, haloalkyl, haloalkoxy, and amino, including mono- and di-substituted amino groups, and the protected derivatives thereof.

As used herein, "alkynyl" refers to an alkyl group that contains in the straight or branched hydrocarbon chain one or more triple bonds. The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atoms, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" refers to heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replace may be in the middle or at the end of the alkyl group. Examples of heteroalkyl include, but are not limited to, —S-alkyl, —O-alkyl, —NH-alkyl, -alkylene-O-alkyl, etc.

As used herein, "aryl" refers to a carbocyclic (all carbon) ring or two or more fused rings (rings that share two adjacent atoms) that have a fully delocalized pi-electron system. Examples of aryl groups include, but are not limited to, benzene, naphthalene and azulene. An aryl group may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. Examples of monocyclic "heteroaryl" include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine, tetrazole, oxadiazole, and triazine. Examples of multicyclic "heteroaryl" include, but are not limited to, quinoline, isoquinoline, quinazoline, quinoxaline, indole, purines, benzofuran, benzothiophene, benzopyranones (e.g. coumarin, chromone, and isocoumarin). A heteroaryl may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a medium size alkylene having 1 to 10 carbon atoms, such as "$C_{1-6}$" The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —$CH_2$—O—, —$CH_2$—$CH_2$—O—, —$CH_2$—$CH_2$—$CH_2$—O—, —$CH_2$—NH—, —$CH_2$—$CH_2$—NH—, —$CH_2$—$CH_2$—$CH_2$—NH—, —$CH_2$—$CH_2$—NH—$CH_2$—, —O—$CH_2$—$CH_2$—O—$CH_2$—$CH_2$—O—, —O—$CH_2$—$CH_2$—O—$CH_2$—$CH_2$—, and the like.

As used herein, "alkylidene" refers to a divalent group, such as =CR'R", which is attached to one carbon of another group, forming a double bond. Alkylidene groups include, but are not limited to, methylidene (=$CH_2$) and ethylidene (=$CHCH_3$). As used herein, "arylalkylidene" refers to an alkylidene group in which either R' or R" is an aryl group. An alkylidene group may be substituted.

As used herein, "alkoxy" refers to the group —OR wherein R is an alkyl, e.g. methoxy, ethoxy, n-propoxy, cyclopropoxy, 1-methylethoxy (isopropoxy), n-butoxy, iso-butoxy, sec-butoxy, tert-butoxy, amoxy, tert-amoxy and the like. An alkoxy may be substituted.

As used herein, "alkylthio" refers to the formula —SR wherein R is an alkyl as defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO— and RS—, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, such as from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. Cycloalkenyl groups may range from $C_3$ to $C_{10}$, such as from $C_3$ to $C_8$ or from $C_5$ to $C_{10}$. For example, $C_{3-8}$ cycloalkenyl includes $C_{4-8}$ cycloalkenyl, $C_{5-8}$ cycloalkenyl or $C_{6-8}$ cycloalkenyl. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered ring which consists of carbon atoms and from one to five heteroatoms selected from the group consisting of nitrogen, oxygen and sulfur. The heteroalicyclic or heteroalicyclyl groups may range from $C_2$ to $C_{10}$, in some embodiments it may range from $C_2$ to $C_9$, and in other embodiments it may range from $C_2$ to $C_8$. The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings, examples are 2H-benzo[b][1,4]oxazin-3 (4H)-one, 3,4-dihydroquinolin-2(1H)-one, 1,2,3,4-tetrahydroquinoline, 3,4-dihydro-2H-benzo[b][1,4]oxazine, 2,3-dihydrobenzo[d]oxazole, 2,3-dihydro-1H-benzo[d]imidazole, indoline, and 1,3-dihydro-2H-benzo[d]imidazol-2-one, and benzo[d]oxazol-2 (3H)-one. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, dioxolanyl, imidazolinyl, morpholinyl, oxetanyl, furanyl, oxiranyl, piperidinyl N-Oxide, piperidinyl, piperazinyl, pyrrolidinyl, pyranyl, 4-piperidonyl, pyrazolidinyl, 2-oxopyrrolidinyl, tetrahydrofuranyl, tetrahydropyranyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "fused bicyclic ring" refers to a ring system where the two rings share two adjacent atoms. The two rings share one covalent bond. An example of a fused bicyclic ring is decalin.

A "spiro bicyclic ring" refers to a bicyclic ring wherein the two rings share one atom.

A "bridged ring system" refers to a ring system where two rings share three or more atoms. The two bridgehead atoms are separated by a bridge containing at least one atom, a specific example is norbornane, also known as bicyclo [2.2.1]heptane. The structure of bicyclo[2.2.1]heptane is shown below, also indicating the bridgehead atoms

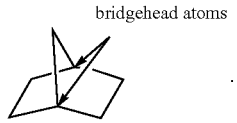

bridgehead atoms

A "(cycloalkyl)alkyl" is a cycloalkyl group connected, as a substituent, via an alkylene group. The alkylene and cycloalkyl of a (cycloalkyl)alkyl may be substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl. A haloalkyl may be substituted.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-1-fluoromethoxy, 2-fluoroisobutyoxy. A haloalkoxy may be substituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(=O)OR" group in which R can be the same as defined with respect to O-carboxy. A C-carboxy may be substituted.

A "trihalomethanesulfonyl" group refers to an "$X_3CSO_2$—" group" wherein X is a halogen.

A dashed bond, ─ ─ ─ ─ ─ , represents an optional unsaturation between the atoms forming the bond. This bond may be unsaturated (e.g. C=C, C=N, C=O) or saturated (e.g. C—C, C—N, C—O). When a dashed bond is present in a ring system it may form part of an aromatic ring system.

A "nitro" group refers to a "—$NO_2$" group.
A "cyano" group refers to a "—CN" group.
A "cyanato" group refers to an "—OCN" group.
An "isocyanato" group refers to a "—NCO" group.
A "thiocyanato" group refers to a "—SCN" group.
A "carbonyl" group refers to a "—C(=O)—" group.
A "thiocarbonyl" group refers to a "—C(=S)—" group.
An "oxo" group refers to a "=O" group.
A "hydroxy" group or "hydroxyl" group refers to an "—OH" group.
An "isothiocyanato" group refers to an "—NCS" group.
A "sulfinyl" group refers to an "—S(=O)—R" group in which R can be the same as defined with respect to O-carboxy. A sulfinyl may be substituted.

A "sulfonyl" group refers to an "$SO_2R$" group in which R can be the same as defined with respect to O-carboxy. A sulfonyl may be substituted.

An "S-sulfonamido" group refers to a "—$SO_2NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted heteroalicyclyl, substituted or unsubstituted aryl, and substituted or unsubstituted heteroaryl. A S-sulfonamido may be substituted.

An "N-sulfonamido" group refers to a "RSO$_2$N(R$_A$)—" group in which R and R$_A$ independently of each other can be the same as defined with respect to the R group as defined for O-carboxy. An N-sulfonamido may be substituted.

A "trihalomethanesulfonamido" group refers to an "X$_3$CSO$_2$N(R)—" group with X as halogen and R can be the same as defined with respect to O-carboxy. A trihalomethanesulfonamido may be substituted.

A "C-amido" group refers to a "—C(=O)NR$_A$R$_B$" group in which R$_A$ and R$_B$ independently of each other can be the same as defined with respect to the R group as defined for O-carboxy, or combined to form a ring system selected from the group consisting of substituted or unsubstituted C$_{3-8}$ cycloalkyl, substituted or unsubstituted C$_{3-8}$ cycloalkenyl, substituted or unsubstituted heteroalicyclyl, substituted or unsubstituted aryl, and substituted or unsubstituted heteroaryl. A C-amido may be substituted.

An "N-amido" group refers to a "RC(=O)NR$_A$—" group in which R and R$_A$ independently of each other can be the same as defined with respect to the R group as defined for O-carboxy. An N-amido may be substituted.

An "ester" refers to a "—C(=O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amine" or "amino" refers to "RNH$_2$" (a primary amine), "R$_2$NH" (a secondary amine), "R$_3$N" (a tertiary amine). An amino group may be substituted.

An aminoalkyl refers to an amino group connected via a lower alkylene group. An aminoalkyl may be substituted.

As used herein "0" (zero), for example in connection with a subscript means that it's absent. For example —(CH$_2$)$_s$—C$_{2-6}$ alkyl, wherein S can be "0" means that the —(CH$_2$)— is absent and the remaining group is —C$_{2-6}$ alkyl.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, 3$^{rd}$ Ed., John Wiley & Sons, New York, N.Y., 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As employed herein, the following terms have their accepted meaning in the chemical literature.
EtOAc Ethylacetate
DIEA N,N-Diisopropylethylamine
HCl Hydrochloric acid
DMF N,N-dimethylformamide
THF Tetrahydrofuran
CDCl$_3$ Chloroform-d
DMSO-D6 Dimethylsulfoxide-d6
MgSO$_4$ Magnesium Sulfate
POCl$_3$ Phosphorus(V) oxychloride
KOH Potassium hydroxide
NaOH Sodium hydroxide
Na$_2$SO$_4$ Sodium Sulfate
K$_2$CO$_3$ Potassium carbonate
Na$_2$CO$_3$ Sodium carbonate
TFA Trifluoroacetic acid
Boc t-butoxycarbonyl
FMOC Fluorenylmethyloxycarbonyl
FMOC-Cl 9-Fluorenylmethoxycarbonyl chloride
TEOC 2-(trimetylsilyl)ethoxycarbonyl
equiv. equivalents
min minutes
cat catalytical
HCl hydrochloric acid
HPLC high performance liquid chromatography It is understood that, in any compound disclosed herein having one or more stereocenters or chiral centers, if an absolute stereochemistry is not expressly indicated, then each center may independently be of R-configuration or S-configuration or a mixture thereof. Thus, the compounds provided herein may be enatiomerically pure or be stereoisomeric mixtures. Further, compounds provided herein may be scalemic mixtures. In addition, it is understood that in any compound having one or more double bond(s) generating geometrical isomers that can be defined as E or Z each double bond may independently be E or Z or a mixture thereof. Likewise, all tautomeric forms are also intended to be included.

As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

It is understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise. For example the term "methyl" includes —CH$_3$, —CD$_3$, —CH$_2$D, etc.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt (NH$_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caprate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, a "prodrug" refers to a compound that may not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a carboxylic acid (the active entity) once inside the cell where water-solubility is beneficial. A further example of a prodrug might be a short peptide (polyaminoacid) bonded to an acid group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985) *Medicinal Chemistry A Biochemical Approach*, Oxford University Press, New York, pages 388-392). A specific example of prodrugs relates to formation of a basic nitrogen comprising the piperidyl group of Formula (I), wherein the basic nitrogen may be formed by the metabolic cleavage of a group attached to the nitrogen of the piperidyl group, forming a basic nitrogen, e.g. as shown in Formula A. Particular examples are acyl and tosyl groups attached to the nitrogen.

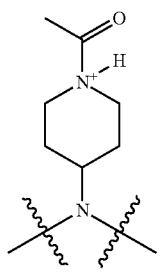

(A)

"Anti-drug" refers to a compound or composition acting against or opposing illicit drugs or their use. Compounds of the present application may act as anti-drugs.

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability, etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any intracellular molecule that in response to ligation generates a signal. A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

"Selective" or "selectivity" is defined as a compound's ability to generate a desired response from a particular receptor type, subtype, class or subclass while generating less or little response from other receptor types. "Selective" or "selectivity" of one or more particular subtypes of a compound means a compound's ability to increase the activity of the subtypes while causing less, little or no increase in the activity of other subtypes. Selectivity of a compound between receptor targets may for example be determined by the ratio of potencies or affinities for those targets. For example, a compound is said to be 10-fold selectivity for Target 1 over Target 2 if said compound has a pKi of 10 nM for Target 1 and 100 nM for Target 2. Said compound is therefore 10-fold more potent at Target 1, i.e. it is 10-fold selective for Target 1.

As used herein, "IC50" refers to an amount, concentration, or dosage of a particular test compound that achieves a 50% inhibition of a maximal response. The IC50 can be determined using an assay. The assay may be an R-SAT® assay as described herein but is not limited to an RSAT assay.

As used herein, "EC50" refers to an amount, concentration or dosage of a particular test compound that elicits a dose-dependent response at 50% of maximal expression of a particular response that is induced, provoked or potentiated by the particular test compound, in an assay that measures such response such as but not limited to R-SAT® assay described herein.

As used herein, "pKi" refers to the negative logarithm of the Ki, the equilibrium dissociation constant of an antagonist-receptor complex measured in a functional antagonist or radioligand binding assay, e.g. R-SAT® assay as described herein.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Compounds

Provided herein are compounds according to Formulas (I)

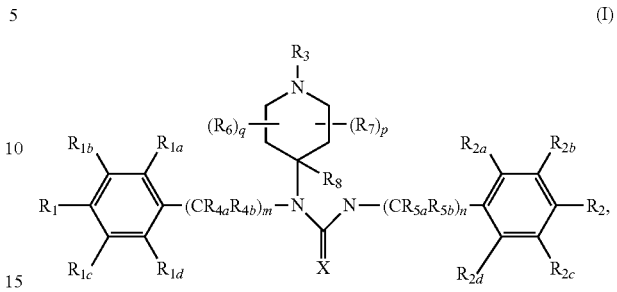

(I)

or a pharmaceutically acceptable salt, hydrate, solvate, polymorph, prodrug, stereoisomer, and deuterated analogue thereof, wherein:

m, and n are independently an integer selected from the group consisting of 0, 1, 2, and 3;

p, and q are independently an integer selected from the group consisting of 0, 1, 2, 3, and 4;

$R_1$, $R_{1a}$, $R_{1b}$, $R_{1c}$ and $R_{1d}$ are independently selected from the group consisting of hydrogen, deuterium, hydroxyl, —OD, halogen, cyano, unsubstituted or substituted amino, —$SO_2R_{10}$, —OC(=O)$R_{11}$, —C(=O)O$R_{11}$, —$NR_{10}$C(=O)$R_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein at least one of $R_1$, $R_{1a}$, $R_{1b}$, $R_{1c}$ and $R_{1d}$ is not hydrogen, wherein $R_{10}$ and $R_{11}$, independently are selected from the group consisting of hydrogen, amino, unsubstituted or substituted $C_{1-6}$ alkyl;

$R_2$, $R_{2a}$, $R_{2b}$, $R_{2c}$ and $R_{2d}$ are independently selected from the group consisting of hydrogen, deuterium, amino, hydroxyl, —OD, halogen, cyano, nitro, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{2-6}$ alkenyloxy, unsubstituted or substituted $C_{2-6}$ alkynyl, unsubstituted or substituted $C_{2-6}$ alkynyloxy, unsubstituted or substituted $C_{1-8}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein $R_2$ is not hydrogen, hydroxy or benzyloxy; or $R_2$ and $R_{2b}$, or $R_2$ and $R_{2c}$, taken together with the atoms to which they are attached form a ring system; or $R_2$ and $R_{2b}$ or $R_{2c}$, taken together with the atoms to which they are attached form a ring system; or $R_{2a}$ and $R_{2b}$, or $R_{2c}$ and $R_{2d}$, taken together with the atoms to which they are attached form a ring system;

$R_3$ is selected from hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

$R_{4a}$, $R_{4b}$, $R_{5a}$, and $R_{5b}$, are independently selected from the group consisting of hydrogen, deuterium, and unsubstituted or substituted $C_{1-6}$ alkyl; wherein when m and n are 1 then $R_{4a}$, $R_{4b}$, $R_{5a}$, $R_{5b}$ are hydrogen;

$R_6$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl; or $R_6$ and $R_3$, taken together with the atoms to which they are attached form a ring system; or $R_6$ and $R_3$, taken together with the atoms to which they are attached form a ring system;

$R_7$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;

$R_8$ is absent, or selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

X is O or S.

Provided herein are also compounds according to Formulas (I).

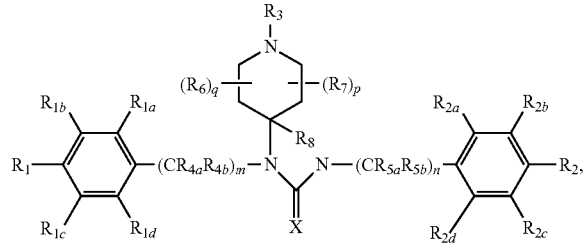

or a pharmaceutically acceptable salt, hydrate, solvate, polymorph, prodrug, stereoisomer, and deuterated analogue thereof, wherein:

m, and n are independently an integer selected from the group consisting of 0, 1, 2, and 3;

p, and q are independently an integer selected from the group consisting of 0, 1, 2, 3, and 4;

$R_1$, $R_{1a}$, $R_{1b}$, $R_{1c}$ and $R_{1d}$ are independently selected from the group consisting of hydrogen, deuterium, hydroxyl, —OD, halogen, cyano, amino, —SO$_2$R$_{10}$, —OC(=O)R$_{11}$, —C(=O)OR$_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein at least one of $R_1$, $R_{1a}$, $R_{1b}$, $R_{1c}$ and $R_{1d}$ is not hydrogen, wherein $R_{10}$ and $R_{11}$, independently are selected from the group consisting of hydrogen, amino, unsubstituted or substituted $C_{1-6}$ alkyl;

$R_2$, $R_{2a}$, $R_{2b}$, $R_{2c}$ and $R_{2d}$ are independently selected from the group consisting of hydrogen, deuterium, amino, hydroxyl, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein at least one of $R_2$, $R_{2a}$, $R_{2b}$, $R_{2c}$ and $R_{2d}$ is not selected from hydrogen; or $R_2$ and $R_{2b}$ or $R_{2c}$, taken together with the atoms to which they are attached form a ring system;

$R_3$ is selected from hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

$R_{4a}$, $R_{4b}$, $R_{5a}$, and $R_{5b}$ are independently selected from the group consisting of hydrogen, deuterium, and unsubstituted or substituted $C_{1-6}$ alkyl; wherein when m and n are 1 then $R_{4a}$, $R_{4b}$, $R_{5a}$, $R_{5b}$ are hydrogen.

$R_6$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl;

$R_7$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;

$R_8$ is absent, or selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

X is O or S.

Provided herein are also compounds according to Formulas (I)

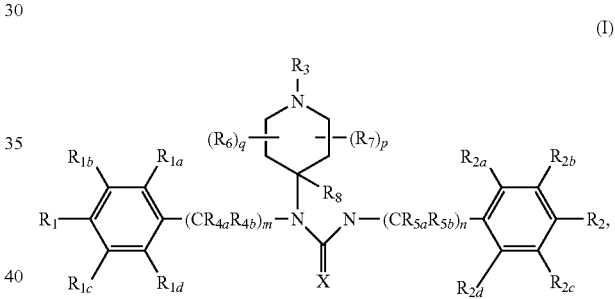

or a pharmaceutically acceptable salt, hydrate, solvate, polymorph, prodrug and stereoisomer thereof, wherein:

m, and n are independently an integer selected from the group consisting of 0, 1, 2, and 3;

p, and q are independently an integer selected from the group consisting of 0, 1, 2, 3, and 4;

$R_1$ is selected from the group consisting of deuterium, hydroxyl, —OD, halogen, cyano, amino, —S(=O)$_2$R$_{10}$, —OC(=O)R$_{11}$, —C(=O)OR$_{11}$, —NR$_{10}$C(=O)R$_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, $R_{1d}$ is selected from the group consisting of hydrogen, deuterium, hydroxyl, —OD, halogen, cyano, amino, —S(=O)$_2$R$_{10}$, —OC(=O)R$_{11}$, —C(=O)OR$_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein $R_{10}$ and $R_{11}$, independently are selected from the group consisting of hydrogen, amino, unsubstituted or substituted $C_{1-6}$ alkyl;

$R_2$ is selected from the group consisting of deuterium, amino, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{2-6}$ alkenyloxy, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl; wherein $R_2$ is not benzyloxy;

$R_{2d}$ is selected from the group consisting of hydrogen, deuterium, amino, hydroxyl, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl; or $R_{2a}$, $R_{2c}$ and $R_{2d}$ are hydrogen and $R_2$ and $R_{2b}$ or $R_{2c}$, taken together with the atoms to which they are attached form a heteroalicyclic or heteroaryl ring system;

or $R_{1a}$, $R_{1b}$, $R_{1c}$, $R_{2a}$, $R_{2b}$, and $R_{2c}$ are hydrogen, and at least one of $R_{1d}$ and $R_{2d}$ is not hydrogen;

$R_3$ is selected from hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

$R_{4a}$, $R_{4b}$, $R_{5a}$, and $R_{5b}$ are independently selected from the group consisting of hydrogen, deuterium, and unsubstituted or substituted $C_{1-6}$ alkyl; wherein when m and n are 1, then $R_{4a}$, $R_{4b}$, $R_{5a}$, $R_{5b}$ are hydrogen;

$R_6$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl; or $R_6$ and $R_3$, taken together with the atoms to which they are attached form a ring system;

$R_7$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;

$R_8$ is absent, or selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

X is O or S.

Provided herein are also compounds according to Formulas (I)

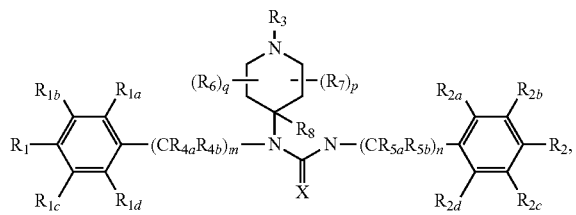

(I)

or a pharmaceutically acceptable salt, hydrate, solvate, polymorph, prodrug and stereoisomer thereof, wherein:

m, and n are independently an integer selected from the group consisting of 0, 1, 2, and 3;

p, and q are independently an integer selected from the group consisting of 0, 1, 2, 3, and 4;

$R_1$ is selected from the group consisting of deuterium, hydroxyl, —OD, halogen, cyano, amino, —S(=O)$_2$R$_{10}$, —OC(=O)R$_{11}$, —C(=O)OR$_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, $R_{1d}$ is selected from the group consisting of hydrogen, deuterium, hydroxyl, —OD, halogen, cyano, amino, —S(=O)$_2$R$_{10}$, —OC(=O)R$_{11}$, —C(=O)OR$_{11}$, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein $R_{10}$ and $R_{11}$, independently are selected from the group consisting of hydrogen, amino, unsubstituted or substituted $C_{1-6}$ alkyl;

$R_2$ is selected from the group consisting of deuterium, amino, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{2-6}$ alkenyloxy, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl; wherein $R_2$ is not benzyloxy;

$R_{2d}$ is selected from the group consisting of hydrogen, deuterium, amino, hydroxyl, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

and $R_{1a}$, $R_{1b}$, $R_{1c}$, $R_{2a}$, $R_{2b}$, and $R_{2c}$ are hydrogen, and at least one of $R_{1d}$ and $R_{2d}$ is not hydrogen;

or $R_{2a}$, $R_{2c}$ and $R_{2d}$ are hydrogen and $R_2$ and $R_{2b}$ or $R_{2c}$, taken together with the atoms to which they are attached form a heteroalicyclic or heteroaryl ring system;

$R_3$ is selected from hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

$R_{4a}$, $R_{4b}$, $R_{5a}$, and $R_{5b}$ are independently selected from the group consisting of hydrogen, deuterium, and unsubstituted or substituted $C_{1-6}$ alkyl; wherein when m and n are 1, then $R_{4a}$, $R_{4b}$, $R_{5a}$, $R_{5b}$ are hydrogen.

$R_6$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl;

$R_7$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;

$R_8$ is absent, or selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

X is O or S.

In some embodiments $R_1$, $R_{1a}$, $R_{1b}$, $R_{1c}$ and $R_{1d}$ independently are selected from the group consisting of hydrogen, deuterium, halogen, amino, —SO$_2$NH$_2$, —SO$_2$N(C$_{1-4}$ alkyl)$_2$, —SO$_2$—C$_{1-4}$ alkyl, —OC(=O)—C$_{1-4}$ alkyl, —N(C$_{1-4}$ alkyl)$_2$, $C_{1-6}$ alkyl, $C_{1-6}$ haloalkyl, $C_{1-6}$ alkoxy, $C_{3-4}$ cycloalkyl, $C_{3-4}$ cycloalkyl-$C_{1-3}$ alkyl and deuterated analogues thereof, e.g. $R_{1a}$, $R_{1b}$, $R_{1c}$ and $R_{1d}$ are independently selected from the group consisting of hydrogen, deuterium, halogen, amino, SO$_2$NH$_2$, —SO$_2$CH$_3$, —OC(=O)CH$_3$, methyl, —CD$_3$, methoxy, —OCD$_3$, —OCF$_3$ and —CF$_3$; and $R_1$ is selected from halogen, amino, SO$_2$NH$_2$, —SO$_2$CH$_3$, —OC(=O)CH$_3$, methyl, —CD$_3$, ethyl, —CD$_2$CD$_3$, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, methoxy, —OCD$_3$, optionally deuterated ethoxy, optionally deuterated n-propoxy, optionally deuterated isopropoxy, optionally deuterated n-butoxy, optionally deuterated iso-butoxy, optionally deuterated pentyl-oxy, optionally deuterated 4-methyl-butoxy, optionally deuterated hexyl-oxy, optionally deuterated 4-methylpentoxy, —OCF$_3$, —OCF$_2$CF$_3$, —OCHF$_2$, —OCDF$_2$, —CF$_3$, —CF$_2$CF$_3$, —CHF$_2$, CDF$_2$—CH$_2$CF$_3$, —CD$_2$CF$_3$, —CH$_2$F, 1,1,2,2-tetrafluorobutyl and 1,1,1,2,2-pentafluorobutyl.

In some embodiments $R_{1a}$, $R_{1b}$, $R_{1c}$ and $R_{1d}$ are independently selected from the group consisting of hydrogen, deuterium, hydroxyl, halogen, amino, —SO$_2$NH$_2$, —SO$_2$CH$_3$, —OC(=O)CH$_3$, —NHC(=O)CH$_3$, methyl, —CD$_3$, methoxy, benzyloxy, dimethylamino, —OCD$_3$, —OCF$_3$, —OCHF$_2$ and —CF$_3$. In some embodiments $R_{1a}$, $R_{1b}$, $R_{1c}$ and $R_{1d}$ are independently selected from the group consisting of hydrogen, deuterium, hydroxyl, halogen, methyl, —CD$_3$, methoxy, —OCD$_3$, OCF$_3$ and —CF$_3$. In some embodiments $R_{1a}$, $R_{1b}$, $R_{1c}$ and $R_{1d}$ are independently selected from the group consisting of hydrogen, deuterium, hydroxyl, halogen, OCF$_3$ and —CF$_3$. In some embodiments $R_{1a}$, $R_{1b}$, $R_{1c}$ and $R_{1d}$ are independently selected from the group consisting of hydrogen, deuterium and halogen. In some embodiments $R_{1a}$, $R_{1b}$, $R_{1c}$ and $R_{1d}$ are independently selected from the group consisting of hydrogen and halogen. In some embodiments $R_{1a}$, $R_{1b}$, and $R_{1c}$ are hydrogen, and $R_{1d}$ is halogen.

In some embodiments $R_1$ is selected from the group consisting of halogen, hydroxyl, —CD$_3$, —CD$_2$CD$_3$, $C_{1-6}$ alkyl, —OCD$_3$, $C_{1-6}$ alkoxy, —OCF$_3$, —OCF$_2$CF$_3$, —OCHF$_2$, —OCDF$_2$, —CF$_3$, —CF$_2$CF$_3$, —CHF$_2$, —CDF$_2$—CH$_2$CF$_3$, —CD$_2$CF$_3$, and —CH$_2$F. In some embodiments $R_1$ is selected from the group consisting of halogen, hydroxyl, —CD$_3$, —CD$_2$CD$_3$, methyl, ethyl, —OCD$_3$, methoxy, ethoxy, —OCF$_3$, —OCF$_2$CF$_3$, —OCHF$_2$, —OCDF$_2$, —CF$_3$, —CF$_2$CF$_3$, —CHF$_2$, —CDF$_2$—CH$_2$CF$_3$, —CD$_2$CF$_3$, and —CH$_2$F. In some embodiments $R_1$ is selected from the group consisting of halogen, hydroxyl, methyl, methoxy, —OCF$_3$, —OCHF$_2$, —CF$_3$, —CHF$_2$ and —CH$_2$F. In some embodiments $R_1$ is selected from the group consisting of halogen, —OCF$_3$, —OCHF$_2$, —CF$_3$, —CHF$_2$ and —CH$_2$F. In some embodiments $R_1$ is halogen. In some embodiments $R_1$ is F or $C_1$. In some embodiments $R_1$ is F.

In some embodiments $R_{1a}$, $R_{1b}$, and $R_{1c}$ are hydrogen, and $R_{1d}$ is deuterium, halogen, amino, SO$_2$NH$_2$, —SO$_2$CH$_3$, —OC(=O)CH$_3$, methyl, —CD$_3$, methoxy, —OCD$_3$, —OCF$_3$ and —CF$_3$; and $R_1$ is selected from halogen, methyl, methoxy, —OCF$_3$ and —CF$_3$, such as fluoro, chloro and —CF$_3$.

In some embodiments $R_{1a}$, $R_{1b}$, and $R_{1c}$ are hydrogen, and $R_{1d}$ is hydrogen or fluoro; and $R_1$ is selected from fluoro, chloro, methyl, methoxy, —OCF$_3$ and —CF$_3$, such as fluoro, and —CF$_3$.

In some embodiments $R_{1a}$, $R_{1b}$, and $R_{1c}$ are hydrogen, and $R_{1d}$ is fluoro; and $R_1$ is selected from fluoro, chloro, methoxy, and methyl, such as fluoro.

In some embodiments $R_{1a}$, $R_{1b}$, and $R_{1c}$ are hydrogen, $R_{1d}$ is halogen, such as fluoro, and $R_1$ is halogen, such as fluoro, e.g. both $R_1$ and $R_{1d}$ are fluoro.

In some embodiments two of $R_{1a}$, $R_{1b}$, $R_{1c}$ and $R_{1d}$ are independently selected from the group consisting of fluoro, chloro, methyl, methoxy, —OCF$_3$ and —CF$_3$, the others are hydrogen; $R_1$ is selected from the group consisting of fluoro, chloro, methyl, methoxy, —OCF$_3$ and —CF$_3$. In some embodiments $R_{1a}$ and $R_{1b}$ are independently selected from the group consisting of fluoro, chloro, methyl, methoxy, —OCF$_3$ and —CF$_3$, $R_{1c}$ and $R_{1d}$ are hydrogen; $R_1$ is selected from the group consisting of fluoro, chloro, methyl, methoxy, —OCF$_3$ and —CF$_3$. In some embodiments $R_{1a}$ and $R_{1c}$ are independently selected from the group consisting of fluoro, chloro, methyl, methoxy, —OCF$_3$ and —CF$_3$, $R_{1b}$ and $R_{1d}$ are hydrogen; $R_1$ is selected from the group consisting of fluoro, chloro, methyl, methoxy, —OCF$_3$ and —CF$_3$. In some embodiments $R_{1a}$ and $R_{1d}$ are independently selected from the group consisting of fluoro, chloro, methyl, methoxy, —OCF$_3$ and —CF$_3$, $R_{1b}$ and $R_{1c}$ are hydrogen; $R_1$ is selected from the group consisting of fluoro, chloro, methyl, methoxy, —OCF$_3$ and —CF$_3$.

In some embodiments $R_2$, $R_{2a}$, $R_{2b}$, $R_{2c}$ and $R_{2d}$ independently are selected from the group consisting of hydrogen, hydroxyl, halogen, cyano, $C_{1-6}$ alkyl, $C_{1-6}$ haloalkyl, $C_{1-6}$ alkoxy, $C_{1-6}$ haloalkoxy, $C_{3-4}$ cycloalkyl, $C_{3-4}$ cycloalkyl-$C_{1-3}$ alkyl and deuterated analogues thereof or $R_{2a}$, $R_{2c}$ and $R_{2d}$ are hydrogen and $R_2$ and $R_{2b}$, taken together with the phenyl ring they attach to and the atoms to which they are attached form a bicyclic fused ring system that has the following formulae:

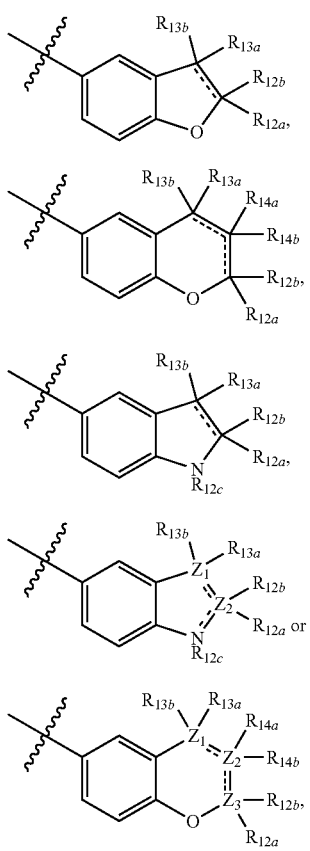

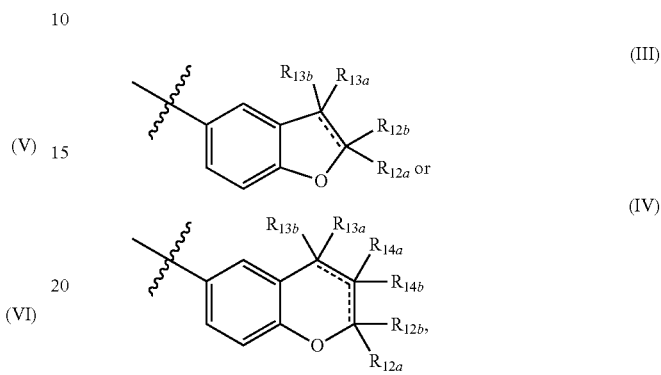

wherein $R_{12a}$, $R_{12b}$, $R_{12c}$, $R_{13a}$, $R_{13b}$, $R_{14a}$, and $R_{14b}$ independently are absent or selected from the group consisting of hydrogen, halogen, hydroxyl, cyano, $C_{1-4}$ alkyl, and $C_{1-4}$ alkoxy, and wherein $Z_1$, $Z_2$ and $Z_3$ independently are selected from the group consisting of C, N, O and S, e.g. $R_{2a}$, $R_{2b}$, $R_{2c}$ and $R_{2d}$ independently are selected from the group consisting of hydrogen, deuterium, hydroxyl, halogen, methyl, —$CD_3$, methoxy, —$OCD_3$, —$OCF_3$ and —$CF_3$; and $R_2$ is selected from halogen, amino, methyl, —$CD_3$, ethyl, —$CD_2CD_3$, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, optionally deuterated methoxy, optionally deuterated ethoxy, optionally deuterated n-propoxy, optionally deuterated isopropoxy, optionally deuterated allyloxy, optionally deuterated prop-2-yn-1-yloxy, optionally deuterated n-butoxy, optionally deuterated iso-butoxy, optionally deuterated tert-butoxy, optionally deuterated pentyl-oxy, optionally deuterated 4-methyl-butoxy, optionally deuterated hexyl-oxy, optionally deuterated 4-methylpentoxy, optionally deuterated cyclopropyloxy, optionally deuterated cyclopropylmethoxy, optionally deuterated cyclopropylethoxy, optionally deuterated cyclobutyloxy, optionally deuterated cyclobutyloxy, optionally deuterated cyclobutylmethoxy, optionally deuterated cyclobutylethoxy, optionally deuterated $C_{1-6}$ haloalkoxy, —$OCF_3$, —$OCF_2CF_3$, —$OCHF_2$, —$OCDF_2$, —$CF_3$, —$CF_2CF_3$, —$CH_2F$, —$CH_2CF_3$, —$CDF_2$—$CH_2CF_3$, —$CD_2CF_3$, —$CF_2$, 1,1,2,2-tetrafluorobutyl and 1,1,1,2,2-pentafluorobutyl.

In some embodiments $R_2$ is not a nitro group.

In some embodiments $R_2$, $R_{2a}$, $R_{2b}$, $R_{2c}$ and $R_{2d}$ independently are selected from the group consisting of hydrogen, hydroxyl, halogen, cyano, $C_{1-6}$ alkyl, $C_{1-6}$ haloalkyl, $C_{1-6}$ alkoxy, $C_{1-6}$ haloalkoxy, $C_{3-4}$ cycloalkyl, $C_{3-4}$ cycloalkyl-$C_{1-3}$ alkyl and deuterated analogues thereof or $R_{2a}$, $R_{2c}$ and $R_{2d}$ are hydrogen and $R_2$ and $R_{2b}$, taken together with the atoms to which they are attached form a heteroalicyclic ring system wherein the formed ring system taken together with the phenyl group to which it is fused has the following general formulae wherein $R_{12a}$, $R_{12b}$, $R_{13a}$, $R_{13b}$, $R_{14a}$, and $R_{14b}$ independently are absent or selected from the group consisting of halogen, hydroxyl, cyano, $C_{1-4}$ alkyl, and $C_{1-4}$ alkoxy, e.g. $R_{2a}$, $R_{2b}$, $R_{2c}$ and $R_{2d}$ independently are selected from the group consisting of hydrogen, deuterium, hydroxyl, halogen, methyl, —$D_3$, methoxy, —$OCD_3$, —$OCF_3$ and —$CF_3$; and $R_2$ is selected from halogen, methyl, —$CD_3$, ethyl, —$CD_2CD_3$, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, optionally deuterated methoxy, optionally deuterated ethoxy, optionally deuterated n-propoxy, optionally deuterated isopropoxy, optionally deuterated allyloxy, optionally deuterated prop-2-yn-1-yloxy, optionally deuterated n-butoxy, optionally deuterated iso-butoxy, optionally deuterated tert-butoxy, optionally deuterated pentyl-oxy, optionally deuterated 4-methyl-butoxy, optionally deuterated hexyl-oxy, optionally deuterated 4-methylpentoxy, optionally deuterated cyclopropyloxy, optionally deuterated cyclopropylmethoxy, optionally deuterated cyclopropylethoxy, optionally deuterated cyclobutyloxy, optionally deuterated cyclobutyloxy, optionally deuterated cyclobutylmethoxy, optionally deuterated cyclobutylethoxy, optionally deuterated $C_{1-6}$ haloalkoxy, —$OCF_3$, —$OCF_2CF_3$, —$OCHF_2$, —$OCDF_2$, —$CF_3$, —$CF_2CF_3$, —$CH_2F$, —$CH_2CF_3$, —$CDF_2$—$CH_2CF_3$, —$CD_2CF_3$, —$CF_2$, 1,1,2,2-tetrafluorobutyl and 1,1,1,2,2-pentafluorobutyl. $R_2$ is not a nitro group.

In some embodiments $R_2$ and $R_{2b}$, taken together with the phenyl ring they attach to and the atoms to which they are attached form a bicyclic fused ring system selected from the group consisting of:

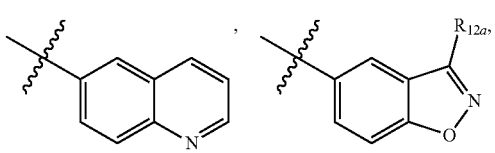

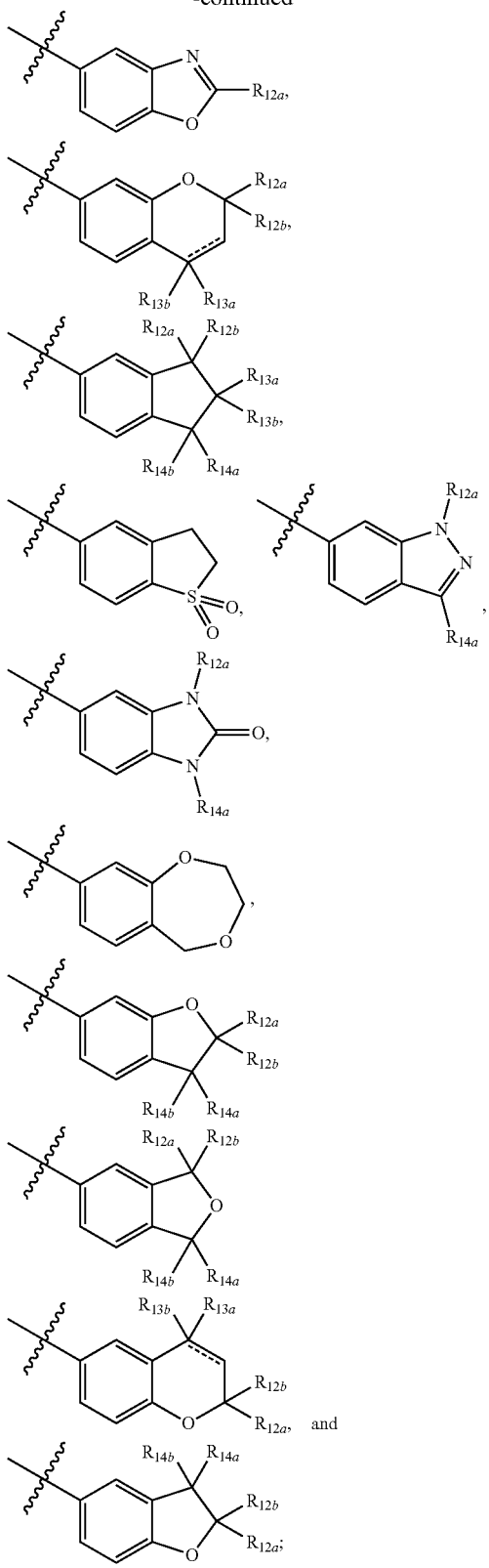

wherein $R_{12a}$, $R_{12b}$, $R_{12c}$, $R_{13a}$, $R_{13b}$, $R_{14a}$, and $R_{14b}$ independently are absent or selected from the group consisting of hydrogen, halogen, hydroxyl, cyano, $C_{1-4}$ alkyl, and $C_{1-4}$ alkoxy.

In some embodiments the ring system formed between $R_2$ and $R_{2b}$ is a ring of Formula (III), and both $R_{12a}$ and $R_{12b}$ are hydrogen or methyl, and both $R_{13a}$ and $R_{13b}$ are hydrogen or methyl.

In some embodiments $R_{2a}$, $R_{2b}$, $R_{2c}$ are hydrogen, $R_{2d}$ is hydrogen, fluoro or hydroxyl, and $R_2$ is selected from methoxy, ethoxy, n-propoxy, isopropoxy, n-butoxy, iso-butoxy, pentyl-oxy, 4-methyl-butoxy, hexyl-oxy and 4-methylpentoxy.

In some embodiments $R_2$, provided $R_2$ is not forming a ring system with $R_{2b}$, is selected from the group consisting of —$OCD_3$, —$OC(CD_3)_3$, methoxy, ethoxy, n-propoxy, isopropoxy, allyloxy, prop-2-yn-1-yloxy n-butoxy, iso-butoxy, tert-butoxy, pentyl-oxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, 2-fluoroethoxy, 3-fluoropropoxy, 2,2-difluoroethoxy, 4-methoxybutoxy, 2-hydroxylethoxy, 1,2-dihydroxyethyl, 2-hydroxy-2,3-dimethylbutoxy, phenoxy, —$OCF_3$ and (1,3-difluoropropan-2-yl)oxy.

In some embodiments $R_2$, provided $R_2$ is not forming a ring system with $R_{2b}$, is selected from the group consisting of methoxy, ethoxy, n-propoxy, isopropoxy, allyloxy, prop-2-yn-1-yloxy n-butoxy, iso-butoxy, tert-butoxy, pentyl-oxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, —$OCF_3$ and (1,3-difluoropropan-2-yl)oxy.

$R_2$ is selected from the group consisting of ethoxy, n-propoxy, isopropoxy, allyloxy, iso-butoxy, tert-butoxy, cyclopropyloxy, cyclopropylmethoxy, 2-fluoroethoxy, 3-fluoropropoxy, 2,2-difluoroethoxy; or $R_2$ and $R_{2b}$, taken together with the phenyl ring they attach to and the atoms to which they are attached form unsubstituted 2,3-dihydrobenzofuran-5-yl, unsubstituted benzofuran-5-yl, and unsubstituted 2,2-dimethyl-2,3-dihydrobenzofuran-5-yl.

In some embodiments $R_1$ and $R_{1d}$ independently are selected from the group consisting of deuterium, halogen, methyl, —$CD_3$, methoxy, —$OCD_3$, —$OCF_3$ and —$CF_3$; or $R_2$ and $R_{2d}$ independently are selected from the group consisting of deuterium, halogen, methyl, —$CD_3$, methoxy, ethoxy, n-propoxy, isopropoxy, n-butoxy, iso-butoxy, pentyl-oxy, 4-methyl-butoxy, hexyl-oxy, 4-methylpentoxy, —$OCD_3$, —$OCF_3$, cyclopropyloxy, 2-fluoroethoxy, 3-fluoropropoxy, 2,2-difluoroethoxy, and —$CF_3$.

In some embodiments $R_1$ and $R_{1d}$ are fluoro, and $R_2$ is $C_{1-6}$ alkoxy, such as methoxy, ethoxy, n-propoxy, isopropoxy, n-butoxy, iso-butoxy, pentyl-oxy, 4-methyl-butoxy, hexyl-oxy and 4-methylpentoxy. In some embodiments $R_1$ and $R_{1d}$ are fluoro, and $R_2$ is n-propoxy, isopropoxy, n-butoxy, iso-butoxy, tert-butoxy, cyclopropylmethoxy, or cyclopropyloxy.

In some embodiments $R_1$ and $R_{1d}$ are fluoro, and $R_{1a}$, $R_{1b}$ and $R_{1c}$ are hydrogen; $R_2$, provided $R_2$ is not forming a ring system with $R_{2b}$, is selected from the group consisting of methoxy, ethoxy, n-propoxy, isopropoxy, allyloxy, prop-2-yn-1-yloxy, n-butoxy, iso-butoxy, tert-butoxy, pentyl-oxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, 2-fluoroethoxy, 3-fluoropropoxy, 2,2-difluoroethoxy, 4-methoxybutoxy, 2-hydroxyethoxy, 1,2-dihydroxyethyl, —$OCF_3$ and (1,3-difluoropropan-2-yl)oxy; and $R_{2a}$, $R_{2b}$, $R_{2c}$ and $R_{2d}$ are hydrogen; or $R_2$ and $R_{2b}$, taken together with the phenyl ring they attach to and the atoms to which they are attached form a bicyclic fused ring system, that has the following general formula:

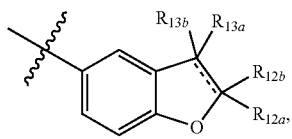
(III)

wherein $R_{12a}$ and $R_{12b}$ are hydrogen or methyl, and both $R_{13a}$ and $R_{13b}$ are hydrogen or methyl, and $R_{2a}$, $R_{2c}$ and $R_{2d}$ are hydrogen.

In some embodiments $R_1$ and $R_{1d}$ are fluoro, and $R_{1a}$, $R_{1b}$ and $R_{1c}$ are hydrogen; and $R_2$ is selected from the group consisting of ethoxy, n-propoxy, isopropoxy, allyloxy, tert-butoxy, n-butoxy, iso-butoxy, cyclopropyloxy, cyclopropylmethoxy, 2-fluoroethoxy, 3-fluoropropoxy and 2,2-difluoroethoxy, and $R_{2a}$, $R_{2b}$, $R_{2c}$ and $R_{2d}$ are hydrogen; or $R_2$ and $R_{2b}$, taken together with the atoms to which they are attached form a heteroalicyclic ring system wherein the formed ring system, taken together with the phenyl group to which it is fused, has the following formulae

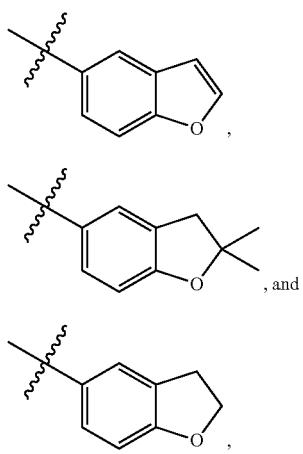

(IIIa)

(IIIb)

(IIIc)

and $R_{2a}$, $R_{2c}$ and $R_{2d}$ are hydrogen.

In some embodiments $R_1$ and $R_{1d}$ are fluoro, and $R_{1a}$, $R_{1b}$ and $R_{1c}$ are hydrogen; and $R_2$ is selected from the group consisting of n-propoxy, isopropoxy, iso-butoxy, and cyclopropyloxy.

In some embodiments $R_3$ is selected from hydrogen, deuterium, hydroxyl, —OD, substituted or unsubstituted $C_{1-6}$ alkyl, substituted or unsubstituted $C_{1-6}$ alkoxy, substituted or unsubstituted —$(CH_2)_s$—$C_{3-6}$ cycloalkyl, substituted or unsubstituted —$(CH_2)_s$—$C_{2-5}$ heteroalicyclyl, substituted or unsubstituted —$(CH_2)_s$—$C_{2-5}$ heteroaryl, and substituted or unsubstituted —$(CH_2)_s$—$C_{5-6}$ aryl, wherein each s is selected from 0, 1, 2 and 3. $R_3$ could for example be hydrogen, methyl, —$CD_3$, ethyl, —$CD_2CD_3$, n-propyl, —$CD_2CD_2CD_3$, iso-propyl, —$CDCD_3CD_3$, and —$(CR_{9a}R_{9b})_tC(=O)OR_{9c}$ and —$(CH_2)_tC(=O)NR_{9a}R_{9b}$, wherein $R_{9a}$, $R_{9b}$, and $R_{9c}$ independently are selected from hydrogen and $C_{1-4}$-alkyl, wherein each t is selected from the group consisting of 0, 1, 2, and 3.

In some embodiments $R_3$ is hydrogen or methyl.

In some embodiments $R_1$ and $R_{1d}$ are fluoro, and $R_{1a}$, $R_{1b}$ and $R_{1c}$ are hydrogen; and $R_2$ is selected from the group consisting of ethoxy, n-propoxy, isopropoxy, allyloxy, iso-butoxy, tert-butoxy, cyclopropyloxy, cyclopropylmethoxy, 2-fluoroethoxy, 3-fluoropropoxy, 2,2-difluoroethoxy; or $R_2$ and $R_{2b}$, taken together with the phenyl ring they attach to and the atoms to which they are attached form unsubstituted 2,3-dihydrobenzofuran-5-yl, unsubstituted benzofuran-5-yl, and unsubstituted 2,2-dimethyl-2,3-dihydrobenzofuran-5-yl, and $R_3$ is hydrogen or methyl.

In some embodiments $R_3$ is taken together with one $R_6$ or $R_7$, which is attached to a carbon atom adjacent the nitrogen atom, to form a heteroalicyclic ring system according to the following formulas:

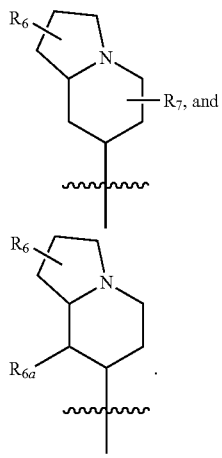

Optionally the formed heteroalicyclic ring systems may comprise additional $R_6$ and/or $R_7$ substituents, as shown above.

In some embodiments $R_{4a}$, $R_{4b}$, $R_{5a}$ and $R_{5b}$ are independently selected from the group consisting of hydrogen, methyl and —$CF_3$, for example $R_{4a}$, $R_{4b}$ and $R_{5a}$ are hydrogen and $R_{5b}$ is methyl or hydrogen; or $R_{4a}$, $R_{5a}$ and $R_{5b}$ are hydrogen and $R_{4b}$ is methyl or hydrogen.

In some embodiments $R_{4a}$, $R_{4b}$, $R_{5a}$ and $R_{5b}$ are independently selected from the group consisting of hydrogen, methyl and —$CF_3$, for example $R_{4a}$, $R_{4b}$ and $R_{5a}$ are hydrogen and $R_{5b}$ is methyl, —$CF_3$ or hydrogen; or $R_{4a}$, $R_{5a}$ and $R_{5b}$ are hydrogen and $R_{4b}$ is methyl, —$CF_3$ or hydrogen.

In some embodiments $R_{4a}$, $R_{4b}$, $R_{5a}$ and $R_{5b}$ are hydrogen.

In some embodiments $R_6$ is absent (e.g. when an unsaturation if present or when q is 0) or selected from the group consisting of hydrogen, deuterium, halogen, hydroxyl, —OD, substituted or unsubstituted $C_{1-4}$ alkyl, and substituted or unsubstituted $C_{1-4}$ alkoxy, for example deuterium, halogen, methyl and methoxy.

In some embodiments $R_6$ is selected from the group consisting of hydrogen, deuterium, halogen, hydroxyl, —OD, substituted or unsubstituted $C_{1-4}$ alkyl, and substituted or unsubstituted $C_{1-4}$ alkoxy, for example deuterium, halogen, methyl and methoxy.

In some embodiments $R_6$ is fluoro and q is 1.

In some embodiments $R_7$ is absent (e.g. when p is 0, or when an unsaturation is present) or selected from hydrogen, deuterium, halogen, and substituted or unsubstituted $C_{1-4}$ alkyl, for example hydrogen, fluoro and methyl. Hence in some embodiments p is 0.

In some embodiments $R_8$ is selected from the group consisting of hydrogen, halogen, methyl, ethyl, propyl, methoxy, ethoxy, $C_{1-2}$-haloalkyl, and $C_{1-2}$-haloalkoxy, e.g. hydrogen, —$CF_3$, —$CHF_2$, —$CF_2CF_3$, —$OCF_3$, —$OCF_2CF_3$ and —$OCHF_2$.

In some embodiments X is O.

In some embodiments m, and n independently are selected from the group consisting of 0 and 1, for example m is 1 and n is 0 or 1.

Some embodiments relate to compounds according to Formula (IIa or IIb)

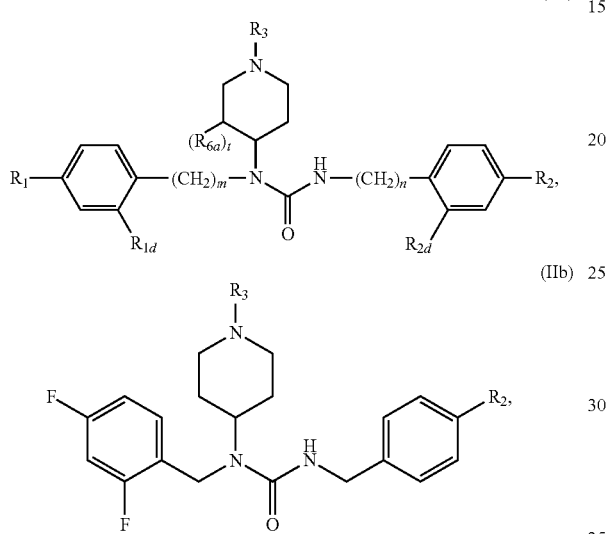

or a pharmaceutically acceptable salt, hydrate, solvate, polymorph, prodrug, stereoisomer, and deuterated analogue thereof, wherein m is 1;
n is 0 or 1;
$R_1$ and $R_{1d}$ are both halogen, such as fluoro;
$R_2$ is unsubstituted or substituted $C_{1-6}$ alkoxy, such as methoxy, ethoxy, n-propoxy, isopropoxy, allyloxy, prop-2-yn-1-yloxy n-butoxy, iso-butoxy, tert-butoxy, pentyl-oxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, —$OCF_3$ and (1,3-difluoropropan-2-yl)oxy;
$R_{2d}$ is hydrogen;
$R_3$ is hydrogen, methyl or ethyl;
t is 0 or 1; and when t is 1 then $R_{6a}$ is halogen such as fluoro.

Some embodiments relate to compounds according to Formula (IIa) or (IIb), or a pharmaceutically acceptable salt, hydrate, solvate, polymorph, prodrug and stereoisomer thereof, wherein m is 1;
n is 0 or 1;
$R_1$ and $R_{1d}$ are both halogen, such as fluoro, or $R_1$ is fluoro and $R_{1d}$ is hydrogen or hydroxyl;
$R_2$ is unsubstituted or substituted $C_{1-6}$ alkoxy, such as methoxy, ethoxy, n-propoxy, isopropoxy, allyloxy, prop-2-yn-1-yloxy n-butoxy, iso-butoxy, tert-butoxy, pentyl-oxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, —$OCF_3$ and (1,3-difluoropropan-2-yl)oxy; $R_{2d}$ is hydrogen, fluoro or hydroxyl; wherein at least one of $R_{1d}$ and $R_{2d}$ is not hydrogen, for example $R_{2d}$ is hydrogen and $R_{1d}$ is halogen;

$R_3$ is hydrogen, methyl or ethyl;
t is 0 or 1; and when t is 1 then $R_{6a}$ is halogen such as fluoro; and In some embodiments of Formulae (IIa) or (IIb), $R_3$ is methyl.

In some embodiments of Formulae (IIa) or (IIb), $R_2$ is ethoxy, n-propoxy, isopropoxy, allyloxy, tert-butoxy, cyclopropyloxy, cyclopropylmethoxy, isobutoxy and 2-fluoroethoxy, or $R_2$ is comprised in a ring taken together with the phenyl ring it attach to and the atoms to which it is attached form a bicyclic fused ring system, that, has the following formulae:

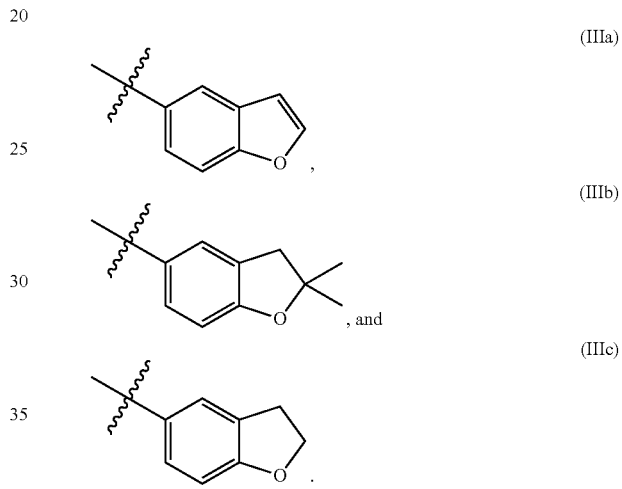

In some embodiments the compound is 1-[(2,4-difluorophenyl)methyl]-1-(1-methylpiperidin-4-yl)-3-{[4-(2-methylpropoxy)phenyl]methyl}urea; 1-[(2,4-difluorophenyl)methyl]-3-{[4-(2-methylpropoxy)phenyl]methyl}-1-(piperidin-4-yl)urea; 1-[(2,4-difluorophenyl)methyl]-1-(1-methylpiperidin-4-yl)-3-{[4-(propan-2-yloxy)phenyl]methyl}urea; 1-[(2,4-difluorophenyl)methyl]-3-[(2,2-dimethyl-2,3-dihydro-1-benzofuran-5-yl)methyl]-1-(1-methylpiperidin-4-yl)urea; 1-[(2,4-difluorophenyl)methyl]-3-[(2,3-dihydro-1-benzofuran-5-yl)methyl]-1-(1-methylpiperidin-4-yl)urea; 3-(4-(tert-butoxy)benzyl)-1-(2,4-difluorobenzyl)-1-(1-methylpiperidin-4-yl)urea; 1-(2,4-difluorobenzyl)-3-(4-ethoxybenzyl)-1-(1-methylpiperidin-4-yl)urea; 3-(4-cyclopropoxybenzyl)-1-(2,4-difluorobenzyl)-1-(1-methylpiperidin-4-yl)urea; 1-(2,4-difluorobenzyl)-3-(4-(2-fluoroethoxy)benzyl)-1-(1-methylpiperidin-4-yl)urea; 3-(4-(allyloxy)benzyl)-1-(2,4-difluorobenzyl)-1-(1-methylpiperidin-4-yl)urea; or 3-(benzofuran-5-ylmethyl)-1-(2,4-difluorobenzyl)-1-(1-methylpiperidin-4-yl)urea.

In some embodiments the compound is 1-[(2,4-difluorophenyl)methyl]-1-(piperidin-4-yl)-3-[(4-propoxyphenyl)methyl]urea; 1-[(2,4-difluorophenyl)methyl]-1-(1-methylpiperidin-4-yl)-3-[(4-propoxyphenyl)methyl]urea; 3-{[4-(cyclopropylmethoxy)phenyl]methyl}-1-[(2,4-difluorophenyl)methyl]-1-(1-methylpiperidin-4-yl)urea; 1-[(4-cyclopropoxyphenyl)methyl]-3-[(2,4-difluorophenyl)methyl]-3-(piperidin-4-yl)urea; 3-{[4-(2,2-difluoroethoxy)

phenyl]methyl}-1-[(2,4-difluorophenyl)methyl]-1-(1-methylpiperidin-4-yl)urea; 3-{[4-(tert-butoxy)phenyl]methyl}-1-[(2,4-difluorophenyl)methyl]-1-(piperidin-4-yl)urea; 3-(4-(allyloxy)benzyl)-1-(2,4-difluorobenzyl)-1-(1-methylpiperidin-4-yl)urea; 3-[(4-cyclopropoxyphenyl)methyl]-1-[(2,4-difluorophenyl)methyl]-1-(1-methylpiperidin-4-yl)urea; 1-[(2,4-difluorophenyl)methyl]-3-{[4-(2-fluoroethoxy)phenyl]methyl}-1-(1-methylpiperidin-4-yl)urea; 3-[(1-benzofuran-5-yl)methyl]-1-[(2,4-difluorophenyl)methyl]-1-(1-methylpiperidin-4-yl)urea; 1-[(2,4-difluorophenyl)methyl]-3-[(2,3-dihydro-1-benzofuran-5-yl)methyl]-1-(1-methylpiperidin-4-yl)urea; 3-[(2,4-difluorophenyl)methyl]-1-{[4-(3-fluoropropoxy)phenyl]methyl}-3-(1-methylpiperidin-4-yl)urea; 3-{[4-(tert-butoxy)phenyl]methyl}-1-[(2,4-difluorophenyl)methyl]-1-(1-methylpiperidin-4-yl)urea; 1-[(2,4-difluorophenyl)methyl]-3-[(2,2-dimethyl-2,3-dihydro-1-benzofuran-5-yl)methyl]-1-(1-methylpiperidin-4-yl)urea; 1-[(2,4-difluorophenyl)methyl]-1-(piperidin-4-yl)-3-{[4-(propan-2-yloxy)phenyl]methyl}urea; 1-[(2,4-difluorophenyl)methyl]-3-[(4-ethoxyphenyl)methyl]-1-(1-methylpiperidin-4-yl)urea; 1-[(2,4-difluorophenyl)methyl]-1-(1-methylpiperidin-4-yl)-3-{[4-(propan-2-yloxy)phenyl]methyl}urea; and 1-[(2,4-difluorophenyl)methyl]-1-(1-methylpiperidin-4-yl)-3-{[4-(2-methylpropoxy)phenyl]methyl}urea.

In some embodiments $R_{1d}$ is F, and $R_1$ is methyl, $C_1$, or F; $R_{1a}$, $R_{1b}$ and $R_{1c}$ are each hydrogen; $R_{4a}$, $R_{4b}$, $R_{5a}$, $R_{5b}$, $R_6$, $R_7$, $R_8$ are each hydrogen; m and n are each 1, and p and q are each 0 or 1; X is O; and $R_3$ is selected from the group consisting of hydrogen, methyl, —CD$_3$, ethyl, —CD$_2$CD$_3$, n-propyl, —CD$_2$CD$_2$CD$_3$, iso-propyl, cyclopropyl, —CDCD$_3$CD$_3$, —(CR$_{9a}$R$_{9b}$)$_t$C(=O)OR$_9$c and —(CH$_2$)$_t$C(=O)NR$_{9a}$R$_{9b}$, wherein R$_{9a}$, R$_{9b}$, and R$_{9c}$ independently are hydrogen or C$_{1-4}$-alkyl, wherein each t is selected from the group consisting of 0, 1, 2 and 3.

In some embodiments $R_{1d}$ is F, and $R_1$ is methyl, $C_1$, or F; $R_{1a}$, $R_{1b}$ and $R_{1c}$ are each hydrogen; $R_{4a}$, $R_{4b}$, $R_{5a}$, $R_{5b}$, $R_6$, $R_7$, $R_8$ are each hydrogen; m and n are each 1, and p and q are each 0; X is O; and $R_3$ is hydrogen or methyl.

In some embodiments $R_{1d}$ and $R_1$ are each F; $R_{1a}$, $R_{1b}$ and $R_{1c}$ are each hydrogen; $R_{4a}$, $R_{4b}$, $R_{5a}$, $R_{5b}$, $R_6$, $R_7$, $R_8$, when present, are each hydrogen; m and n are each 1, and p and q are each 0; X is O; and $R_3$ is selected from the group consisting of hydrogen, methyl, —CD$_3$, ethyl, —CD$_2$CD$_3$, n-propyl, —CD$_2$CD$_2$CD$_3$, iso-propyl, cyclopropyl, —CDCD$_3$CD$_3$, —(CR$_{9a}$R$_{9b}$)$_t$C(=O)OR$_9$c and —(CH$_2$)$_t$C(=O)NR$_{9a}$R$_{9b}$, wherein R$_{9a}$, R$_{9b}$, and R$_{9c}$ independently are hydrogen or C$_{1-4}$-alkyl, wherein each t is selected from the group consisting of 0, 1, 2 and 3.

In some embodiments $R_{1d}$ and $R_1$ are each F; $R_{1a}$, $R_{1b}$ and $R_{1c}$ are each hydrogen; $R_{4a}$, $R_{4b}$, $R_{5a}$, $R_{5b}$, $R_6$, $R_7$, $R_8$, when present, are each hydrogen; m and n are each 1, and p and q are each 0; X is O; and $R_3$ is hydrogen or methyl.

In some embodiments $R_{1d}$ and $R_1$ are each F; $R_{1a}$, $R_{1b}$ and $R_{1c}$ are each hydrogen; $R_{4a}$, $R_{4b}$, $R_{5a}$, $R_{5b}$, $R_6$, $R_7$, $R_8$, when present, are each hydrogen; m and n are each 1, and p and q are each 0; X is O; $R_3$ is hydrogen or methyl; and $R_2$ is selected from the group consisting of ethoxy, n-propoxy, isopropoxy, allyloxy, iso-butoxy, tert-butoxy, cyclopropyloxy, cyclopropylmethoxy, 2-fluoroethoxy, 3-fluoropropoxy and 2,2-difluoroethoxy; or $R_2$ and $R_{2b}$, taken together with the phenyl ring they attach to and the atoms to which they are attached form unsubstituted 2,3-dihydrobenzofuran-5-yl, unsubstituted benzofuran-5-yl, and unsubstituted 2,2-dimethyl-2,3-dihydrobenzofuran-5-yl.

In some embodiments $R_{1d}$ and $R_1$ are each F; $R_{1a}$, $R_{1b}$ and $R_{1c}$ are each hydrogen; $R_{4a}$, $R_{4b}$, $R_{5a}$, $R_{5b}$, $R_6$, $R_7$, $R_8$, when present, are each hydrogen; m and n are each 1, and p and q are each 0; X is O; $R_3$ is hydrogen or methyl; and $R_2$ is selected from the group consisting of ethoxy, n-propoxy, isopropoxy, allyloxy, iso-butoxy, tert-butoxy, cyclopropyloxy, cyclopropylmethoxy, 2-fluoroethoxy, 3-fluoropropoxy and 2,2-difluoroethoxy; or $R_2$ and $R_{2b}$, taken together with the phenyl ring they attach to and the atoms to which they are attached form unsubstituted 2,3-dihydrobenzofuran-5-yl, unsubstituted benzofuran-5-yl, and unsubstituted 2,2-dimethyl-2,3-dihydrobenzofuran-5-yl.

Some embodiments relate to compounds according to Formulae (Va) or (Vb),

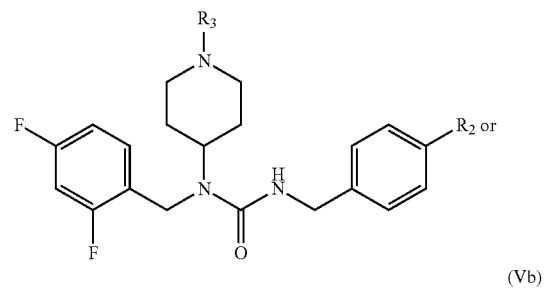

(Va)

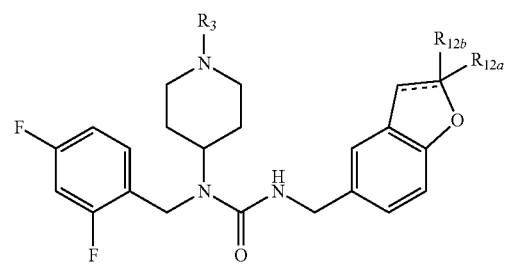

(Vb)

or a pharmaceutically acceptable salt, hydrate, solvate, polymorph, prodrug and stereoisomer thereof, wherein $R_2$ is selected from the group consisting of substituted or unsubstituted $C_{1-6}$ alkoxy; $R_3$ is hydrogen or methyl, and $R_{12a}$ and $R_{12b}$ are the same and selected from hydrogen or methyl.

In some embodiments of Formula (Va) $R_2$ is ethoxy, n-propoxy, isopropoxy, allyloxy, iso-butoxy, tert-butoxy, cyclopropyloxy, cyclopropylmethoxy, 2-fluoroethoxy, 3-fluoropropoxy, and 2,2-difluoroethoxy.

In some embodiments of Formula (Va) $R_2$ is n-propoxy, isopropoxy, iso-butoxy, and cyclopropyloxy.

In some embodiments of Formula (Vb) the bicyclic ring system is selected from has the following formulae:

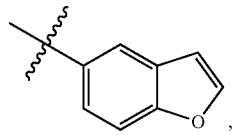

(IIIa)

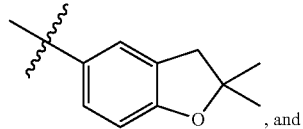

(IIIb)

, and

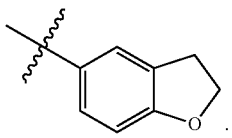
(IIIc)

In certain embodiments a compound provided herein has hERG % inhibition of less than 65%. In some embodiments the hERG % inhibition is less than 50%. %. In certain embodiments a compound provided herein has hERG % inhibition of less than 40%, such as less than 30%.

In certain embodiments a compound provided herein has hERG % inhibition of less than 65% and a 5-HT2A pKi of 8.4 or greater. In some embodiments the hERG % inhibition is less than 50%. In certain embodiments a compound provided herein has hERG % inhibition of less than 40%, such as less than 30%, and a 5-HT2A pKi of 8.4 or greater.

Some embodiments disclosed herein relate to a method for treating a disease in a patient comprising administering to the patient an effective amount of a compound, pharmaceutically acceptable salt, polymorph or stereoisomer of a compound according to Formulas (I) and (II), wherein the disease is selected from the group consisting of Abnormal hormonal activity, Alzheimer's disease, Alzheimer's disease dementia, Alzheimer's disease psychosis, Addiction (alcohol, cocaine, methamphetamine, nicotine and opioid), Addison's disease, ADHD, Alzheimer's disease psychosis, Affective disorders, Aggressiveness, Agitation, Akathisia, Alcohol addiction, Alcohol withdrawal, Amenorrhea, Amyotrophic lateral sclerosis, Anhedonia, Anorexia, Anti-NMDAR encephalitis, Anxiety, Appetite disorders, Asthma, Autism, Behavioral disorders, Behavioral disturbances associated with dementia, Binge eating disorder associated with impulse control disorder (ICD), Bipolar disorder, Blindness, Borderline disorder, Borderline personality disorder, Bradykinesia, Bulimia, Buying associated with ICD, Cardiac arrhythmia, Cerebral vascular accidents, Charles Bonnet disease, Chemotherapy-induced emesis, Childhood autism, Chronic pain, Chronic insomnia, cocaine addiction, Cognitive disorders, craniofacial pain, temporomandibular joint (TMJ)/temporomandibular disorder (TMD), Cushing's disease, Delusion, Dementia, Dementia with Lewy Body or Lewy Body dementia, dementia and psychosis associated with Creutzfeld-Jakob disease (CJD), Gerstmann-Strausser-Schenker disease (GSSD) and fatal familiar insomnia (FFI), Depression, Diabetes mellitus (non-insulin dependent), Diabetic peripheral neuropathy, Drug addiction, Double vision, Down's syndrome, Dyskinesia, Dysthymia, Dystonia, Ejaculatory problem, Emphysema, Epilepsy, Extrapyramidal disorder, Fibromyalgia, Frailty, Friedrich's Ataxia, Frontotemperal Dementia, Gambling associated with ICD, Galactorrhea, General anxiety disorder, Glaucoma, Hair loss or thinning, Hallucination, Headache, Hemorrhoids, Huntington's disease, Hyperprolactinemia, Hypertension, Hypersexuality associated with ICD, Hypotension, Hypoglutamateriga disorders, Impulse control disorder, Idiopathic thrombocytopenic purpura, Impotence, Incontinence, Increased intraocular pressure, Infertility, Inflammatory pain, Insomnia, Ischemia, Ischemic stroke, Lewy body disease (LBD), Learning disorders, Libido (decreased), Loss of libido, Low male fertility, Low sperm mobility, Lupus, Machado-Joseph disease, Major depression, Mania, Menopausal symptoms, Metabolic syndrome, methamphetamine addiction, Migraine, mild cognitive impairment (MCI), Motor tics, Multi-infarct dementia, Multiple sclerosis, Multiplex development disorder, Myocardial infarction, Myoclonus, Neuropathic pain, Neurodegenerative disorder, Neuropsychiatric disease, Nicotine addiction, Non motor symptoms of Parkinson's disease selected from dementia, depression, apathy, hallucinations, dribbling saliva (sialorrhea), constipation, pain, genitourinary problems and sleep disorders, Obsessive compulsive disorder, On/off phenomena, Opioid addiction, Osteoporosis, Pancreatis, Panic attacks, Parkinson's disease, Parkinson's disease dementia, Parkinson's disease psychosis, Periodic limb movement during sleep (PLMS), Peripheral vascular disease, Pituitary tumor, Postherpetic neuralgia, Progressive Supranucelar Palsy, Prion disease including Creutzfeld-Jakob disease (CJD), Gerstmann-Strausser-Schenker disease (GSSD) and fatal familiar insomnia (FFI), Prolactinoma, Pseudobulbar affect (PBA), Psychomotor slowing, Psychosis, Psychoses secondary to neurodegenerative disorders, Psychosomatic disorders, Psychotic depression, post-traumatic stress disorder (PTSD), Raynaud's disease, Reflex sympathetic dystrophy, Restless legs syndrome, Retinal disease, Schizoaffective disorders, Schizophrenia, negative symptoms of schizophrenia, cognitive impairment associated with schizophrenia, Sepsis, Serotonin syndrome, Sexual dysfunction, Sexual dysfunction associated with antidepressant use, Sleep apnea, Sleep disorders, Sleep maintenance insomnia, social anxiety disorder, Spinal injury, Spinocerebellar Atrophy, Suicidal tendency, Thrombosis, Thrombotic stroke, Thrombotic thrombocytopenic purpura, Tinnitus, Tiredness, Tourette's syndrome, Transient insomnia, Traumatic brain injury, Treatment-resistant depression, Treatment-resistant schizophrenia, Tremor, Vaginal dryness, Vasospasm Wakefulness, vascular dementia, Hallucinations associated with Parkinson's disease, Delusions associated with Parkinson's disease; cancer, brain cancer, glioma, Pancreatic cancer, Hypoactive sexual desire disorder, adult type 2 diabetes mellitus with Parkinson's disease or dementia and Liver fibrosis.

Suitable routes of administration of compounds of Formula (I) may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

EXAMPLES

Unless otherwise stated, starting materials were obtained from commercial suppliers, such as (but not limited to); Chemtronica, Merck (Sigma-Aldrich), Fluorochem, Fisher, Bepharm, Broadpharm, Larodan, Activate Scientific, and Enamine.

Nuclear Magnetic Resonance (NMR) spectra were recorded on Varian instrument at 400 MHz, at 25° C. Chemical shifts are reported in ppm (δ) using the residual solvent as internal standard. Peak multiplicities are expressed as follow: s, singlet; d, doublet; t, triplet; q, quartet; p, pentet; h, heptet; m, multiplet; b s, broad singlet or combinations thereof, including but not limited to dd, doublet of doublets and dt, doublet of triplet.

LC-MS were acquired on an Agilent 1100 HPLC coupled with an Agilent MSD mass spectrometer operating in ES (+) ionization mode. Column: Waters symmetry 2.1×30 mm C18 or Chromolith RP-18 2×50 mm. Solvent A water+0.1% TFA and solvent B Acetonitrile+0.1% TFA. Wavelength: 254 nM Preparative HPLC were acquired on a Gilson system. Flow: 10 ml/min Column: kromasil 100-5-C18 column. Wavelength: 220 nM. Solvent A water+0.1% TFA and solvent B Acetonitrile+0.1% TFA. Gradient: 40% to 95% B in 15 min The following are examples of abbreviations used EtOAc Ethylacetate DIEA N,N-Diisopropylethylamine HCl Hydrochloric acid DMF N,N-dimethylformamide THF Tetrahydrofuran CDCl$_3$ Chloroform-d DMSO-D6 Dimethylsulfoxide-d6

MgSO$_4$ Magnesium Sulfate

POCl$_3$ Phosphorus(V) oxychloride

KOH Potassium hydroxide

NaOH Sodium hydroxide

Na$_2$SO$_4$ Sodium Sulfate

K$_2$CO$_3$ Potassium carbonate

Na$_2$CO$_3$ Sodium carbonate

TFA Trifluoroacetic acid

Boc t-butoxycarbonyl

FMOC Fluorenylmethyloxycarbonyl

FMOC-Cl 9-Fluorenylmethoxycarbonyl chloride

TEOC 2-(trimetylsilyl)ethoxycarbonyl equiv. equivalents min minutes cat catalytical HCl hydrochloric acid HPLC high performance liquid chromatography Preparation of Starting Materials and Intermediate Compounds Intermediate 1:
2-[4-(2-methylpropoxy)phenyl]acetyl chloride

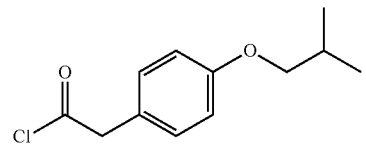

Thionyl chloride (21.6 ml, 298 mmol) was added to 2-[4-(2-methylpropoxy)phenyl]acetic acid (6.21 g, 29.8 mmol) in dichloromethane (29.8 ml). The mixture was stirred at ambient temperature for 18 hours before it was concentrated to afford the title compound (6.77 g, 100%).

Intermediate 2: 2-[4-(propan-2-yloxy)phenyl]acetyl chloride

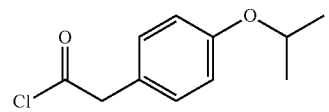

The compound was prepared in analogy with 2-[4-(2-methylpropoxy)phenyl]acetyl chloride, using 2-[4-(propan-2-yloxy)phenyl]acetic acid.

Intermediate 3:
1-(isocyanatomethyl)-4-(2-methylpropoxy)benzene

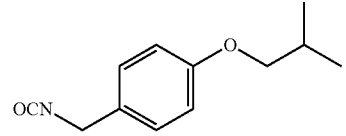

2-[4-(2-methylpropoxy)phenyl]acetyl chloride (6.12 g, 27 mmol) was dissolved in acetone (8 ml) and the resulting solution was added over 10 minutes to sodium azide (2.46 g, 37.8 mmol) in water (8 ml). After stirring for additionally 1 hour the mixture was diluted with water and extracted with toluene (3×25 ml). The organic phase was dried using sodium sulfate and filtered. The filtrate was gently concentrated to about 25 ml. The mixture was stirred at 65° C. for 20 minutes before it was concentrated to afford the title compound (5.41 g, 98%).

Intermediate 4:
1-(isocyanatomethyl)-4-(propan-2-yloxy)benzene

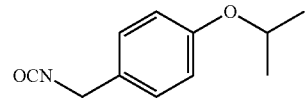

The compound was prepared in analogy with 1-(isocyanatomethyl)-4-(2-methylpropoxy)benzene, using 2-[4-(propan-2-yloxy)phenyl]acetyl chloride.

Intermediate 5: N-[(4-fluorophenyl)methyl]-1-methylpiperidin-4-amine

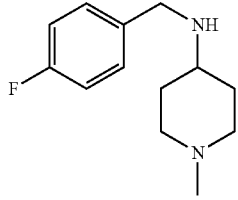 [SMILES: CN1CCC(NCc2ccc(F)cc2)CC1]

4-fluorobenzylamine (80.8 mmol, 10.4 g) was dissolved in ethanol (80 ml) and N-methyl-4-piperidone (80.8 mmol, 9.43 g) was added. Sodium triacetoxyborohydride (161.6 mmol, 35.4 g) was added in portions and the mixture was stirred at room temperature for 4 hours. Sodium hydroxide (aqueous, 5M) was added until pH>13 and the resulting mixture was stirred for 1 hour and then partitioned between diethyl ether and water. The organic phase was collected and the aqueous phase was extracted once again with diethyl ether. The combined organic phases were dried and evaporated to give the desired intermediate as a yellow oil (17.48 g, 97%).

Intermediate 6: N-[(2,4-difluorophenyl)methyl]-1-methylpiperidin-4-amine

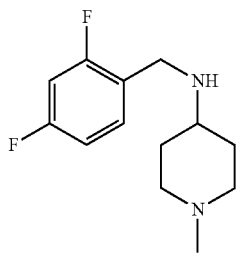 [SMILES: CN1CCC(NCc2ccc(F)cc2F)CC1]

2,4-difluorobenzylamine (4.0 g, 27.1 mmol) was dissolved in ethanol (30 ml) and N-methyl-4-piperidone (3.16 g, 27.1 mmol) was added followed by sodium triacetoxyborohydride (54.2 mmol, 11.85 g). The mixture was stirred at room temperature for 2 hours, then partitioned between diethyl ether and 2 M sodium hydroxide (100 ml). The organic phase was collected and extracted with 2M hydrochloric acid (50 ml), then the acidic aqueous phase was made basic with 5 M sodium hydroxide (30 ml) and extracted with diethyl ether. The organic extract was dried and evaporated to give the title compound as a yellow oil (5.96 g, 91% yield).

Intermediate 7: (3S,4R)-3-Fluoro-N-[(4-fluorophenyl)methyl]-1-methylpiperidin-4-amine and (3R,4S)-3-Fluoro-N-[(4-fluorophenyl)methyl]-1-methylpiperidin-4-amine

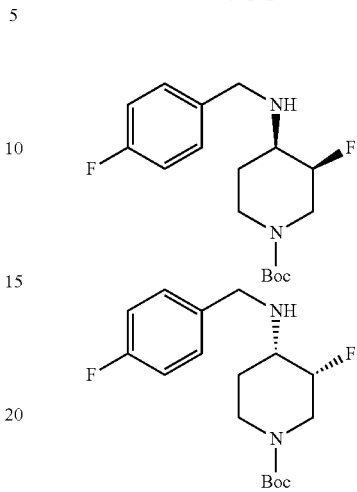

Sodium triacetoxyborohydride (100 mmol, 21.2 g) was added to a solution of tert-butyl 3-fluoro-4-oxopiperidine-1-carboxylate (10.86 g, 50 mmol) and 4-fluorobenzylamine (6.286 ml, 55 mmol) in ethanol (100 ml). After 4 hours of stirring at ambient temperature saturated sodium bicarbonate (100 ml) was added. The mixture was extracted with dichloromethane (3×100 ml), dried using a phase separator and concentrated. The crude material was purified by column chromatography using silicone dioxide gel, eluting with 25-100% ethyl acetate in petroleum ether to afford the title compounds as a 1:1 mixture of enantiomers (8.90 g, 55%).

(3S,4R)-3-Fluoro-N-[(4-fluorophenyl)methyl]-1-methylpiperidin-4-amine and (3R,4S)-3-Fluoro-N-[(4-fluorophenyl)methyl]-1-methylpiperidin-4-amine

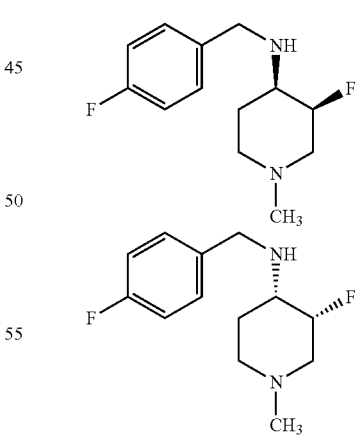

Trifluoroacetic acid (5 ml) was added to a 1:1 mixture of tert-butyl (3S,4R)-3-fluoro-4-{[(4-fluorophenyl)methyl]amino}piperidine-1-carboxylate and tert-butyl (3R,4S)-3-fluoro-4-{[(4-fluorophenyl)methyl]amino}piperidine-1-carboxylate (1.73 g, 5.31 mmol) in dichloromethane (15 ml). After 50 minutes the mixture was concentrated and redissolved in ethanol (53 ml). Formaldehyde (37% aqueous, 198

µl, 2.66 mmol) and sodium triacetoxyborohydride (1.13 g, 5.31 mmol) were added. After 30 minutes of stirring at ambient temperature additional formaldehyde (37% aqueous, 99 µl, 1.33 mmol) and sodium triacetoxyborohydride (565 mg, 2.66 mmol) were added. After additionally 45 minutes of stirring the mixture was concentrated. Sodium bicarbonate (saturated, 100 ml) was added and the resulting mixture was extracted with dichloromethane (3×100 ml). The organic phase was dried using a phase separator and concentrated. The crude material was purified by column chromatography using silicone dioxide gel, eluting with 5-15% methanol in dichloromethane to afford the title compounds as a 1:1 mixture of enantiomers (545 mg, 43%).

Intermediate 8: tert-butyl (3R,4R)-3-fluoro-4-{[(4-fluorophenyl)methyl]amino}piperidine-1-carboxylate and tert-butyl (3S,4S)-3-fluoro-4-{[(4-fluorophenyl)methyl]amino}piperidine-1-carboxylate

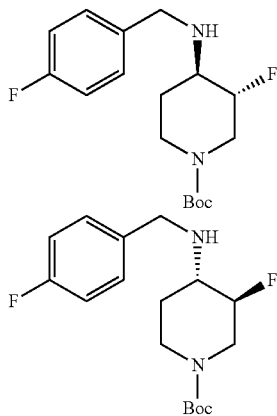

To a mixture of (4-fluorophenyl)methanamine (1.07 mL, 9.44 mmol) and tert-butyl 3-fluoro-4-oxopiperidine-1-carboxylate (1.87 g, 8.58 mmol) in dichloromethane (35 ml) sodium triacetoxyborohydride (2.73 g, 12.9 mmol) was added in portions over 20 minutes and stirring was continued for 1 hour at room temperature. The reaction was diluted with sodium hydrogen carbonate (saturated, aqueous, 100 ml) and extracted with dichloromethane (3×50 ml). The organic phase was dried (phase-separator) and concentrated. The crude (3 g) was purified by column chromatography using silicon dioxide gel, eluting with 30% ethyl acetate in petroleum ether to afford (2.2 g, 78%) of tert-butyl (3S,4R)-3-fluoro-4-{[(4-fluorophenyl)methyl]amino}piperidine-1-carboxylate and tert-butyl (3R,4S)-3-fluoro-4-{[(4-fluorophenyl)methyl]amino}piperidine-1-carboxylate as the racemic mixture and (0.25 g, 9%) of tert-butyl (3R,4R)-3-fluoro-4-{[(4-fluorophenyl)methyl]amino}piperidine-1-carboxylate and tert-butyl (3S,4S)-3-fluoro-4-{[(4-fluorophenyl)methyl]amino}piperidine-1-carboxylate as the racemic mixture.

Intermediate 9: 2-[3-fluoro-4-(2-methylpropoxy)phenyl]acetyl chloride

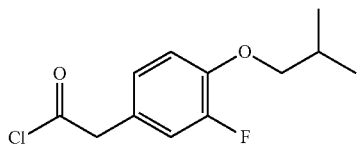 [SMILES: CC(C)COc1ccc(CC(=O)Cl)cc1F]

Sulfuric acid (49 µl, 882 µmol) was added to 2-(3-fluoro-4-hydroxyphenyl)acetic acid (500 mg, 2.94 mmol) in methanol (5 ml). After 1.5 hours, sodium acetate trihydrate (2 mmol) was added and the mixture was concentrated. The crude was suspended in ethyl acetate (5 ml), filtered and concentrated. Dimethylformamide (3 ml), isobutyl bromide (799 µl, 7.35 mmol), potassium carbonate (813 mg, 5.88 mmol) and tetrabutylammonium iodide (109 mg, 294 µmol) were added. The mixture was heated to 70° C. and stirred for 16 hours before it was cooled to ambient temperature and diluted with ethyl acetate (50 ml). The mixture was washed with water (5×30 ml), dried (phase-separator) and concentrated. The crude material was purified by column chromatography using silicon dioxide gel, eluting with 0-10% ethyl acetate in petroleum ether to give the intermediate ether (619 mg, 88%). The material was dissolved in methanol (4 ml) and sodium hydroxide (aqueous, 2M, 2.58 ml, 5.15 mmol) was added. After 1 hour, hydrochloric acid (aqueous, 2M, 3 ml) was added and the mixture was extracted with ethyl acetate (3×10 ml). The combined organic phases were dried (phase-separator), concentrated and re-dissolved in dichloromethane (2 ml). Thionyl chloride (1.87 ml, 25.8 mmol) was added and mixture was stirred at ambient temperature for 16 hours before it was concentrated to give the desired acyl chloride (633 mg, quantitative).

Intermediate 10: 2-[2-fluoro-4-(2-methylpropoxy)phenyl]acetyl chloride

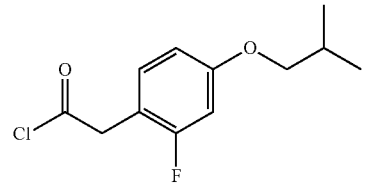 [SMILES: CC(C)COc1ccc(CC(=O)Cl)c(F)c1]

The compound was prepared in analogy with 2-[3-fluoro-4-(2-methylpropoxy)phenyl]acetyl chloride using 2-(2-fluoro-4-hydroxyphenyl)acetic acid. Yield: 87%.

Intermediate 11: tert-butyl 4-{[(2,4-difluorophenyl)methyl]amino}piperidine-1-carboxylate

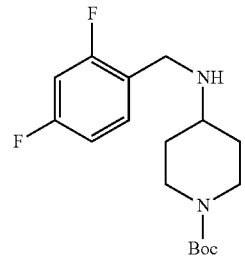 [SMILES: CC(C)(C)OC(=O)N1CCC(NCc2ccc(F)cc2F)CC1]

The compound was prepared in analogy with N-[(4-fluorophenyl)methyl]-1-methylpiperidin-4-amine using (2,4-difluorophenyl)methanamine and tert-butyl 4-oxopiperidine-1-carboxylate to yield the desired intermediate (quantitative).

Intermediate 12: N-[(2,4-dimethoxyphenyl)methyl]-1-methylpiperidin-4-amine

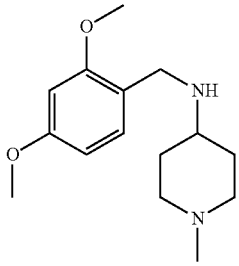 [SMILES: COc1ccc(CNC2CCN(C)CC2)c(OC)c1]

The compound was prepared in analogy with N-[(4-fluorophenyl)methyl]-1-methylpiperidin-4-amine, using 2,4-dimethoxybenzylamine and 1-methylpiperidin-4-one. Yield: 71%.

Intermediate 13: N-[(3,5-dimethoxyphenyl)methyl]-1-methylpiperidin-4-amine

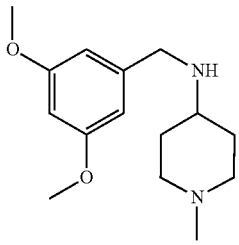 [SMILES: COc1cc(CNC2CCN(C)CC2)cc(OC)c1]

The compound was prepared in analogy with N-[(4-fluorophenyl)methyl]-1-methylpiperidin-4-amine using (3,5-dimethoxyphenyl)methanamine and 1-methylpiperidin-4-one to yield the desired intermediate (88%). Tetrahydrofuran was used instead of ethanol.

Intermediate 13A: N-[(3,5-difluorophenyl)methyl]-1-methylpiperidin-4-amine

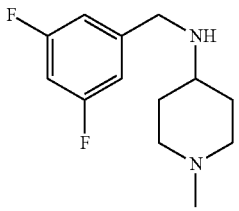

The compound was prepared in analogy with N-[(4-fluorophenyl)methyl]-1-methylpiperidin-4-amine using (3,5-difluorophenyl)methanamine and 1-methylpiperidin-4-one to yield the desired intermediate (54%). Tetrahydrofuran was used instead of ethanol.

Intermediate 14: methyl 2-[3-hydroxy-2-(2-methylprop-2-en-1-yl)phenyl]acetate and methyl 2-[3-hydroxy-4-(2-methylprop-2-en-1-yl)phenyl]acetate

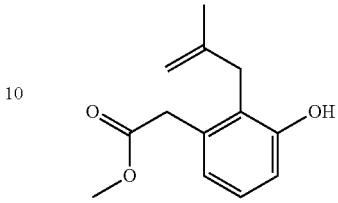

A mixture of 3-bromo-2-methylprop-1-ene (4.15 ml, 41.2 mmol), methyl 2-(3-hydroxyphenyl)acetate (4.56 g, 27.4 mmol), tetrabutylammonium iodide (1.01 g, 2.74 mmol), and $K_2CO_3$ (7.58 g, 54.9 mmol) in DMF (20 ml) was heated to 60° C. for 15 hours. The mixture was purified by column chromatography using silicon dioxide gel, eluting with 17% ethyl acetate in petroleum ether to afford methyl 2-{3-[(2-methylprop-2-en-1-yl)oxy]phenyl}acetate (4.7 g).

A solution of methyl 2-{3-[(2-methylprop-2-en-1-yl)oxy]phenyl}acetate (3.6 g, 16.3 mmol) in NMP (50 ml) was heated to 220° C. for 8 hours. Water (160 ml) was added and the mixture was extracted with diethyl ether (800 ml). The organic phase was washed with water (3×300 ml), dried with $Na_2SO_4$, filtered, and concentrated under reduced pressure. The crude material was purified by column chromatography using silicon dioxide gel, eluting with 25% ethyl acetate in petroleum ether to afford methyl 2-[3-hydroxy-2-(2-methylprop-2-en-1-yl)phenyl]acetate (700 mg) and methyl 2-[3-hydroxy-4-(2-methylprop-2-en-1-yl)phenyl]acetate.

Intermediate 15: 4-(isocyanatomethyl)-2,2-dimethyl-2,3-dihydro-1-benzofuran

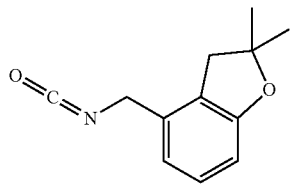

A solution of methyl 2-[3-hydroxy-2-(2-methylprop-2-en-1-yl)phenyl]acetate (700 mg) in formic acid (10 ml) was heated to 100° C. for 20 minutes. The solvent was concentrated to afford methyl 2-(2,2-dimethyl-2,3-dihydro-1-benzofuran-4-yl)acetate (670 mg). Sodium hydroxide (1.98 ml, 5 M aq., 9.89 mmol) was added to a solution of methyl 2-(2,2-dimethyl-2,3-dihydro-1-benzofuran-4-yl)acetate (670 mg) in methanol (6 ml). The mixture was stirred at room temperature for 1 hour. Diethyl ether (100 ml) and HCl (3 ml, 5 M aq.) was added. The organic phase was washed with water (30 ml), dried with $Na_2SO_4$, filtered and concentrated under reduced pressure to afford 2-(2,2-dimethyl-2,3-dihydro-1-benzofuran-4-yl)acetic acid (540 mg). Thionyl chloride (2.0 ml, 27.5 mmol) was added to 2-(2,2-dimethyl-2,3-dihydro-1-benzofuran-4-yl)acetic acid (540 mg, 2.62 mmol) in $CH_2Cl_2$ (3 ml). The mixture was stirred at room temperature overnight, then concentrated under reduced pressure. The residue was dissolved in acetone (3 ml), cooled to 0° C. and NaN$_3$ (238 mg, 3.67 mmol) in water (3 ml) was added dropwise. The mixture was stirred at 0° C. for 1 hour. The mixture was extracted with toluene (100 ml), the organic phase was dried with Na$_2$SO$_4$, filtered and concentrated (to 20 ml) under reduced pressure. The solution was heated to 60° C. for 1 hour, then concentrated under reduced pressure to afford 4-(isocyanatomethyl)-2,2-dimethyl-2,3-dihydro-1-benzofuran (492 mg) that was used without further purification.

Intermediate 16: 6-(isocyanatomethyl)-2,2-dimethyl-2,3-dihydro-1-benzofuran

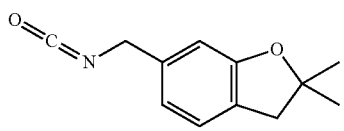

6-(isocyanatomethyl)-2,2-dimethyl-2,3-dihydro-1-benzofuran was made in analogy with 4-(isocyanatomethyl)-2,2-dimethyl-2,3-dihydro-1-benzofuran and was used without further purification.

Intermediate 17: (4-{[2-($^2$H$_3$)methyl($^2$H$_6$)propan-2-yl]oxy}phenyl)methanamine

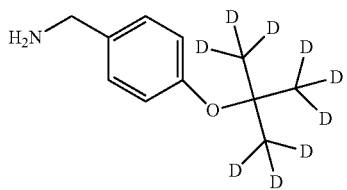 [SMILES: [2H]C([2H])([2H])C(Oc1ccc(CN)cc1)(C([2H])([2H])[2H])C([2H])([2H])[2H]]

Sodium hydride (39.6 mg, 1.65 mmol) was added to a solution of tert-butanol-d$_{10}$ (100 mg, 1.19 mmol) in tetrahydrofuran (1 ml). After 35 minutes gas evolution had stopped and the mixture was concentrated to white solids. The solids were resuspended in tetrahydrofuran (1 ml) and a solution of 4-fluorobenzonitrile (100 mg, 0.826 mmol) in tetrahydrofuran (1 ml) was added. After 2 hours the mixture was heated to 65° C. After 21 hours NaOH (2 ml, 1 M aqueous) was added and the mixture was extracted with ethyl acetate (1 ml). The organic phase was separated, dried using a phase separator and concentrated. The crude material was purified by column chromatography using silicon dioxide gel, eluting with 1-6% ethyl acetate in petroleum ether to afford 4-{[2-($^2$H$_3$)methyl($^2$H$_6$)propan-2-yl]oxy}benzonitrile (63.7 mg, 42%).

Cold borane (2 ml, 1 M in tetrahydrofuran) was added to 4-{[2-($^2$H$_3$)methyl($^2$H$_6$)propan-2-yl]oxy}benzonitrile (61.4 mg, 0.333 mmol) and the resulting mixture was heated to 65° C. After 18 hours the mixture was concentrated and methanol (2 ml) was added. The mixture was heated to 50° C. for 15 minutes when gas evolution stopped. The mixture was concentrated, redissolved in ethyl acetate (3 ml), washed with NaOH (1 ml, 1 M aqueous), the organic phase was separated, dried using a phase separator and concentrated to afford the desired intermediate as oil (32.4 mg, 52%).

Intermediate 18: (3,5-dihydro-2H-1,4-benzodioxepin-8-yl)methanamine

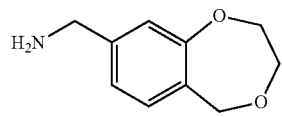

Sodium hydride (15.3 mg, 0.638 mmol) was added to a solution of 2-[5-(aminomethyl)-2-fluorophenoxy]ethan-1-ol (50.6 mg, 0.254 mmol) in tetrahydrofuran (5 ml). After 20 minutes of stirring at room temperature the mixture was heated to 50° C. After 3.5 hours K$_2$CO$_3$ (spatula tip) was added and the mixture heated to 60° C. After 2 hours the mixture was heated in a microwave reactor to 200° C. for 30 minutes giving a brown solution. Sodium hydroxide (2 ml, 1 M aqueous) was added and the mixture extracted with ethyl acetate (3×3 ml), the combined organic phases were dried using a phase separator and concentrated to afford a solution of the desired intermediate (1 ml). This material was used without further purification.

Intermediate 19: 2-(aminomethyl)-5-fluoro-N,N-dimethylaniline

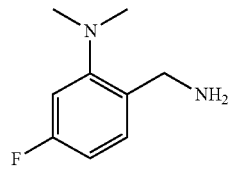

Sodium hydride (88 mg, 60%, 3.67 mmol) was added to a stirred solution of 2-amino-4-fluorobenzonitrile (100 mg, 0.735 mmol) in tetrahydrofuran (1 ml), followed by methyl iodide (183 µl, 2.94 mmol). After 2 hours additional sodium hydride (42 mg, 60%, 1.75 mmol) was added followed by methyl iodide (90 µl, 1.45 mmol). After 17 hours of stirring at room temperature NaOH (2 ml, 1 M aqueous) was added, the aqueous phase was extracted with ethyl acetate (3×3 ml), the combined organic phases were dried using a phase separator, and concentrated. The crude material was purified by column chromatography using silicon dioxide gel, eluting with 1-15% ethyl acetate in petroleum ether to afford 2-(dimethylamino)-4-fluorobenzonitrile (111 mg, 92%).

Borane (2.0 ml, 1 M in THF, 2.0 mmol) was added to 2-(dimethylamino)-4-fluorobenzonitrile (111 mg, 0.676 mmol). After 18 hours of stirring at room temperature, additional borane (2 ml, 1 M in THF, 2 mmol) was added and the mixture heated to 45° C. After another 24 hours of stirring at 45° C. the mixture was diluted with ethyl acetate (5 ml) washed with NaOH (3×4 ml, 1 M aqueous). The organic phase was dried using a phase separator and concentrated to afford the desired intermediate (112 mg).

Intermediate 20: (4-cyclopropoxyphenyl)methanamine

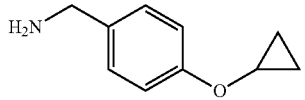 [SMILES: NCc1ccc(OC2CC2)cc1]

4-cyanophenol (1.0 g, 7.97 mmol), cesium carbonate (16.0 mmol, 5.25 g), sodium iodide (0.8 mmol, 121 mg), cyclopropyl bromide (31.9 mmol, 2.64 ml) and N,N-dimethylacetamide (4.0 ml) were stirred at 150° C. for 20 hours in a sealed thick-walled vessel and then partitioned between water and diethyl ether. The organic phase was washed with water several times, then dried and evaporated, and the residue was purified by silica gel chromatography, eluting with 25-50% ethyl acetate in petroleum ether to afforded 4-cyclopropyloxy-benzonitrile (832 mg, 5.22 mmol, 65% yield). 4-cyclopropyloxy-benzonitrile (1.188 g, 7.46 mmol) was cooled on an ice-bath and borane (1 M in tetrahydrofuran, 30 ml, 30 mmol) was added. The mixture was stirred at room temperature for 20 hours and 60° C. for 30 min, then quenched with methanol (10 ml), evaporated and heated in methanol (20 ml) at reflux for 2 hours. The mixture was evaporated and partitioned between diethyl ether and sodium hydroxide (aqueous, 1 M). The organic phase was collected and extracted with hydrochloric acid (aqueous, 1 M). The aqueous phase was made basic with sodium hydroxide (aqueous, 5 M), then extracted with diethyl ether. The organic phase was dried and evaporated to give crude (4-cyclopropoxyphenyl)methanamine (878 mg, 72% yield).

Intermediate 21: tert-butyl 4-{[(2,4-difluorophenyl)methyl]amino}piperidine-1-carboxylate

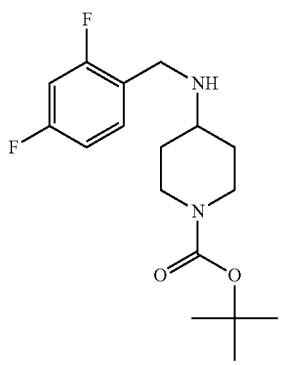 [SMILES: CC(C)(C)OC(=O)N1CCC(NCc2ccc(F)cc2F)CC1]

(2,4-difluorophenyl)methanamine (8.0 g, 54.7 mmol) was added to tert-butyl 4-oxopiperidine-1-carboxylate (11.3 g, 54.7 mmol) in ethanol (60 ml) followed by addition of sodium triacetoxyborohydride (23.9 g, 110 mmol). The reaction was stirred for 2 hours at room temperature. Then NaOH (160 ml, 2 M, aq.) was added and the mixture extracted with diethyl ether. The organic phase was washed with water and brine, dried using MgSO$_4$, filtered and concentrated under reduced pressure to afford the desired intermediate (18.3 g). This intermediate was used without further purification.

Intermediate 22: 2-(trimethylsilyl)ethyl 4-[(chlorocarbonyl)[(2,4-difluorophenyl)methyl]amino]piperidine-1-carboxylate

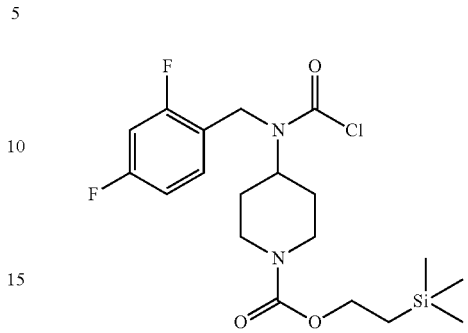

(2,4-difluorophenyl)methanamine (1.68 g, 11.4 mmol) was added to 2-(trimethylsilyl)ethyl 4-oxopiperidine-1-carboxylate (2.4 g, 9.27 mmol) in CH$_2$Cl$_2$ (20 ml) followed by addition of sodium triacetoxyborohydride (4.46 g, 20.4 mmol). The reaction was stirred for 1 hours at room temperature. Then NaOH (0.5 M, aq.) was added and the mixture extracted with CH$_2$Cl$_2$. The organic phase was dried using MgSO$_4$, filtered, and concentrated under reduced pressure. The crude intermediate was purified by column chromatography using silicon dioxide gel, eluting with ethyl acetate to afford 2-(trimethylsilyl)ethyl 4-{[(2,4-difluorophenyl)methyl]amino}piperidine-1-carboxylate (3.49 g).

A solution of 2-(trimethylsilyl)ethyl 4-{[(2,4-difluorophenyl)methyl]amino}piperidine-1-carboxylate (2.04 g, 5.49 mmol) and pyridine (1.8 ml, 22.0 mmol) in CH$_2$Cl$_2$ (10 ml) was added to a solution of triphosgene (1.09 g, 3.66 mmol) in CH$_2$Cl$_2$ (10 ml) at 0° C. The reaction was stirred for 1 hour at this temperature. Then the mixture was concentrated under reduced pressure, dissolved in diethyl ether and washed with HCl (0.5 M aq.). The organic phase was dried using MgSO$_4$, filtered, and concentrated under reduced pressure. The crude intermediate was purified by column chromatography using silicon dioxide gel, eluting with 25% ethyl acetate in hexanes to afford the desired intermediate (1.98 g).

Intermediate 23: 7-(aminomethyl)-2,2-dimethyl-3,4-dihydro-2H-1-benzopyran-4-ol

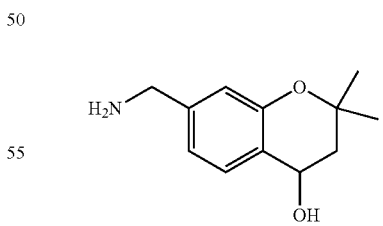

LiAlH$_4$ (28.3 mg, 0.745 mmol) was added in portions to 2,2-dimethyl-4-oxo-3,4-dihydro-2H-1-benzopyran-7-carbonitrile (30 mg, 0.149 mmol) in THF (4.0 ml) at room temperature. The mixture was heated to 50° C. overnight, then NaSO$_4$*10 H$_2$O was added in portions until gas evolution ceased, the mixture was diluted with ethyl acetate (5 ml), filtered, and concentrated to afford the desired intermediate (30.0 mg, 97% yield).

Intermediate 24: (2,2-dimethyl-2H-chromen-7-yl)methanamine

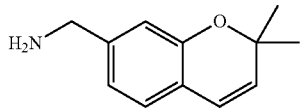

LiAlH₄ (37.7 mg, 0.993 mmol) was added in portions to 2,2-dimethyl-2H-chromene-7-carbonitrile (46 mg, 0.248 mmol) in THF (4.0 ml) at room temperature. The mixture was heated to 50° C. overnight, then NaSO₄*10 H₂O was added in portions until gas evolution ceased, the mixture was diluted with ethyl acetate (5 ml), filtered, and concentrated to afford the desired intermediate (46.0 mg, 97% yield).

Intermediate 25: (3-methyl-1H-indazol-5-yl)methanamine

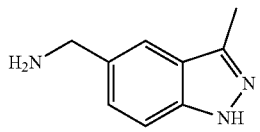

LiAlH₄ (84.5 mg, 2.23 mmol) was added in portions to 3-methyl-1H-indazole-5-carbonitrile (70 mg, 0.445 mmol) in THF (10.0 ml) at room temperature. The mixture was heated to 50° C. overnight, then NaSO₄*10 H₂O was added in portions until gas evolution ceased, the mixture was diluted with ethyl acetate (15 ml), filtered, and concentrated to afford the desired intermediate (23.7 mg, 31% yield).

Intermediate 26: N-{[2-(benzyloxy)-4-fluorophenyl]methyl}-1-methylpiperidin-4-amine

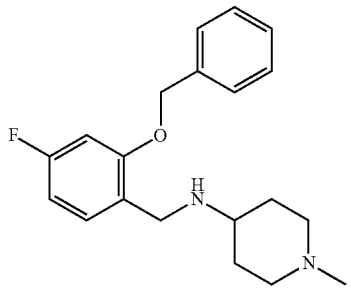 [SMILES: CN1CCC(NCc2ccc(F)cc2OCc2ccccc2)CC1]

Benzyl alcohol (0.77 g, 7.2 mmol) was added to a stirred suspension of potassium tert-butoxide (0.97 g, 8.6 mg) in dioxane (15 ml) at room temperature. After 10 minutes of stirring at room temperature 2,4-difluorobenzonitrile (1.00 g, 7.2 mmol) was added in one portion. After another 90 minutes water (10 ml) was added and the mixture extracted with diethyl ether (3×10 ml), the combined organic phases were dried using a phase separator and concentrated to solids. The crude material was purified by column chromatography using silicon dioxide gel, eluting with 25-50% dichloromethane in petroleum ether to afford 2-(benzyloxy)-4-fluorobenzonitrile as a white solid (1.33 g, 81%).

A cold solution of borane (1.4 ml, 1 M in tetrahydrofuran) was added to 2-(benzyloxy)-4-fluorobenzonitrile (208 mg, 915 µmol). After 15 hours of stirring at room temperature additional borane (1.4 ml, 1 M in tetrahydrofuran) was added. After another 19 hours of stirring additional borane (1.0 ml, 1 M in tetrahydrofuran) was added. After 3 hours the mixture was added to sodium hydroxide (5 ml, 1 M aqueous), extracted with ethyl acetate (3×5 ml), the combined organic phases were dried using a phase separator and concentrated afford [2-(benzyloxy)-4-fluorophenyl]methanamine as oil (260 mg, quantitative). This material was used without further purification.

N-Methyl-4-piperidone (150 mg, 1.32 mmol) was added to a stirred solution of [2-(benzyloxy)-4-fluorophenyl]methanamine (204 mg, 882 µmol) in ethanol (5 ml), after 5 minutes sodium triacetoxyborohydride (372 mg, 1.76 mmol) was added. After 6 hours the reaction mixture was concentrated, redissolved in dichloromethane (5 ml), washed with sodium hydroxide (5 ml, 1 M aqueous), the aqueous phase was extracted with additional dichloromethane (2×1 ml), the combined organic phases were dried using a phase separator, and concentrated to afford the desired intermediate as a yellow oil (253 mg, 87%).

Intermediate 27: tert-butyl 4-[(chlorocarbonyl)[(2,4-difluorophenyl)methyl]amino]piperidine-1-carboxylate

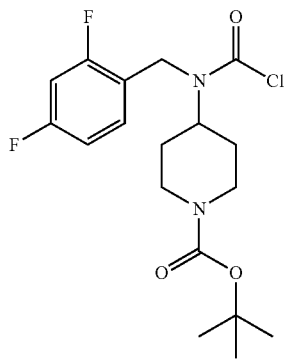 [SMILES: CC(C)(C)OC(=O)N1CCC(N(Cc2ccc(F)cc2F)C(=O)Cl)CC1]

Diphosgene (184 µl, 1.54 mmol) in CH₂Cl₂ (2 ml) was added dropwise to a mixture of tert-butyl 4-{[(2,4-difluorophenyl)methyl]amino}piperidine-1-carboxylate (1.00 g, 3.07 mmol) and DIPEA (1.07 ml, 6.15 mmol) in CH₂Cl₂ (8 ml) at room temperature. After 10 minutes of stirring at room temperature additional diphosgene (100 µl, 0.837 mmol) in CH₂Cl₂ (1 ml) was added. After another 2 hours of stirring NaOH (1 ml, 1 M aq.) was added. The organic phase was dried using a phase separator and concentrated. The crude material was purified by silica gel chromatography, eluting with 3-12% ethyl acetate in petroleum ether to afford the desired intermediate (1.34 g).

Intermediate 28: phenyl N-[(4-cyclopropoxyphenyl)methyl]carbamate

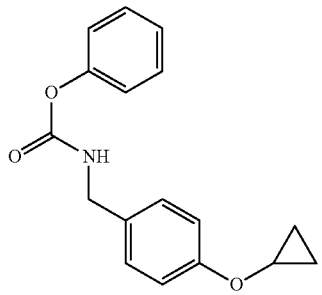 [SMILES: O=C(NCc1ccc(OC2CC2)cc1)Oc1ccccc1]

4-cyanophenol (1 g, 7.97 mmol), cesium carbonate (16.0 mmol, 5.25 g), sodium iodide (0.8 mmol, 121 mg), cyclopropyl bromide (31.9 mmol, 2.64 ml) and dimethylacetamide (4.0 ml) were stirred at 150° C. for 20 hours in a sealed vessel and then partitioned between water and diethyl ether. The organic phase was washed with water several times, then dried and evaporated, and the crude was purified by column chromatography using silicon dioxide gel, eluting with 20-30% ethyl acetate in petroleum ether and gave 4-cyclopropyloxy-benzonitrile (405 mg, 2.54 mmol, 32% yield). This procedure was repeated once and gave 4-cyclopropyloxy-benzonitrile (832 mg, 5.22 mmol, 65% yield). The two batches were combined and gave 1.188 g (7.46 mmol) which was cooled on an ice-bath and a $BH_3$ solution (30 ml, 1 M in tetrahydrofuran, 30 mmol) was added. The mixture was stirred at room temperature for 20 hours and at 60° C. for 30 min, it was then quenched with methanol (10 ml), evaporated and heated in methanol (20 ml) at reflux for 2 hours. The mixture was evaporated and partitioned between ether and 1 M NaOH. The organic phase was collected and extracted with 1 M HCl, the aqueous phase was separated and made basic with 5 M NaOH, then extracted with diethyl ether and the organic phase was collected, dried, and evaporated to give crude 4-cyclopropyloxy-benzylamine (878 mg, 5.37 mmol, 72% yield). This material was dissolved in dichloromethane (5 ml), pyridine (8.1 mmol, 660 µl) was added followed by phenyl chloroformate (7.0 mmol, 906 µl) dissolved in dichloromethane (4.0 ml) dropwise on an ice-bath and the mixture was stirred 30 min, then partitioned between dichloromethane and 1 M HCl, the organic phase was separated, dried, and evaporated to give a crystalline material. This was recrystallized from EtOAc/hexanes and gave the title compound (881 mg, 3.1 mmol, 58% yield). From the mother liquor was another crop crystallized (218 mg, 0.77 mmol). The combined yield of phenyl N-[(4-cyclopropoxyphenyl)methyl]carbamate was 72%.

Intermediate 29: 1-butoxy-4-(isocyanatomethyl)benzene

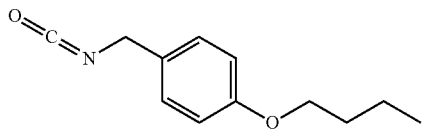

2-(4-butoxyphenyl)acetic acid (4.0 g, 18.81 mmol) was refluxed 2 hours in a mixture of dichloromethane (24 ml), thionyl chloride (16 ml) and DMF (160 µl). The mixture was evaporated, and diethyl ether was added. The solids were removed and the ether extract was evaporated and gave 2-(4-butoxyphenyl)acetyl chloride (4.35 g, 100% yield). This acid chloride (3.5 g, 14.7 mmol) was dissolved in acetone (10 ml) and added at 0° C. during 10 min to a solution of sodium azide (1.35 g, 20.53 mmol) in water (10 ml). After stirring at 0° C. for 1 hour the mixture was diluted with cold water (40 ml) and extracted with toluene 2×40 ml. The organic extracts were combined, dried ($Na_2SO_4$), and concentrated to 60 ml on a rotary evaporator using a water bath at 30° C. The toluene solution was then heated to 65° C. in an oil bath until the gas evolution stopped (30 min). The mixture was stirred for additional 5 min and thereafter evaporated to give an oil that was dissolved in n-heptane (40 ml). The solution was filtered to remove any solids and the filtrate was evaporated to give the title compound as an oil (3.21 g, 100% yield).

Intermediate 30: 1-ethoxy-4-(isocyanatomethyl)benzene

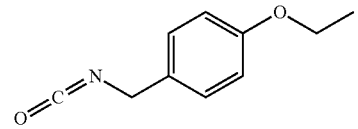

The compound was prepared in analogy to 1-butoxy-4-(isocyanatomethyl)benzene.

Intermediate 31: phenyl N-({4-[(tert-butyldimethylsilyl)oxy]-2-fluorophenyl}methyl)carbamate

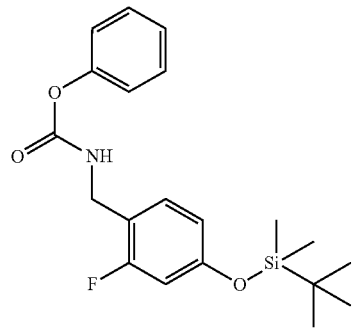 [SMILES: CC(C)(C)[Si](C)(C)Oc1ccc(CNC(=O)Oc2ccccc2)c(F)c1]

2-Fluoro-4-hydroxy-benzaldehyde (982 mg, 7.0 mmol), imidazole (20.0 mmol, 1.375 g), and DMF (4.0 ml) were stirred and a solution of t-butyldimethylsilyl chloride (14.0 mmol, 2.175 g) dissolved in DMF (4.0 ml) was added. The mixture was stirred at 20° C. for 20 hours and then partitioned between water and diethyl ether. The organic phase was washed with water several times, dried, evaporated and the residue was purified by column chromatography using silicon dioxide gel, eluting with 30% ethyl acetate in petroleum ether to afford the silylated benzaldehyde as an oil. This material was dissolved in ethanol (5 ml) and sodium borohydride (7.0 mmol, 270 mg) was added. The mixture was stirred for 1 hour, then concentrated and partitioned between water and diethyl ether. The organic phase was separated and evaporated to afford the intermediate benzylic alcohol (961 mg, 3.75 mmol, 54% yield for two steps). This alcohol (961 mg, 3.75 mmol) was dissolved in dichloromethane (4 ml) and diisopropylethylamine (9.4 mmol, 1.64 ml) was added followed by p-toluenesulfonyl chloride (5.63 mmol, 1.083 g). The mixture was stirred 72 hours and then purified column chromatography using silicon dioxide gel, eluting with 30% ethyl acetate in petroleum ether to afford the intermediate benzyl tosylate (866 mg, 2.11 mmol, 56% yield). This material (853 mg, 2.07 mmol), potassium phtalimide (4.0 mmol, 750 mg), and DMF (3.0 ml) were stirred and pyridine (1.0 mmol, 81 µl) was added. The mixture was stirred 22 hours, then partitioned between 0.5 M HCl and diethyl ether. The organic phase was separated, then evaporated, and the residue was purified by column chromatography using silicon dioxide gel, eluting with 30% ethyl acetate in petroleum ether to afford the intermediate phtalimide derivative (735 mg, 1.9 mmol). This material was stirred in a mixture of ethanol (5 ml) and methylamine solution (8 M, 40 mmol, 5.0 ml) for 20 hours, then concentrated, and the residue was purified by column chromatography using silicon dioxide gel, eluting with methanol to afford the intermediate benzylamine (104 mg, 0.407 mmol, 20% yield for two steps). This material (104 mg, 0.407 mmol) was dissolved in dichloromethane (2.0 ml) and pyridine (1.0 mmol, 82 µl) was added, the mixture was cooled on an ice bath and phenyl chloroformate (0.8 mmol, 104 µl) was added. The mixture was stirred 1 hour, then partitioned between water and diethyl ether, the organic phase was separated, evaporated, and the residue was purified by column chromatography using silicon dioxide gel, eluting with 30% ethyl acetate in petroleum ether to afford phenyl N-({4-[(tert-butyldimethyl silyl)oxy]-2-fluorophenyl}methyl)carbamate (165 mg, 100% yield).

Intermediate 33: 2-[3-fluoro-4-(propan-2-yloxy)phenyl]acetyl chloride

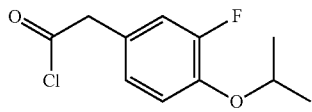

The compound was prepared in analogy with 2-[3-fluoro-4-(2-methyl propoxy)phenyl]acetyl chloride using 2-(3-fluoro-4-hydroxyphenyl)acetic acid and 2-iodopropane instead of isobutyl bromide. Tetrabutylammonium iodide was omitted.

Intermediate 34: 2-fluoro-4-(isocyanatomethyl)-1-(propan-2-yloxy)benzene

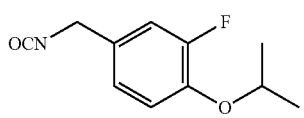

The compound was prepared in analogy with 1-(isocyanatomethyl)-4-(2-methylpropoxy)benzene using 2-[3-fluoro-4-(propan-2-yloxy)phenyl]acetyl chloride.

Intermediate 35: 2-[2-fluoro-4-(propan-2-yloxy)phenyl]acetyl chloride

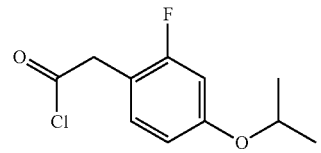

The compound was prepared in analogy with 2-[2-fluoro-4-(2-methyl propoxy)phenyl]acetyl chloride using 2-(2-fluoro-4-hydroxyphenyl)acetic acid and 2-iodopropane.

Intermediate 36: 2-fluoro-1-(isocyanatomethyl)-4-(propan-2-yloxy)benzene

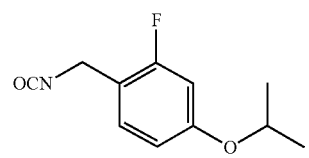

The compound was prepared in analogy with 1-(isocyanatomethyl)-4-(2-methylpropoxy)benzene using 2-[2-fluoro-4-(propan-2-yloxy)phenyl]acetyl chloride.

Intermediate 37: 2-[3-methyl-4-(propan-2-yloxy)phenyl]acetyl chloride

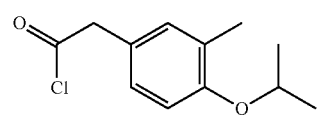

The compound was prepared in analogy with 2-[2-fluoro-4-(2-methyl propoxy)phenyl]acetyl chloride using 2-(4-hydroxy-3-methylphenyl)acetic acid and 2-iodopropane instead of isobutyl bromide. Tetrabutylammonium iodide was omitted.

Intermediate 38: 4-(isocyanatomethyl)-2-methyl-1-(propan-2-yloxy)benzene

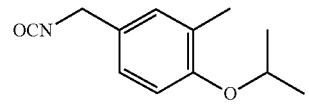

The compound was prepared in analogy with 1-(isocyanatomethyl)-4-(2-methylpropoxy)benzene using 2-[3-methyl-4-(propan-2-yloxy)phenyl]acetyl chloride.

Example 1: 1-[(2,4-dimethoxyphenyl)methyl]-3-[(3R,4S)-3-fluoro-1-methylpiperidin-4-yl]-3-[(4-fluorophenyl)methyl]urea; trifluoroacetic acid (1a) and 1-[(2,4-dimethoxyphenyl)methyl]-3-[(3S,4R)-3-fluoro-1-methylpiperidin-4-yl]-3-[(4-fluorophenyl)methyl]urea; trifluoroacetic acid (1b)

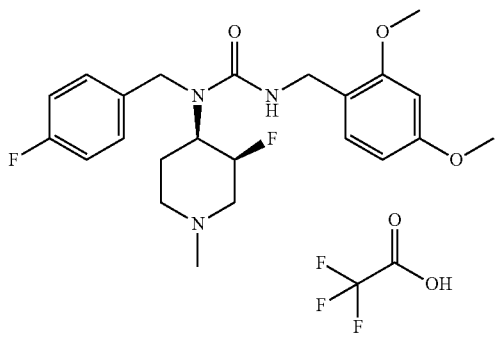

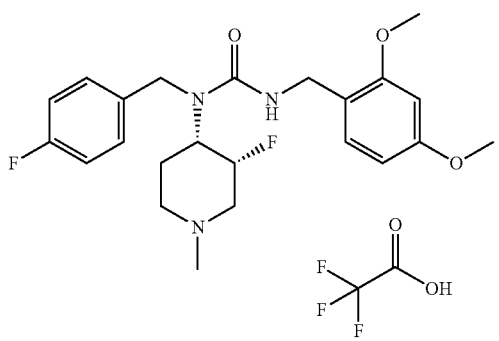

(2,4-dimethoxyphenyl)methanamine (104 µmol) and triethylamine (35 µl, 250 mol) in dichloromethane were added to diphosgene (6 µl, 50 µmol) in dichloromethane (0.5 ml), using a syringe pump (0.5 ml/hour). The mixture was stirred for additionally 1 hour at ambient temperature before (3R,4S)-3-Fluoro-N-[(4-fluorophenyl)methyl]-1-methylpiperidin-4-amine and (3S,4R)-3-fluoro-N-[(4-fluorophenyl)methyl]-1-methylpiperidin-4-amine (1:1, 83 mol) in dichloromethane (0.5) ml was added. After 24 hours, the mixture was washed with water (1.5 ml). The aqueous phase was extracted with dichloromethane (1.5 ml). The combined organic phase was dried (phase-separator) and concentrated. The crude material was purified by HPLC, eluting with 20-85% acetonitrile in water (containing 0.1% trifluoroacetic acid) to afford the title compounds. Yield: 31.3 mg, 55%: $^1$H NMR (400 MHz, Chloroform-d) δ 7.18-7.08 (m, 2H), 7.05 (d, 1H), 7.00 (t, 2H), 6.38 (dd, 1H), 6.32 (d, 1H), 5.17-4.95 (m, 2H), 4.79 (dd, 1H), 4.51 (d, 1H), 4.43 (d, 1H), 4.20 (qd, 2H), 3.91-3.72 (m, 5H), 3.45 (s, 3H), 3.03 (dd, 1H), 2.94-2.75 (m, 4H), 2.63-2.45 (m, 1H), 1.77 (d, 1H); LC-MS: 434.3 [M+H]$^+$.

Example 2: 3-[(2,4-dimethoxyphenyl)methyl]-3-(1-methylpiperidin-4-yl)-1-{[4-(2-methylpropoxy)phenyl]methyl}urea (2)

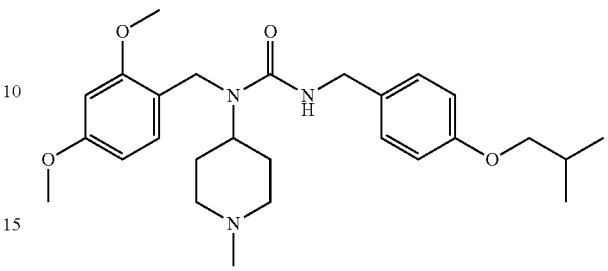

N-[(2,4-dimethoxyphenyl)methyl]-1-methylpiperidin-4-amine (0.34 mmol, 90 mg) in dichloromethane was added to 1-(isocyanatomethyl)-4-(2-methylpropoxy)benzene (0.37 mmol, 77 mg) in dichloromethane. The solution was stirred for 1 hour and then partitioned between dichloromethane and sodium hydroxide (aqueous, 0.5 M). The organic phase was separated, dried (sodium sulfate), filtered and evaporated. The crude product was purified by column chromatography using silicon dioxide gel. Yield: 101 mg, 63%: $^1$H NMR (400 MHz, Chloroform-d) δ 7.11-7.03 (m, 3H), 6.78 (d, 2H), 6.41 (dd, 1H), 6.38 (d, 1H), 4.72 (t, 1H), 4.45 (m, 1H), 4.29 (d, 2H), 4.24 (s, 2H), 3.80 (s, 3H), 3.73-3.65 (m, 5H), 2.86 (d, 2H), 2.26 (s, 3H), 2.14-1.99 (m, 3H), 1.77-1.61 (m, 4H), 1.01 (d, 6H); LC-MS: 470.3 [M+H]$^+$.

Example 3: 1-[(2,4-difluorophenyl)methyl]-1-(1-methylpiperidin-4-yl)-3-{[4-(2-methylpropoxy)phenyl]methyl}urea; trifluoroacetic acid (3)

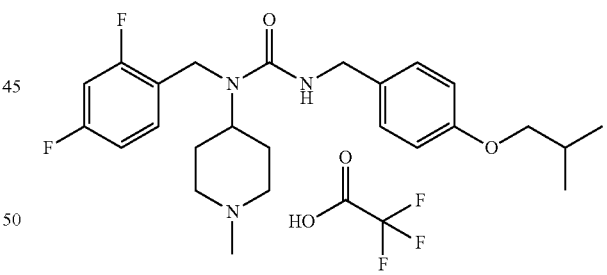

1-(Isocyanatomethyl)-4-(2-methylpropoxy)benzene (61.5 mg, 300 µmol) in dichloromethane (1 ml) was added to N-[(2,4-difluorophenyl)methyl]-1-methylpiperidin-4-amine (60.0 mg, 250 µmol) in dichloromethane (1 ml). The mixture was stirred overnight and then concentrated. The crude material was purified by HPLC, eluting with 38-72% acetonitrile in water (containing 0.1% trifluoroacetic acid) to afford the title compound (31 mg, 22%). $^1$H NMR (400 MHz, Chloroform-d) δ 7.13 (m, 1H), 7.04 (m, 2H), 6.79 (m, 4H), 4.78-4.65 (m, 2H), 4.36 (s, 2H), 4.29 (s, 2H), 3.72-3.65 (m, 2H), 3.65-3.56 (m, 2H), 2.85 (m, 2H), 2.79 (s, 3H), 2.16 (d, 2H), 2.07 (m, 1H), 1.96-1.85 (m, 2H), 1.02 (d, 6H); LC-MS: 446.3 [M+H]$^+$.

Example 4: 1-[(2,4-difluorophenyl)methyl]-3-{[4-(2-methylpropoxy)phenyl]methyl}-1-(piperidin-4-yl)urea; trifluoroacetic acid (4)

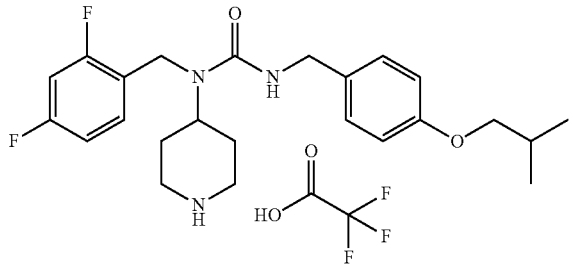

tert-butyl 4-{[(2,4-difluorophenyl)methyl]({[4-(2-methylpropoxy)phenyl]methyl}carbamoyl)amino}piperidine-1-carboxylate

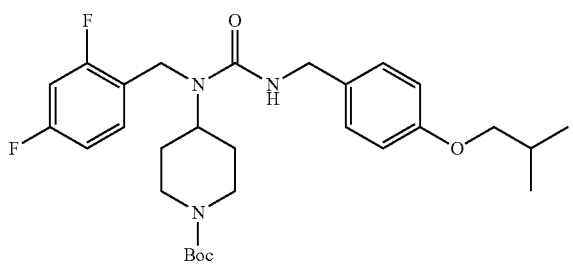 [SMILES: CC(C)COc1ccc(CNC(=O)N(Cc2ccc(F)cc2F)C2CCN(C(=O)OC(C)(C)C)CC2)cc1]

To a stirred solution of tert-butyl 4-{[(2,4-difluorophenyl)methyl]amino}piperidine-1-carboxylate (469 mg, 1.61 mmol) in dichloromethane (5 ml) at room temperature was added a solution of 1-(isocyanatomethyl)-4-(2-methylpropoxy)benzene (396 mg, 1.93 mmol) in dichloromethane (0.2 ml) dropwise over 1 minute. The mixture was stirred for 2.5 hours, then additional 1-(isocyanatomethyl)-4-(2-methylpropoxy)benzene (198 mg, 0.96 mmol) was added in one portion. The mixture was stirred for 1.5 hours, then concentrated to yield the desired intermediate (811 mg).

1-[(2,4-difluorophenyl)methyl]-3-{[4-(2-methylpropoxy)phenyl]methyl}-1-(piperidin-4-yl)urea; trifluoroacetic acid To a stirred solution of tert-butyl 4-{[(2,4-difluorophenyl)methyl]({[4-(2-methylpropoxy)phenyl]methyl}carbamoyl)amino}piperidine-1-carboxylate (57 mg, 0.11 mmol) in dichloromethane (1.5 ml) at room temperature was added trifluoroacetic acid (0.5 ml). After 1 hour, the reaction mixture was concentrated. The crude material was purified by HPLC, eluting with 30-80% acetonitrile in water (containing 0.1% trifluoroacetic acid) to afford the title compound (23 mg, 39%). $^1$H NMR (400 MHz, Chloroform-d) δ 9.60 (bs, 1H), 9.08 (bs, 1H), 7.13 (q, 1H), 7.03 (d, 2H), 6.80 (t, 4H), 4.69-4.53 (m, 2H), 4.36 (s, 2H), 4.28 (s, 2H), 3.68 (d, 2H), 3.41 (d, 2H), 2.95 (d, 2H), 2.13-1.98 (m, 1H), 2.00-1.84 (m, 4H), 1.01 (d, 6H); LC-MS: 432.2 [M+H]$^+$.

Example 5: 1-[(2,4-difluorophenyl)methyl]-1-(1-methylpiperidin-4-yl)-3-{[4-(propan-2-yloxy)phenyl]methyl}urea; trifluoroacetic acid (5)

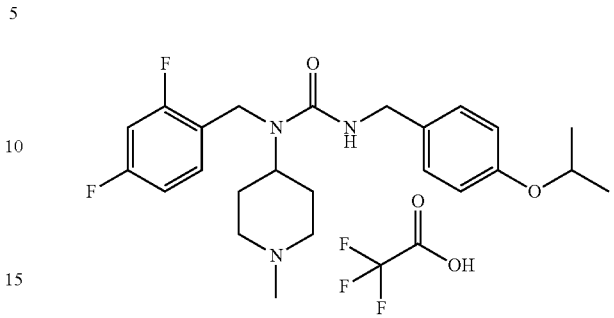

1-(isocyanatomethyl)-4-(propan-2-yloxy)benzene (23.9 mg, 125 μmol) was added to N-[(2,4-difluorophenyl)methyl]-1-methylpiperidin-4-amine (20.0 mg, 83.2 μmol) in dichloromethane (500 μl). The mixture was stirred overnight and then concentrated. The crude material was purified by HPLC, eluting with 30-60% acetonitrile in water (containing 0.1% trifluoroacetic acid) to afford the title compound (32 mg, 71%). $^1$H NMR (400 MHz, Chloroform-d) δ 11.99 (bs, 1H), 7.12 (q, 1H), 7.02 (d, 2H), 6.87-6.75 (m, 4H), 4.83-4.66 (m, 2H), 4.51 (hept, 1H), 4.37 (s, 2H), 4.29 (s, 2H), 3.63 (d, 2H), 2.97-2.84 (m, 2H), 2.81 (s, 3H), 2.29-2.13 (m, 2H), 1.93 (d, 2H), 1.32 (d, 6H); LC-MS: 432.3 [M+H]$^+$.

Example 6: 3-{[3-fluoro-4-(2-methylpropoxy)phenyl]methyl}-1-[(4-fluorophenyl)methyl]-1-(1-methylpiperidin-4-yl)urea; trifluoroacetic acid (6)

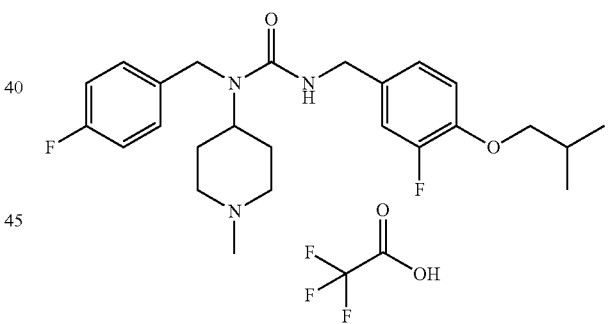

2-[3-Fluoro-4-(2-methylpropoxy)phenyl]acetyl chloride (48.9 μl, 200 μmol) in acetone (100 μl) was added to sodium azide (18.2 mg, 280 μmol) in water (100 μl) at 0° C. After 1 hour, the mixture was diluted with water (1 ml) and extracted with toluene (3×1 ml). The organic phase was dried using sodium sulfate and filtered. The filtrate was gently concentrated to about 1 ml. The mixture was stirred at 60° C. for 15 minutes and then cooled to 0° C. N-[(4-fluorophenyl)methyl]-1-methylpiperidin-4-amine (48.9 mg, 220 μmol) in toluene (1 ml) was added and the mixture was heated to ambient temperature. After 2 hours, the mixture was concentrated and the crude was purified by HPLC, eluting with 25-45% acetonitrile in water (containing 0.1% trifluoroacetic acid) to afford the title compound (69.8 mg, 62%). $^1$H NMR (400 MHz, Chloroform-d) δ 12.41 (bs, 1H), 7.16 (dd, 2H), 7.01 (t, 2H), 6.86-6.71 (m, 3H), 4.80 (s, 1H), 4.69 (ddd, 1H), 4.35 (s, 2H), 4.22 (s, 2H), 3.73 (d, 2H), 3.55

(d, 2H), 2.84 (t, 2H), 2.76 (s, 3H), 2.26-2.12 (m, 2H), 2.08 (dq, 1H), 1.88 (d, 2H), 1.01 (d, 6H); LC-MS: 446.3 [M+H]+.

Example 7: 3-{[2-fluoro-4-(2-methylpropoxy)phenyl]methyl}-1-[(4-fluorophenyl)methyl]-1-(1-methylpiperidin-4-yl)urea; trifluoroacetic acid (7)

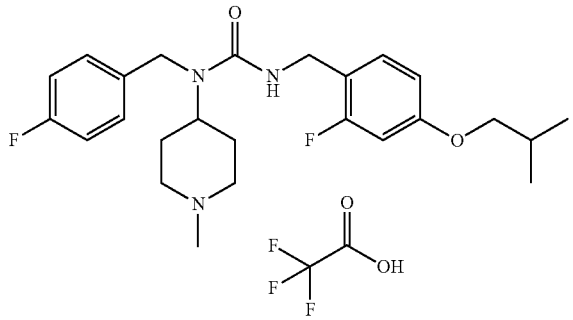 [SMILES: CC(C)COc1ccc(CNC(=O)N(Cc2ccc(F)cc2)C2CCN(C)CC2)c(F)c1 ; O=C(O)C(F)(F)F]

The compound was prepared in analogy with example 6 using 2-[2-fluoro-4-(2-methylpropoxy)phenyl]acetyl chloride. Yield: 29%. $^1$H NMR (400 MHz, Chloroform-d) δ 12.55 (bs, 1H), 7.13 (dd, 2H), 7.04 (t, 1H), 6.99 (t, 2H), 6.58 (dd, 1H), 6.51 (dd, 1H), 4.81-4.62 (m, 2H), 4.32 (s, 2H), 4.28 (s, 2H), 3.66 (d, 2H), 3.55 (d, 2H), 2.83 (t, 2H), 2.76 (s, 3H), 2.16 (tt, 2H), 2.05 (dq, 1H), 1.87 (d, 2H), 1.01 (d, 6H); LC-MS: 446.3 [M+H]+.

Example 8: 1-[(2,4-difluorophenyl)methyl]-3-[(2,2-dimethyl-2,3-dihydro-1-benzofuran-5-yl)methyl]-1-(1-methylpiperidin-4-yl)urea; trifluoroacetic acid (8)

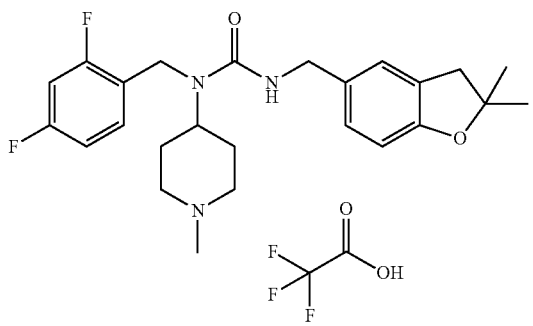 [SMILES: CN1CCC(N(Cc2ccc(F)cc2F)C(=O)NCc2ccc3c(c2)CC(C)(C)O3)CC1 ; O=C(O)C(F)(F)F]

Methyl 2-{4-[(2-methylprop-2-en-1-yl)oxy]phenyl}acetate

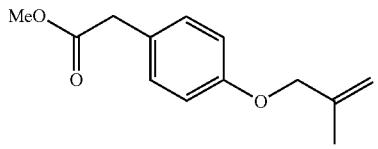 [SMILES: C=C(C)COc1ccc(CC(=O)OC)cc1]

3-bromo-2-methylprop-1-ene (1.41 ml, 14 mmol) was added to methyl 2-(4-hydroxyphenyl)acetate (1.66 g, 10 mmol) and potassium carbonate (3.46 g, 25 mmol) in acetone (50 ml). The mixture was heated to reflux and stirred overnight before it was cooled to ambient temperature, diluted with ethyl acetate (20 ml), filtered through a plug of celite and concentrated (2.11 g, 96%).

Methyl 2-[4-hydroxy-3-(2-methylprop-2-en-1-yl)phenyl]acetate

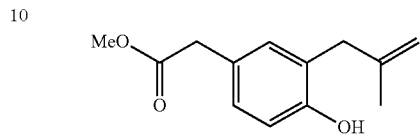

Methyl 2-{4-[(2-methylprop-2-en-1-yl)oxy]phenyl}acetate (1.94 g, 8.81 mmol) was dissolved in N-methyl-2-pyrrolidone (45 ml). The mixture was heated to 200° C. and stirred overnight before it was cooled to ambient temperature and concentrated (2.56 g, quantitative, containing 20% N-methyl-2-pyrrolidone).

Methyl 2-(2,2-dimethyl-2,3-dihydro-1-benzofuran-5-yl)acetate

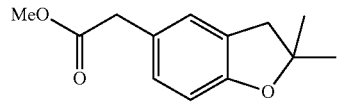 [SMILES: COC(=O)Cc1ccc2c(c1)CC(C)(C)O2]

methyl 2-[4-hydroxy-3-(2-methylprop-2-en-1-yl)phenyl]acetate (2.43 g, containing 20% N-methyl-2-pyrrolidone, 8.81 mmol) was dissolved in formic acid (33.2 ml). The mixture was heated to 100° C. and stirred overnight before it was cooled to ambient temperature and concentrated. The crude was purified by column chromatography using silicon dioxide gel, eluting with 0-15% ethyl acetate in petroleum ether to afford the desired intermediate (1.84 g, 95%).

5-(isocyanatomethyl)-2,2-dimethyl-2,3-dihydro-1-benzofuran

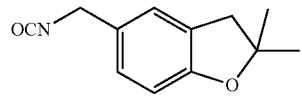

Methyl 2-(2,2-dimethyl-2,3-dihydro-1-benzofuran-5-yl)acetate (1.84 g, 8.35 mmol) was dissolved in methanol (15 ml) and sodium hydroxide (aqueous, 2M, 8.35 ml, 16.7 mmol) was added. After 30 minutes, hydrochloric acid (aqueous, 1M, 50 ml) was added and the mixture was extracted with ethyl acetate (3×20 ml). The combined organic phases were washed with brine (20 ml), dried (phase-separator), concentrated and re-dissolved in dichloromethane (2 ml). Thionyl chloride (6.08 ml, 83.5 mmol) was added and mixture was stirred at ambient temperature for 18 hours before it was concentrated. The crude was dissolved in acetone (5.52 ml) and cooled to 0° C. Sodium azide (760 mg, 11.7 mmol) in water (5.52 ml) was added. After stirring for 1 hour the mixture was diluted with water (50 ml) and extracted with toluene (3×50 ml). The organic phase was dried using magnesium sulfate and filtered. The filtrate was gently concentrated to about 55 ml. The mixture was stirred at 60° C. for 20 minutes before it was concentrated (1.77 g, quantitative).

1-[(2,4-difluorophenyl)methyl]-3-[(2,2-dimethyl-2,3-dihydro-1-benzofuran-5-yl)methyl]-1-(1-methylpiperidin-4-yl)urea; trifluoroacetic acid 5-(isocyanatomethyl)-2,2-dimethyl-2,3-dihydro-1-benzofuran (203 mg, 1 mmol) in dichloromethane (2.5 ml) was added to N-[(2,4-difluorophenyl)methyl]-1-methylpiperidin-4-amine (288 mg, 1.2 mmol) in dichloromethane (2.5 ml). The mixture was stirred for 30 minutes and then concentrated. The crude material was purified by reversed phase chromatography, eluting with 10-40% acetonitrile in water (containing 0.1% trifluoroacetic acid) to afford the title compound (448 mg, 80%). $^1$H NMR (400 MHz, Chloroform-d) δ 12.72 (bs, 1H), 7.13 (q, 1H), 6.89-6.77 (m, 4H), 6.61 (d, 1H), 4.74 (tt, 1H), 4.66 (s, 1H), 4.36 (s, 2H), 4.26 (s, 2H), 3.60 (d, 2H), 2.94 (s, 2H), 2.90-2.73 (m, 5H), 2.18 (qd, 2H), 1.91 (d, 2H), 1.46 (s, 6H); LC-MS: 444.3 [M+H]$^+$.

Example 9: 1-[(2,4-difluorophenyl)methyl]-3-[(3,3-dimethyl-2,3-dihydro-1-benzofuran-5-yl)methyl]-1-(1-methylpiperidin-4-yl)urea; trifluoroacetic acid (9)

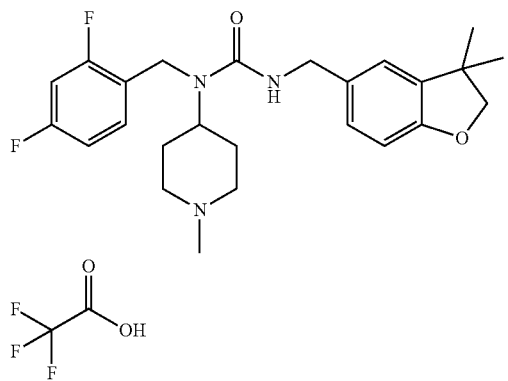

(3,3-dimethyl-2,3-dihydro-1-benzofuran-5-yl)methanamine

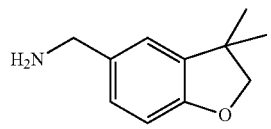

3,3-dimethyl-2,3-dihydro-1-benzofuran-5-carboxylic acid (115 mg, 600 μmol) was dissolved in dichloromethane (2 ml) and oxalyl chloride (56.7 μl, 660 μmol) was added. The mixture was stirred at ambient temperature for 5 minutes before N,N-dimethylformamide (2.3 μl) was added. After 40 minutes, ammonia (28% aqueous, 1.02 ml, 54 mmol) was added and the resulting mixture was stirred vigorously for additionally 30 minutes. The organic phase was separated. The aqueous phase was extracted with dichloromethane (2 ml). The combined organic phase was dried (phase separator) and concentrated. Borane (1M in tetrahydrofuran, 2.4 ml, 2.4 mmol) was added and the mixture was stirred at ambient temperature for 14 hours before it was heated to 50° C. After additionally 7 hours, more borane (1M in tetrahydrofuran, 1.2 ml, 1.2 mmol) was added and the mixture was stirred for 17 hours. The reaction was quenched with methanol and concentrated. Sodium hydroxide (aqueous, 1M, 10 ml) was added and the mixture was extracted with dichloromethane (3×10 ml). The organic phase was extracted with hydrochloric acid (aqueous, 1M, 10 ml). The aqueous phase was made basic using sodium hydroxide (aqueous, 5M) and extracted with dichloromethane (3×10 ml). The organic phase was dried (phase separator) and concentrated (45 mg, 42%).

1-[(2,4-difluorophenyl)methyl]-3-[(3,3-dimethyl-2,3-dihydro-1-benzofuran-5-yl)methyl]-1-(1-methylpiperidin-4-yl)urea; trifluoroacetic acid To a stirred solution of diphosgene (12 μl, 100 μmol) in dichloromethane (1 ml) was added (3,3-dimethyl-2,3-dihydro-1-benzofuran-5-yl)methanamine (35.4 mg, 200 μmol) in dichloromethane (1 ml). Diisopropylethylamine (105 μl, 600 μmol) was added. The mixture was stirred for 15 minutes before N-[(2,4-difluorophenyl)methyl]-1-methylpiperidin-4-amine (71 mg, 295 μmol) was added. After additionally 30 minutes the mixture was washed with sodium hydroxide (aqueous, 1M, 2 ml). The aqueous phase was extracted with dichloromethane (1 ml). The combined organic phase was dried (phase separator) and concentrated. The crude material was purified by HPLC, eluting with 20-50% acetonitrile in water (containing 0.1% trifluoroacetic acid) to afford the title compound (91 mg, 82%). $^1$H NMR (400 MHz, Chloroform-d) δ 12.56 (bs, 1H), 7.14 (q, 1H), 6.89 (dd, 1H), 6.86-6.77 (m, 3H), 6.68 (d, 1H), 4.75 (tt, 1H), 4.67 (s, 1H), 4.37 (s, 2H), 4.30 (s, 2H), 4.21 (s, 2H), 3.61 (d, 2H), 2.86 (t, 2H), 2.79 (s, 3H), 2.18 (qd, 2H), 1.92 (d, 2H), 1.29 (s, 6H); LC-MS: 444.0 [M+H]$^+$.

Example 10: 1-[(2,4-difluorophenyl)methyl]-3-[(2,3-dihydro-1-benzofuran-5-yl)methyl]-1-(1-methylpiperidin-4-yl)urea (10)

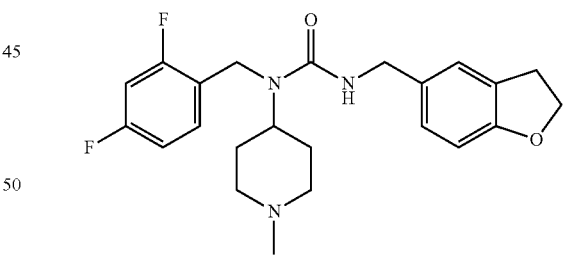

Bis(phenyl N-[(2,3-dihydro-1-benzofuran-5-yl)methyl]carbamate)

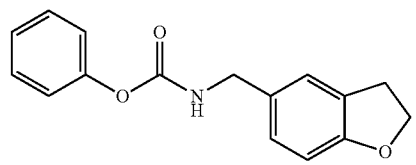 [SMILES: O=C(NCc1ccc2c(c1)CCO2)Oc1ccccc1]

(2,3-dihydro-1-benzofuran-5-yl)methanamine, (59 mg, 0.39 mmol) and pyridine (65 µl, 0.8 mmol) were stirred in dichloromethane (1 ml) and phenyl chloroformate (71 µl, 0.55 mmol) was added dropwise. The mixture was stirred at room temperature for 2 hours, then partitioned between dichloromethane and sodium hydroxide (aqueous, 0.5 M). The organic phase was separated, dried, evaporated and the residue was purified by column chromatography using silicon dioxide gel, eluting with 67% ethyl acetate in petroleum ether to afford the desired intermediate (88 mg, 83%).

1-(2,4-difluorobenzyl)-3-((2,3-dihydrobenzofuran-5-yl)methyl)-1-(1-methylpiperidin-4-yl)urea N-[(2,4-difluorophenyl)methyl]-1-methylpiperidin-4-amine (101 mg, 0.40 mmol) and bis(phenyl N-[(2,3-dihydro-1-benzofuran-5-yl)methyl]carbamate) (88 mg, 0.326 mmol) were dissolved in toluene (2.0 ml) and diisopropylethylamine (105 µl, 6.0 mmol) was added. The mixture was stirred at 120° C. for 17 h, then partitioned between sodium hydroxide (aqueous, 0.5 M) and ether. The organic phase was separated and concentrated. The residue was purified by column chromatography using silicon dioxide gel, eluting with 0-33% methanol in ethyl acetate. Fractions containing the desired material were pooled, concentrated, suspended in diethyl ether and filtered to remove the solids. The clear solution was evaporated to afford the title compound as an oil (92 mg, 68%). This oil was triturated in ether/hexanes to give the title compound as the crystalline non-hygroscopic free base (69.2 mg, 51%). $^1$H NMR (400 MHz, Chloroform-d) δ 7.22 (q, 1H), 7.01 (s, 1H), 6.91 (d, 1H), 6.85-6.74 (m, 2H), 6.68 (d, 1H), 4.55 (t, 2H), 4.52 (t, 1H), 4.40 (s, 2H), 4.30 (d, 2H), 4.29 (m, 1H), 3.15 (t, 2H), 2.90 (d, 2H), 2.29 (s, 3H), 2.11 (m, 2H), 1.71 (m, 4H); LC-MS: 416.2 [M+H]$^+$.

Example 11 (comparative): 1-[(3,5-difluorophenyl)methyl]-1-(1-methylpiperidin-4-yl)-3-{[4-(2-methylpropoxy)phenyl]methyl}urea; trifluoroacetic acid (11)

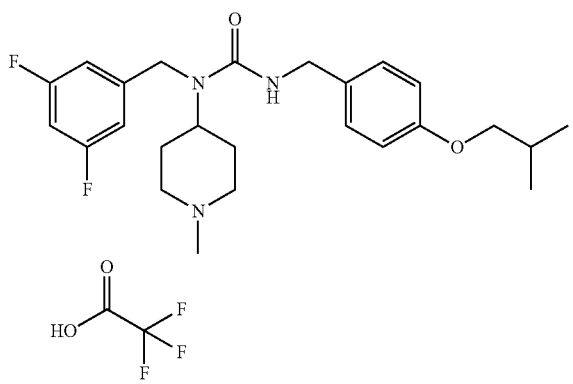

The compound was prepared in analogy with example 2 using N-[(3,5-difluorophenyl)methyl]-1-methylpiperidin-4-amine and 1-(isocyanatomethyl)-4-(2-methylpropoxy)benzene. Yield: 62%. $^1$H NMR (400 MHz, Chloroform-d) δ 7.02 (d, 2H), 6.83-6.78 (m, 2H), 6.74 (d, 2H), 6.73-6.67 (m, 1H), 4.73 (m, 1H), 4.60 (s, 1H), 4.37 (s, 2H), 4.32-4.25 (m, 2H), 3.68 (d, 2H), 3.61-3.52 (m, 2H), 2.84 (m, 2H), 2.78 (s, 3H), 2.27-2.13 (m, 2H), 2.05 (dq, 1H), 1.96-1.85 (m, 2H), 1.01 (d, 6H); LC-MS: 446.3 [M+H]$^+$.

Example 12 (comparative): 1-[(3,5-dimethoxyphenyl)methyl]-1-(1-methylpiperidin-4-yl)-3-{[4-(2-methylpropoxy)phenyl]methyl}urea; trifluoroacetic acid (12)

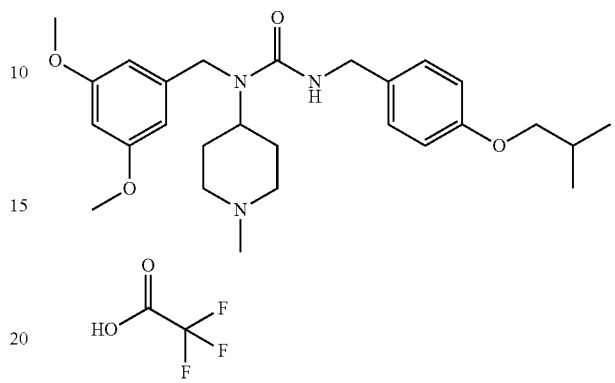

The compound was prepared in analogy with example 2 using N-[(3,5-dimethoxyphenyl)methyl]-1-methylpiperidin-4-amine and 1-(isocyanatomethyl)-4-(2-methylpropoxy)benzene. Yield: 34%. $^1$H NMR (400 MHz, Chloroform-d) δ 7.02 (d 2H), 6.80-6.74 (m, 2H), 6.34 (m, 3H), 4.62-4.54 (m, 1H), 4.46-4.36 (m, 1H), 4.29 (s, 2H), 4.27 (d, 2H), 3.72 (s, 6H), 3.68 (d, 2H), 2.94-2.85 (m, 2H), 2.27 (s, 3H), 2.15-2.01 (m, 3H), 1.81-1.63 (m, 4H), 1.01 (d, 6H); LC-MS: 470.3 [M+H]$^+$.

Example 13: 1-[(4-fluoro-2-hydroxyphenyl)methyl]-1-(1-methylpiperidin-4-yl)-3-{[4-(2-methylpropoxy)phenyl]methyl}urea; trifluoroacetic acid (13)

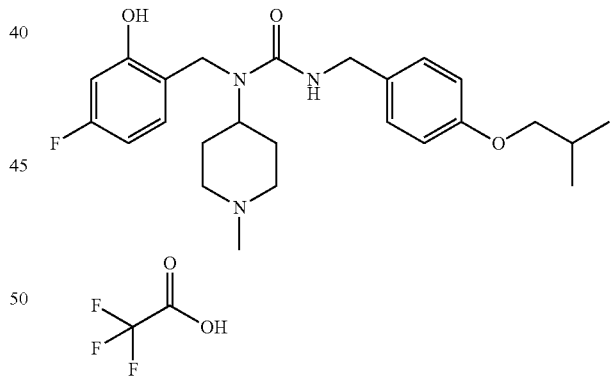

2-(benzyloxy)-4-fluorobenzonitrile

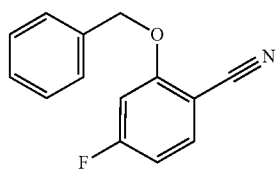 [SMILES: N#Cc1ccc(F)cc1OCc1ccccc1]

To a stirred suspension of potassium tert-butoxide (2.34 g, 21 mmol) in dioxane (15 ml) at room temperature was added benzyl alcohol (2.33 g, 22 mmol) in one portion. The mixture was stirred for 10 minutes then 2,4-difluorobenzonitrile (1.00 g, 7.2 mmol) was added in one portion. The mixture was stirred for 1.5 hours then water (10 ml) was added and the mixture extracted with diethyl ether (3×10 ml). The combined organic phases were dried using a phase separator and concentrated to solids. The crude material was purified by column chromatography using silicon dioxide gel, eluting with 25-50% dichloromethane in petroleum ether to afford the desired intermediate (1.33 g, 5.8 mmol, 81%).

[2-(benzyloxy)-4-fluorophenyl]methanamine

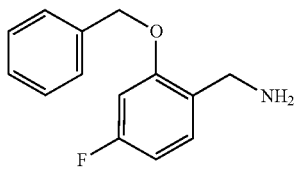 [SMILES: NCc1ccc(F)cc1OCc1ccccc1]

2-(benzyloxy)-4-fluorobenzonitrile (208 mg, 0.92 mmol) was dissolved in a 4° C. solution of BH$_3$ (1.4 ml, 1 M in tetrahydrofuran). After 5 hours addition BH$_3$ solution (1.4 ml) was added at room temperature, after another 19 hours additional BH$_3$ solution (1 ml) was added and stirring continued for 3 hours then NaOH (5 ml, 1 M aqueous) was added dropwise and the mixture extracted with ethyl acetate (3×5 ml). The combined organic phases were dried using a phase separator and concentrated to oil (260 mg).

N-{[2-(benzyloxy)-4-fluorophenyl]methyl}-1-methylpiperidin-4-amine

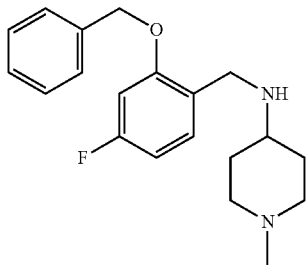 [SMILES: CN1CCC(NCc2ccc(F)cc2OCc2ccccc2)CC1]

To a stirred solution of [2-(benzyloxy)-4-fluorophenyl]methanamine (204 mg) in ethanol (5 ml) at room temperature was added 1-methylpiperidin-4-one (163 μl), followed by sodium triacetoxyborohydride (372 mg) in one portion. The mixture was stirred 6 hours then concentrated, diluted with NaOH (5 ml, 1 M aqueous) and washed with dichloromethane (3×5 ml). The combined organic phases were dried using a phase separator and concentrated to oil (253 mg).

1-{[2-(benzyloxy)-4-fluorophenyl]methyl}-1-(1-methylpiperidin-4-yl)-3-{[4-(2-methylpropoxy)phenyl]methyl}urea (13b)

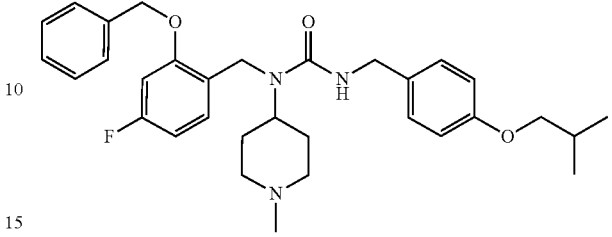

To a stirred solution of N-{[2-(benzyloxy)-4-fluorophenyl]methyl}-1-methylpiperidin-4-amine (127 mg) in dichloromethane (2 ml) at room temperature was added a solution of 1-(isocyanatomethyl)-4-(2-methylpropoxy)benzene (112 mg) in dichloromethane (1 ml). The mixture was stirred 3 hours, then washed with NaOH (3×1 ml, 1 M aqueous). The organic phase was dried using a phase separator and concentrated to oil (229 mg).

1-[(4-fluoro-2-hydroxyphenyl)methyl]-1-(1-methylpiperidin-4-yl)-3-{[4-(2-methylpropoxy)phenyl]methyl}urea; trifluoroacetic acid To a stirred solution of 1-{[2-(benzyloxy)-4-fluorophenyl]methyl}-1-(1-methylpiperidin-4-yl)-3-{[4-(2-methylpropoxy)phenyl]methyl}urea (90 mg) in ethanol (5 ml) under a nitrogen atmosphere was added palladium (10% by weight) on charcoal (58 mg) in one portion at room temperature. The nitrogen atmosphere was exchanged for a hydrogen atmosphere and the mixture was stirred for 2.5 hours. The hydrogen atmosphere was removed, the mixture was filtered through a plug of celite with ethanol and the filtered solvent was concentrated to crude oil. The crude material was purified by HPLC, eluting with 55-75% acetonitrile in water (containing 0.1% trifluoroacetic acid) to afford the title compound (33 mg, 0.059 mmol, 41% over 4 steps). $^1$H NMR (400 MHz, Chloroform-d) δ 12.13 (bs, 1H), 7.12 (d, 2H), 6.98 (t, 1H), 6.79 (d, 2H), 6.61 (d, 1H), 6.47 (t, 1H), 5.63 (s, 1H), 4.31 (s, 4H), 4.19 (s, 1H), 3.67 (d, 2H), 3.45 (d, 2H), 2.82 (s, 2H), 2.72 (s, 3H), 2.36 (q, 2H), 2.12-1.94 (m, 1H), 1.82 (d, 2H), 1.00 (d, 6H); LC-MS: 444.3 [M+H]$^+$.

Example 14: 1-[(4-fluorophenyl)methyl]-3-{[2-hydroxy-4-(2-methylpropoxy)phenyl]methyl}-1-(1-methylpiperidin-4-yl)urea; trifluoroacetic acid (14)

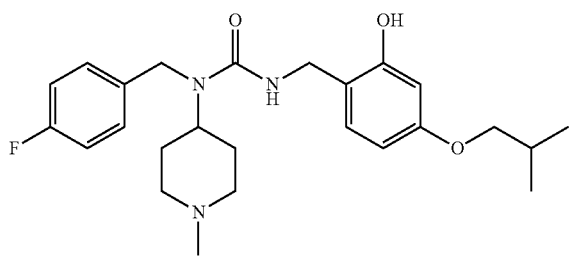

-continued

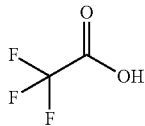

2-(benzyloxy)-4-(2-methylpropoxy)benzonitrile

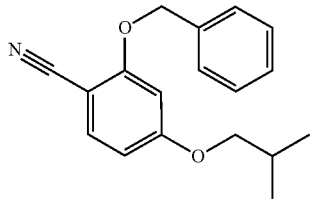 [SMILES: CC(C)COc1ccc(C#N)c(OCc2ccccc2)c1]

To a stirred solution of 2-(benzyloxy)-4-fluorobenzonitrile (208 mg, 0.92 mmol) in dioxane (2 ml) at room temperature was added isobutanol (126 μl), followed by potassium tert-butoxide (146 mg) in one portion. The mixture was stirred for 17 hours then then water (10 ml) was added and the mixture extracted with diethyl ether (3×10 ml). The combined organic phases were dried using a phase separator and concentrated to oil (287 mg).

[2-(benzyloxy)-4-(2-methylpropoxy)phenyl]methanamine

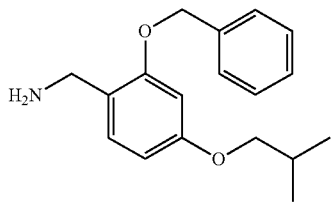 [SMILES: CC(C)COc1ccc(CN)c(OCc2ccccc2)c1]

2-(benzyloxy)-4-(2-methylpropoxy)benzonitrile (287 mg mmol) was dissolved in a 4° C. solution of $BH_3$ (1 ml, 1 M in tetrahydrofuran). After 1.5 hours the mixture was heated to 60° C., after 1.5 hours additional $BH_3$ solution (1 ml) was added and stirring continued for 17 hours. The mixture was cooled to room temperature, NaOH (4 ml, 1 M aqueous) was added dropwise and the mixture extracted with diethyl ether (3×5 ml). The combined organic phases were dried using a phase separator and concentrated to oil (393 mg).

3-{[2-(benzyloxy)-4-(2-methylpropoxy)phenyl]methyl}-1-[(4-fluorophenyl)methyl]-1-(1-methylpiperidin-4-yl)urea

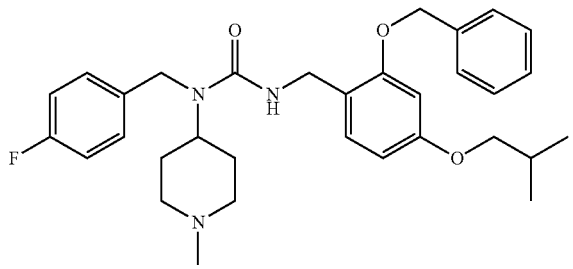 [SMILES: CC(C)COc1ccc(CNC(=O)N(Cc2ccc(F)cc2)C2CCN(C)CC2)c(OCc2ccccc2)c1]

To a stirred solution of diphosgene (50 μl) in dichloromethane (1 ml) at 0° C. was added a mixture of [2-(benzyloxy)-4-(2-methylpropoxy)phenyl]methanamine (102 mg) and pyridine (87 μl) in dichloromethane (1 ml) dropwise over 2 minutes. The mixture was stirred for 1 hour then added to a stirred solution of N-[(4-fluorophenyl)methyl]-1-methylpiperidin-4-amine (71 mg) in dichloromethane (1 ml) at room temperature dropwise over 2 minutes. The mixture was stirred 3 hours, then washed with NaOH (3×1 ml, 1 M aqueous). The organic phase was dried using a phase separator and concentrated to oil (168 mg).

1-[(4-fluorophenyl)methyl]-3-{[2-hydroxy-4-(2-methylpropoxy)phenyl]methyl}-1-(1-methylpiperidin-4-yl)urea; trifluoroacetic acid To a stirred solution of 3-{[2-(benzyloxy)-4-(2-methylpropoxy)phenyl]methyl}-1-[(4-fluorophenyl)methyl]-1-(1-methylpiperidin-4-yl)urea (168 mg) in ethanol (5 ml) under a nitrogen atmosphere was added palladium (10% by weight) on charcoal (70 mg) in one portion at room temperature. The nitrogen atmosphere was exchanged for a hydrogen atmosphere and the mixture was stirred for 2.5 hours. The hydrogen atmosphere was removed, the mixture was filtered through a plug of celite with ethanol and the filtered solvent was extracted with dichloromethane (3×5 ml). The combined organic phases were dried using a phase separator and concentrated to crude oil. One third of the crude material was purified by HPLC, eluting with 40-70% acetonitrile in water (containing 0.1% trifluoroacetic acid) to afford the title compound (15 mg, 0.026 mmol, 33% over 4 steps). $^1$H NMR (400 MHz, Chloroform-d) δ 12.65 (bs, 1H), 7.10 (dd, 2H), 6.99 (t, 2H), 6.81 (d, 1H), 6.47 (d, 1H), 6.33 (dd, 1H), 5.05 (t, 1H), 4.64 (t, 1H), 4.36 (s, 2H), 4.19 (d, 2H), 3.67 (d, 2H), 3.55 (d, 2H), 2.89-2.74 (m, 5H), 2.23 (q, 2H), 2.05 (p, 1H), 1.85 (d, 2H), 1.00 (d, 6H); LC-MS: 444.3 $[M+H]^+$.

Example 15: 1-[(2,4-difluorophenyl)methyl]-3-{[4-(2-fluoroethoxy)phenyl]methyl}-1-(1-methylpiperidin-4-yl)urea; trifluoroacetic acid (15)

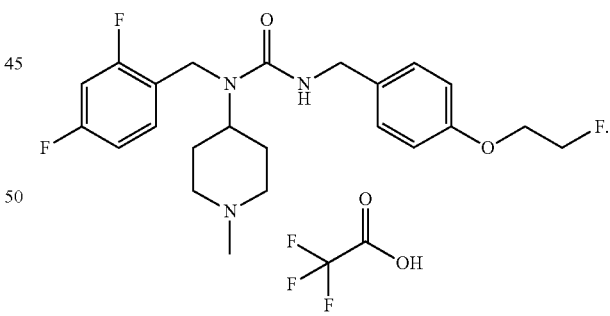

4-(2-fluoroethoxy)benzonitrile

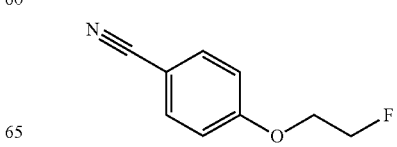

2-fluoroethanol (145 μl, 2.46 mmol) was added to a mixture of potassium tert-butoxide (277 mg, 2.46 mmol) in dioxane (2 ml). After 5 minutes of stirring at room temperature 4-fluorobenzonitrile (199 mg, 1.64 mmol) in dioxane (2 ml) was added to the mixture. After 16 hours of stirring at room temperature the mixture was added to a layer of diethyl ether (5 ml) on water (5 ml). The water phase was extracted with diethyl ether (3×5 ml), the combined organic layers were dried using a phase separator and concentrated to afford the desired intermediate as a white solid (261.3 mg).

[4-(2-fluoroethoxy)phenyl]methanamine

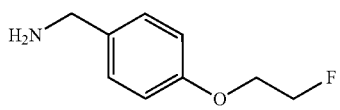

Borane (2 ml, 1 M in tetrahydrofuran, 2 mmol) was added to 4-(2-fluoroethoxy)benzonitrile (133 mg, 0.805 mmol). After 1 hour of stirring at room temperature the mixture was heated to 40° C. After 1 hour of stirring the mixture was concentrated. The residue was re-dissolved in methanol (2 ml), refluxed for 1 hour and concentrated to an oil. NaOH (1 ml, 1 M aqueous) was added and the product was extracted with ethyl acetate (2×1 ml). The organic layer was dried using a phase separator and concentrated to afford the desired intermediate as an oil (113.8 mg).

3-[(2,4-difluorophenyl)methyl]-1-{[4-(2-fluoroethoxy)phenyl]methyl}-3-(1-methylpiperidin-4-yl)urea; trifluoroacetic acid

[4-(2-fluoroethoxy)phenyl]methanamine (51.3 mg, 0.303 mmol) dissolved in dichloromethane (0.5 ml) was added to diphosgene (18.3 μl, 0.152 mmol) dissolved in dichloromethane (0.5 ml) then diisopropylethylamine (106 μl, 0.606 mmol) was added dropwise. After 15 minutes of stirring at room temperature N-[(2,4-difluorophenyl)methyl]-1-methylpiperidin-4-amine (87.4 mg, 0.364 mmol) dissolved in dichloromethane (0.5 ml) was added. After another 2 hours of stirring the mixture was concentrated. The crude material was purified by HPLC, eluting with 15-50% acetonitrile in water (containing 0.1% trifluoroacetic acid) to afford the title compound (87.0 mg, 52%): $^1$H NMR (400 MHz, Chloroform-d) δ 12.88 (bs, 1H), 7.12 (q, 1H), 7.05 (d, 2H), 6.86-6.75 (m, 4H), 4.84-4.76 (m, 1H), 4.75-4.63 (m, 3H), 4.36 (s, 2H), 4.28 (d, 2H), 4.23-4.19 (m, 1H), 4.17-4.12 (m, 1H), 3.57 (d, 2H), 2.90-2.73 (m, 5H), 2.17 (qd, 2H), 1.89 (d, 2H); LCMS: 436.3 [M+H]$^+$.

Example 16: 1-[(2,4-difluorophenyl)methyl]-3-[(4-ethoxyphenyl)methyl]-1-(1-methylpiperidin-4-yl)urea (16)

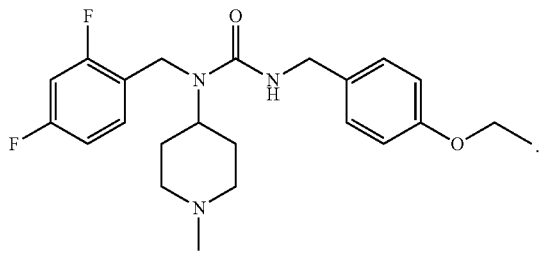 [SMILES: CCOc1ccc(CNC(=O)N(Cc2ccc(F)cc2F)C2CCN(C)CC2)cc1]

1-ethoxy-4-(isocyanatomethyl)-benzene

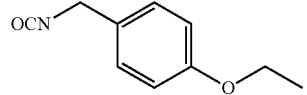

4-Ethoxyphenylacetic acid (10.0 g, 53.38 mmol) was refluxed for 2 hours in a mixture of dichloromethane (60 ml), thionyl chloride (40 ml) and N,N-dimethylformamide (200 ul). The mixture was evaporated and triturated in diethyl ether. The diethyl ether extract was evaporated to give 2-(4-ethoxyphenyl)acetyl chloride (10.98 g, 100% yield). This material (7.0 g, 95% purity, 33.4 mmol) was dissolved in acetone (15 ml) and added at 0° C. during 10 minutes to a solution of sodium azide (3.07 g, 46.8 mmol) in water (15 ml). After stirring at 0° C. for 1 hour the mixture was diluted with cold water (40 ml) and extracted with toluene 2×40 ml. The organic extracts were combined, dried (sodium sulfate) and concentrated to 60 ml on a rotary evaporator using a water bath at 30° C. The toluene solution was heated to 65° C. in an oil bath until the gas evolution stopped (30 minutes). The mixture was stirred for additional 5 minutes and thereafter evaporated to give an oil that was dissolved in heptane (40 ml). The solution was filtered to remove solids and the filtrate was evaporated to afford the title compound as an oil (6.81 gram, 100% yield).

3-[(2,4-difluorophenyl)methyl]-1-[(4-ethoxyphenyl)methyl]-3-(1-methylpiperidin-4-yl)urea 1-Ethoxy-4-(isocyanatomethyl)benzene (87% pure, 200 mg 1.08 mmol) was dissolved in dichloromethane (2 ml) and N-[(2,4-difluorophenyl)methyl]-1-methylpiperidin-4-amine (200 mg, 832 μmol) dissolved in dichloromethane (1 ml) was added. The mixture was stirred for 20 min, then partitioned between sodium hydroxide (aqueous, 0.5 M) and dichloromethane. The organic phase was evaporated and the residue was recrystallized consecutive from diethyl ether/hexanes, acetone/water and diethyl ether/hexanes to give 109 mg of impure compound. The material was purified by silica gel chromatography, eluting with 0-33% methanol in ethyl acetate to afforded the title compound (71 mg, 21% yield); $^1$H NMR (400 MHz, Chloroform-d) δ 7.26-7.16 (m, 1H), 7.09 (d, 2H), 6.86-6.73 (m, 4H), 4.53 (t, 1H), 4.40 (s, 2H), 4.32 (d, 2H), 4.32-4.20 (m, 1H), 4.01 (q, 2H), 2.89 (d, 2H), 2.27 (s, 3H), 2.16-2.02 (m, 2H), 1.74-1.62 (m, 4H), 1.40 (t, 3H); 418.0 [M+H]$^+$.

Example 17: 3-[(4-cyclopropoxyphenyl)methyl]-1-[(2,4-difluorophenyl)methyl]-1-(1-methylpiperidin-4-yl)urea; hemitartrate (17)

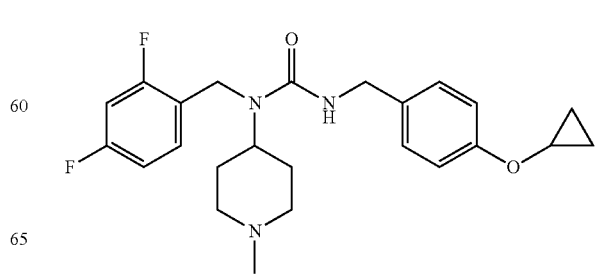

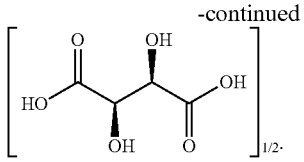

3-[(4-cyclopropoxyphenyl)methyl]-1-[(2,4-difluoro-phenyl)methyl]-1-(1-methylpiperidin-4-yl)urea; hemitartrate N-[(2,4-difluorophenyl)methyl]-1-methylpiperidin-4-amine (1.89 mmol, 478 mg), phenyl N-[(4-cyclopropoxyphenyl)methyl]carbamate (97%, 585 mg, 2.0 mmol) and potassium carbonate (2.5 mmol, 350 mg) were suspended in toluene (5.0 ml). The mixture was stirred at 70° C. for 16 hours, then partitioned between toluene and sodium hydroxide (aqueous, 0.5 M). The organic phase was separated and concentrated. The material was purified by silica gel chromatography, eluting with 0-50% methanol in ethyl acetate. Fractions containing the desired product were pooled and concentrated. Diethyl ether (10 ml) was added. The mixture was filtered and concentrated to give 3-[(4-cyclopropoxyphenyl)methyl]-1-[(2,4-difluorophenyl)methyl]-1-(1-methylpiperidin-4-yl)urea (725 mg, 1.688 mmol, 89% yield). This material (725 mg, 1.688 mmol) and L-(+)-tartaric acid (0.844 mmol, 127.3 mg) were dissolved in ethanol (5.0 ml) using an ultrasonication bath. The solvents were then evaporated to give the title compound as the hemitartrate salt (glassy foam, 906 mg). $^1$H NMR (400 MHz, Chloroform-d) δ 7.16 (q, 1H), 7.05 (d, 2H), 6.94 (d, 2H), 6.84-6.73 (m, 2H), 4.70 (bt, 1H), 4.62-4.48 (m, 1H), 4.41 (s, 2H), 4.33 (s, 1H), 4.28 (d, 2H), 3.70 (m, 1H), 3.42 (t, 2H), 2.72-2.56 (m, 2H), 2.63 (s, 3H), 2.18 (m, 2H), 1.81 (d, 2H), 0.76 (m, 4H); LC-MS: 430.3 [M+H]$^+$.

Example 18: 3-{[4-(tert-butoxy)phenyl]methyl}-1-[(2,4-difluorophenyl)methyl]-1-(1-methylpiperidin-4-yl)urea; trifluoroacetic acid (18)

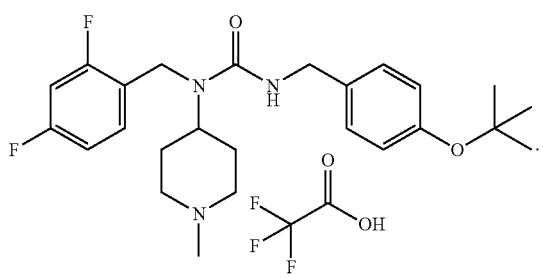

The compound was prepared in analogy with 1-[(2,4-difluorophenyl)methyl]-3-{[4-(2-fluoroethoxy)phenyl]methyl}-1-(1-methylpiperidin-4-yl)urea (example 15) using 4-fluorobenzonitril and potassium tert-butoxide. 2-fluoro-ethanol was not added. The crude material was purified by HPLC, eluting with 20-55% acetonitrile in water (containing 0.1% trifluoroacetic acid) to afford the title compound (19.7 mg, 32%): $^1$H NMR $^1$H NMR (400 MHz, Chloroform-d) δ 12.57 (bs, 1H), 7.12 (q, 1H), 7.00 (d, 2H), 6.88 (d, 2H), 6.81 (t, 2H), 4.81-4.65 (m, 2H), 4.37 (s, 2H), 4.31 (s, 2H), 3.59 (d, 2H), 2.93-2.72 (m, 5H), 2.17 (q, 2H), 1.91 (d, 2H), 1.31 (s, 9H); LCMS: 446.3 [M+H]$^+$.

Example 19: 3-(4-(allyloxy)benzyl)-1-(2,4-difluorobenzyl)-1-(1-methylpiperidin-4-yl)urea; trifluoroacetic acid (19)

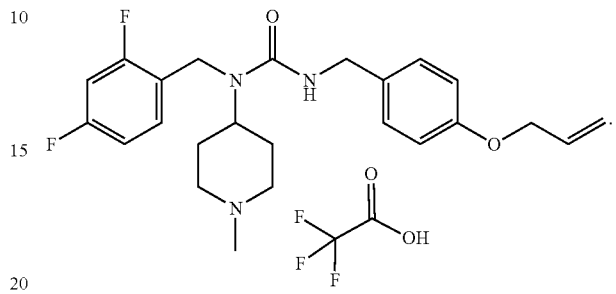

phenyl N-{[4-(prop-2-en-1-yloxy)phenyl]methyl}carbamate

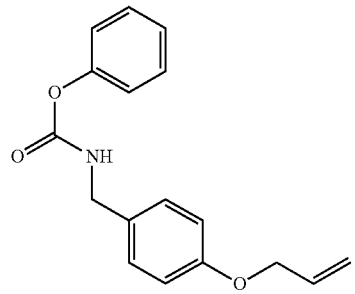 [SMILES: C=CCOc1ccc(CNC(=O)Oc2ccccc2)cc1]

4-(hydroxy)-benzaldehyde (10.0 g, 80.25 mmol), potassium carbonate (163.8 mmol, 22.6 g), tetrabutylammonium iodide (1.0 mmol, 377 mg), allyl bromide (121 mmol, 10.6 ml) and N,N-dimethylformamide (4.0 ml) were stirred at 20° C. for 6 hours and then partitioned between water and diethyl ether. The organic phase was washed with water several times, then dried and evaporated to give 4-(allyloxy)-benzaldehyde as an oil (13.3 g, 100%). This material (11.17 g, 68.8 mmol) was dissolved in ethanol (40 ml) and sodium borohydride (35 mmol, 1.351 g) was added in portions. The mixture was stirred 1 hour and then concentrated, sodium hydroxide (aqueous, 5 M, 30 ml) and water (100 mL) were added and the mixture was extracted with diethyl ether. The organic phase was washed with water and brine and then evaporated to give 4-(allyloxy)-benzylalcohol (10.49 g, 63.9 mmol, 93%). This alcohol (3.0 g, 18.2 mmol) was dissolved in dichloromethane (10 ml) and thionyl chloride (37 mmol, 2.8 ml) was added. The mixture was stirred at 40° C. for 10 min and then evaporated. The residue was dissolved in N,N-dimethylformamide (7 ml) and potassium phthalimide (20 mmol, 3.75 g) followed by pyridine (5 mmol, 410 µl) were added. The mixture was stirred at room temperature 20 hours and then at 50° C. for 30 min. Hydrochloric acid (aqueous, 1 M, 20 ml) was added. The crystals were isolated by filtration, washed with 33% methanol in water and dried to give 5.18 g material which was recrystallized from 95% ethanol to give the phthalimide derivative (4.7 g, 88% yield). This material was stirred in 33% methylamine in ethanol (16 ml) and ethanol (15 ml) for 18 hours, then at 60° C. for 30 min. The mixture was partitioned between diethyl ether and sodium hydroxide (0.2 M). The organic phase was separated and extracted with hydrochloric acid (aqueous, 1 M). The aqueous phase was made basic with sodium hydroxide (5 M), then extracted with diethyl ether. The organic phase was dried and evaporated to give the intermediate 4-allyloxy-benzylamine (2.247 g, 86%). This material (1.5 g, 9.1 mmol) and pyridine (11.83 mmol, 0.96 mL) were stirred in dichloromethane (10 ml) on an ice bath and phenyl chloroformate (10.01 mmol, 1.614 g, 1.3 ml) dissolved in dichloromethane (5 ml) was added dropwise during 20 minutes. The mixture was stirred at room temperature for 1 hour, then partitioned between dichloromethane and hydrochloric acid (aqueous, 0.5 M). The organic phase was dried and evaporated to an oil (2.3 g). Recrystallization from ethanol/water gave the desired intermediate as crystals (4.62 mmol, 1.31 g, 51%).

3-[(2,4-difluorophenyl)methyl]-3-(1-methylpiperidin-4-yl)-1-{[4-(prop-2-en-1-yloxy)phenyl]methyl}urea; trifluoroacetic acid N-[(2,4-difluorophenyl)methyl]-1-methylpiperidin-4-amine (0.588 mmol, 149 mg) and phenyl N-{[4-(prop-2-en-1-yloxy)phenyl]methyl}carbamate (200 mg, 0.705 mmol) were dissolved in toluene (1.5 ml) and cesium carbonate (1.0 mmol, 326 mg) was added. The mixture was stirred at 80° C. for 2 hours, then partitioned between diethyl ether and sodium hydroxide (aqueous, 0.5 M). The organic phase was concentrated and purified by silica gel chromatography, eluting with 0-50% methanol in ethyl acetate. Fractions containing the desired product were pooled and concentrated. Diethyl ether was added. The mixture was filtered and concentrated to give the desired compound as the free base (112 mg, 0.261 mmol, 44% yield). This material was dissolved in dioxane (3 ml) and trifluoroacetic acid (0.27 mmol, 21 ul) was added followed by freeze drying to afford the title compound (0.27 mmol, 146 mg, 100% yield). $^1$H NMR (400 MHz, Chloroform-d) δ 12.96 (s, 1H), 7.13 (q, 1H), 7.04 (d, 2H), 6.87-6.75 (m, 4H), 6.04 (m, 1H), 5.40 (qd, 1H), 5.29 (qd, 1H), 4.78-4.63 (m, 2H), 4.51 (d, 2H), 4.37 (s, 2H), 4.29 (d, 2H), 3.58 (d, 2H), 2.83 (t, 2H), 2.78 (s, 3H), 2.20 (m, 2H), 1.90 (d, 2H); LC-MS: 430.3 [M+H]$^+$.

Example 20: 3-[(1-benzofuran-5-yl)methyl]-1-[(2,4-difluorophenyl)methyl]-1-(1-methylpiperidin-4-yl)urea; trifluoroacetic acid (20)

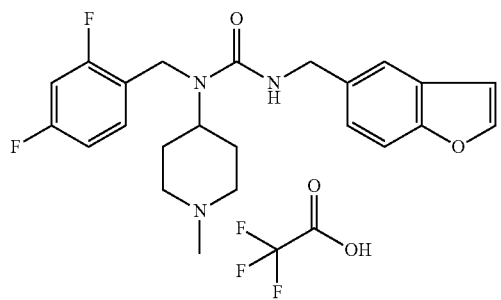

To a stirred solution of diphosgene (21.2 mg, 107 µmol) in dichloromethane (700 µl) was added (1-benzofuran-5-yl) methanamine (30.0 mg, 204 µmol) and triethylamine (56.8 µl, 408 mmol) in dichloromethane (700 µl). The mixture was stirred for 30 minutes before N-[(2,4-difluorophenyl)methyl]-1-methylpiperidin-4-amine (51.4 mg, 214 µmol) was added. After additionally 5 hours the mixture was concentrated. The crude material was purified by HPLC, eluting with 15-50% acetonitrile in water (containing 0.1% trifluoroacetic acid) to afford the title compound (79 mg, 74%). $^1$H NMR (400 MHz, Chloroform-d) δ $^1$H NMR (400 MHz, Chloroform-d) δ 12.07 (bs, 1H), 7.62 (d, 1H), 7.40 (d, 1H), 7.32 (s, 1H), 7.12 (q, 1H), 7.08-7.01 (m, 1H), 6.80 (t, 2H), 6.70 (d, 1H), 4.90 (bs, 1H), 4.79-4.64 (m, 1H), 4.43 (s, 2H), 4.38 (s, 2H), 3.59 (d, 2H), 2.86 (t, 2H), 2.78 (s, 3H), 2.17 (qd, 2H), 1.91 (d, 2H); LC-MS: 414.2 [M+H]$^+$.

General Procedures

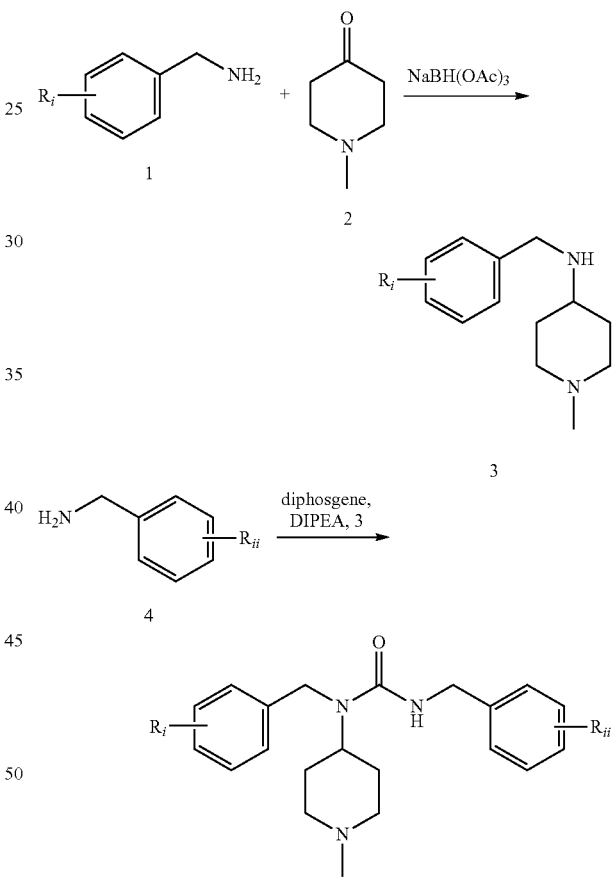

Scheme S1: General procedure A (GP A).

Amine 1 (1.1 equiv.) was added to ketone 2 (1.0 equiv.) in CH$_2$Cl$_2$ followed by addition of sodium triacetoxyborohydride (1.5 equiv.). The reaction mixture was stirred for 3 hours at room temperature, then concentrated under reduced pressure. The residue was diluted with NaOH (1 M, aq.) and extracted with CH$_2$Cl$_2$. The organic phase was dried and concentrated under reduced pressure to give secondary amines 3, that was used in the next step without purification or purified by silica gel column chromatography. A solution of amine 4 (1.0 equiv.) in CH$_2$Cl$_2$ was added dropwise to a solution of diphosgene (0.5 equiv.) in CH$_2$Cl$_2$ at room temperature. DIPEA (3.0 equiv.) was added and the resulting mixture was stirred for 5 minutes at room temperature. Thereafter a solution of secondary amine 3 (1.1 equiv.) in CH$_2$Cl$_2$ was added and the reaction mixture was stirred overnight at room temperature. The mixture was concentrated under reduced pressure and the desired urea 5 was purified by preparative HPLC eluting with acetonitrile in water (containing 0.1% trifluoroacetic acid) to afford the TFA salt of the product or purified by preparative HPLC eluting with acetonitrile in water, containing 6 ppm ammonia (28% aq.), to afford the product as the free base.

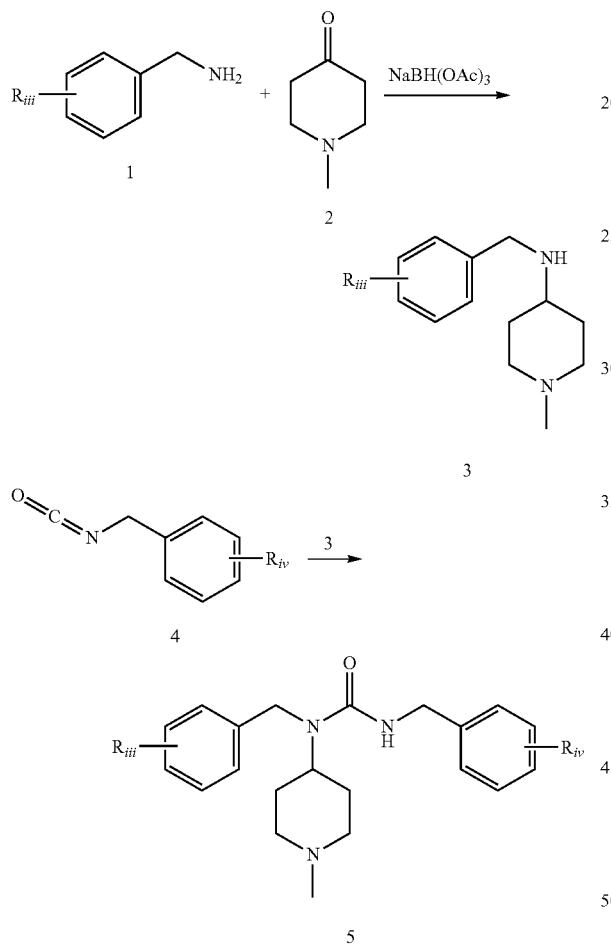

Scheme S2: General procedure B (GP B).

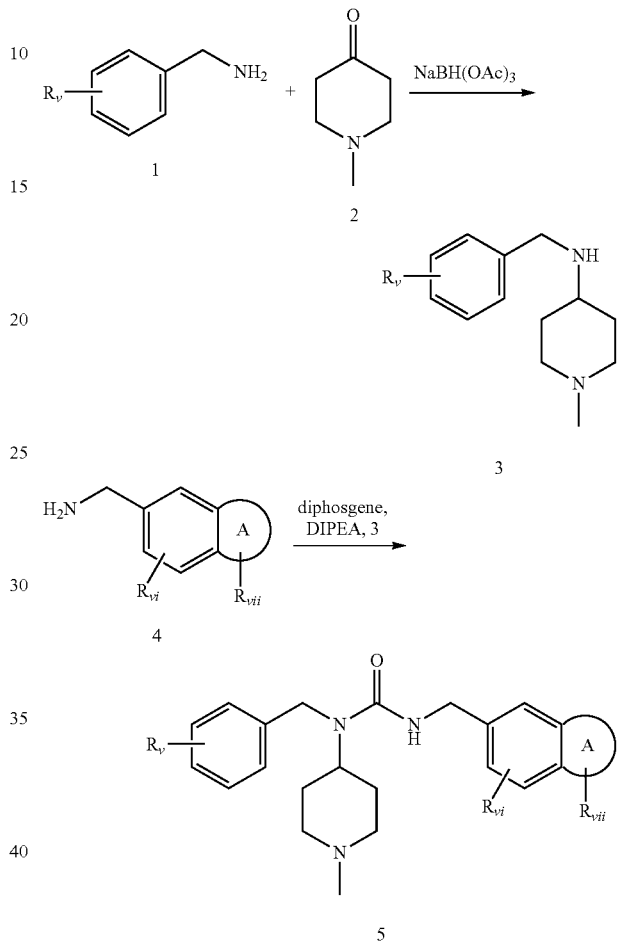

Scheme S3: General procedure C(GP C).

Amine 1 (1.1 equiv.) was added to ketone 2 (1.0 equiv.) in CH$_2$Cl$_2$ followed by addition of sodium triacetoxyborohydride (1.5 equiv.). The reaction mixture was stirred for 3 hours at room temperature, then concentrated under reduced pressure. The residue was diluted with NaOH (1 M, aq.) and extracted with CH$_2$Cl$_2$. The organic phase was dried and concentrated under reduced pressure to give secondary amines 3, that was used in the next step without purification or purified by silica gel column chromatography. Isocyanate 4 (1.0 equiv.) in CH$_2$Cl$_2$ was added to a solution of secondary amine 3 (1.0 equiv.) in CH$_2$Cl$_2$ at room temperature, the reaction mixture was stirred for 3 hours. The mixture was concentrated under reduced pressure and the desired urea 5 was purified by preparative HPLC eluting with acetonitrile in water (containing 0.1% trifluoroacetic acid) to afford the TFA salt of the product or purified by preparative HPLC eluting with acetonitrile in water, containing 6 ppm ammonia (28% aq.), to afford the product as the free base.

Amine 1 (1.1 equiv.) was added to ketone 2 (1.0 equiv.) in CH$_2$Cl$_2$ followed by addition of sodium triacetoxyborohydride (1.5 equiv.). The reaction mixture was stirred for 3 hours at room temperature, then concentrated under reduced pressure. The residue was diluted with NaOH (1 M, aq.) and extracted with CH$_2$Cl$_2$. The organic phase was dried and concentrated under reduced pressure to give secondary amines 3, that was used in the next step without purification or purified by silica gel column chromatography. A solution of amine 4 (1.0 equiv.) in CH$_2$Cl$_2$ was added dropwise to a solution of diphosgene (0.5 equiv.) in CH$_2$Cl$_2$ at room temperature. DIPEA (3.0 equiv.) was added and the resulting mixture was stirred for 5 minutes at room temperature. Thereafter a solution of secondary amine 3 (1.1 equiv.) in CH$_2$Cl$_2$ was added and the reaction mixture was stirred overnight at room temperature. The mixture was concentrated under reduced pressure and the desired urea 5 was purified by preparative HPLC eluting with acetonitrile in water (containing 0.1% trifluoroacetic acid) to afford the TFA salt of the product or purified by preparative HPLC eluting with acetonitrile in water, containing 6 ppm ammonia (28% aq.), to afford the product as the free base.

Scheme S4: General procedure D (GP D).

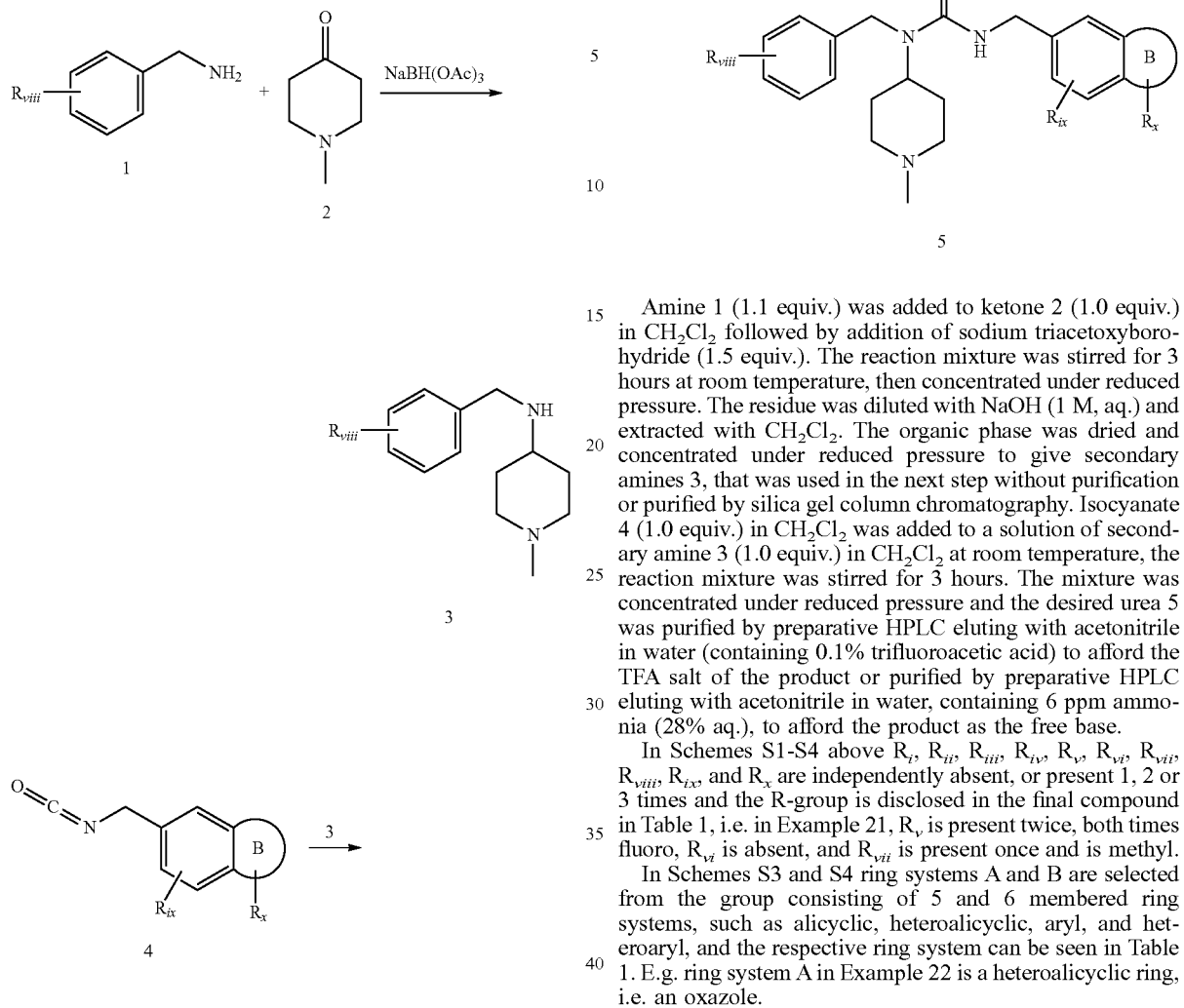

Amine 1 (1.1 equiv.) was added to ketone 2 (1.0 equiv.) in $CH_2Cl_2$ followed by addition of sodium triacetoxyborohydride (1.5 equiv.). The reaction mixture was stirred for 3 hours at room temperature, then concentrated under reduced pressure. The residue was diluted with NaOH (1 M, aq.) and extracted with $CH_2Cl_2$. The organic phase was dried and concentrated under reduced pressure to give secondary amines 3, that was used in the next step without purification or purified by silica gel column chromatography. Isocyanate 4 (1.0 equiv.) in $CH_2Cl_2$ was added to a solution of secondary amine 3 (1.0 equiv.) in $CH_2Cl_2$ at room temperature, the reaction mixture was stirred for 3 hours. The mixture was concentrated under reduced pressure and the desired urea 5 was purified by preparative HPLC eluting with acetonitrile in water (containing 0.1% trifluoroacetic acid) to afford the TFA salt of the product or purified by preparative HPLC eluting with acetonitrile in water, containing 6 ppm ammonia (28% aq.), to afford the product as the free base.

In Schemes S1-S4 above $R_i$, $R_{ii}$, $R_{iii}$, $R_{iv}$, $R_v$, $R_{vi}$, $R_{vii}$, $R_{viii}$, $R_{ix}$, and $R_x$ are independently absent, or present 1, 2 or 3 times and the R-group is disclosed in the final compound in Table 1, i.e. in Example 21, $R_v$ is present twice, both times fluoro, $R_{vi}$ is absent, and $R_{vii}$ is present once and is methyl.

In Schemes S3 and S4 ring systems A and B are selected from the group consisting of 5 and 6 membered ring systems, such as alicyclic, heteroalicyclic, aryl, and heteroaryl, and the respective ring system can be seen in Table 1. E.g. ring system A in Example 22 is a heteroalicyclic ring, i.e. an oxazole.

TABLE 1

Compounds prepared by GP A, GP B, GP C and GP D.

| Example/Compound | Structure | Starting materials | | | Procedure |
|---|---|---|---|---|---|
| 21 | 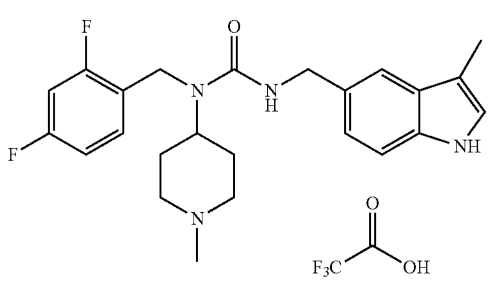 | (2,4-difluorophenyl)methanamine* | 1-methylpiperidin-4-one* | (3-methyl-1H-indol-5-yl)methanamine* | C |

TABLE 1-continued

Compounds prepared by GP A, GP B, GP C and GP D.

| Example/Compound | Structure | Starting materials | | | Procedure |
|---|---|---|---|---|---|
| 22 | 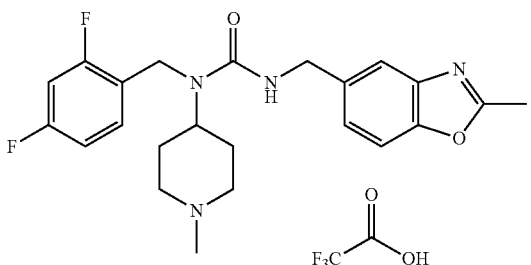 | (2,4-difluorophenyl)methanamine* | 1-methylpiperidin-4-one* | (2-methyl-1,3-benzoxazol-5-yl)methanamine* | C |
| 23 | 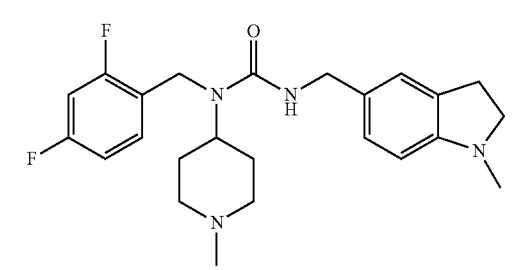 [SMILES: CN1CCC(N(Cc2ccc(F)cc2F)C(=O)NCc2ccc3c(c2)CCN3C)CC1] | (2,4-difluorophenyl)methanamine* | 1-methylpiperidin-4-one* | (1-methyl-2,3-dihydro-1H-indol-5-yl)methanamine* | C |
| 24 | 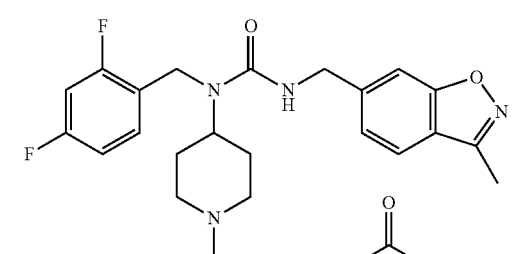 | (2,4-difluorophenyl)methanamine* | 1-methylpiperidin-4-one* | (3-methyl-1,2-benzoxazol-6-yl)methanamine* | C |
| 25 | 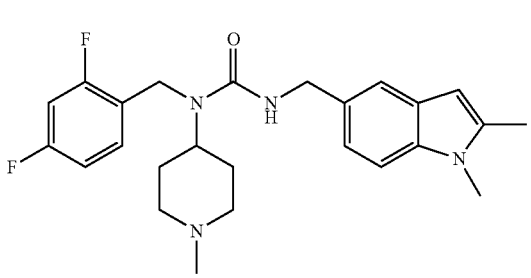 [SMILES: Cc1cc2cc(CNC(=O)N(Cc3ccc(F)cc3F)C3CCN(C)CC3)ccc2n1C] | (2,4-difluorophenyl)methanamine* | 1-methylpiperidin-4-one* | (1,2-dimethyl-1H-indol-5-yl)methanamine* | C |
| 26 | 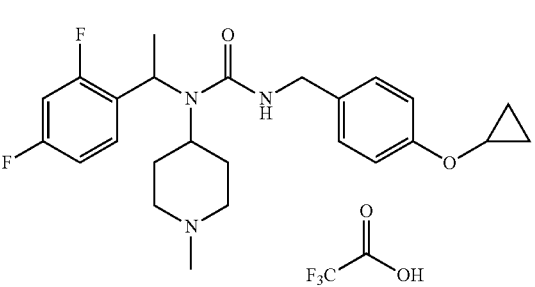 | 1-(2,4-difluorophenyl)ethan-1-amine* | 1-methylpiperidin-4-one* | (4-cyclopropoxyphenyl)methanamine** | A |

TABLE 1-continued

Compounds prepared by GP A, GP B, GP C and GP D.

| Example/Compound | Structure | Starting materials | | | Procedure |
|---|---|---|---|---|---|
| 27 | 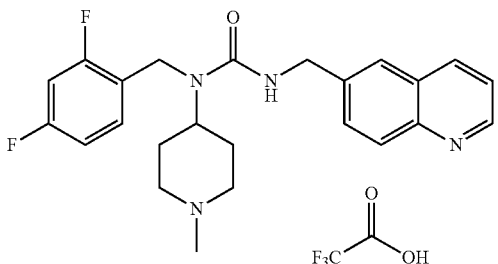 | (2,4-difluoro-phenyl)methan-amine* | 1-methyl-piperidin-4-one* | (quinolin-6-yl)methan-amine | C |
| 28 | 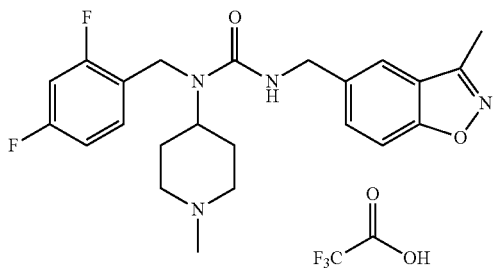 | (2,4-difluoro-phenyl)methan-amine* | 1-methyl-piperidin-4-one* | (3-methyl-1,2-benzoxazol-5-yl)methan-amine* | C |
| 29 | 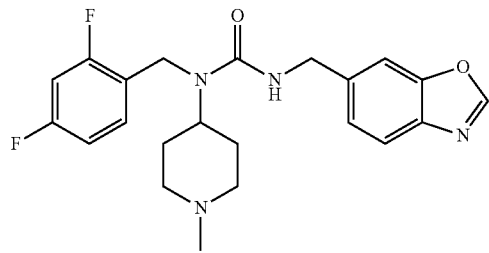 | (2,4-difluoro-phenyl)methan-amine* | 1-methyl-piperidin-4-one* | (1,3-benzoxazol-6-yl)methan-amine* | C |
| 30 | 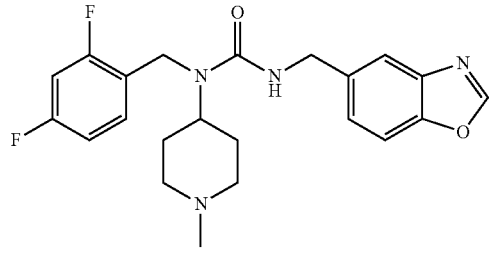 | (2,4-difluoro-phenyl)methan-amine* | 1-methyl-piperidin-4-one* | (1,3-benzoxazol-5-yl)methan-amine* | C |
| 31 | 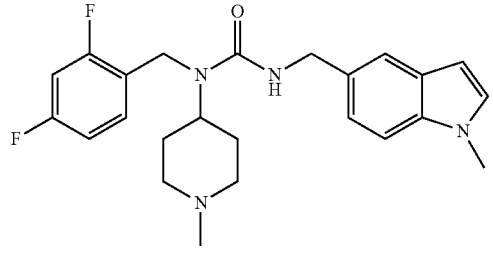 [SMILES: CN1CCC(N(Cc2ccc(F)cc2F)C(=O)NCc2ccc3c(ccn3C)c2)CC1] | (2,4-difluoro-phenyl)methan-amine* | 1-methyl-piperidin-4-one* | (1-methyl-1H-indol-5-yl)methan-amine* | C |

TABLE 1-continued

Compounds prepared by GP A, GP B, GP C and GP D.

| Example/Compound | Structure | Starting materials | | | Procedure |
|---|---|---|---|---|---|
| 32 | 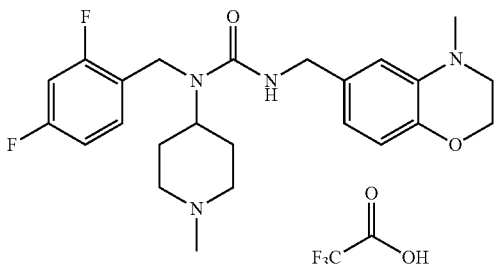 | (2,4-difluorophenyl)methanamine* | 1-methylpiperidin-4-one* | (4-methyl-3,4-dihydro-2H-1,4-benzoxazin-6-yl)methanamine* | C |
| 33 | 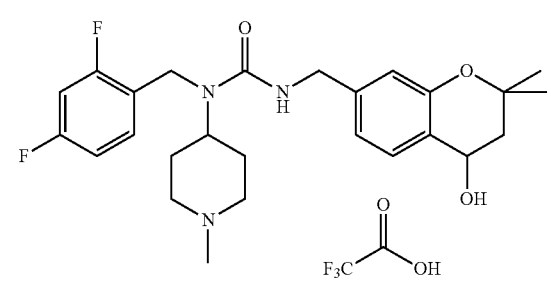 | (2,4-difluorophenyl)methanamine* | 1-methylpiperidin-4-one* | 7-(aminomethyl)-2,2-dimethyl-3,4-dihydro-2H-1-benzopyran-4-ol** | C |
| 34 | 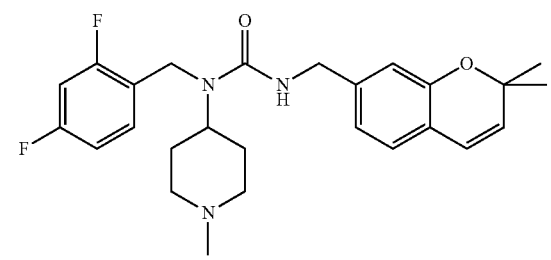 [SMILES: CN1CCC(N(Cc2ccc(F)cc2F)C(=O)NCc2ccc3c(c2)OC(C)(C)C=C3)CC1] | (2,4-difluorophenyl)methanamine* | 1-methylpiperidin-4-one* | (2,2-dimethyl-2H-chromen-7-yl)methanamine** | C |
| 35 | 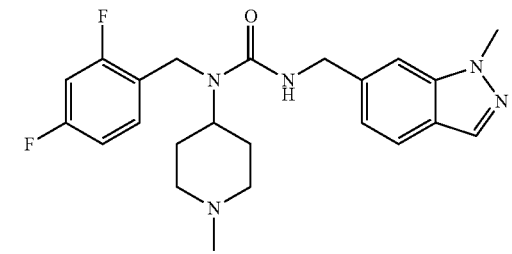 [SMILES: CN1CCC(N(Cc2ccc(F)cc2F)C(=O)NCc2ccc3cnn(C)c3c2)CC1] | (2,4-difluorophenyl)methanamine* | 1-methylpiperidin-4-one* | (1-methyl-1H-indazol-6-yl)methanamine* | C |
| 36 | 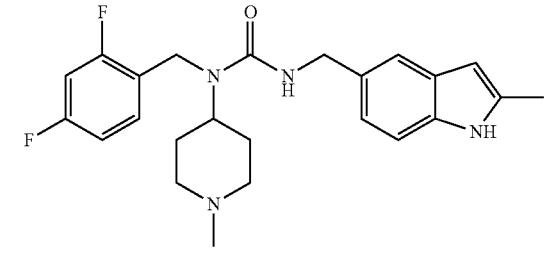 [SMILES: Cc1cc2cc(CNC(=O)N(Cc3ccc(F)cc3F)C3CCN(C)CC3)ccc2[nH]1] | (2,4-difluorophenyl)methanamine* | 1-methylpiperidin-4-one* | (2-methyl-1H-indol-5-yl)methanamine* | C |

TABLE 1-continued

Compounds prepared by GP A, GP B, GP C and GP D.

| Example/Compound | Structure | Starting materials | | | Procedure |
|---|---|---|---|---|---|
| 37 | 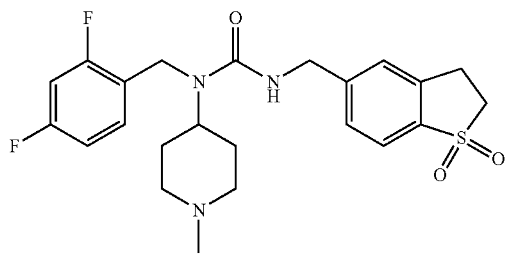 [SMILES: CN1CCC(N(Cc2ccc(F)cc2F)C(=O)NCc2ccc3c(c2)CCS3(=O)=O)CC1] | (2,4-difluorophenyl)methanamine* | 1-methylpiperidin-4-one* | 5-(aminomethyl)-2,3-dihydro-1λ6-benzothiophene-1,1-dione* | C |
| 38 | 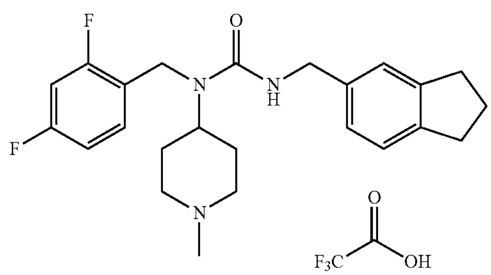 | (2,4-difluorophenyl)methanamine* | 1-methylpiperidin-4-one* | (2,3-dihydro-1H-inden-5-yl)methanamine* | C |
| 39 | 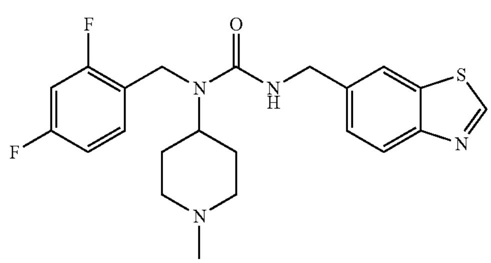 [SMILES: CN1CCC(N(Cc2ccc(F)cc2F)C(=O)NCc2ccc3ncsc3c2)CC1] | (2,4-difluorophenyl)methanamine* | 1-methylpiperidin-4-one* | (1,3-benzothiazol-6-yl)methanamine* | C |
| 40 | 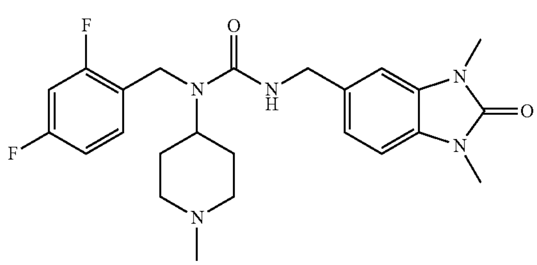 [SMILES: CN1CCC(N(Cc2ccc(F)cc2F)C(=O)NCc2ccc3c(c2)n(C)c(=O)n3C)CC1] | (2,4-difluorophenyl)methanamine* | 1-methylpiperidin-4-one* | 5-(aminomethyl)-1,3-dimethyl-2,3-dihydro-1H-1,3-benzodiazol-2-one* | C |
| 41 | 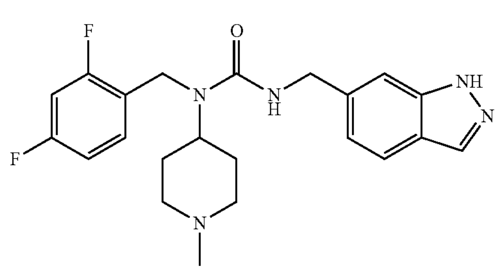 [SMILES: CN1CCC(N(Cc2ccc(F)cc2F)C(=O)NCc2ccc3cn[nH]c3c2)CC1] | (2,4-difluorophenyl)methanamine* | 1-methylpiperidin-4-one* | (1H-indazol-6-yl)methanamine* | C |

TABLE 1-continued

Compounds prepared by GP A, GP B, GP C and GP D.

| Example/Compound | Structure | Starting materials | | | Procedure |
|---|---|---|---|---|---|
| 42 | 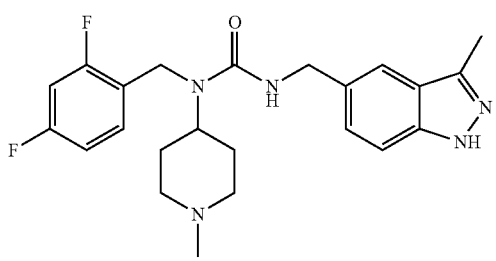 [SMILES: Cc1n[nH]c2ccc(CNC(=O)N(Cc3ccc(F)cc3F)C3CCN(C)CC3)cc12] | (2,4-difluoro-phenyl)methan-amine* | 1-methyl-piperidin-4-one* | (3-methyl-1H-indazol-5-yl)methan-amine* | C |
| 43 | 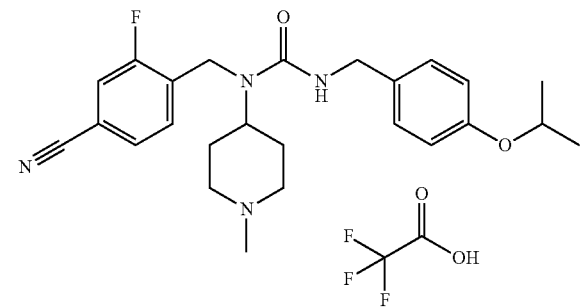 | 4-(amino-methyl)-3-fluoro-benzo nitrile* | 1-methyl-piperidin-4-one* | [4-(propan-2-yloxy)phenyl]methan-amine* | A |
| 44 | 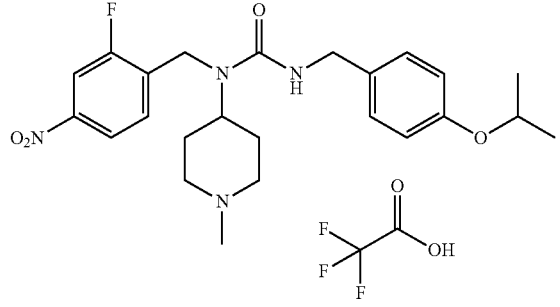 | (2-fluoro-4-nitro-phenyl)methan-amine* | 1-methyl-piperidin-4-one* | [4-(propan-2-yloxy)phenyl]methan-amine* | A |
| 45 | 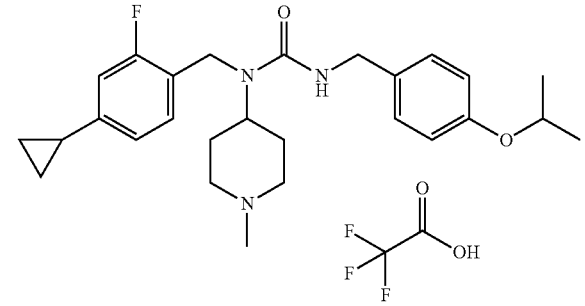 | (4-cyclopropyl-2-fluoro-phenyl)metan-amine* | 1-methyl-piperidin-4-one* | [4-(propan-2-yloxy)phenyl]methan-amine* | A |
| 46 | 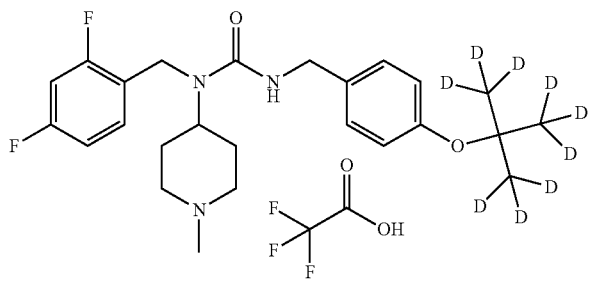 | (2,4-difluoro-phenyl)methan-amine* | 1-methyl-piperidin-4-one* | (4-{[2-($^{2}$H$_{3}$)methyl($^{2}$H$_{6}$)propan-2-yl]oxy}phenyl)methan-amine** | A |

TABLE 1-continued

Compounds prepared by GP A, GP B, GP C and GP D.

| Example/Compound | Structure | Starting materials | | | Procedure |
|---|---|---|---|---|---|
| 47 | 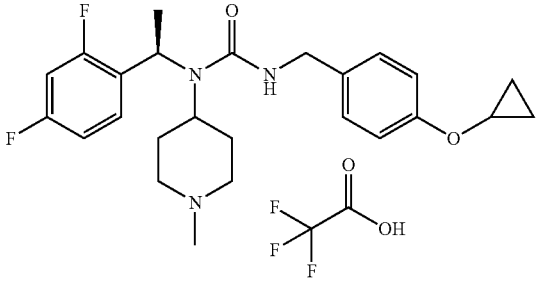 | (1R)-1-(2,4-difluoro-phenyl)ethan-1-amine* | 1-methyl-piperidin-4-one* | (4-cyclopropoxyphenyl)methan-amine** | A |
| 48 | 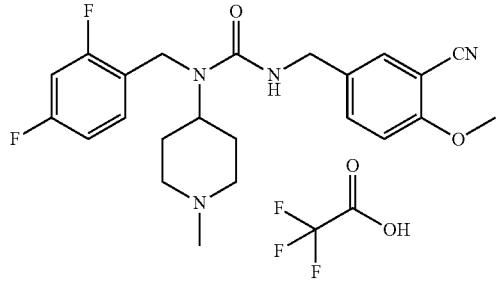 | (2,4-difluoro-phenyl)methan-amine* | 1-methyl-piperidin-4-one* | 5-(amino-methyl)-2-methoxy-benzonitrile | A |
| 49 | 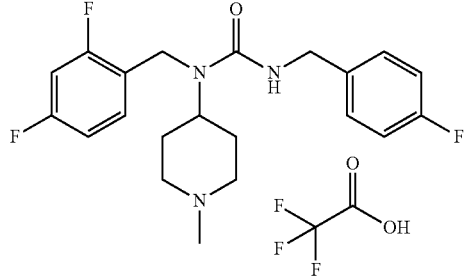 | (2,4-difluoro-phenyl)methan-amine* | 1-methyl-piperidin-4-one* | (4-fluorophenyl)methan-amine* | A |
| 50 | 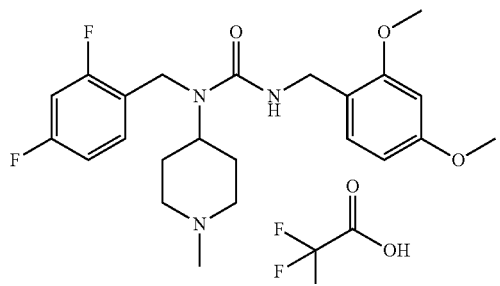 | (2,4-difluoro-phenyl)methan-amine* | 1-methyl-piperidin-4-one* | (2,4-dimethoxy-phenyl)methan-amine* | A |
| 51 | 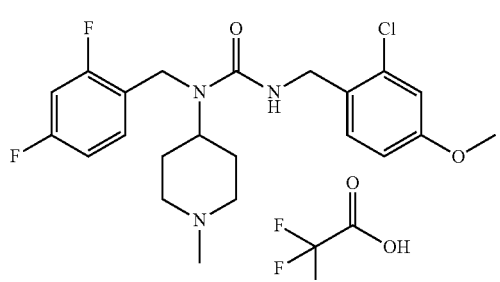 | (2,4-difluoro-phenyl)methan-amine* | 1-methyl-piperidin-4-one* | (2-chloro-4-methoxy-phenyl)methan-amine | A |

TABLE 1-continued

Compounds prepared by GP A, GP B, GP C and GP D.

| Example/Compound | Structure | Starting materials | | | Procedure |
|---|---|---|---|---|---|
| 52 | 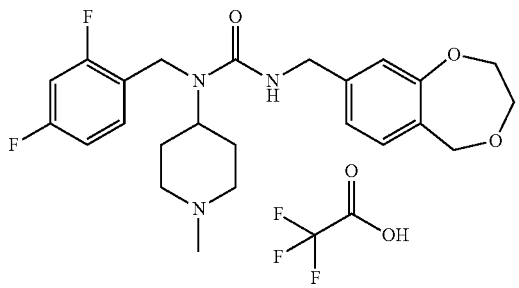 | (2,4-difluoro-phenyl)methan-amine* | 1-methyl-piperidin-4-one* | (3,5-dihydro-2H-1,4-benzo-dioxepin-8-yl)methan-amine** | C |
| 53 | 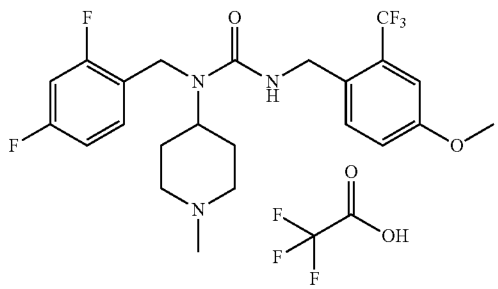 | (2,4-difluoro-phenyl)methan-amine* | 1-methyl-piperidin-4-one* | [4-methoxy-2-(trifluoro-methyl)phenyl]methan-amine* | A |
| 54 | 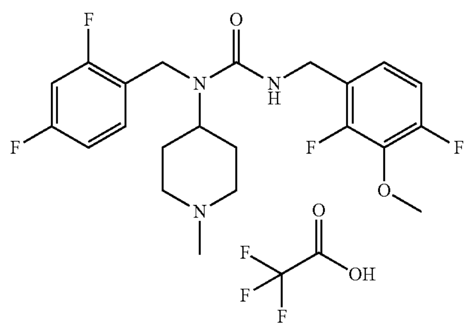 | (2,4-difluoro-phenyl)methan-amine* | 1-methyl-piperidin-4-one* | (2,4-difluoro-3-methoxy-phenyl)methan-amine* | A |
| 55 | 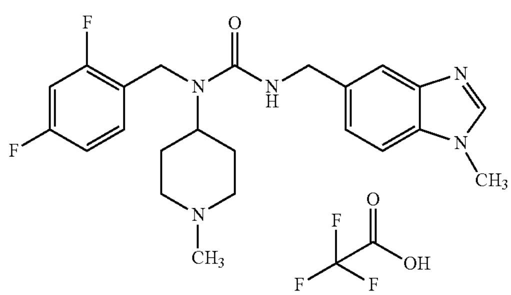 | (2,4-difluoro-phenyl)methan-amine* | 1-methyl-piperidin-4-one* | (1-methtyl-1H-1,3-benzodiazol-5-yl)methan-amine* | C |
| 56 | 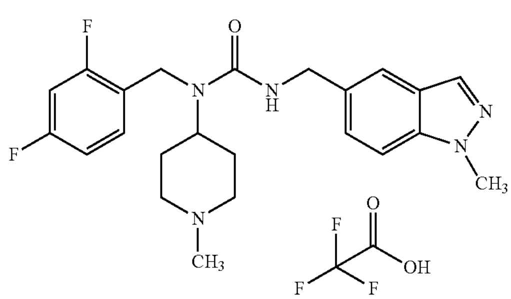 | (2,4-difluoro-phenyl)methan-amine* | 1-methyl-piperidin-4-one* | (1-methtyl-1H-indazol-5-yl)methan-amine* | C |

TABLE 1-continued

Compounds prepared by GP A, GP B, GP C and GP D.

| Example/Compound | Structure | Starting materials | | | Procedure |
|---|---|---|---|---|---|
| 57 | 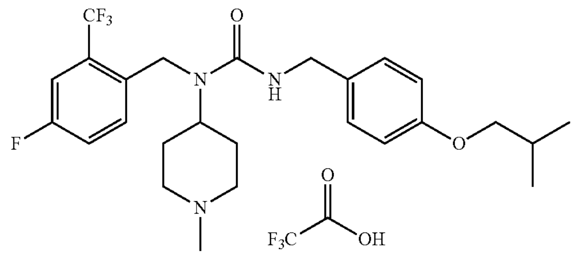 | [4-fluoro-2-(trifluoromethyl)phenyl]methanamine* | 1-methyl-piperidin-4-one* | 1-(isocyanatomethyl)-4-(2-methylpropoxy)benzene** | B |
| 58 | 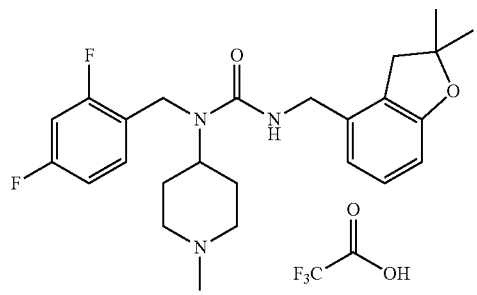 | (2,4-difluorophenyl)methanamine* | 1-methyl-piperidin-4-one* | 4-(isocyanatomethyl)-2,2-dimethyl-2,3-dihydro-1-benzofuran** | D |
| 59 | 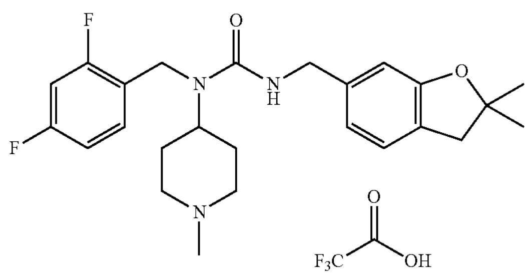 | (2,4-difluorophenyl)methanamine* | 1-methyl-piperidin-4-one* | 6-(isocyanatomethyl)-2,2-dimethyl-2,3-dihydro-1-benzofuran** | D |
| 60 | 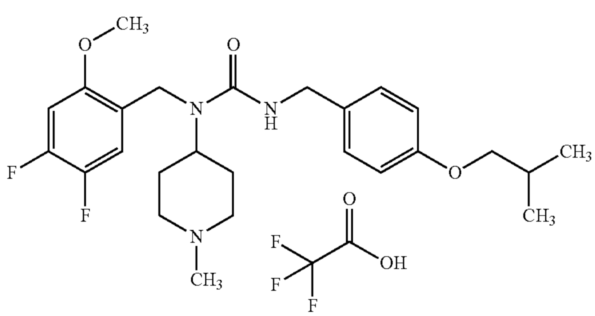 | (4,5-difluoro-2-methoxyphenyl)metanamine* | 1-methyl-piperidin-4-one* | 1-(isocyanatomethyl)-4-(2-methylpropoxy)benzene** | B |
| 61 | 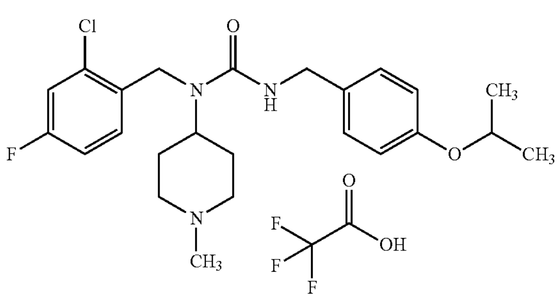 | (2-chloro-4-fluorophenyl)methanamine* | 1-methyl-piperidin-4-one* | 1-(isocyanatomethyl)-4-(propan-2-yloxy)benzene** | B |

TABLE 1-continued

Compounds prepared by GP A, GP B, GP C and GP D.

| Example/Compound | Structure | Starting materials | | | Procedure |
|---|---|---|---|---|---|
| 62 | 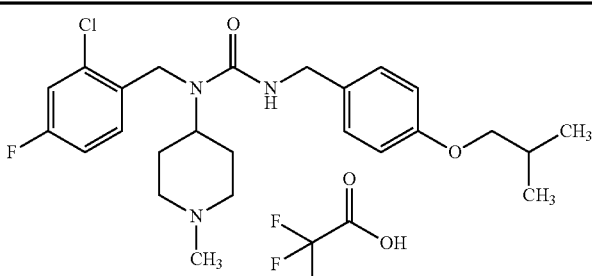 | (2-chloro-4-fluoro-phenyl)methan-amine* | 1-methyl-piperidin-4-one* | 1-(isocyanato-methyl)-4-(2-methyl-propoxy)benzene** | B |
| 63 | 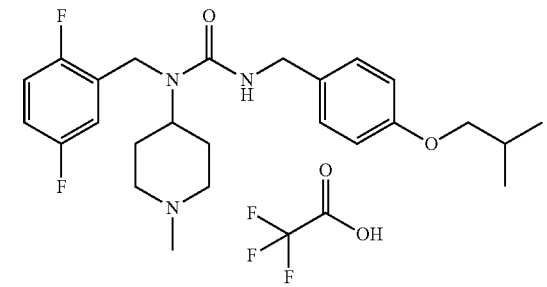 | (2,5-difluoro-phenyl)methan-amine* | 1-methyl-piperidin-4-one* | 1-(isocyanato-methyl)-4-(2-methyl-propoxy)benzene** | B |
| 64 | 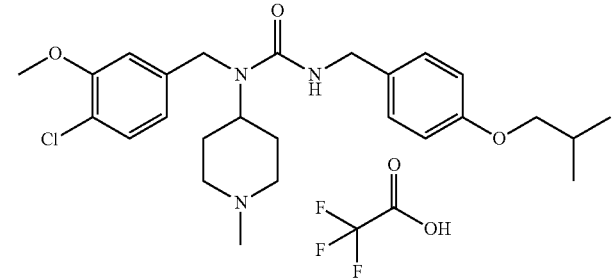 | (4-chloro-3-methoxy-phenyl)methan-amine* | 1-methyl-piperidin-4-one* | 1-(isocyanato-methyl)-4-(2-methyl-propoxy)benzene** | B |
| 65 | 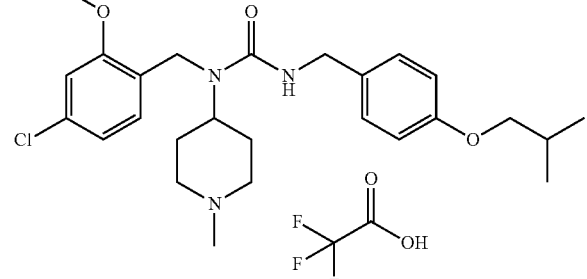 | (4-chloro-2-methoxy-phenyl)methan-amine* | 1-methyl-piperidin-4-one* | 1-(isocyanato-methyl)-4-(2-methyl-propoxy)benzene** | B |
| 66 | 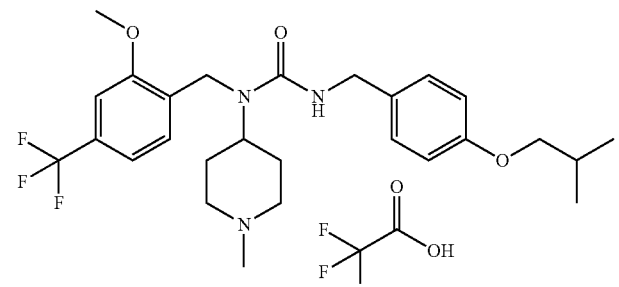 | [2-methoxy-4-(trifluoro-methyl)phenyl]methan-amine* | 1-methyl-piperidin-4-one* | 1-(isocyanato-methyl)-4-(2-methyl-propoxy)benzene** | B |

TABLE 1-continued

Compounds prepared by GP A, GP B, GP C and GP D.

| Example/ Compound | Structure | Starting materials | | | Procedure |
|---|---|---|---|---|---|
| 67 | 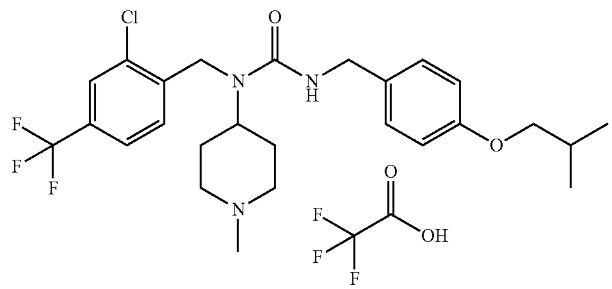 | [2-chloro-4-(trifluoromethyl)phenyl]methanamine* | 1-methyl-piperidin-4-one* | 1-(isocyanatomethyl)-4-(2-methylpropoxy)benzene** | B |
| 68 | 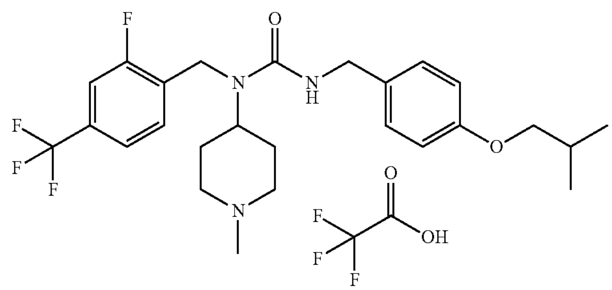 | [2-fluoro-4-(trifluoromethyl)phenyl]methanamine* | 1-methyl-piperidin-4-one* | 1-(isocyanatomethyl)-4-(2-methylpropoxy)benzene** | B |
| 69 | 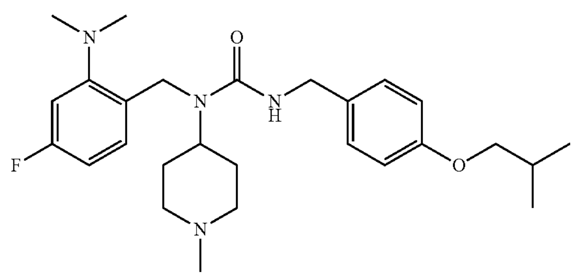 [SMILES: CC(C)COc1ccc(CNC(=O)N(Cc2ccc(F)cc2N(C)C)C2CCN(C)CC2)cc1] | 2-(aminomethyl)-5-fluoro-N,N-dimethylaniline* | 1-methyl-piperidin-4-one* | 1-(isocyanatomethyl)-4-(2-methylpropoxy)benzene** | B |
| 70 | 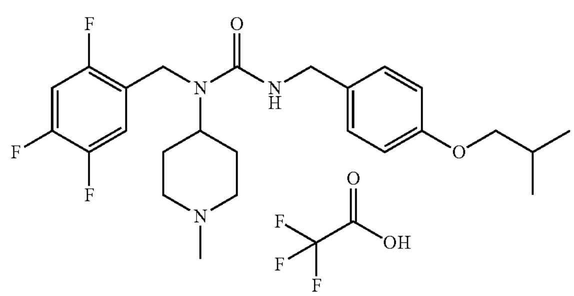 | (2,4,5-trifluorophenyl)methanamine* | 1-methyl-piperidin-4-one* | 1-(isocyanatomethyl)-4-(2-methylpropoxy)benzene** | B |
| 71 | 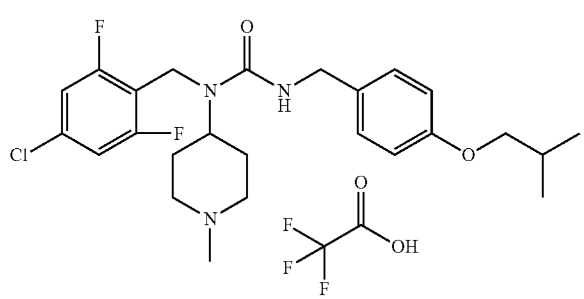 | (4-chloro-2,6-difluorophenyl)methanamine* | 1-methyl-piperidin-4-one* | 1-(isocyanatomethyl)-4-(2-methylpropoxy)benzene** | B |

TABLE 1-continued

Compounds prepared by GP A, GP B, GP C and GP D.

| Example/Compound | Structure | Starting materials | | | Procedure |
|---|---|---|---|---|---|
| 72 | 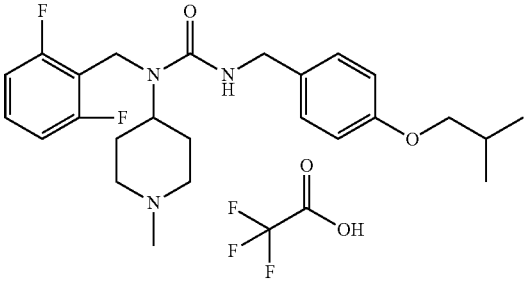 | (2,6-difluorophenyl)methanamine* | 1-methyl-piperidin-4-one* | 1-(isocyanato-methyl)-4-(2-methyl-propoxy)benzene** | B |

*Commercially available
**prepared intermediate descried herein

| Example/Compound | NMR | m/z [M + H]⁺ |
|---|---|---|
| 21 | ¹H NMR (400 MHz, DMSO-d6) δ 10.62 (s, 1H), 9.21 (s, 1H), 7.30-7.16 (m, 4H), 7.08-7.01 (m, 2H), 7.00-6.95 (m, 1H), 4.43 (s, 2H), 4.35 (d, 2H), 4.25 (t, 1H), 3.51-3.25 (m, 2H), 2.98 (q, 2H), 2.72 (d, 3H), 2.21 (s, 3H), 1.89-1.66 (m, 4H). | 426.9 |
| 22 | ¹H NMR (400 MHz, DMSO-d6) δ 9.19 (s, 1H), 7.56 (d, 1H), 7.48 (s, 1H), 7.30-7.16 (m, 4H), 7.13-6.95 (m, 1H), 4.42 (s, 2H), 4.35 (d, 2H), 4.28-4.16 (m, 1H), 3.53-3.14 (m, 2H), 2.98 (q, 2H), 2.72 (d, 3H), 2.59 (s, 3H), 1.90-1.69 (m, 4H). | 429.3 |
| 23 | ¹H NMR (400 MHz, DMSO-d6) δ 7.19 (q, 2H), 7.00 (t, 1H), 6.87 (d, 3H), 6.41 (dd, 1H), 4.39 (s, 2H), 4.11 (s, 2H), 4.00-3.85 (m, 1H), 3.23-3.12 (m, 2H), 2.86-2.76 (m, 2H), 2.71 (d, 2H), 2.65 (d, 3H), 2.09 (d, 3H), 1.88 (t, 2H), 1.59-1.37 (m, 4H). | 429.3 |
| 24 | ¹H NMR (400 MHz, Chloroform-d) δ 13.22 (s, 1H), 7.51 (d, 1H), 7.30 (s, 1H), 7.17 (q, 1H), 7.09 (d, 1H), 6.82 (q, 2H), 4.99 (t, 1H), 4.73-4.61 (m, 1H), 4.50 (d, 2H), 4.42 (s, 2H), 3.58 (d, 2H), 2.89-2.72 (m, 5H), 2.55 (s, 3H), 2.22 (q, 2H), 1.90 (d, 2H). | 429.3 |
| 25 | ¹H NMR (400 MHz, DMSO-d6) δ 7.31-7.14 (m, 4H), 7.06-6.90 (m, 3H), 6.13 (s, 1H), 4.41 (s, 2H), 4.31 (d, 2H), 3.99-3.87 (m, 1H), 3.63 (s, 3H), 2.76-2.65 (m, 2H), 2.38 (s, 3H), 2.09 (s, 3H), 1.88 (t, 2H), 1.59-1.40 (m, 4H). | 441.3 |
| 26 | ¹H NMR (400 MHz, Methanol-d4) δ 7.55 (q, 1H), 7.21 (d, 2H), 7.05-6.94 (m, 4H), 5.29 (q, 1H), 4.44-4.20 (m, 2H), 3.72 (tt, 1H), 3.44 (d, 1H), 3.23 (d, 1H), 3.12-2.77 (m, 4H), 2.72 (s, 3H), 2.70-2.51 (m, 1H), 1.77 (d, 1H), 1.57 (d, 3H), 0.94 (d, 1H), 0.81-0.72 (m, 2H), 0.68-0.57 (m, 2H). | 444.3 |
| 27 | ¹H NMR (400 MHz, DMSO-d6) δ 9.51 (s, 1H), 8.99 (d, 1H), 8.56 (d, 1H), 8.05 (d, 1H), 7.84 (s, 1H), 7.78 (d, 1H), 7.70 (dd, 1H), 7.34 (t, 1H), 7.30-7.19 (m, 2H), 7.07 (t, 1H), 4.48 (d, 2H), 4.45 (s, 2H), 3.40 (d, 2H), 2.99 (q, 2H), 2.72 (s, 3H), 1.92-1.73 (m, 4H). | 425.3 |
| 28 | ¹HNMR (400 MHz, Chloroform-d) δ 12.37 (br. s, 1H), 7.46 (d, 1H), 7.40 (s, 1H), 7.34 (dd, 1H), 7.15 (q, 1H), 6.89-6.77 (m, 2H), 4.97 (br. s, 1H), 4.76-4.63 (m, 1H), 4.51-4.45 (m, 2H), 4.42 (s, 2H), 3.63-3.56 (m, 2H), 2.94-2.75 (m, 5H), 2.54 (s, 3H), 2.32 (dq, 2H), 1.97-1.86 (m, 2H). | 429.3 |
| 29 | ¹H NMR (400 MHz, Chloroform-d) δ 8.07 (s, 1H), 7.69 (d, 1H), 7.39 (s, 1H), 7.25-7.15 (m, 2H), 6.87-6.76 (m, 2H), 4.89-4.77 (m, 1H), 4.62-4.33 (m, 5H), 3.20 (br. s, 2H), 2.65-2.36 (m, 5H), 2.06 (br. s, 2H), 1.81 (d, 2H). | 415.3 |
| 30 | ¹H NMR (400 MHz, Chloroform-d) δ 8.09 (s, 1H), 7.60 (s, 1H), 7.49 (d, 1H), 7.27-7.18 (m, 2H), 6.87-6.74 (m, 2H), 4.82-4.73 (m, 1H), 4.51 (d, 2H), 4.47-4.32 (m, 3H), 3.08 (br. s, 2H), 2.52-2.21 (m, 5H), 1.93 (br. s, 2H), 1.78 (d, 2H). | 415.3 |
| 31 | ¹H NMR (400 MHz, Chloroform-d) δ 7.40 (s, 1H), 7.26-7.19 (m, 2H), 7.09-7.00 (m, 2H), 6.87-6.68 (m, 2H), 6.45-6.35 (m, 1H), 4.57 (t, 1H), 4.49 (d, 2H), 4.44-4.29 (m, 3H), 3.78 (s, 3H), 2.99 (d, 2H), 2.36 (s, 3H), 2.29-2.14 (m, 2H), 1.92-1.68 (m, 4H). | 427.3 |
| 32 | ¹H NMR (400 MHz, Chloroform-d) δ 11.79 (br.s, 1H), 7.20-7.11 (m, 1H), 6.87-6.79 (m, 2H), 6.73 (d, 1H), 6.66 (d, 1H), 6.56 (dd, 1H), 4.86 (br. s, 1H), 4.78-4.65 (m, 1H), 4.40 (s, 2H), 4.34-4.30 (m, 2H), 4.27 (d, 2H), 3.61 (d, 2H), 3.38-3.30 (m, 2H), 2.97-2.84 (m, 5H), 2.85-2.77 (m, 3H), 2.34-2.20 (m, 2H), 1.93 (d, 2H). | 445.3 |
| 33 | ¹H NMR (400 MHz, Chloroform-d) δ 12.37 (s, 1H), 7.41-7.31 (m, 1H), 7.18 (q, 1H), 6.94-6.78 (m, 2H), 6.70-6.53 (m, 1H), 6.47 (s, 1H), 4.96- | 474.3 |

| Example/ Compound | NMR | m/z [M + H]⁺ |
|---|---|---|
| | 4.64 (m, 3H), 4.41 (s, 2H), 4.36-4.26 (m, 2H), 3.58 (d, 2H), 2.94-2.82 (m, 2H), 2.79 (s, 4H), 2.40-2.24 (m, 2H), 2.17 (dd, 1H), 1.92 (d, 2H), 1.83 (dd, 1H), 1.43 (s, 3H), 1.30 (s, 3H). | |
| 34 | ¹H NMR (400 MHz, Chloroform-d) δ 7.26-7.17 (m, 1H), 6.89-6.75 (m, 3H), 6.63 (d, 1H), 6.53 (s, 1H), 6.28 (d, 1H), 5.58 (d, 1H), 4.57 (t, 1H), 4.47-4.28 (m, 5H), 3.05 (br. s, 2H), 2.39 (s, 3H), 2.26 (br. s, 2H), 1.94-1.72 (m, 4H), 1.41 (s, 6H). | 456.3 |
| 35 | ¹H NMR (400 MHz, Chloroform-d) δ 7.93 (s, 1H), 7.63 (d, 1H), 7.25-7.17 (m, 2H), 6.95 (d, 1H), 6.83-6.73 (m, 2H), 4.80-4.70 (m, 1H), 4.53 (d, 2H), 4.48-4.29 (m, 3H), 4.03 (s, 3H), 3.02 (br. s, 2H), 2.37 (s, 3H), 2.26 (br. s, 2H), 1.96-1.71 (m, 4H). | 428.3 |
| 36 | ¹H NMR (400 MHz, Chloroform-d) δ 7.93 (s, 1H), 7.29 (s, 1H), 7.25-7.15 (m, 2H), 6.93 (d, 1H), 6.86-6.69 (m, 2H), 6.15 (s, 1H), 4.60-4.51 (m, 1H), 4.46 (d, 2H), 4.39 (s, 2H), 4.34 (br. s, 1H), 2.96 (br. s, 2H), 2.44 (s, 3H), 2.34 (s, 3H), 2.18 (br. s, 2H), 1.74 (br. s, 4H). | 427.3 |
| 37 | ¹H NMR (400 MHz, Chloroform-d) δ 7.65 (d, 1H), 7.28 (s, 1H), 7.25-7.17 (m, 2H), 6.84 (q, 2H), 4.80 (br. s, 1H), 4.48-4.39 (m, 4H), 4.28 (br.s, 1H), 3.48 (t, 2H), 3.33 (t, 2H), 2.95 (d, 2H), 2.32 (s, 3H), 2.15 (br. s, 2H), 1.86-1.67 (m, 4H). | 464.2 |
| 38 | ¹H NMR (400 MHz, Chloroform-d) δ 12.82 (br. s, 1H), 7.20-7.09 (m, 2H), 6.95 (s, 1H), 6.91-6.77 (m, 3H), 4.82-4.62 (m, 2H), 4.48-4.28 (m, 4H), 3.60 (d, 2H), 2.85 (q, 6H), 2.79 (s, 3H), 2.29-2.12 (m, 2H), 2.06 (p, 2H), 1.92 (d, 2H). | 414.3 |
| 39 | ¹H NMR (400 MHz, DMSO-d₆) δ 9.33 (s, 1H), 8.01 (d, 1H), 7.91 (s, 1H), 7.41 (d, 1H), 7.30-7.08 (m, 3H), 7.01 (t, 1H), 4.54-4.31 (m, 4H), 4.03-3.89 (m, 1H), 2.72 (d, 2H), 2.10 (s, 3H), 1.96-1.83 (m, 2H), 1.60-1.44 (m, 4H). | 431.2 |
| 40 | ¹H NMR (400 MHz, Chloroform-d) δ 7.21 (q, 1H), 6.94-6.74 (m, 5H), 4.70 (br. s, 1H), 4.53-4.35 (m, 5H), 3.40 (s, 3H), 3.38 (s, 3H), 3.18 (br. s, 2H), 2.66-2.27 (m, 5H), 1.97 (br. s, 2H), 1.80 (d, 2H). | 458.3 |
| 41 | ¹H NMR (400 MHz, Chloroform-d) δ 8.11-7.93 (m, 2H), 7.64 (d, 1H), 7.41 (q, 1H), 7.25 (s, 1H), 6.90-6.68 (m, 2H), 4.91-3.95 (m, 5H), 3.11 (d, 2H), 2.79 (br. s, 2H), 2.43 (s, 3H), 2.35-2.04 (m, 4H), 1.98 (d, 2H). | 414.3 |
| 42 | ¹H NMR (400 MHz, Chloroform-d) δ 9.86 (br. s, 1H), 7.45 (s, 1H), 7.34 (d, 1H), 7.25-7.18 (m, 2H), 6.84-6.73 (m, 2H), 4.71-4.62 (m, 1H), 4.50 (d, 2H), 4.43 (s, 2H), 4.36 (br. s, 1H), 2.96 (br. s, 2H), 2.54 (s, 3H), 2.34 (s, 3H), 2.18 (br. s, 2H), 1.90-1.69 (m, 4H). | 428.3 |
| 43 | ¹H NMR (400 MHz, DMSO-d6) δ 9.15 (s, 1H), 7.85 (d, 1H), 7.68 (d, 1H), 7.35 (t, 1H), 7.10 (d, 3H), 6.82 (d, 2H), 4.56 (p, 1H), 4.49 (s, 2H), 4.28-4.21 (m, 1H), 4.18 (d, 2H), 3.42-3.33 (m, 2H), 3.05-2.89 (m, 2H), 2.77-2.69 (m, 3H), 1.85-1.69 (m, 4H), 1.24 (d, 6H). | 439.3 |
| 44 | ¹H NMR (400 MHz, DMSO-d6) δ 9.22 (s, 1H), 8.09 (dd, 2H), 7.45 (t, 1H), 7.11 (d, 3H), 6.82 (d, 2H), 4.61-4.48 (m, 3H), 4.33-4.21 (m, 1H), 4.19 (d, 2H), 3.39 (d, 2H), 3.07-2.90 (m, 2H), 2.72 (s, 3H), 1.88-1.71 (m, 4H), 1.24 (d, 6H). | 459.3 |
| 45 | ¹H NMR (400 MHz, Chloroform-d) δ 12.81 (s, 1H), 7.05-6.97 (m, 3H), 6.85-6.75 (m, 3H), 6.75-6.68 (m, 1H), 4.79-4.69 (m, 2H), 4.51 (p, 1H), 4.34 (s, 2H), 4.28 (d, 2H), 3.59 (d, 2H), 2.92-2.81 (m, 2H), 2.77 (s, 3H), 2.18 (q, 2H), 1.96-1.91 (m, 1H), 1.91-1.81 (m, 2H), 1.32 (d, 6H), 1.05-0.95 (m, 2H), 0.72-0.63 (m, 2H). | 454.3 |
| 46 | ¹H NMR (400 MHz, Chloroform-d) δ 12.79 (s, 1H), 7.13 (q, 1H), 7.00 (d, 2H), 6.87 (d, 2H), 6.81 (t, 2H), 4.79-4.66 (m, 2H), 4.37 (s, 2H), 4.31 (d, 2H), 3.58 (d, 2H), 2.83 (t, 2H), 2.77 (s, 3H), 2.19 (q, 2H), 1.90 (d, 2H). | 455.4 |
| 47 | ¹H NMR (400 MHz, Methanol-d4) δ 7.66-7.54 (m, 1H), 7.26 (d, 2H), 7.04 (dd, 4H), 5.34 (q, 1H), 4.49-4.27 (m, 2H), 3.78 (tt, 1H), 3.50 (d, 1H), 3.29 (d, 1H), 3.19-3.01 (m, 2H), 2.97-2.82 (m, 1H), 2.78 (s, 3H), 2.74-2.54 (m, 2H), 1.82 (d, 1H), 1.63 (d, 3H), 1.01 (d, 1H), 0.88-0.63 (m, 4H). | 444.3 |
| 48 | ¹H NMR (400 MHz, Chloroform-d) δ 12.66 (bs, 1H), 7.37-7.29 (m, 2H), 7.13 (q, 1H), 6.91-6.78 (m, 3H), 5.04 (s, 1H), 4.68-4.56 (m, 1H), 4.40 (s, 2H), 4.28 (d, 2H), 3.90 (s, 3H), 3.57 (d, 2H), 2.84 (t, 2H), 2.78 (s, 3H), 2.24 (qd, 2H), 1.89 (d, 2H). | 429.3 |
| 49 | ¹H NMR (400 MHz, Chloroform-d) δ 12.94 (s, 1H), 7.17-7.07 (m, 3H), 6.95 (t, 2H), 6.82 (t, 2H), 4.77 (s, 1H), 4.75-4.63 (m, 1H), 4.38 (s, 2H), 4.32 (d, 2H), 3.58 (d, 2H), 2.88-2.73 (m, 5H), 2.21 (qd, 2H), 1.90 (d, 2H). | 392.2 |
| 50 | ¹H NMR (400 MHz, Chloroform-d) δ 12.80 (bs, 1H), 7.10 (d, 1H), 7.02 (q, 1H), 6.89-6.81 (m, 1H), 6.75 (t, 1H), 6.40 (dd, 1H), 6.34 (d, 1H), 5.05 (t, 1H), 4.77-4.65 (m, 1H), 4.33 (s, 2H), 4.24 (d, 2H), 3.79 (s, 3H), 3.57 (d, 2H), 3.51 (s, 3H), 2.87-2.73 (m, 5H), 2.14 (q, 2H), 1.87 (d, 2H). | 434.3 |
| 51 | ¹H NMR (400 MHz, Chloroform-d) δ 12.66 (bs, 1H), 7.18 (q, 1H), 7.05 (q, 1H), 6.86-6.70 (m, 4H), 4.91 (t, 1H), 4.75-4.63 (m, 1H), 4.38-4.30 (m, 4H), 3.77 (s, 3H), 3.58 (d, 2H), 2.91-2.71 (m, 5H), 2.17 (q, 2H), 1.88 (d, 2H). | 438.3 |
| 52 | ¹H NMR (400 MHz, Chloroform-d) δ 12.94 (bs, 1H), 7.16 (q, 1H), 7.06 (d, 1H), 6.90-6.72 (m, 4H), 4.79-4.66 (m, 2H), 4.62 (s, 2H), 4.38 (s, | 446.3 |

| Example/Compound | NMR | m/z [M + H]⁺ |
|---|---|---|
| | 2H), 4.32 (d, 2H), 4.04 (d, 2H), 3.98 (d, 2H), 3.57 (d, 2H), 2.88-2.73 (m, 5H), 2.20 (q, 2H), 1.90 (d, 2H). | |
| 53 | ¹H NMR (400 MHz, Chloroform-d) δ 12.70 (bs, 1H), 7.33 (d, 1H), 7.09 (d, 1H), 7.08-7.00 (m, 1H), 6.97 (dd, 1H), 6.87-6.69 (m, 2H), 4.80-4.62 (m, 2H), 4.43 (d, 2H), 4.33 (s, 2H), 3.82 (s, 3H), 3.59 (d, 2H), 2.95-2.71 (m, 5H), 2.30-2.11 (m, 2H), 1.90 (d, 2H). | 472.3 |
| 54 | ¹H NMR (400 MHz, Chloroform-d) δ 12.63 (s, 1H), 7.08 (q, 1H), 6.91-6.74 (m, 4H), 4.84 (s, 1H), 4.78-4.59 (m, 1H), 4.37 (s, 2H), 4.33 (d, 2H), 3.94 (s, 3H), 3.58 (d, 2H), 2.90-2.72 (m, 5H), 2.28-2.13 (m, 2H), 1.89 (d, 2H). | 440.3 |
| 55 | ¹H NMR (400 MHz, Chloroform-d) δ 8.90 (s, 1H), 7.85 (d,1H), 7.42 (d, 1H), 7.24 (s, 1H), 6.87 (t, 1H), 6.80 (t, 1H) 5.37 (m, 1H), 4.55 (s, 2H), 4.44 (s, 2H), 4.05 (s, 3H), 3.58 (d, 2H), 2.87 (s, 2H), 2.77 (s, 3H), 2.24 (d, 2H), 1.95 (d, 2H). | 428.3 |
| 56 | ¹H NMR (400 MHz, Chloroform-d) δ 12.49 (bs, 1H), 7.92 (s, 1H), 7.46 (s, 1H), 7.32 (d 1H), 7.19 (dd 1H), 7.14 (q 1H), 6.80 (t 2H), 4.73 (t 1H), 4.46 (s, 2H), 4.38 (s, 2H), 4.07 (s, 3H), 3.62 (d 2H), 2.89 (d 2H), 2.80 (s, 3H), 2.28-2.09 (m, 2H), 1.93 (d 2H). | 428.3 |
| 57 | ¹H NMR (400 MHz, Chloroform-d) δ 12.80 (bs, 1H), 7.41-7.31 (m, 2H), 7.20-7.14 (m, 1H), 6.99 (d, 2H), 6.78 (d, 2H), 4.81-4.71 (m, 1H), 4.53 (s, 1H), 4.48 (s, 2H), 4.26 (s, 2H), 3.67 (d, 2H), 3.60 (d, 2H), 2.90-2.74 (m, 5H), 2.26-2.10 (m, 2H), 2.10-2.00 (m, 1H), 1.92 (d, 2H), 1.01 (d, 6H). | 496.3 |
| 58 | ¹H NMR (400 MHz, Chloroform-d) δ 7.20-7.10 (m, 1H), 7.02 (t, 1H), 6.83 (ddt, 2H), 6.62 (d, 1H), 6.51 (d, 1H), 4.69 (ddt, 2H), 4.37 (s, 2H), 4.26 (d, 2H), 3.58 (d, 2H), 2.83 (s, 3H), 2.77 (s, 4H), 2.19 (qd, 2H), 1.90 (d, 2H), 1.42 (s, 6H). | 444.3 |
| 59 | ¹H NMR (400 MHz, DMSO-d6) δ 9.23 (s, 1H), 7.28-7.18 (m, 2H), 7.10-7.00 (m, 3H), 6.65 (d, 1H), 6.54 (s, 1H), 4.41 (s, 2H), 4.21 (s, 1H), 4.18 (d, 2H), 3.39 (d, 2H), 2.98 (d, 2H), 2.94 (s, 2H), 2.73 (s, 2H), 1.87-1.67 (m, 4H), 1.38 (s, 6H). | 444.3 |
| 60 | ¹H NMR (400 MHz, Chloroform-d) δ 12.35 (s, 1H), 7.04 (d, 2H), 6.97-6.88 (m, 1H), 6.81 (d, 2H), 6.66 (dd, 1H), 4.83-4.72 (m, 2H), 4.29 (d, 2H), 4.24 (s, 2H), 3.73 (s, 3H), 3.69 (d, 2H), 3.59 (d, 2H), 2.91-2.83 (m, 2H), 2.79 (d, 3H), 2.30-2.16 (m, 2H), 2.07 (dp, 1H), 1.92 (d, 2H), 1.02 (d, 6H). | 476.3 |
| 61 | ¹H NMR (400 MHz, Chloroform-d) δ 12.93 (bs, 1H), 7.19-7.08 (m, 2H), 7.03 (d, 2H), 6.93 (td, 1H), 6.79 (d, 2H), 4.83-4.71 (m, 1H), 4.60-4.53 (m, 1H), 4.56-4.44 (m, 1H), 4.36 (s, 2H), 4.29 (d, 2H), 3.59 (d, 2H), 2.91-2.80 (m, 2H), 2.78 (s, 3H), 2.27-2.08 (m, 2H), 1.91 (d, 2H), 1.32 (d, 6H). | 448.0 |
| 62 | ¹H NMR (400 MHz, Chloroform-d) δ 12.57 (bs, 1H), 7.19-7.09 (m, 2H), 7.03 (d, 2H), 6.93 (td, 1H), 6.80 (d, 2H), 4.82-4.71 (m, 1H), 4.61-4.53 (m, 1H), 4.35 (s, 2H), 4.29 (d, 2H), 3.69 (d, 2H), 3.60 (d, 2H), 2.94-2.81 (m, 2H), 2.79 (s, 3H), 2.26-2.10 (m, 2H), 2.13-1.99 (m, 1H), 1.92 (d, 2H), 1.02 (d, 6H). | 462.0 |
| 63 | ¹H NMR (400 MHz, Chloroform-d) 12.35 (bs, 1H), 7.06-6.98 (m, 3H), 6.98-6.91 (m, 1H), 6.86 (s, 1H), 6.79 (d, 2H), 4.80-4.57 (m, 2H), 4.38 (s, 2H), 4.29 (s, 2H), 3.68 (d, 2H), 3.60 (d, 2H), 2.96-2.82 (m, 2H), 2.79 (s, 3H), 2.27-2.12 (m, 2H), 2.11-1.99 (m, 1H), 1.92 (d, 2H), 1.00 (d, 6H). | 446.3 |
| 64 | ¹H NMR (400 MHz, DMSO-d6) δ 9.23 (s, 1H), 7.36 (d, 1H), 7.12 (d, 2H), 7.01 (t, 1H), 6.93 (s, 1H), 6.85-6.77 (m, 3H), 4.41 (s, 2H), 4.25-4.16 (m, 3H), 3.74 (s, 3H), 3.70 (d, 2H), 3.39 (d, 2H), 3.04-2.90 (m, 2H), 2.71 (d, 3H), 1.99 (dt, 1H), 1.88-1.67 (m, 4H), 0.97 (d, 6H). | 474.3 |
| 65 | ¹H NMR (400 MHz, DMSO-d6) δ 9.10 (s, 1H), 7.14-7.05 (m, 3H), 7.05-6.93 (m, 2H), 6.90 (t, 1H), 6.83 (d, 2H), 4.27 (s, 3H), 4.15 (d, 2H), 3.84 (s, 3H), 3.70 (d, 2H), 3.37 (d, 2H), 3.05-2.92 (m, 2H), 2.71 (d, 3H), 2.06-1.92 (m, 1H), 1.74 (d, 4H), 0.97 (d, 6H) | 474.3 |
| 66 | ¹H NMR (400 MHz, Chloroform-d) δ 12.87 (bs, 1H), 7.17 (q, 2H), 7.04-6.98 (m, 3H), 6.78 (d, Hz, 2H), 4.77 (t, 1H), 4.70 (s, 1H), 4.32 (s, 2H), 4.28 (d, 2H), 3.82 (s, 3H), 3.67 (d, 2H), 3.57 (d, 2H), 2.85-2.81 (m, 2H), 2.77 (s, 3H), 2.15 (q, 2H), 2.10-2.01 (m, 1H), 1.89 (d, 2H), 1.00 (d, 6H). | 508.4 |
| 67 | ¹H NMR (400 MHz, Chloroform-d) δ 12.90 (bs, 1H), 7.65 (s, 1H), 7.45 (d, 1H), 7.29 (d, 1H), 7.01 (d, 2H), 6.78 (d, 2H), 4.77 (t, 1H), 4.49 (s, 1H), 4.44 (s, 2H), 4.28 (d, 2H), 3.67 (d, 2H), 3.58 (d, 2H), 2.91-2.78 (m, 2H), 2.77 (s, 3H), 2.40-2.13 (m, 2H), 2.14-1.98 (m, 1H), 1.91 (d, 2H), 1.01 (d, 6H). | 512.3 |
| 68 | ¹HNMR (400 MHz, Chloroform-d) δ 12.76 (bs, 1H), 7.38-7.23 (m, 3H), 7.01 (d, 2H), 6.78 (d, 2H), 4.74 (t, 1H), 4.60 (bs, 1H), 4.46 (s, 2H), 4.29 (s, 2H), 3.67 (d, 2H), 3.59 (d, 2H), 2.84 (t, 2H), 2.78 (s, 3H), 2.20 (q, 2H), 2.13-1.98 (m, 1H), 1.91 (d, 2H), 1.01 (d, 6H). | 496.3 |
| 69 | ¹H NMR (400 MHz, Chloroform-d) δ 12.11 (s, 1H), 7.61 (s, 1H), 7.18-7.02 (m, 3H), 6.94 (d, 1H), 6.79 (d, 2H), 4.64 (t, 1H), 4.49 (s, 2H), 4.27 (s, 2H), 3.67 (d, 2H), 3.50 (d, 2H), 3.15 (s, 2H), 2.80 (d, 3H), 2.72 (s, 6H), 2.58-2.40 (m, 2H), 2.13-1.99 (m, 1H), 1.87 (d, 2H), 1.01 (d, 6H). | 471.3 |

| Example/Compound | NMR | m/z [M + H]+ |
|---|---|---|
| 70 | ¹H NMR (400 MHz, Chloroform-d) δ 12.78 (bs, 1H), 7.04 (d, 2H), 7.02-6.88 (m, 2H), 6.80 (d, 2H), 4.76-4.54 (m, 2H), 4.34 (s, 2H), 4.29 (s, 2H), 3.68 (d, 2H), 3.58 (d, 2H), 2.93-2.73 (m, 5H), 2.19 (q, 2H), 2.12-1.99 (m, 1H), 1.89 (d, 2H), 1.01 (d, 6H). | 464.3 |
| 71 | ¹H NMR (400 MHz, Chloroform-d) δ 12.62 (bs, 1H), 7.05 (d, 2H), 6.89 (d, 2H), 6.81 (d, 2H), 4.91 (s, 1H), 4.60-4.48 (m, 1H), 4.36 (s, 2H), 4.29 (s, 2H), 3.70 (d, 2H), 3.62 (d, 2H), 2.89-2.71 (m, 5H), 2.32 (q, 2H), 2.15-2.01 (m, 1H), 1.92 (d, 2H), 1.02 (d, 6H). | 480.3 |
| 72 | ¹H NMR (400 MHz, Chloroform-d) δ 12.34 (bs, 1H), 7.31-7.22 (m, 1H), 7.06 (d, 2H), 6.87 (t, 2H), 6.80 (d, 2H), 5.04 (s, 1H), 4.61-4.50 (m, 1H), 4.40 (s, 2H), 4.29 (s, 2H), 3.69 (d, 2H), 3.62 (d, 2H), 2.87-2.73 (m, 5H), 2.41-2.22 (m, 2H), 2.14-2.00 (m, 1H), 1.92 (d, 2H), 1.01 (d, 6H), | 446.3 |

Example 73: 1-[(2,4-difluorophenyl)methyl]-3-{[4-(²H₃)methoxyphenyl]methyl})-1-(1-methylpiperidin-4-yl)urea (73)

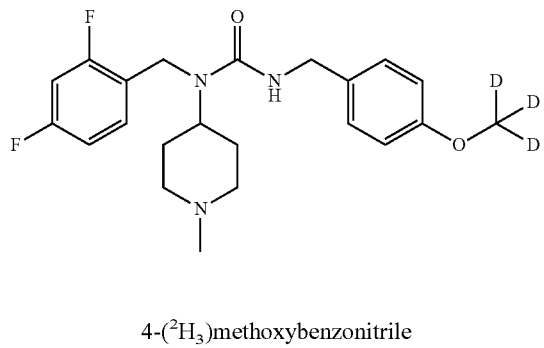

4-(²H₃)methoxybenzonitrile

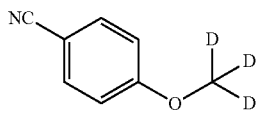

A mixture of 4-hydroxybenzonitrile (1.20 g, 10.1 mmol), iodo(²H₃)methane (2.19 mg, 15.1 mmol) and K₂CO₃ (2.78 g, 20.1 mmol) in DMF (10.0 mmol) was heated to 37° C. for 20 hours. Water (20 ml) was added and the mixture extracted with diethyl ether (200 ml). The organic phase was washed with water (3×40 ml), dried with Na₂SO₄, filtered and concentrated under reduced pressure to afford the desired intermediate (1.29 g) that was used without further purification.

[4-(²H₃)methoxyphenyl]methanamine

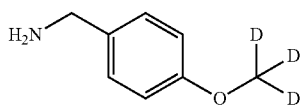 [SMILES: [2H]C([2H])([2H])Oc1ccc(CN)cc1]

LiAlH₄ (713 mg, 18.8 mmol) was added to a solution of 4-(²H₃)methoxybenzonitrile (1.28 g, 9.40 mmol) in THF (30 ml). The mixture was heated to reflux for 4 hours, then cooled to room temperature. Water (0.7 ml), THF (10 ml), NaOH (0.7 ml, 15% aq.), and water (2.1 ml) was added. The mixture was stirred for 30 minutes, filtered, concentrated under reduced pressure, re-dissolved in acetonitrile and concentrated again to afford the desired intermediate (1.1 g) that was used without further purification.

phenyl N-{[4-(²H₃)methoxyphenyl]methyl}carbamate

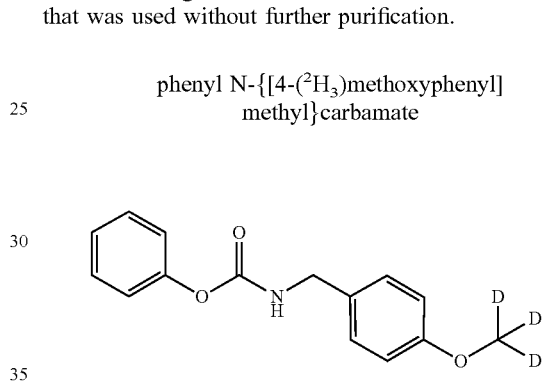

Phenyl chloroformate (1.60 g, 10.2 mmol) in CH₂Cl₂ (10 ml) was added dropwise to a solution of [4-(²H₃)methoxyphenyl]methanamine (1.10 g, 7.85 mmol) and pyridine (0.95 ml) in CH₂Cl₂ (10 ml) at 0° C. The mixture was stirred at this temperature for 20 minutes, then concentrated under reduced pressure. The residue was partitioned between diethyl ether (250 ml) and HCl (15.7 ml, 1 M aq.). The organic phase was washed with water (50 ml), dried with Na₂SO₄, filtered, and concentrated under reduced pressure. The crude material was purified by crystallization from ethyl acetate and n-heptane to afford the desired intermediate (1.56 g).

1-[(2,4-difluorophenyl)methyl]-3-{[4-(²H₃)methoxyphenyl]methyl}-1-(1-methylpiperidin-4-yl)urea A mixture of phenyl N-{[4-(²H₃)methoxyphenyl]methyl}carbamate (676 mg, 2.60 mmol), N-[(2,4-difluorophenyl)methyl]-1-methylpiperidin-4-amine (480 mg, 2.00 mmol) and K₂CO₃ (414 mg, 3.00 mmol) in toluene (6 ml) was heated to 75° C. for 12 hours. The mixture was purified by column chromatography using silicon dioxide gel, eluting with 10% methanol in CH₂Cl₂, containing 1% ammonia (28% aq.) to afford the title compound (760 mg, 94%). ¹H NMR (400 MHz, DMSO-d6) δ 7.26-7.10 (m, 4H), 7.01 (dt, 2H), 6.85 (d, 2H), 4.40 (s, 2H), 4.18 (d, 2H), 3.91 (dt, 1H), 2.71 (d, 2H), 2.10 (s, 3H), 1.88 (td, 2H), 1.57-1.42 (m, 4H); LCMS: 407.3 [M+H]⁺.

Example 74: 1-[(2,4-difluorophenyl)methyl]-3-{[2-methoxy-4-(propan-2-yloxy)phenyl]methyl}-1-(1-methylpiperidin-4-yl)urea (74)

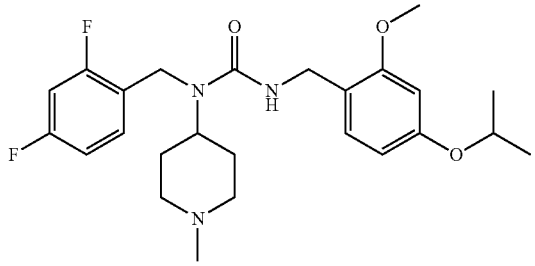 [SMILES: COc1cc(OC(C)C)ccc1CNC(=O)N(Cc1ccc(F)cc1F)C1CCN(C)CC1]

[2-methoxy-4-(propan-2-yloxy)phenyl]methanamine

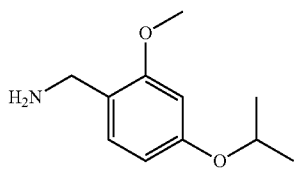

LiAlH$_4$ (445 mg, 11.7 mmol) was added to a solution of 2-methoxy-4-(propan-2-yloxy)benzonitrile (1.12 g, 5.86 mmol) in THF (25 ml). The mixture was heated to reflux for 2 hours, then cooled to room temperature. Water (0.5 ml), THF (10 ml), NaOH (0.5 ml, 15% aq.), and water (1.5 ml) was added. The mixture was stirred for 30 minutes, filtered, concentrated under reduced pressure to afford the desired intermediate (1.00 g) that was used without further purification.

phenyl N-{[2-methoxy-4-(propan-2-yloxy)phenyl]methyl}carbamate

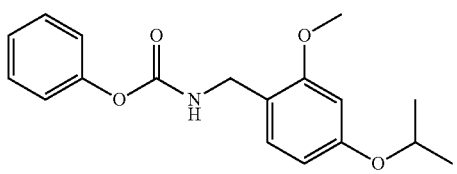 [SMILES: COc1cc(OC(C)C)ccc1CNC(=O)Oc1ccccc1]

Phenyl chloroformate (1.04 g, 6.66 mmol) in CH$_2$Cl$_2$ (7 ml) was added dropwise to a solution of [2-methoxy-4-(propan-2-yloxy)phenyl]methanamine (1.00 g, 5.12 mmol) and pyridine (0.62 ml) in CH$_2$Cl$_2$ (7 ml) at 0° C. The mixture was stirred at this temperature for 20 minutes, then concentrated under reduced pressure. The residue was partitioned between diethyl ether (250 ml) and HCl (10.2 ml, 1 M aq.). The organic phase was washed with water (50 ml), dried with Na$_2$SO$_4$, filtered, and concentrated under reduced pressure. The crude material was purified by column chromatography using silicon dioxide gel, eluting with 20% ethyl acetate in petroleum ether to afford the desired intermediate (1.00 g).

1-[(2,4-difluorophenyl)methyl]-3-{[2-methoxy-4-(propan-2-yloxy)phenyl]methyl}-1-(1-methylpiperidin-4-yl)urea A mixture of phenyl N-{[2-methoxy-4-(propan-2-yloxy)phenyl]methyl}carbamate (938 mg, 2.98 mmol), N-[(2,4-difluorophenyl)methyl]-1-methylpiperidin-4-amine (550 mg, 2.29 mmol) and K$_2$CO$_3$ (474 mg, 3.43 mmol) in toluene (7 ml) was heated to 75° C. for 12 hours. The mixture was concentrated under reduced pressure, NaOH (16 ml, 0.4 M aq.) and diethyl ether (200 ml) was added. The organic phase was washed with water (250 ml), dried with Na$_2$SO$_4$, filtered, and concentrated under reduced pressure. The mixture was purified by column chromatography using silicon dioxide gel, eluting with 7% methanol in CH$_2$Cl$_2$, containing 1% ammonia (28% aq.) to afford the title compound (700 mg, 66%). $^1$H NMR (400 MHz, Chloroform-d) δ 7.12 (dd, 2H), 6.83-6.70 (m, 2H), 6.38 (dd, 1H), 6.32 (d, 1H), 4.92 (t, 1H), 4.50 (h, 1H), 4.35 (s, 2H), 4.30 (dd, 1H), 4.25 (d, 2H), 3.52 (s, 3H), 2.86 (d, 2H), 2.26 (s, 3H), 2.12-2.01 (m, 2H), 1.69-1.59 (m, 4H), 1.32 (d, 6H); LCMS: 462.3. [M+H]$^+$.

Example 75: 1-[(2,4-difluorophenyl)methyl]-1-{1-[(1,1,1,3,3,3-$^2$H$_6$)propan-2-yl]piperidin-4-yl}-3-{[4-(propan-2-yloxy)phenyl]methyl}urea; trifluoroacetic acid (75)

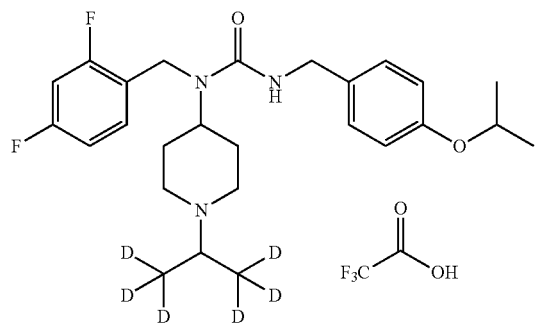 [SMILES: [2H]C([2H])([2H])C(N1CCC(N(Cc2ccc(F)cc2F)C(=O)NCc2ccc(OC(C)C)cc2)CC1)C([2H])([2H])[2H] ; O=C(O)C(F)(F)F]

phenyl N-{[4-(propan-2-yloxy)phenyl]methyl}carbamate

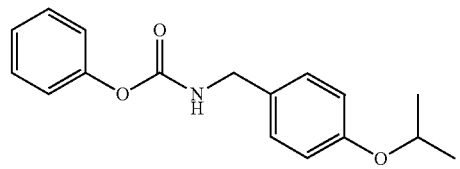 [SMILES: CC(C)Oc1ccc(CNC(=O)Oc2ccccc2)cc1]

Phenyl chloroformate (1.84 ml, 15.4 mmol) in CH$_2$Cl$_2$ (5 ml) was added dropwise to a solution of [4-(propan-2-yloxy)phenyl]methanamine (2.0 g, 11.9 mmol) and pyridine (1.2 ml, 15.4 mmol) in CH$_2$Cl$_2$ (10 ml) at 0° C. The mixture was stirred at this temperature for 1 hour, then partitioned between dichloromethane and HCl (0.4 M aq.). The organic phase was dried with Na$_2$SO$_4$, filtered, and concentrated under reduced pressure. The crude material was purified by crystallization from ethyl acetate and n-heptane to afford the desired intermediate (2.93 g).

tert-butyl 4-{[(2,4-difluorophenyl)methyl]({[4-(propan-2-yloxy)phenyl]methyl}-carbamoyl)amino}piperidine-1-carboxylate

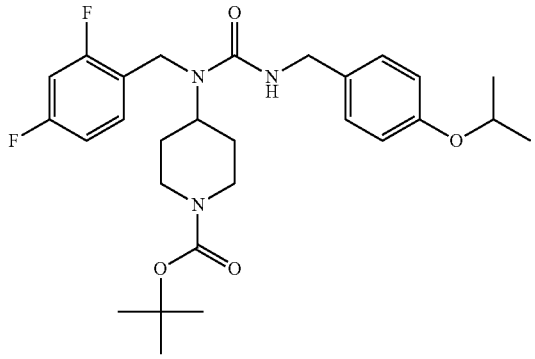 [SMILES: CC(C)Oc1ccc(CNC(=O)N(Cc2ccc(F)cc2F)C2CCN(C(=O)OC(C)(C)C)CC2)cc1]

A mixture of phenyl N-{[4-(propan-2-yloxy)phenyl]methyl}carbamate (892 mg, 3.13 mmol), tert-butyl 4-{[(2,4-difluorophenyl)methyl]amino}piperidine-1-carboxylate (1.02 g, 3.13 mmol) and K$_2$CO$_3$ (605 mg, 4.38 mmol) in toluene (10 ml) was heated to 75° C. for 21 hours. The mixture was concentrated under reduced pressure, diethyl ether (200 ml) and NaOH (30 ml, 1 M aq.) was added. The water phase was extracted again with diethyl ether (100 ml). The combined organic phases were washed with water (100 ml), dried with Na$_2$SO$_4$, filtered and concentrated. The crude material was purified by column chromatography using silicon dioxide gel, eluting with 50% ethyl acetate in petroleum ether to afford the title compound (1.2 g, 74%).

1-[(2,4-difluorophenyl)methyl]-1-(piperidin-4-yl)-3-{[4-(propan-2-yloxy)phenyl]methyl}urea (142)

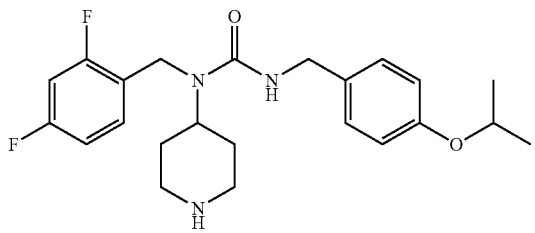 [SMILES: CC(C)Oc1ccc(CNC(=O)N(Cc2ccc(F)cc2F)C2CCNCC2)cc1]

TFA (4 ml) was added to tert-butyl 4-{[(2,4-difluorophenyl)methyl]({[4-(propan-2-yloxy)phenyl]methyl}carbamoyl)amino}piperidine-1-carboxylate (1.20 g, 2.32 mmol) in CH$_2$Cl$_2$ (10 ml) at room temperature. After 20 minutes of stirring at room temperature the mixture concentrated under reduced pressure, NaHCO$_3$(10 ml, sat. aq.) and diethyl ether (150 ml) was added. The organic phase dried with Na$_2$SO$_4$, filtered, and concentrated under reduced pressure to afford the desired intermediate (0.80 g) that was used without further purification, or to obtained concentrate purified by preparative HPLC, eluting with 20-40% acetonitrile in water (containing 0.1% trifluoroacetic acid) to afford 1-[(2,4-difluorophenyl)methyl]-1-(piperidin-4-yl)-3-{[4-(propan-2-yloxy)phenyl]methyl}urea.

1-[(2,4-difluorophenyl)methyl]-1-{1-[(1,1,1,3,3,3-$^2$H$_6$)propan-2-yl]piperidin-4-yl}-3-{[4-(propan-2-yloxy)phenyl]methyl}urea; trifluoroacetic acid NaBH$_3$CN (117 mg, 1.87 mmol) was added to ($^2$H$_6$)propan-2-one (120 mg, 1.87 mmol) and 1-[(2,4-difluorophenyl)methyl]-1-(piperidin-4-yl)-3-{[4-(propan-2-yloxy)phenyl]methyl}urea (260 mg, 0.623 mmol) in ethanol (4 ml). The mixture was stirred at room temperature for 18 hours, then additional ($^2$H$_6$)propan-2-one (90 mg, 1.40 mmol) was added. The mixture was stirred for another 4 days, then concentrated under reduced pressure. The crude material was purified by preparative HPLC, eluting with 20-40% acetonitrile in water (containing 0.1% trifluoroacetic acid) to afford the title compound (10 mg, 3%): $^1$H NMR (400 MHz, DMSO-d6) δ 8.91 (s, 1H), 7.22 (dt, 2H), 7.15-7.02 (m, 4H), 6.83 (d, 2H), 4.56 (dt, 1H), 4.41 (s, 2H), 4.27 (d, 2H), 4.19 (d, 2H), 3.34 (d, 2H), 2.98 (d, 2H), 1.94-1.79 (m, 2H), 1.75 (d, 2H), 1.24 (d, 6H); LCMS: 466.4 [M+H]$^+$.

Example 76: 1-[(2,4-difluorophenyl)methyl]-1-(piperidin-4-yl)-3-[(4-propoxyphenyl)methyl]urea; trifluoroacetic acid (76)

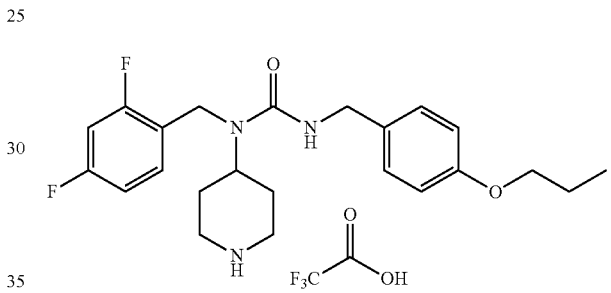

tert-butyl 4-{[(2,4-difluorophenyl)methyl]({[(4-propoxyphenyl)methyl]carbamoyl})amino}piperidine-1-carboxylate

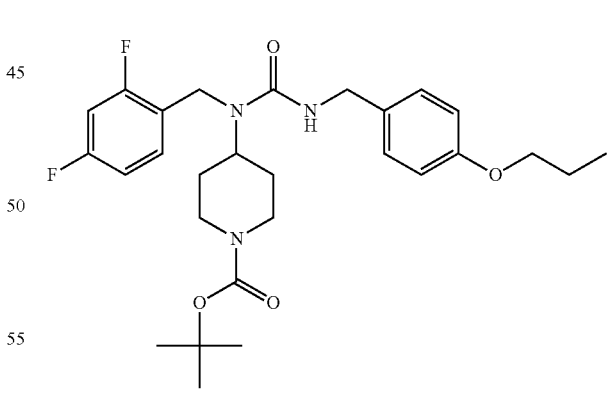

A solution of (4-propoxyphenyl)methanamine (52.0 mg, 0.315 mmol) in CH$_2$Cl$_2$ (1.0 ml) was added dropwise to a solution of diphosgene (23.0 μl, 0.192 mmol) in CH$_2$Cl$_2$ (0.5 ml) at room temperature. DIPEA (132 μl, 0.758 mmol) was added and the resulting mixture was stirred for 10 minutes at room temperature. Thereafter a solution of tert-butyl 4-{[(2,4-difluorophenyl)methyl]amino}piperidine-1-carboxylate (133 mg, 0.407 mmol) in CH$_2$Cl$_2$ (1.0 ml) was added and the reaction mixture was stirred overnight at room temperature. The mixture was concentrated under reduced pressure. The crude material was purified by column chromatography using silicon dioxide gel, eluting with 1-5% methanol in CH$_2$Cl$_2$, containing 1% ammonia (28% aq.) to afford the desired intermediate (150 mg).

1-[(2,4-difluorophenyl)methyl]-1-(piperidin-4-yl)-3-[(4-propoxyphenyl)methyl]-urea; trifluoroacetic acid TFA (0.5 ml) was added to tert-butyl 4-{[(2,4-difluorophenyl)methyl]({[(4-propoxyphenyl)methyl]carbamoyl}) amino}piperidine-1-carboxylate (80.4 mg, 0.155 mmol) in CH$_2$Cl$_2$ (1.5 ml) at room temperature. After 30 minutes of stirring at room temperature toluene (1.5 ml) was added and the mixture concentrated under reduced pressure. The crude material was purified by preparative HPLC, eluting with 20-40% acetonitrile in water (containing 0.1% trifluoroacetic acid) to afford the title compound (42 mg, 51%): $^1$H NMR (400 MHz, DMSO-d6) δ 8.50 (d, 1H), 8.10 (d, 1H), 7.27-7.16 (m, 2H), 7.13 (d, 2H), 7.08-7.01 (m, 2H), 6.84 (d, 2H), 4.41 (s, 2H), 4.29-4.05 (m, 3H), 3.89 (t, 2H), 3.27 (d, 2H), 2.89 (q, 2H), 1.84-1.62 (m, 6H), 0.96 (t, 3H); LCMS: 418.3 [M+H]$^+$.

Example 77: 3-[(1H-1,3-benzodiazol-5-yl)methyl]-1-[(2,4-difluorophenyl)methyl]-1-(1-methylpiperidin-4-yl)urea; trifluoroacetic acid (77)

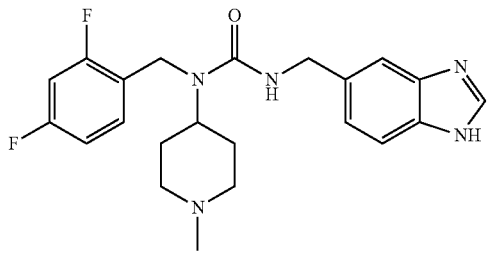

2-(trimethylsilyl)ethyl 4-({[(1H-1,3-benzodiazol-5-yl)methyl]carbamoyl}[(2,4-difluorophenyl)methyl]amino)piperidine-1-carboxylate

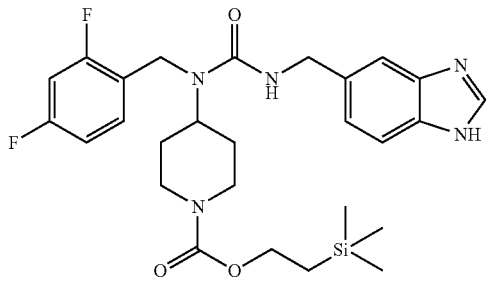 [SMILES: C[Si](C)(C)CCOC(=O)N1CCC(N(Cc2ccc(F)cc2F)C(=O)NCc2ccc3[nH]cnc3c2)CC1]

2-(trimethylsilyl)ethyl 4-[(chlorocarbonyl)[(2,4-difluorophenyl)methyl]amino]piperidine-1-carboxylate (102 mg, 0.240 mmol) in DMF (2.0 ml) was added dropwise to a solution of (1H-1,3-benzodiazol-5-yl)methanamine dihydrochloride (51.6 mg, 0.234 mmol) and DIPEA (143 μl, 0.821 mmol) in DMF (1.0 ml). The mixture was stirred for 4 days at room temperature, then additional 2-(trimethylsilyl)ethyl 4-[(chlorocarbonyl)[(2,4-difluorophenyl)methyl]amino]piperidine-1-carboxylate (34.4 mg, 0.081 mmol) was added. The mixture stirred for another hour, then concentrated under reduced pressure. The crude material was purified by column chromatography using silicon dioxide gel, eluting with 1-10% methanol in CH$_2$Cl$_2$, containing 1% ammonia (28% aq.) to afford the desired intermediate (111 mg).

3-[(1H-1,3-benzodiazol-5-yl)methyl]-1-[(2,4-difluorophenyl)methyl]-1-(piperidin-4-yl)urea

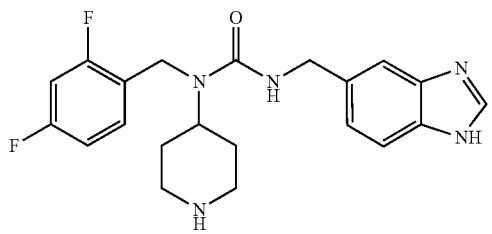 [SMILES: O=C(NCc1ccc2[nH]cnc2c1)N(Cc1ccc(F)cc1F)C1CCNCC1]

TBAF (0.6 ml, 1 M in THF) was added to 2-(trimethylsilyl)ethyl 4-({[(1H-1,3-benzodiazol-5-yl)methyl]carbamoyl}[(2,4-difluorophenyl)methyl]amino)piperidine-1-carboxylate (111 mg, 0.204 mmol) in THF (1.5 ml) at room temperature. After 3 hours the mixture was heated to 50° C. and stirred at this temperature overnight, then concentrated under reduced pressure. The crude material was purified by column chromatography using silicon dioxide gel, eluting with 1-100% methanol in CH$_2$Cl$_2$, containing 1% ammonia (28% aq.) to afford the desired intermediate (110 mg).

3-[(1H-1,3-benzodiazol-5-yl)methyl]-1-[(2,4-difluorophenyl)methyl]-1-(1-methylpiperidin-4-yl)urea; trifluoroacetic acid Formaldehyde (30.5 μl, 37% aq., 0.303 mmol) was added dropwise to a solution of 3-[(1H-1,3-benzodiazol-5-yl)methyl]-1-[(2,4-difluorophenyl)methyl]-1-(piperidin-4-yl)urea (110 mg, 0.275 mmol) in ethanol (2.0 ml) at room temperature. NaBH$_3$CN (26.0 mg, 0.414 mmol) was added in portions and the reaction mixture was stirred for 3 hours at room temperature. The mixture was concentrated under reduced pressure, partitioned between CH$_2$Cl$_2$ (3.0 ml) and NaOH (3.0 ml, 1 M aq.). The water phase was extracted with CH$_2$Cl$_2$ (3×3 ml), the combined organic phases were, dried using a phase separator and concentrated under reduced pressure. The crude material was purified by column chromatography using silicon dioxide gel, eluting with 5-10% methanol in CH$_2$Cl$_2$, containing 1% ammonia (28% aq.) followed by preparative HPLC, eluting with 5-30% acetonitrile in water (containing 0.1% trifluoroacetic acid) to afford the title compound (31 mg, 21%): $^1$H NMR (400 MHz, DMSO-d6) δ 9.60 (bs, 1H), 9.33 (s, 1H), 7.75 (d, 1H), 7.65 (s, 1H), 7.41 (d, 1H), 7.32 (t, 1H), 7.26-7.15 (m, 2H), 7.04 (t, Hz, 1H), 4.43 (s, 4H), 4.31-4.18 (m, 1H), 3.40 (d, 2H), 2.98 (t, 2H), 2.72 (s, 3H), 1.91-1.67 (m, 4H); LCMS: 414.3 [M+H]$^+$.

Example 78 (comparative): 1-[(2,4-difluorophenyl)methyl]-1-(1-methylazepan-4-yl)-3-{[4-(propan-2-yloxy)phenyl]methyl}urea; trifluoroacetic acid (78)

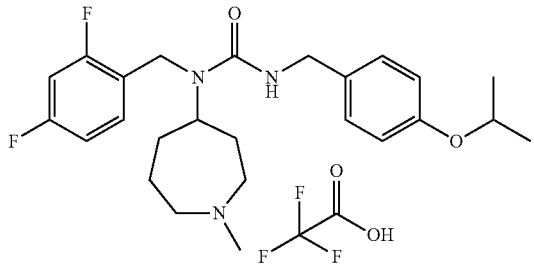

tert-butyl 4-{[(2,4-difluorophenyl)methyl]amino}azepane-1-carboxylate

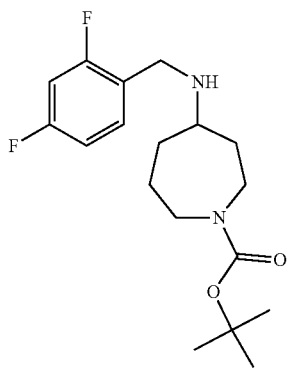 [SMILES: CC(C)(C)OC(=O)N1CCCC(NCc2ccc(F)cc2F)CC1]

(2,4-difluorophenyl)methanamine (112 mg, 0.779 mmol) was added to tert-butyl 4-oxoazepane-1-carboxylate (153 mg, 0.719 mmol) in CH$_2$Cl$_2$ (2.0 ml) followed by addition of sodium triacetoxyborohydride (248 mg, 1.17 mmol). The reaction was stirred for 20 hours at room temperature. Then NaOH (2 ml, 1 M, aq.) was added and the mixture extracted with CH$_2$Cl$_2$ (2×1.0 ml). The organic phase was dried using a phase separator and concentrated under reduced pressure. The crude material was purified by column chromatography using silicon dioxide gel, eluting with 1-10% methanol in CH$_2$Cl$_2$, containing 1% ammonia (28% aq.) to afford the desired racemic intermediate (219 mg).

tert-butyl 4-{[(2,4-difluorophenyl)methyl]({[4-(propan-2-yloxy)phenyl]methyl}carbamoyl)amino}azepane-1-carboxylate)

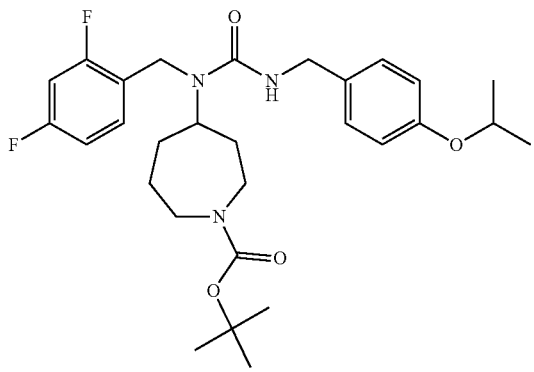 [SMILES: CC(C)Oc1ccc(CNC(=O)N(Cc2ccc(F)cc2F)C2CCCN(C(=O)OC(C)(C)C)CC2)cc1]

A solution of [4-(propan-2-yloxy)phenyl]methanamine (100 mg, 0.294 mmol) in CH$_2$Cl$_2$ (1.0 ml) was added dropwise to a solution of diphosgene (17.6 µl, 0.147 mmol) in CH$_2$Cl$_2$ (0.5 ml) at room temperature. DIPEA (102 µl, 0.588 mmol) was added and the resulting mixture was stirred for 17 minutes at room temperature. Thereafter a solution of tert-butyl 4-{[(2,4-difluorophenyl)methyl]amino}azepane-1-carboxylate (58.0 mg, 0.351 mmol) in CH$_2$Cl$_2$ (1.0 ml) was added and the reaction mixture was stirred for 1 hour at room temperature. The mixture was concentrated under reduced pressure. The crude material was purified by column chromatography using silicon dioxide gel, eluting with 1-10% methanol in CH$_2$Cl$_2$, containing 1% ammonia (28% aq.) to afford the desired intermediate (83.0 mg).

1-(azepan-4-yl)-1-[(2,4-difluorophenyl)methyl]-3-{[4-(propan-2-yloxy)phenyl]methyl}urea

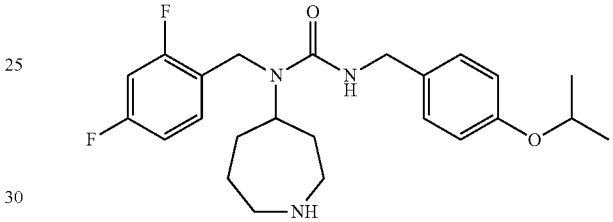

TFA (0.3 ml) was added to tert-butyl 4-{[(2,4-difluorophenyl)methyl]({[4-(propan-2-yloxy)phenyl]methyl}carbamoyl)amino}azepane-1-carboxylate (82.0 mg, 0.154 mmol) in CH$_2$Cl$_2$ (3.0 ml) at room temperature. After 2 hours of stirring at room temperature, toluene (1.0 ml) was added and the mixture concentrated under reduced pressure. The crude material was purified by column chromatography using silicon dioxide gel, eluting with 1-10% methanol in CH$_2$Cl$_2$, containing 1% ammonia (28% aq.) to afford the desired intermediate (13.7 mg, 21%).

1-[(2,4-difluorophenyl)methyl]-1-(1-methylazepan-4-yl)-3-{[4-(propan-2-yloxy)phenyl]methyl}urea; trifluoroacetic acid Formaldehyde (9.6 µl, 37% aq., 0.096 mmol) was added dropwise to a solution of 1-(azepan-4-yl)-1-[(2,4-difluorophenyl)methyl]-3-{[4-(propan-2-yloxy)phenyl]methyl}urea (13.7 mg, 0.032 mmol) in ethanol (2.0 ml) at room temperature. NaBH$_3$CN (6.7 mg, 0.107 mmol) was added and the reaction mixture was stirred for 16 hours at room temperature. The mixture was concentrated under reduced pressure. The crude material was purified by preparative HPLC, eluting with 20-40% acetonitrile in water (containing 0.1% trifluoroacetic acid) to afford the title compound (12 mg, 68%): $^1$H NMR (400 MHz, Methanol-d4) δ 7.24 (q, 1H), 7.15 (d, 2H), 6.95 (dt, 2H), 6.83 (d, 2H), 4.63-4.47 (m, 3H), 4.28 (s, 2H), 4.26-4.04 (m, 1H), 3.56-3.42 (m, 2H), 3.29-3.02 (m, 2H), 2.89 (s, 3H), 2.33-1.62 (m, 7H), 1.31 (d, 6H); LCMS: 446.3 [M+H]$^+$.

Example 79: 1-[(7R,8aS)-octahydroindolizin-7-yl]-3-[(4-cyclopropoxyphenyl)methyl]-1-[(2,4-difluorophenyl)methyl]urea; trifluoroacetic acid (79)

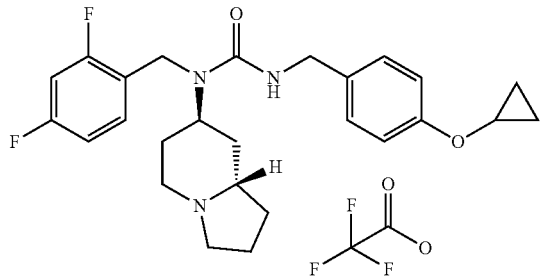

A solution of a (4-cyclopropoxyphenyl)methanamine (0.040 ml, 0.257 mmol) in dichloromethane (1 ml) was added dropwise to a solution of diphosgene (0.015 ml, 0.129 mmol) in dichloromethane (1 ml) at room temperature. DIPEA (0.134 ml, 0.772 mmol) was added and the resulting mixture was stirred for 5 minutes at room temperature. Thereafter a solution of a (7R,8aS)—N-[(2,4-difluorophenyl)methyl]-octahydroindolizin-7-amine (75.4 mg, 0.283 mmol) in dichloromethane (1 ml) was added and the reaction mixture was stirred overnight at room temperature. The mixture was concentrated under reduced pressure and the crude material was purified by preparative HPLC, eluting with acetonitrile in water (containing 0.1% trifluoroacetic acid) to afford the title compound (84 mg, 54%). $^1$H NMR (400 MHz, Chloroform-d) δ 12.20 (br. s, 1H), 7.17-7.08 (m, 1H), 7.06-7.00 (m, 2H), 6.98-6.91 (m, 2H), 6.87-6.78 (m, 2H), 4.96-4.84 (m, 1H), 4.69 (br. s, 1H), 4.37 (s, 2H), 4.29 (s, 2H), 3.93 (br. s, 1H), 3.74-3.66 (m, 1H), 3.61-3.49 (m, 1H), 3.48-3.40 (m, 1H), 3.16-3.06 (m, 1H), 3.04-2.90 (m, 1H), 2.34-2.08 (m, 6H), 1.98 (d, 1H), 1.86 (d, 1H), 0.82-0.70 (m, 4H). LCMS: 456.3 [M+H]$^+$.

Example 80: 1-[(7R,8aS)-octahydroindolizin-7-yl]-1-[(2,4-difluorophenyl)methyl]-3-{[4-(propan-2-yloxy)phenyl]methyl}urea; trifluoroacetic acid (80)

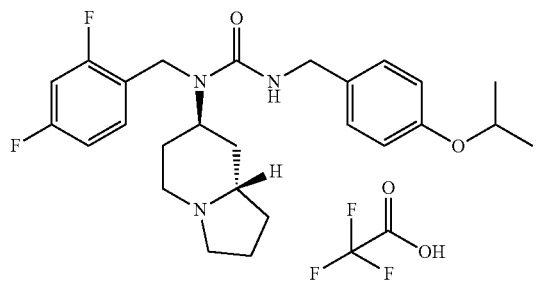

A solution of [4-(propan-2-yloxy)phenyl]methanamine (0.023 ml, 0.148 mmol) in dichloromethane (1 ml) was added dropwise to a solution of diphosgene (0.009 ml, 0.074 mmol) in dichloromethane (1 ml) at room temperature. DIPEA (0.077 ml, 0.445 mmol) was added and the resulting mixture was stirred for 5 minutes at room temperature. Thereafter a solution of a (7R,8aS)—N-[(2,4-difluorophenyl)methyl]-octahydroindolizin-7-amine (43.4 mg, 0.163 mmol) in dichloromethane (1 ml) was added and the reaction mixture was stirred overnight at room temperature. The mixture was concentrated under reduced pressure and the crude material was purified by preparative HPLC, eluting with acetonitrile in water (containing 0.1% trifluoroacetic acid) to afford the title compound (42 mg, 48%). $^1$H NMR (400 MHz, Chloroform-d) δ 12.20 (s, 1H), 7.13 (q, 1H), 7.01 (d, 2H), 6.87-6.76 (m, 4H), 4.97-4.83 (m, 1H), 4.72-4.61 (m, 1H), 4.51 (sep, 1H), 4.37 (s, 2H), 4.28 (s, 2H), 3.96 (br. s, 1H), 3.62-3.49 (m, 1H), 3.48-3.40 (m, 1H), 3.17-3.06 (m, 1H), 3.04-2.90 (m, 1H), 2.36-2.10 (m, 6H), 1.98 (d, 1H), 1.86 (d, 1H), 1.32 (d, 6H). LCMS: 458.3 [M+H]$^+$.

Example 81: 1-[(2,4-difluorophenyl)methyl]-1-(piperidin-4-yl)-3-[(quinoxalin-6-yl)methyl]urea (81)

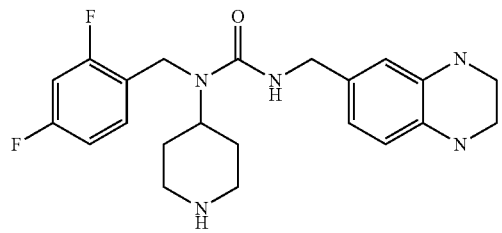 [SMILES: O=C(NCc1ccc2c(c1)NCCN2)N(Cc1ccc(F)cc1F)C1CCNCC1]

To the solution of (quinoxalin-6-yl)methanamine (24 mg, 0.150 mmol) in CH$_2$Cl$_2$ (5 ml), DIPEA (0.1 ml, 0.600 mmol) and followed by 2-(trimethylsilyl)ethyl 4-[(chlorocarbonyl)[(2,4-difluorophenyl)methyl]amino]piperidine-1-carboxylate (78 mg, 0.180 mmol) were added. Reaction was stirred overnight at room temperature. Volatiles were evaporated in vacuo. Brine (5.0 ml) was added and compound was extracted with CH$_2$Cl$_2$ (4×7 ml). The combined organic layers were dried over Na$_2$SO$_4$ and the solvent was removed by rotary evaporation. The crude material was purified by column chromatography using silicon dioxide gel, eluting with ethyl acetate in petroleum ether to afford 2-(trimethylsilyl)ethyl 4-{[(2,4-difluorophenyl)methyl]({[(quinoxalin-6-yl)methyl]carbamoyl})amino}piperidine-1-carboxylate (80 mg, 95%).

TBAF (2 ml, 1 M in THF) was added to 2-(trimethylsilyl)ethyl 4-{[(2,4-difluorophenyl)methyl]({[(quinoxalin-6-yl)methyl]carbamoyl})amino}piperidine-1-carboxylate (80 mg, 0.144 mmol) in THF (1 ml) at room temperature. After 3 hours the mixture was heated to 50° C. and stirred at this temperature overnight. The mixture was concentrated under reduced pressure and the crude material was purified by preparative HPLC, eluting with acetonitrile in water (containing 6 ppm ammonia) to afford the title compound (40 mg, 65%). $^1$H-NMR (400 MHz, Chloroform-d) δ 8.83 (d, 2H), 8.05 (d, 1H), 7.88 (s, 1H), 7.65 (dd, 1H), 7.35-7.27 (m, 1H), 6.93-6.72 (m, 2H), 4.86 (d, 1H), 4.66 (d, 2H), 4.43 (d, 3H), 3.16 (d, 2H), 2.73 (t, 2H), 2.13 (s, 1H), 1.78 (d, 2H), 1.68-1.52 (m, 2H). LCMS: 412.2 [M+H]$^+$.

Example 82: 1-[(2,4-difluorophenyl)methyl]-1-(1-methylpiperidin-4-yl)-3-[(quinoxalin-6-yl)methyl]urea (82)

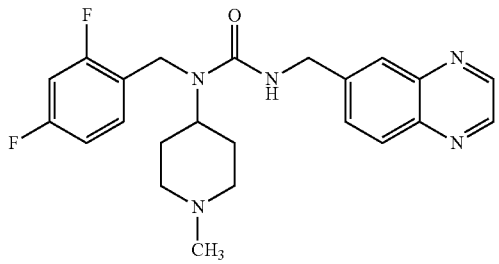 [SMILES: CN1CCC(N(Cc2ccc(F)cc2F)C(=O)NCc2ccc3nccnc3c2)CC1]

Formaldehyde (0.010 ml, 37% aq., 0.122 mmol) was added to a stirred solution of 1-[(2,4-difluorophenyl)methyl]-1-(piperidin-4-yl)-3-[(quinoxalin-6-yl)methyl]urea (23 mg, 0.056 mmol) in ethanol (3 ml). Hereafter NaBH(OAc)$_3$ (35.5 mg, 0.168 mmol) was added in portions and the reaction mixture was stirred for 4 hours at room temperature. Volatiles were evaporated in vacuo. CH$_2$Cl$_2$ (7 ml) was added and the organic phase was washed with NaHCO$_3$ (sat. aq.). The crude material was purified by preparative HPLC, eluting with acetonitrile in water (containing 6 ppm ammonia) to afford the title compound (15 mg, 60%). $^1$H NMR (400 MHz, Chloroform-d) δ 8.83 (d, 2H), 8.05 (d, 1H), 7.88 (s, 1H), 7.65 (dd, 1H), 7.33-7.23 (m, 1H), 6.95-6.68 (m, 2H), 4.93-4.83 (m, 1H), 4.65 (d, 2H), 4.48 (s, 2H), 4.40-4.27 (m, 1H), 2.97 (d, 2H), 2.33 (s, 3H), 2.24-2.10 (m, 2H), 1.92-1.70 (m, 4H). LCMS: 426.3 [M+H]$^+$.

Example 83: 3-[(4,5-difluoro-2-methoxyphenyl)methyl]-3-(piperidin-4-yl)-1-{[4-(propan-2-yloxy)phenyl]methyl}urea; trifluoroacetic acid (83)

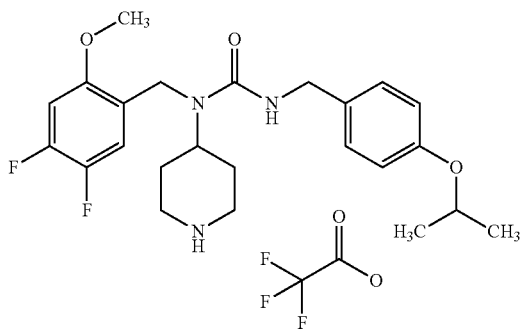

tert-butyl 4-{[(4,5-difluoro-2-methoxyphenyl)methyl]amino}piperidine-1-carboxylate

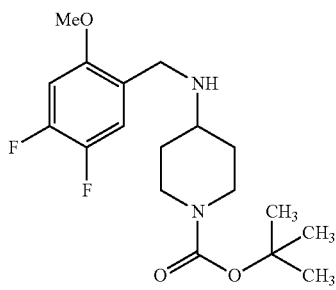 [SMILES: COc1cc(F)c(F)cc1CNC1CCN(C(=O)OC(C)(C)C)CC1]

(4,5-difluoro-2-methoxyphenyl)methanamine (191 mg) and tert-butyl 4-oxopiperidine-1-carboxylate (200 mg) were dissolved in ethanol. Sodium triactetoxyborohydride (319 mg) was added. The reaction was stirred at room temperature overnight. The mixture was concentrated, the residue diluted with Na$_2$CO$_3$ (sat. aq.) and extracted with dichloromethane. The organic phase was dried and concentrated to afford the desired intermediate (379 mg).

tert-butyl 4-{[(4,5-difluoro-2-methoxyphenyl)methyl]({[4-(propan-2-yloxy)phenyl]methyl}carbamoyl)amino}piperidine-1-carboxylate

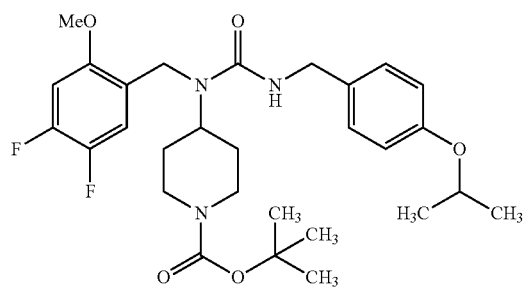 [SMILES: COc1cc(F)c(F)cc1CN(C(=O)NCc1ccc(OC(C)C)cc1)C1CCN(C(=O)OC(C)(C)C)CC1]

tert-butyl 4-{[(4,5-difluoro-2-methoxyphenyl)methyl]amino}piperidine-1-carboxylate (82 mg) was stirred in dichloromethane (1 ml) at room temperature. 1-(isocyanatomethyl)-4-(propan-2-yloxy)benzene (44 mg) dissolved in dichloromethane (0.5 ml) was drop-wise added. Stir the reaction overnight. The mixture was concentrated under reduced pressure and the desired urea was purified by column chromatography using silicon dioxide gel, eluting with 50-70% ethyl acetate in petroleum ether to afford the desired intermediate (77 mg).

3-[(4,5-difluoro-2-methoxyphenyl)methyl]-3-(piperidin-4-yl)-1-{[4-(propan-2-yloxy)phenyl]methyl}urea; trifluoroacetic acid tert-butyl 4-{[(4,5-difluoro-2-methoxyphenyl)methyl]({[4-(propan-2-yloxy)phenyl]methyl}carbamoyl)amino}piperidine-1-carboxylate (77 mg) was dissolved in dichloromethane (1.4 ml). The solution was cooled to 0° C. and trifluoroacetic acid was added and the reaction was stirred for 90 minutes. The mixture was concentrated and the crude material was purified by HPLC, eluting with 20-55% acetonitrile in water (containing 0.1% trifluoroacetic acid) to afford the title compound (49 mg, 62%): $^1$H NMR (400 MHz, Chloroform-d) δ 9.57 (s, 1H), 9.09 (s, 1H), 7.05 (d, 2H), 7.00-6.91 (m, 1H), 6.80 (d, 2H), 6.65 (dd, 1H), 4.73 (s, 1H), 4.67 (dq, 1H), 4.51 (hept, 1H), 4.28 (s, 2H), 4.24 (s, 2H), 3.72 (s, 3H), 3.42 (d, 2H), 3.03-2.79 (m, 2H), 2.03-1.85 (m, 4H), 1.32 (d, 6H); LCMS: 448.3 [M+H]$^+$.

Example 84 (comparative): 3-[(2,4-difluorophenyl)methyl]-3-[(1R,3R,5S)-8-methyl-8-azabicyclo[3.2.1]octan-3-yl]-1-{[4-(propan-2-yloxy)phenyl]methyl}urea; trifluoroacetic acid (84)

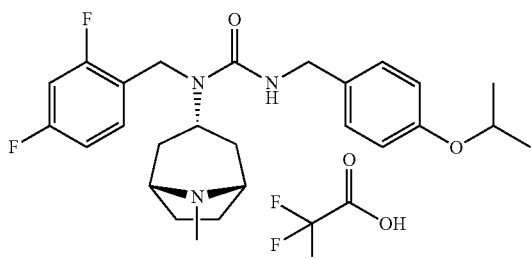

(1R,3R,5S)—N-[(2,4-difluorophenyl)methyl]-8-methyl-8-azabicyclo[3.2.1]octan-3-amine

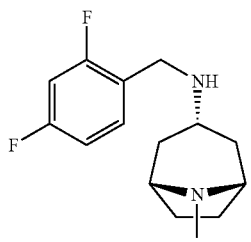 [SMILES: CN1[C@@H]2CC[C@H]1C[C@@H](NCc1ccc(F)cc1F)C2]

(2,4-difluorophenyl)methanamine (112 mg, 779 mol) was added to 8-methyl-8-azabicyclo[3.2.1]octan-3-one (99.6 mg, 716 μmol) in dichloromethane (2 ml). After 10 minutes of stirring at room temperature sodium triacetoxyborohydride (224 mg, 1.06 μmol) was added. After another 21 hour of stirring sodium hydroxide (2 ml, 1 M aqueous) was added. The mixture was extracted with dichloromethane (3×1 ml), the organic phase was dried using a phase separator and concentrated to oil. The crude material was purified by column chromatography using silicon dioxide gel, eluting with 5-10% methanol in dichloromethane, containing 1% ammonia (28% aqueous) to afford the desired intermediate (174 mg).

3-[(2,4-difluorophenyl)methyl]-3-[(1R,3R,5S)-8-methyl-8-azabicyclo[3.2.1]-octan-3-yl]-1-{[4-(propan-2-yloxy)phenyl]methyl}urea; trifluoroacetic acid A solution of [4-(propan-2-yloxy)phenyl]methanamine (75.0 mg, 0.454 mmol) in CH$_2$Cl$_2$ (1 ml) was added dropwise to a solution of diphosgene (16.9 μl, 0.141 mmol) in CH$_2$Cl$_2$ (0.5 ml) at room temperature. DIPEA (98.1 μl, 0.563 mmol) was added and the resulting mixture was stirred for 5 minutes at room temperature. Thereafter a solution of (1R,3R,5S)—N-[(2,4-difluorophenyl)methyl]-8-methyl-8-azabicyclo[3.2.1]octan-3-amine (56.0 mg, 0.210 mmol) in CH$_2$Cl$_2$ (1 ml) was added and the reaction mixture was stirred for 1 hour at room temperature. The mixture was concentrated under reduced pressure. The crude material was purified by preparative HPLC, eluting with 20-40% acetonitrile in water (containing 0.1% trifluoroacetic acid) to afford the title compound (101 mg, 78%): $^1$H NMR (400 MHz, Chloroform-d) δ 11.75 (s, 1H), 7.33-7.24 (m, 1H), 7.15 (d, 2H), 6.90-6.72 (m, 4H), 4.52 (hept, 1H), 4.32 (s, 2H), 4.30 (s, 2H), 4.06 (p, 1H), 3.74 (d, 2H), 2.69-2.54 (m, 5H), 2.36-2.12 (m, 6H), 1.32 (d, 6H); LCMS: 458.3 [M+H]$^+$.

Example 85: 1-[(2,4-difluorophenyl)methyl]-1-[(3R,4S)-1,3-dimethylpiperidin-4-yl]-3-{[4-(propan-2-yloxy)phenyl]methyl}urea; trifluoroacetic acid and 1-[(2,4-difluorophenyl)methyl]-1-[(3S,4R)-1,3-dimethylpiperidin-4-yl]-3-{[4-(propan-2-yloxy)phenyl]methyl}urea; trifluoroacetic acid (85)

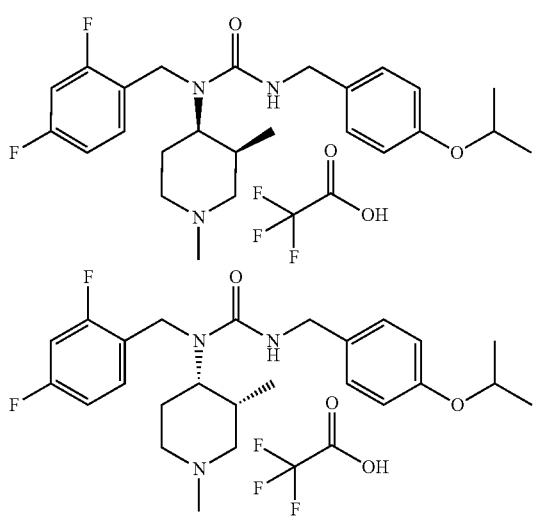

1-[(2,4-difluorophenyl)methyl]-1-[(3R,4S)-1,3-dimethylpiperidin-4-yl]-3-{[4-(propan-2-yloxy)phenyl]methyl}urea; trifluoroacetic acid and 1-[(2,4-difluorophenyl)methyl]-1-[(3S,4R)-1,3-dimethylpiperidin-4-yl]-3-{[4-(propan-2-yloxy)phenyl]methyl}urea; trifluoroacetic acid

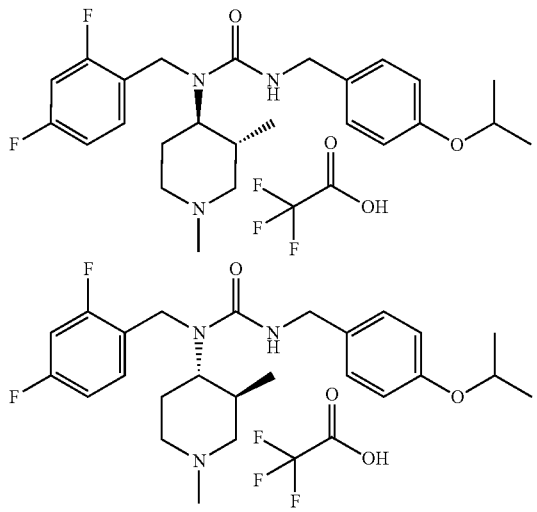

(3R,4S)—N-[(2,4-difluorophenyl)methyl]-1,3-dimethylpiperidin-4-amine and (3S,4R)—N-[(2,4-difluorophenyl)methyl]-1,3-dimethylpiperidin-4-amine

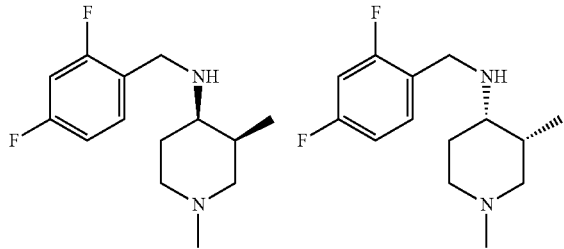

(3R,4R)—N-[(2,4-difluorophenyl)methyl]-1,3-dimethylpiperidin-4-amine and (3S,4S)—N-[(2,4-difluorophenyl)methyl]-1,3-dimethylpiperidin-4-amine

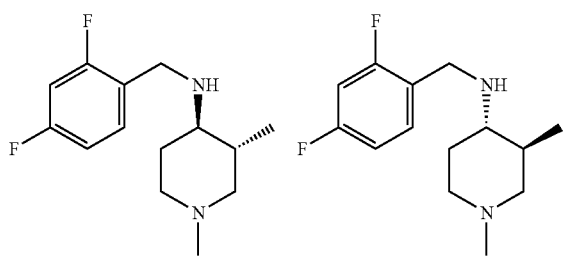

1,3-dimethylpiperidin-4-one (91.0 mg, 715 μmol) was added to (2,4-difluorophenyl)methanamine (105 mg, 734 μmol) in dichloromethane (1 ml). After 5 minutes of stirring at room temperature sodium triacetoxyborohydride (234 mg, 1.10 mmol) was added. After another 3 hours of stirring sodium hydroxide (1 ml, 1 M aqueous) was added. The mixture was extracted with dichloromethane (1 ml), the organic phase was dried using a phase separator and concentrated. The crude material was purified by column chromatography using silicon dioxide gel, eluting with 1-10% methanol in dichloromethane, containing 1% ammonia (28% aqueous) to afford the cis intermediates: (3R,4S)—N-[(2,4-difluorophenyl)methyl]-1,3-dimethylpiperidin-4-amine and (3S,4R)—N-[(2,4-difluorophenyl)methyl]-1,3-dimethylpiperidin-4-amine (105 mg) and the trans intermediates: (3R,4R)—N-[(2,4-difluorophenyl)methyl]-1,3-dimethylpiperidin-4-amine and (3S,4S)—N-[(2,4-difluorophenyl)methyl]-1,3-dimethylpiperidin-4-amine (14 mg).

1-[(2,4-difluorophenyl)methyl]-1-[(3R,4S)-1,3-dimethylpiperidin-4-yl]-3-{[4-(propan-2-yloxy)phenyl]methyl}urea; trifluoroacetic acid and 1-[(2,4-difluorophenyl)methyl]-1-[(3S,4R)-1,3-dimethylpiperidin-4-yl]-3-{[4-(propan-2-yloxy)phenyl]methyl}urea; trifluoroacetic acid A solution of [4-(propan-2-yloxy)phenyl]methanamine (24.9 mg, 0.151 mmol) in CH$_2$Cl$_2$ (1 ml) was added dropwise to a solution of diphosgene (9.1 μl, 0.076 mmol) in CH$_2$Cl$_2$ (0.5 ml) at room temperature. DIPEA (52.0 μl, 0.298 mmol) was added and the resulting mixture was stirred for 10 minutes at room temperature. Thereafter a solution of the cis intermediates: (3R,4S)—N-[(2,4-difluorophenyl)methyl]-1,3-dimethylpiperidin-4-amine and (3S,4R)—N-[(2,4-difluorophenyl)methyl]-1,3-dimethylpiperidin-4-amine (43.4 mg, 0.171 mmol) in CH$_2$Cl$_2$ (1 ml) was added and the reaction mixture was stirred for 2 hour at room temperature. The mixture was concentrated under reduced pressure. The crude material was purified by HPLC, eluting with 20-40% acetonitrile in water (containing 0.1% trifluoroacetic acid) to afford the title cis compounds (62 mg, 74%): $^1$H NMR (400 MHz, Chloroform-d) δ 12.59 (bs, 1H), 7.13-7.01 (m, 1H), 6.98 (d, 2H), 6.89-6.71 (m, 4H), 4.71-4.11 (m, 7H), 3.71 (d, 1H), 3.38 (d, 1H), 3.13-3.01 (m, 1H), 2.85-2.66 (m, 5H), 2.40 (qd, 1H), 1.63 (d, 1H), 1.36-1.19 (m, 9H); LCMS: 446.3 [M+H]$^+$.

1-[(2,4-difluorophenyl)methyl]-1-[(3R,4R)-1,3-dimethylpiperidin-4-yl]-3-{[4-(propan-2-yloxy)phenyl]methyl}urea; trifluoroacetic acid and 1-[(2,4-difluorophenyl)methyl]-1-[(3S,4S)-1,3-dimethylpiperidin-4-yl]-3-{[4-(propan-2-yloxy)phenyl]methyl}urea; trifluoroacetic acid A solution of [4-(propan-2-yloxy)phenyl]methanamine (8.7 mg, 0.053 mmol) in CH$_2$Cl$_2$ (0.5 ml) was added dropwise to a solution of diphosgene (3.1 μl, 0.026 mmol) in CH$_2$Cl$_2$ (0.5 ml) at room temperature. DIPEA (18.0 μl, 0.103 mmol) was added and the resulting mixture was stirred for 10 minutes at room temperature. Thereafter a solution of the trans intermediates: (3R,4R)—N-[(2,4-difluorophenyl)methyl]-1,3-dimethylpiperidin-4-amine and (3S,4S)—N-[(2,4-difluorophenyl)methyl]-1,3-dimethylpiperidin-4-amine (14.1 mg, 0.055 mmol) in CH$_2$Cl$_2$ (1 ml) was added and the reaction mixture was stirred for 2 hour at room temperature. The mixture was concentrated under reduced pressure. The crude material was purified by HPLC, eluting with 20-40% acetonitrile in water (containing 0.1% trifluoroacetic acid) to afford the title trans compounds (14 mg, 48%): $^1$H NMR (400 MHz, Chloroform-d) δ 12.96 (bs, 1H), 7.13 (q, 1H), 7.05-6.91 (m, 2H), 6.85-6.72 (m, 4H), 4.84-4.43 (m, 3H), 4.42-4.17 (m, 4H), 3.53 (dd, 2H), 2.89-2.70 (m, 4H), 2.54 (t, 1H), 2.49-2.32 (m, 1H), 2.16-1.95 (m, 1H), 1.86 (d, 1H), 1.31 (d, 6H), 0.93 (d, 3H); LCMS: 446.3 [M+H]$^+$.

Example 86: 1-[(2,4-difluorophenyl)methyl]-1-(1,4-dimethylpiperidin-4-yl)-3-{[4-(propan-2-yloxy)phenyl]methyl}urea; trifluoroacetic acid (86)

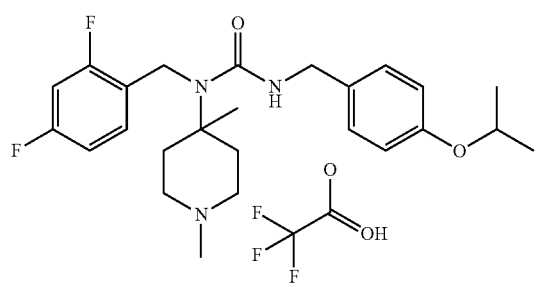

tert-butyl 4-{[(2,4-difluorophenyl)methyl]amino}-4-methylpiperidine-1-carboxylate

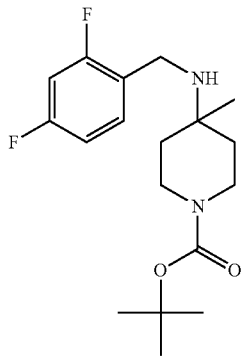

2,4-difluorobenzaldehyde (199 mg, 1.40 mmol) in dichloromethane (0.5 ml) was added to tert-butyl 4-amino-4-methylpiperidine-1-carboxylate (330 mg, 1.54 mmol) in dichloromethane (0.5 ml). After 10 minutes of stirring at room temperature sodium triacetoxyborohydride (445 mg, 2.10 mmol) was added. After another 18 hours of stirring sodium hydroxide (2 ml, 1 M aqueous) was added, the mixture was extracted with dichloromethane (2×1 ml), the combined organic phases were separated, dried using a phase separator, and concentrated. The crude material was purified by column chromatography using silicon dioxide gel, eluting with 0-10% methanol in dichloromethane, containing 1% ammonia (28% aqueous) to afford the desired intermediate (366 mg).

tert-butyl 4-{[(2,4-difluorophenyl)methyl]({[4-(propan-2-yloxy)phenyl]methyl}carbamoyl)amino}-4-methylpiperidine-1-carboxylate

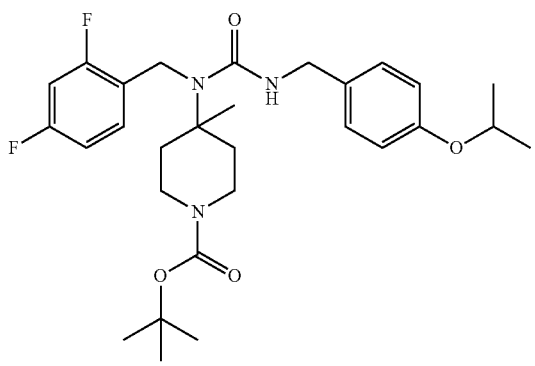 [SMILES: CC(C)Oc1ccc(CNC(=O)N(Cc2ccc(F)cc2F)C2(C)CCN(C(=O)OC(C)(C)C)CC2)cc1]

A solution of [4-(propan-2-yloxy)phenyl]methanamine (45 mg, 0.272 mmol) in dichloromethane (0.5 ml) was added to a stirred solution of diphosgene (16.3 µl, 136 µmol) in dichloromethane (0.5 ml) at room temperature giving a suspension. After complete addition diisopropylethylamine (95 µl, 0.545 mmol) was added dropwise giving a clear solution and gas evolution. After 5 minutes of stirring at room temperature a solution of tert-butyl 4-{[(2,4-difluorophenyl)methyl]amino}-4-methylpiperidine-1-carboxylate (100 mg, 0.294 mmol) in dichloromethane (0.5 ml) was added rapidly. After another 90 minutes of stirring at room temperature the mixture was concentrated to oil. The crude material was purified by column chromatography using silicon dioxide gel, eluting with 6-25% ethyl acetate in petroleum ether to afford the desired intermediate (146 mg).

1-[(2,4-difluorophenyl)methyl]-1-(4-methylpiperidin-4-yl)-3-{[4-(propan-2-yloxy)phenyl]methyl}urea

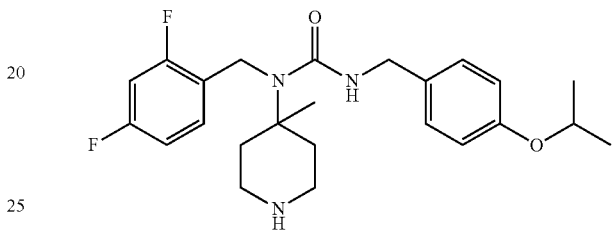

Trifluoroacetic acid (100 µl) was added to tert-butyl 4-{[(2,4-difluorophenyl)methyl]({[4-(propan-2-yloxy)phenyl]methyl}carbamoyl)amino}-4-methylpiperidine-1-carboxylate (62 mg, 117 µmol) in dichloromethane (0.9 ml). After 2 hours of stirring at room temperature sodium hydroxide (2 ml, 1 M aqueous) and water (2 ml) was added. The mixture was extracted with dichloromethane (3 ml), the organic phase was dried using a phase separator, and concentrated. The crude material was purified by column chromatography using silicon dioxide gel, eluting with 5-10% methanol in dichloromethane, containing 1% $NH_3$ (28% aqueous) to afford the desired intermediate (45 mg).

1-[(2,4-difluorophenyl)methyl]-1-(1,4-dimethylpiperidin-4-yl)-3-{[4-(propan-2-yloxy)phenyl]methyl}urea; trifluoroacetic acid Formaldehyde (13 µl, 37%, 129 µmol) was added to 1-[(2,4-difluorophenyl)methyl]-1-(4-methylpiperidin-4-yl)-3-{[4-(propan-2-yloxy)phenyl]methyl}urea (45 mg, 104 µmol) in ethanol (1 ml). After 70 minutes of stirring at room temperature sodium triacetoxyborohydride (67 mg, 316 µmol) was added. After 2 hours of stirring at room temperature the mixture was concentrated to oil. The crude material was purified by HPLC, eluting with 20-50% acetonitrile in water (containing 0.1% trifluoroacetic acid) to afford the title compound (28.1 mg, 48%): $^1$H NMR (400 MHz, Chloroform-d) δ 12.49 (bs, 1H), 7.36-7.17 (m, 1H), 7.09-6.96 (m, 2H), 6.95-6.70 (m, 4H), 4.62-4.55 (m, 1H), 4.50 (p, 1H), 4.43 (s, 2H), 4.26-4.19 (m, 2H), 3.49 (d, 2H), 2.90-2.71 (m, 5H), 2.58 (d, 2H), 2.26 (t, 2H), 1.62 (s, 3H), 1.33-1.28 (m, 6H); LCMS: 446.3 [M+H]$^+$.

Example 87: 1-[(2,4-difluorophenyl)methyl]-3-{[4-(2-hydroxy-2,3-dimethylbutoxy)phenyl]methyl}-1-(1-methylpiperidin-4-yl)urea; trifluoroacetic acid (87)

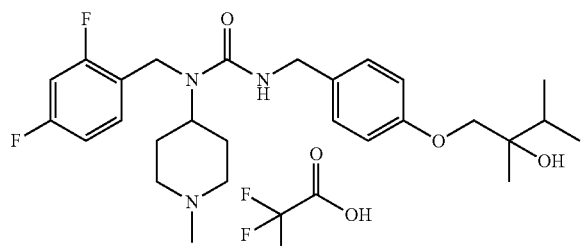

4-(2-hydroxy-2,3-dimethylbutoxy)benzonitrile

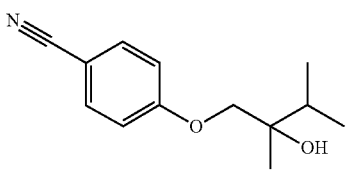 [SMILES: CC(C)C(C)(O)COc1ccc(C#N)cc1]

Isopropylmagnesium bromide (1.48 ml, 1.3 M in tetrahydrofuran) was added dropwise to 4-(2-oxopropoxy)benzonitrile (260 mg, 1.48 mmol) in diethyl ether (20 ml) at room temperature. After 1 day of stirring at room temperature ammonium chloride (10 ml, sat. aq.) was added. The mixture was extracted with diethyl ether (50 ml), the organic phase was washed with brine, dried using magnesium sulfate, filtered, and concentrated. The crude material was purified by column chromatography using silicon dioxide gel, eluting with ethyl acetate in petroleum ether to afford the desired intermediate (63 mg).

1-[4-(aminomethyl)phenoxy]-2,3-dimethylbutan-2-ol

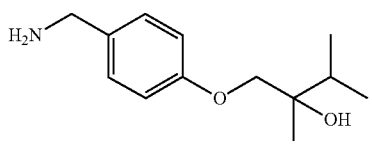 [SMILES: CC(C)C(C)(O)COc1ccc(CN)cc1]

Borane (862 µl, 1 M in tetrahydrofuran) was added to 4-(2-hydroxy-2,3-dimethylbutoxy)benzonitrile (63 mg, 287 µmol) in tetrahydrofuran (1 ml). After 2 days of stirring at room temperature methanol (6 ml) was added and the mixture was heated to 75° C. concentrated. After 15 hours the mixture was concentrated to afford the desired intermediate (69 mg).

tert-butyl 4-{[(2,4-difluorophenyl)methyl]({[4-(2-hydroxy-2,3-dimethylbutoxy)phenyl]methyl}carbamoyl)amino}piperidine-1-carboxylate

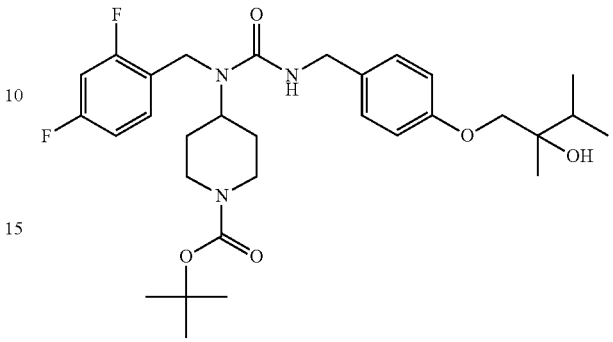

1-[4-(aminomethyl)phenoxy]-2,3-dimethylbutan-2-ol (68.9 mg, 309 µmol) and diisopropylethylamine (131 µl, 936 µmol) was added to tert-butyl 4-[(chlorocarbonyl)[(2,4-difluorophenyl)methyl]amino]piperidine-1-carboxylate (120 mg, 309 µmol) in dichloromethane (2 ml). After 18 hours of stirring at room temperature sodium hydroxide (1 ml, 1 M aqueous) was added, the organic phase was dried using a phase separator and concentrated to oil (223 mg).

1-[(2,4-difluorophenyl)methyl]-3-{[4-(2-hydroxy-2,3-dimethylbutoxy)phenyl]methyl}-1-(piperidin-4-yl)urea

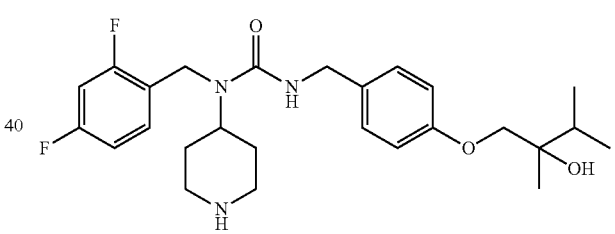

Trifluoroacetic acid (100 µl) was added to tert-butyl 4-{[(2,4-difluorophenyl)-methyl]({[4-(2-hydroxy-2,3-dimethylbutoxy)phenyl]methyl}carbamoyl)amino}piperidine-1-carboxylate (223 mg, 387 µmol) in dichloromethane (0.9 ml). After 17 hours of stirring at room temperature additional trifluoroacetic acid (100 µl) was added. After 5 hours of stirring at room temperature additional trifluoroacetic acid (100 µl) was added. After 22 hours of stirring at room temperature sodium hydroxide (1 ml, 1 M aqueous) was added, the organic phase was dried using a phase separator, and concentrated. The crude material was purified by column chromatography using silicon dioxide gel, eluting with a 1:1:1:1 ratio of butanol, water, ethyl acetate and acetic acid to afford the desired intermediate (49.6 mg).

1-[(2,4-difluorophenyl)methyl]-3-{[4-(2-hydroxy-2,3-dimethylbutoxy)phenyl]methyl}-1-(1-methylpiperidin-4-yl)urea; trifluoroacetic acid Formaldehyde (12.6 µl, 37%. 125 µmol) was added to 1-[(2,4-difluorophenyl)methyl]-3-{[4-(2-hydroxy-2,3-dimethylbutoxy)phenyl]methyl}-1-(piperidin-4-yl)urea (49.6 mg, 104 µmol) in tetrahydrofuran (1 ml). After 50 minutes of stirring at room temperature sodium triacetoxyborohydride (45 mg, 212 µmol) was added. After 19 hours of stirring at room temperature the mixture was concentrated to oil. The crude material was purified by HPLC, eluting with 20-40% acetonitrile in water (containing 0.1% trifluoroacetic acid) to afford the title compound (18 mg, 29%): ¹H NMR (400 MHz, Chloroform-d) δ 12.78 (bs, 1H), 7.12 (q, 1H), 7.04 (d, 2H), 6.84-6.78 (m, 4H), 4.78-4.64 (m, 2H), 4.36 (s, 2H), 4.28 (d, 2H), 3.87 (d, 1H), 3.77 (d, 1H), 3.57 (d, 2H), 2.83 (t, 2H), 2.76 (s, 3H), 2.21 (q, 2H), 2.03-1.94 (m, 1H), 1.89 (d, 2H), 1.18 (s, 3H), 1.00 (d, 3H), 0.92 (d, 3H); LCMS: 490.3 [M+H]⁺.

Example 88: 1-[(2,4-difluorophenyl)methyl]-3-({3-fluoro-4-[(2-hydroxyethoxy)methyl]phenyl}methyl)-1-(1-methylpiperidin-4-yl)urea; trifluoroacetic acid (88)

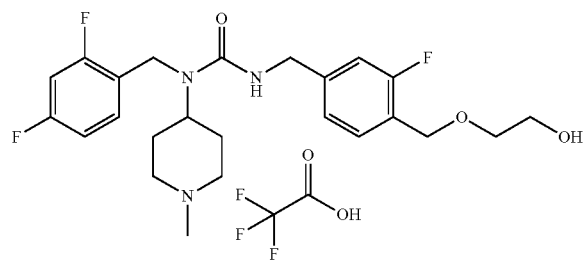

[4-({2-[(tert-butyldiphenylsilyl)oxy]ethoxy}methyl)-3-fluorophenyl]methanamine

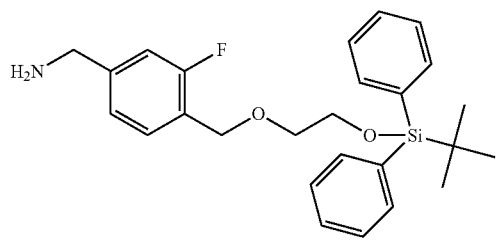 [SMILES: CC(C)(C)[Si](OCCOCc1ccc(CN)cc1F)(c1ccccc1)c1ccccc1]

tert-Butyl(chloro)diphenylsilane (97.7 µl, 0.376 mmol) and 4-dimethylaminopyridine (3.06 mg, 0.025 mmol) was added to a solution of 2-{[4-(aminomethyl)-2-fluorophenyl]methoxy}ethan-1-ol (49.9 mg, 0.250 mmol) and triethylamine (105 µl, 0.751 mmol) in dichloromethane (1 ml). After 2 hours of stirring at room temperature NaOH (1 ml, 1 M aqueous) was added. The mixture was extracted with dichloromethane (3×2 ml), the combined organic phases were dried using a phase separator and concentrated to afford the desired intermediate as oil (110 mg).

3-{[4-({2-[(tert-butyldiphenylsilyl)oxy]ethoxy}methyl)-3-fluorophenyl]methyl}-1-[(2,4-difluorophenyl)methyl]-1-(1-methylpiperidin-4-yl)urea

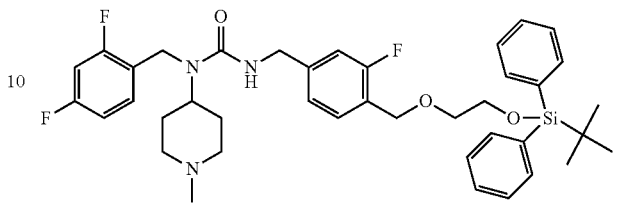

A solution of [4-({2-[(tert-butyldiphenylsilyl)oxy]ethoxy}methyl)-3-fluorophenyl]methanamine (110 mg, 0.251 mmol) in CH₂Cl₂ (1 ml) was added dropwise to a solution of diphosgene (15.5 µl, 0.128 mmol) in CH₂Cl₂ (0.5 ml) at room temperature. DIPEA (131 µl, 0.753 mmol) was added and the resulting mixture was stirred for 10 minutes at room temperature. Thereafter a solution of N-[(2,4-difluorophenyl)methyl]-1-methylpiperidin-4-amine (103 mg, 0.427 mmol) in CH₂Cl₂ (1 ml) was added and the reaction mixture was stirred for 2 hours at room temperature. The mixture was concentrated under reduced pressure and used without further purification.

1-[(2,4-difluorophenyl)methyl]-3-({3-fluoro-4-[(2-hydroxyethoxy)methyl]phenyl}methyl)-1-(1-methylpiperidin-4-yl)urea; trifluoroacetic acid Tetrabutylammonium fluoride (0.5 ml, 1 M in tetrahydrofuran) was added to a solution of 3-{[4-({2-[(tert-butyldiphenylsilyl)oxy]ethoxy}methyl)-3-fluorophenyl]methyl}-1-[(2,4-difluorophenyl)methyl]-1-(1-methylpiperidin-4-yl)urea (117 mg, 0.166 mmol) in tetrahydrofuran (0.5 ml). After 1.5 hours of stirring at room temperature the mixture was concentrated. The crude material was purified by HPLC, eluting with 20-50% acetonitrile in water (containing 0.1% trifluoroacetic acid) to afford the title compound (26.5 mg, 18% over 3 steps): ¹H NMR (400 MHz, Chloroform-d) δ 13.01 (bs, 1H), 7.30 (t, 1H), 7.15 (q, 1H), 6.90 (d, 1H), 6.87-6.78 (m, 3H), 4.88 (t, 1H), 4.72-4.61 (m, 1H), 4.57 (s, 2H), 4.40 (s, 2H), 4.33 (d, 2H), 3.78-3.71 (m, 2H), 3.63-3.50 (m, 4H), 2.90-2.73 (m, 5H), 2.23 (q, 2H), 1.89 (d, 2H); LCMS: 466.3 [M+H]⁺.

Example 89: N-(5-fluoro-2-{[1-(1-methylpiperidin-4-yl)({[4-(propan-2-yloxy)phenyl]methyl}carbamoyl)amino]methyl}phenyl)acetamide; trifluoroacetic acid (89)

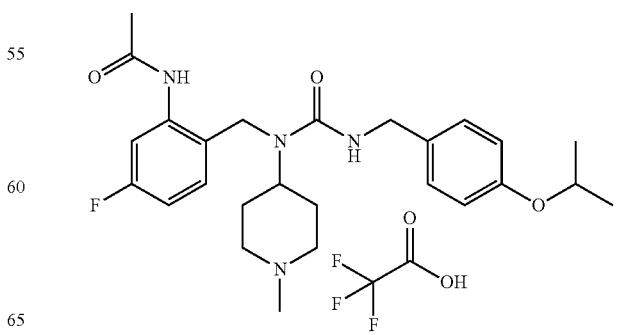

N-(5-fluoro-2-formylphenyl)acetamide

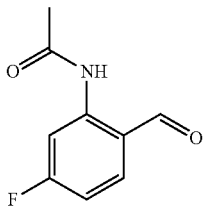

Acetic anhydride (143 µl, 1.29 mmol) was added to a solution of 2-amino-4-fluorobenzaldehyde (119 mg, 0.858 mmol) in tetrahydrofuran (1 ml). After 5 hours of stirring at room temperature acetic anhydride (143 µl, 1.29 mmol) was added. After 16 hours of stirring at room temperature the mixture was concentrated. The crude material was purified by column chromatography using silicon dioxide gel, eluting with 3-25% ethyl acetate in petroleum ether to afford the desired intermediate as oil (115 mg).

N-(5-fluoro-2-{[(1-methylpiperidin-4-yl)amino]methyl}phenyl)acetamide

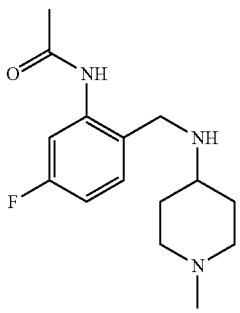

1-methylpiperidin-4-amine (42.0 µl, 0.335 mmol) was added to a solution of N-(5-fluoro-2-formylphenyl)acetamide (66.6 mg, 0.368 mmol) in dichloromethane (1 ml), sodium triacetoxyborohydride (118 mg, 0.555 mmol) was added in one portion. After 3 hours of stirring at room temperature dichloromethane (1 ml) was added and the mixture heated to 40° C. After 3 hours the mixture was cooled to room temperature and stirred for 4 days, then NaOH (2 ml, 1 M aqueous) was added. The mixture was extracted with dichloromethane (1 ml), the combined organic phases were dried using a phase separator and concentrated to afford the desired intermediate as oil (126 mg).

N-(5-fluoro-2-{[1-(1-methylpiperidin-4-yl)({[4-(propan-2-yloxy)phenyl]methyl}carbamoyl)amino]methyl}phenyl)acetamide; trifluoroacetic acid 1-(isocyanatomethyl)-4-(propan-2-yloxy)benzene (150 mg, 0.668 mmol) was added to a solution of N-(5-fluoro-2-{[(1-methylpiperidin-4-yl)amino]methyl}phenyl)acetamide (126 mg, 0.450 mmol) in dichloromethane (1 ml). After 17 hours of stirring at room temperature the mixture was concentrated. The crude material was purified by HPLC, eluting with 30-60% acetonitrile in water (containing 0.1% trifluoroacetic acid) to afford the title compound (12.1 mg, 5%): $^1$H NMR (400 MHz, Chloroform-d) δ 12.45 (bs, 1H), 9.22 (s, 1H), 7.37 (d, 1H), 7.12 (d, 2H), 7.06 (dd, 1H), 6.85-6.74 (m, 3H), 5.28 (s, 1H), 4.73-4.40 (m, 4H), 4.30 (d, 2H), 3.43 (d, 2H), 2.79 (d, 5H), 2.46 (q, 2H), 2.20 (s, 3H), 1.78 (d, 2H), 1.31 (d, 6H); LCMS: 471.3 [M+H]$^+$.

Example 90: 1-{[2-hydroxy-4-(trifluoromethyl)phenyl]methyl}-1-(1-methylpiperidin-4-yl)-3-{[4-(2-methylpropoxy)phenyl]methyl}urea; trifluoroacetic acid (90)

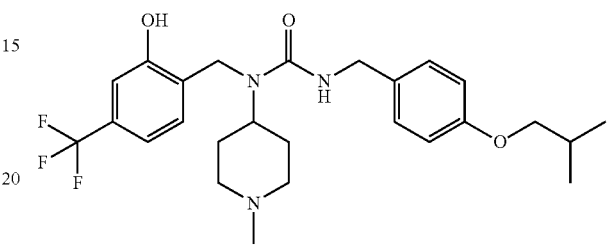

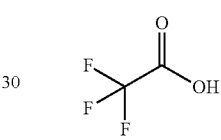

2-[(tert-butyldiphenylsilyl)oxy]-4-(trifluoromethyl)benzaldehyde

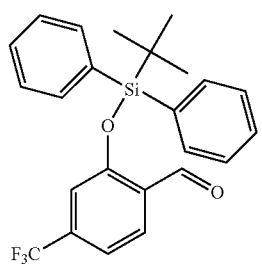 [SMILES: CC(C)(C)[Si](Oc1cc(C(F)(F)F)ccc1C=O)(c1ccccc1)c1ccccc1]

tert-Butyl(chloro)diphenylsilane (210 µl, 0.808 mmol) was added to a solution of 2-hydroxy-4-(trifluoromethyl)benzaldehyde (102 mg, 0.536 mmol), 4-dimethylaminopyridine (12.6 mg, 0.103 mmol), and triethylamine (220 µl, 1.58 mmol) in dichloromethane (2 ml). After 17 hours of stirring at room temperature HCl (2 ml, 1 M aqueous) was added. The mixture was extracted with dichloromethane (3×2 ml), the combined organic phases were dried using a phase separator, and concentrated. The crude material was purified by column chromatography using silicon dioxide gel, eluting with 3-25% ethyl acetate in petroleum ether to afford the desired intermediate as oil (248 mg).

131

N-({2-[(tert-butyldiphenylsilyl)oxy]-4-(trifluoromethyl)phenyl}methyl)-1-methylpiperidin-4-amine

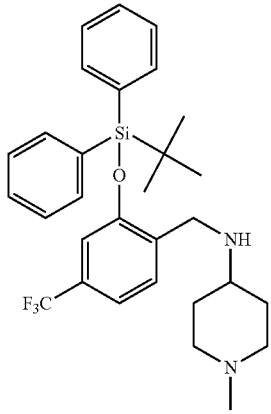 [SMILES: CN1CCC(NCc2ccc(C(F)(F)F)cc2O[Si](c2ccccc2)(c2ccccc2)C(C)(C)C)CC1]

1-methylpiperidin-4-amine (72.6 µl, 0.579 mmol) was added to a solution of 2-[(tert-butyldiphenylsilyl)oxy]-4-(trifluoromethyl)benzaldehyde (248 mg, 0.579 mmol) in dichloromethane (3 ml), sodium triacetoxyborohydride (193 mg, 0.911 mmol) was added in one portion. After 18 hours of stirring at room temperature NaOH (2 ml, 1 M aqueous) was added. The mixture was extracted with dichloromethane (3×2 ml), the combined organic phases were dried using a phase separator and concentrated to afford the desired intermediate as oil (219 mg).

1-({2-[(tert-butyldiphenylsilyl)oxy]-4-(trifluoromethyl)phenyl}methyl)-1-(1-methylpiperidin-4-yl)-3-{[4-(2-methylpropoxy)phenyl]methyl}urea

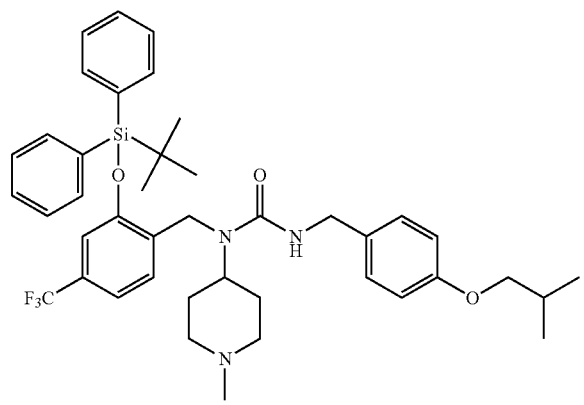 [SMILES: CC(C)COc1ccc(CNC(=O)N(Cc2ccc(C(F)(F)F)cc2O[Si](c2ccccc2)(c2ccccc2)C(C)(C)C)C2CCN(C)CC2)cc1]

A solution of 1-(isocyanatomethyl)-4-(2-methylpropoxy)benzene (48 mg, 0.187 mmol) in dichloromethane (0.5 ml) was added to a solution of N-({2-[(tert-butyldiphenylsilyl)oxy]-4-(trifluoromethyl)phenyl}methyl)-1-methylpiperidin-4-amine (54 mg, 0.103 mmol) in dichloromethane (1.5 ml). After 3 hours of stirring at room temperature NaOH (2 ml, 1 M aqueous) was added. The mixture was extracted with dichloromethane (3×2 ml), the combined organic phases were dried using a phase separator and concentrated to afford the desired intermediate (114 mg).

132

1-{[2-hydroxy-4-(trifluoromethyl)phenyl]methyl}-1-(1-methylpiperidin-4-yl)-3-{[4-(2-methylpropoxy)phenyl]methyl}urea; trifluoroacetic acid Tetrabutylammonium fluoride (0.5 ml, 1 M in tetrahydrofuran) was added to a solution of 1-({2-[(tert-butyldiphenylsilyl)oxy]-4-(trifluoromethyl)phenyl}methyl)-1-(1-methylpiperidin-4-yl)-3-{[4-(2-methylpropoxy)phenyl]methyl}urea (114 mg, 0.156 mmol) in tetrahydrofuran (0.5 ml). After 2 hours of stirring at room temperature the mixture was concentrated. The crude material was purified by HPLC, eluting with 30-70% acetonitrile in water (containing 0.1% trifluoroacetic acid), followed by column chromatography using silicon dioxide gel, eluting with 10% methanol in dichloromethane, followed by HPLC, eluting with 30-60% acetonitrile in water (containing 0.1% trifluoroacetic acid) to afford the title compound (4.4 mg, 5%): $^1$H NMR (400 MHz, Chloroform-d) δ 12.10 (s, 1H), 7.17-7.08 (m, 4H), 7.01 (d, 1H), 6.79 (d, 2H), 5.43 (s, 1H), 4.42 (s, 2H), 4.35-4.20 (m, 3H), 3.67 (d, 2H), 3.50 (d, 2H), 2.91-2.80 (m, 2H), 2.77 (s, 3H), 2.44 (q, 2H), 2.11-1.96 (m, 1H), 1.84 (d, 2H), 1.00 (d, 6H); LCMS: 494.3 [M+H]$^+$.

Example 91: 1-[(4-fluoro-2-methoxyphenyl)methyl]-1-(1-methylpiperidin-4-yl)-3-{[4-(2-methylpropoxy)phenyl]methyl}urea; trifluoroacetic acid (90)

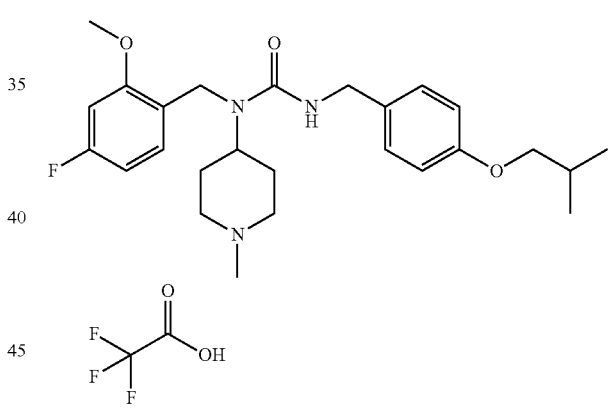

Trimethylsilyldiazomethane (49.8 µl, 0.099 mmol) was added to 1-[(4-fluoro-2-hydroxyphenyl)methyl]-1-(1-methylpiperidin-4-yl)-3-{[4-(2-methylpropoxy)phenyl]methyl}urea (36.8 mg, 0.083 mmol) in a mixture of methanol (0.5 ml) and ethyl acetate (1.5 ml) at 0° C. After 4 hours of stirring while reaching room temperature HCl (2 ml, 1 M aqueous) was added, followed by NaOH (5 ml, 1 M aqueous). The water phase was extracted with ethyl acetate (3×3 ml) and the combined organic phases were dried using a phase separator and concentrated. The crude material was purified by preparative HPLC, eluting with 30-60% acetonitrile in water (containing 0.1% trifluoroacetic acid) to afford the title compound (8.7 mg, 18%): $^1$H NMR (400 MHz, Chloroform-d) δ 12.67 (bs, 1H), 7.02 (d, 3H), 6.79 (d, 2H), 6.61-6.52 (m, 2H), 4.86 (s, 1H), 4.81-4.69 (m, 1H), 4.27 (d, 2H), 4.23 (s, 2H), 3.72 (s, 3H), 3.68 (d, 2H), 3.57 (d, 2H), 2.94-2.80 (m, 2H), 2.76 (s, 3H), 2.15 (q, 2H), 2.09-1.97 (m, 1H), 1.89 (d, 2H), 1.01 (d, 6H); LCMS: 458.3 [M+H]$^+$.

Example 92: 5-fluoro-2-{[1-(1-methylpiperidin-4-yl)({[4-(2-methylpropoxy)-phenyl]methyl}carbamoyl)amino]methyl}phenyl acetate; trifluoroacetic acid (92)

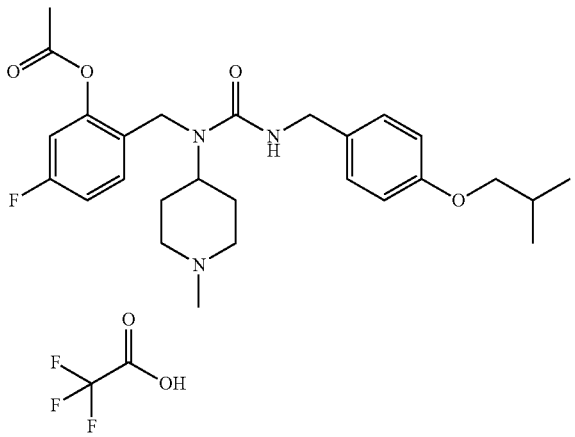

5-fluoro-2-{[1-(1-methylpiperidin-4-yl)({[4-(2-methylpropoxy)phenyl]methyl}carbamoyl)amino]methyl}phenyl acetate; trifluoroacetic acid Acetic anhydride (15 mg, 147 μmol) was added to 1-[(4-fluoro-2-hydroxyphenyl)methyl]-1-(1-methylpiperidin-4-yl)-3-{[4-(2-methylpropoxy)phenyl]methyl}urea (42.4 mg, 95.6 μmol) in dichloromethane (1 ml). After 20 hours of stirring at room temperature NaOH (2 ml, 1 M aqueous) was added and the mixture extracted with dichloromethane (3×2 ml). The combined organic phases were dried using a phase separator and concentrated. The crude material was purified by preparative HPLC, eluting with 30-60% acetonitrile in water (containing 0.1% trifluoroacetic acid) to afford the title compound (7 mg, 15%): $^1$H NMR (400 MHz, Chloroform-d) δ 12.55 (bs, 1H), 7.14 (dd, 1H), 6.98 (d, 2H), 6.86 (ddd, 2H), 6.76 (d, 2H), 5.04 (t, 1H), 4.83-4.70 (m, 1H), 4.24 (d, 2H), 4.18 (s, 2H), 3.67 (d, 2H), 3.56 (d, 2H), 2.91-2.80 (m, 2H), 2.77 (s, 3H), 2.35 (s, 3H), 2.30-2.15 (m, 2H), 2.13-1.98 (m, 1H), 1.91 (d, 2H), 1.01 (d, 6H); LCMS: 486.4 [M+H]$^+$.

Example 93: 1-[(2,4-difluorophenyl)methyl]-3-[(1H-indazol-5-yl)methyl]-1-(1-methylpiperidin-4-yl)urea; trifluoroacetic acid (93)

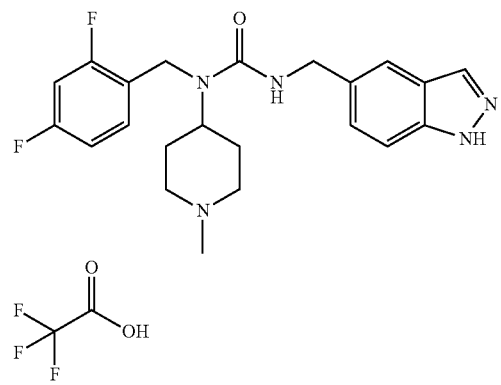

To tert-butyl 4-[(chlorocarbonyl)[(2,4-difluorophenyl)methyl]amino]piperidine-1-carboxylate (50 mg, 129 μmol) and diisopropylethylamine (33.6 μl, 193 μmol) in dichloromethane 1 ml was added (1H-indazol-5-yl)methanamine. The mixture was sonicated for 2 hours and then the crude product collected by filtration. To the crude TFA 500 μl in 1 ml THF was added and the reaction was heated to 60° C. for 1.5 hours. The mixture was concentrated and then suspended in methanol filtered and concentrated. This material, formaldehyde (11.5 μl, 155 mol) and sodium triacetoxyborohydride (54.7 mg, 258 μmol) were stirred in tetrahydrofuran (1.0 ml) for 2 hours, more formaldehyde (17.3 μl, 233 μmol) and sodium triacetoxyborohydride (109 mg, 516 μmol) were added and the reaction stirred for 1 hour. Ammonia (27% aqueous, 1 ml) was added and the reaction was stirred overnight. The reaction was concentrated and the crude material purified by HPLC, eluting with 10-40% acetonitrile in water (containing 0.1% trifluoroacetic acid). Yield: 9% from carbamoyl chloride. $^1$H NMR (400 MHz, Methanol-d4) δ 7.97 (s, 1H), 7.60 (s, 1H), 7.47 (d, 1H), 7.32 (d, 1H), 7.22 (q, 1H), 6.99-6.90 (m, 1H), 6.87 (t, 1H), 4.53 (s, 2H), 4.46 (s, 2H), 4.40-4.26 (m, 1H), 3.50 (d, 2H), 3.15-3.00 (m, 2H), 2.82 (s, 3H), 2.09-1.85 (m, 4H); LCMS: 414.3 [M+H]$^+$.

Example 94: 1-[(2,4-difluorophenyl)methyl]-3-({4-[(1R)-1,2-dihydroxyethyl]phenyl}methyl)-1-(1-methylpiperidin-4-yl)urea; trifluoroacetic acid and 1-[(2,4-difluorophenyl)methyl]-3-({4-[(1 S)-1,2-dihydroxyethyl]phenyl}methyl)-1-(1-methylpiperidin-4-yl)urea; trifluoroacetic acid (94)

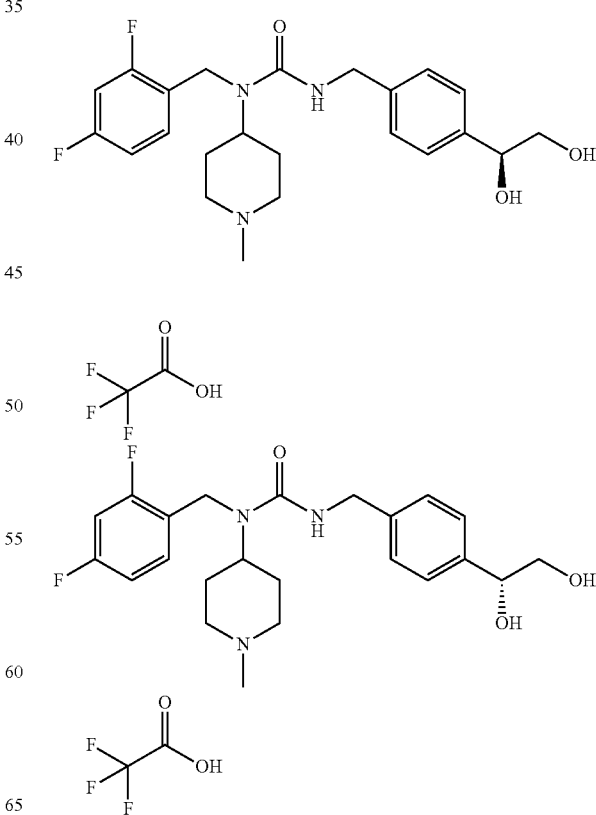

1-[(2,4-difluorophenyl)methyl]-3-[(4-ethenylphenyl)methyl]-1-(1-methylpiperidin-4-yl)urea

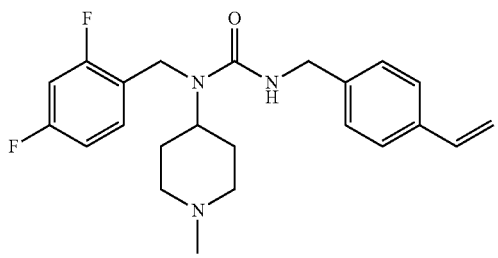 [SMILES: C=Cc1ccc(CNC(=O)N(Cc2ccc(F)cc2F)C2CCN(C)CC2)cc1]

The compounds were prepared in analogy with GP A using (4-ethenylphenyl)methanamine and N-[(2,4-difluorophenyl)methyl]-1-methylpiperidin-4-amine (1:1.2).

1-[(2,4-difluorophenyl)methyl]-3-({4-[(1R)-1,2-dihydroxyethyl]phenyl}methyl)-1-(1-methylpiperidin-4-yl)urea; trifluoroacetic acid and 1-[(2,4-difluorophenyl)methyl]-3-({4-[(1S)-1,2-dihydroxyethyl]phenyl}methyl)-1-(1-methylpiperidin-4-yl)urea; trifluoroacetic acid 1-[(2,4-difluorophenyl)methyl]-3-[(4-ethenylphenyl)methyl]-1-(1-methylpiperidin-4-yl)urea (39.9 mg, 100 µmol) in acetone (4 ml) was added to potassium osmate(VI) dihydrate (1.8 mg, 5 µmol) and N-methylmorpholine N-oxide (50% aqueous, 51.8 µl, 250 µl) in water (2 ml). After 21 hours of stirring at ambient temperature the reaction was quenched with sodium thiosulfate (aqueous) and filtered through a plug of celite. The acetone was removed under reduced pressure and the resulting mixture was diluted with sodium hydroxide (aqueous, 1M, 1 ml). The product was extracted with dichloromethane (3×1 ml), dried (phase separator) and concentrated. The crude material was purified by HPLC, eluting with 10-40% acetonitrile in water (containing 0.1% trifluoroacetic acid). The compounds were isolated as a racemic mixture. Yield: 43.1 mg, 79%. $^1$H NMR (400 MHz, Methanol-d4) δ 7.30 (d, 2H), 7.27-7.18 (m, 3H), 7.01-6.87 (m, 2H), 4.66 (dd, 1H), 4.52 (s, 2H), 4.39-4.24 (m, 3H), 3.63-3.54 (m, 2H), 3.51 (d, 2H), 3.14-3.02 (m, 2H), 2.83 (s, 3H), 2.09-1.83 (m, 4H); LCMS: 434.3 [M+H]$^+$.

Example 95: 1-[(2,4-difluorophenyl)methyl]-3-[(1,3-dihydro-2-benzofuran-5-yl)methyl]-1-(1-methylpiperidin-4-yl)urea; trifluoroacetic acid (95)

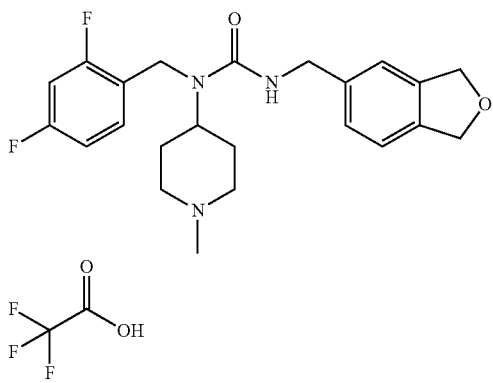

(1,3-dihydro-2-benzofuran-5-yl)methanamine

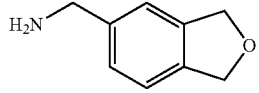

Oxalyl chloride (56.7 µl, 660 µmol) and dimethylformamide (2.3 µl, 30 µmol) were added to 1,3-dihydro-2-benzofuran-5-carboxylic acid (98.5 mg, 600 µmol) in dichloromethane (2 ml). After 40 minutes of stirring at ambient temperature, ammonia (27% aqueous, 1.02 ml, 54 mmol) was added and the resulting two-phase system was stirred vigorously for 30 minutes before it filtered through a plug of celite. The phases were separated and the aqueous phase was extracted with dichloromethane (2 ml). The combined organic phase was dried (phase separator) and concentrated. Borane (1M in tetrahydrofuran, 2.4 ml, 2.4 mmol) was added and the mixture was stirred for 14 hours at ambient temperature before it was heated to 50° C. After 7 hours, more borane (1M in tetrahydrofuran, 1.2 ml, 1.2 mmol) was added and the reaction was stirred for additionally 17 hours before it was quenched with methanol and concentrated. Sodium hydroxide (aqueous, 1M, 10 ml) was added. The product was extracted with dichloromethane (3×10 ml), dried (phase separator) and concentrated. The crude was dissolved in dichloromethane (10 ml) and extracted with hydrochloric acid (1M, aqueous, 10 ml). The aqueous phase was made basic using sodium hydroxide (5M) and extracted with dichloromethane (3×10 ml). The organic phase was dried (phase separator) and concentrated to give the desired benzyl amine (27.4 mg, 31%).

1-[(2,4-difluorophenyl)methyl]-3-[(1,3-dihydro-2-benzofuran-5-yl)methyl]-1-(1-methylpiperidin-4-yl)urea; trifluoroacetic acid was prepared in analogy with GP C using (1,3-dihydro-2-benzofuran-5-yl)methanamine and N-[(2,4-difluorophenyl)methyl]-1-methylpiperidin-4-amine (1:1.5). Yield: 69%. $^1$H NMR (400 MHz, Chloroform-d) δ 12.64 (bs, 1H), 7.21-7.07 (m, 2H), 7.02 (d, 1H), 6.99 (s, 1H), 6.83 (t, 2H), 5.05 (d, 4H), 4.84 (s, 1H), 4.71 (tt, 1H), 4.44-4.32 (m, 4H), 3.60 (d, 2H), 2.94-2.70 (m, 5H), 2.20 (qd, 2H), 1.91 (d, 2H); LCMS: 415.9 [M+H]$^+$.

Example 96: 1-[(2,4-difluorophenyl)methyl]-3-{[4-(3-methoxypropoxy)phenyl]methyl}-1-(1-methylpiperidin-4-yl)urea; trifluoroacetic acid (96)

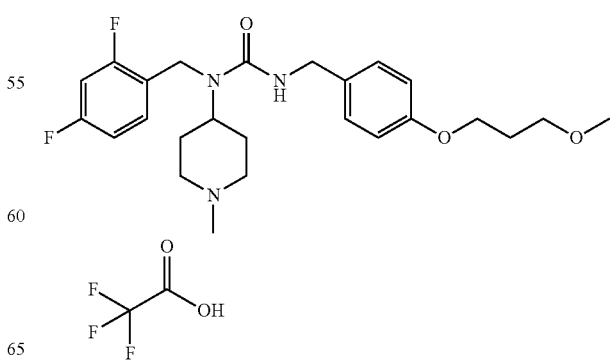

The compound was prepared in analogy with example 15 (1-[(2,4-difluorophenyl)methyl]-3-{[4-(2-fluoroethoxy)phenyl]methyl}-1-(1-methylpiperidin-4-yl)urea) using 3-methoxypropan-1-ol. Yield: 35%. $^1$H NMR (400 MHz, Chloroform-d) δ 12.62 (bs, 1H), 7.12 (q, 1H), 7.03 (d, 2H), 6.86-6.77 (m, 4H), 4.79-4.62 (m, 2H), 4.36 (s, 2H), 4.29 (s, 2H), 4.03 (t, 2H), 3.60 (d, 2H), 3.55 (t, 2H), 3.36 (s, 3H), 2.94-2.80 (m, 2H), 2.79 (s, 3H), 2.28-2.10 (m, 2H), 2.04 (p, 2H), 1.91 (d, 2H); LCMS: 462.3 [M+H]$^+$.

Example 97: 1-[(2,4-difluorophenyl)methyl]-3-[(2-fluoro-4-nitrophenyl)methyl]-1-(1-methylpiperidin-4-yl)urea; trifluoroacetic acid (97)

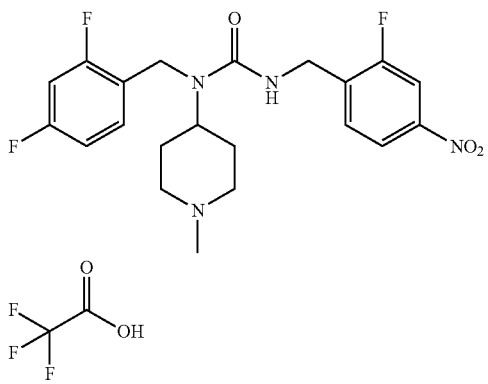

The compounds were prepared in analogy with GP A using (2-fluoro-4-nitrophenyl)methanamine hydrochloride and N-[(2,4-difluorophenyl)methyl]-1-methylpiperidin-4-amine (1:1). Yield: 75%. $^1$H NMR (400 MHz, Chloroform-d) δ 12.36 (bs, 1H), 7.98 (dd, 1H), 7.88 (dd, 1H), 7.46-7.37 (m, 1H), 7.18-7.08 (m, 1H), 6.92-6.82 (m, 2H), 5.14-5.08 (m, 1H), 4.63 (ddd, 1H), 4.47 (d, 2H), 4.42 (s, 2H), 3.61 (d, 2H), 2.94-2.75 (m, 5H), 2.36-2.15 (m, 2H), 1.90 (d, 2H); LCMS: 437.3 [M+H]$^+$.

Example 98: 3-[(4-chloro-3-methoxyphenyl)methyl]-1-[(2,4-difluorophenyl)methyl]-1-(1-methylpiperidin-4-yl)urea; trifluoroacetic acid (98)

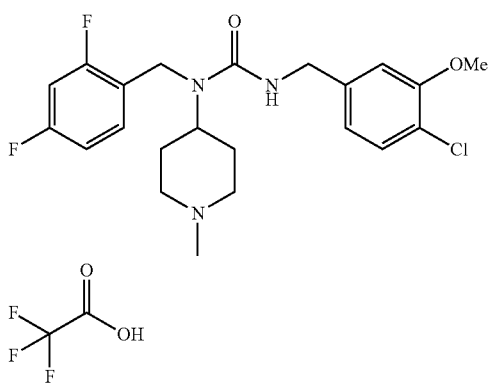

The compounds were prepared in analogy with GP A using (4-chloro-3-methoxyphenyl)methanamine and N-[(2,4-difluorophenyl)methyl]-1-methylpiperidin-4-amine (1:1) Yield: 69%. $^1$H NMR (400 MHz, Chloroform-d) δ 12.22 (s, 1H), 7.29-7.22 (m, 1H), 7.22-7.11 (m, 1H), 6.93-6.79 (m, 2H), 6.73 (s, 1H), 6.64 (d, 1H), 4.88 (s, 1H), 4.79-4.64 (m, 1H), 4.44 (s, 2H), 4.33 (d, 2H), 3.85 (s, 3H), 3.58 (d, 2H), 2.93-2.87 (m, 2H), 2.80 (d, 3H), 2.43 (q, 2H), 1.92 (d, 2H); LCMS: 438.3 [M+H]$^+$.

Example 99: 1-[(2,4-difluorophenyl)methyl]-3-{[4-fluoro-2-(trifluoromethoxy)phenyl]methyl}-1-(1-methylpiperidin-4-yl)urea; trifluoroacetic acid (99)

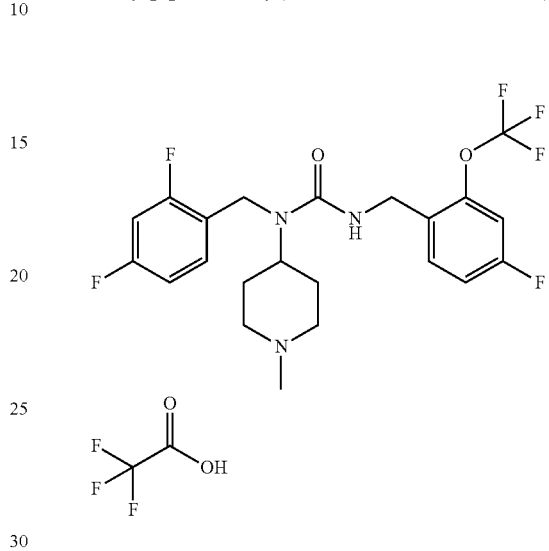

The compounds were prepared in analogy with GP A using N-[(2,4-difluorophenyl)methyl]-1-methylpiperidin-4-amine and [4-fluoro-2-(trifluoromethoxy)phenyl]methanamine (1:1). Yield: 70%. $^1$H NMR (400 MHz, Chloroform-d) δ 12.19 (bs, 1H), 7.32-7.23 (m, 1H), 7.16-7.05 (m, 1H), 7.00-6.91 (m, 2H), 6.90-6.79 (m, 2H), 4.85 (s, 1H), 4.78-4.67 (m, 1H), 4.40 (s, 2H), 4.36 (d, 2H), 3.59 (d, 2H), 2.96-2.82 (m, 2H), 2.80 (s, 3H), 2.47-2.30 (m, 2H), 1.92 (d, 2H); LCMS: 476.2 [M+H]$^+$.

Example 100: 3-[(2,4-difluorophenyl)methyl]-1-[(4-fluorophenyl)methyl]-1-(1-methylpiperidin-4-yl)urea; trifluoroacetic acid (100)

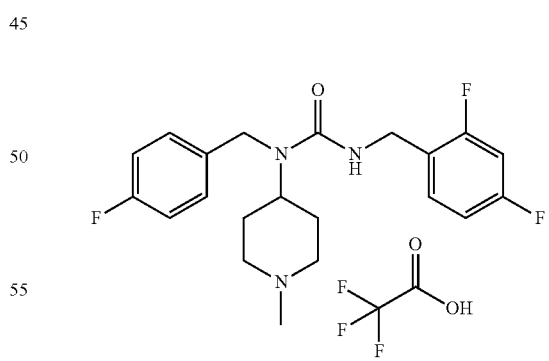

The compounds were prepared in analogy with GP A using (2,4-difluorophenyl)methanamine and N-[(4-fluorophenyl)methyl]-1-methylpiperidin-4-amine (1:1). Yield: 57%. $^1$H NMR (400 MHz, Chloroform-d) δ 12.50 (bs, 1H), 7.21-7.10 (m, 3H), 7.02 (t, 2H), 6.79 (td, 1H), 6.73 (ddd, 1H), 4.79 (t, 1H), 4.73 (ddd, 1H), 4.37 (s, 2H), 4.32 (d, 2H), 3.58 (d, 2H), 2.93-2.73 (m, 5H), 2.36-2.18 (m, 2H), 1.90 (d, 2H); LCMS: 392.3 [M+H]$^+$.

Example 101: 1-{[2-(difluoromethoxy)-4-fluorophenyl]methyl}-1-(1-methylpiperidin-4-yl)-3-{[4-(2-methylpropoxy)phenyl]methyl}urea; trifluoroacetic acid (101

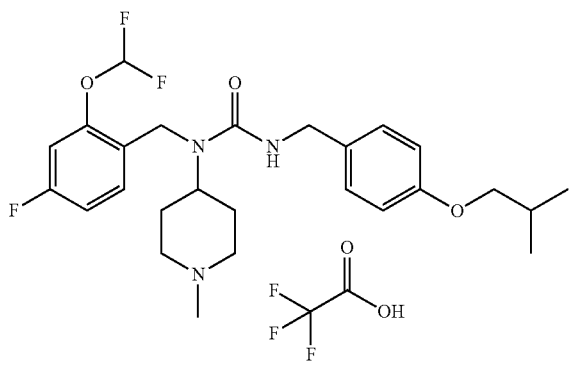

tert-butyl 4-{[(4-fluoro-2-hydroxyphenyl)methyl]({[4-(2-methylpropoxy)phenyl]methyl}carbamoyl)amino}piperidine-1-carboxylate

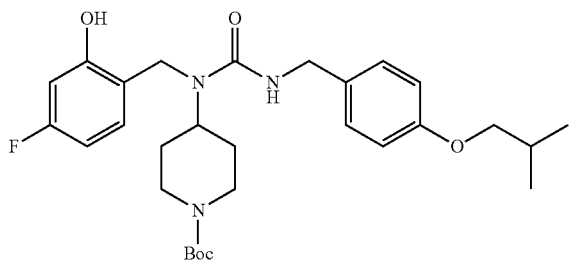 [SMILES: CC(C)COc1ccc(CNC(=O)N(Cc2ccc(F)cc2O)C2CCN(C(=O)OC(C)(C)C)CC2)cc1]

The compound was prepared in analogy with example 13 (1-[(4-fluoro-2-hydroxyphenyl)methyl]-1-(1-methylpiperidin-4-yl)-3-{[4-(2-methylpropoxy)phenyl]methyl}urea) using tert-butyl 4-oxopiperidine-1-carboxylate.

1-{[2-(difluoromethoxy)-4-fluorophenyl]methyl}-1-(1-methylpiperidin-4-yl)-3-{[4-(2-methylpropoxy)phenyl]methyl}urea; trifluoroacetic acid Sodium chlorodifluoroacetate (76.2 mg, 500 μmol), tert-butyl 4-{[(4-fluoro-2-hydroxyphenyl)methyl]({[4-(2-methylpropoxy)phenyl]methyl}carbamoyl)amino}piperidine-1-carboxylate (106 mg, 200 μmol) and cesium carbonate (130 mg, 400 μmol) were suspended in water (200 μl) and dimethylformamide (2 ml). The mixture was heated to 80° C. for 5 hours before it was cooled to ambient temperature, diluted with ethyl acetate (20 ml), washed with water (5×20 ml), dried (phase separator) and concentrated. The crude was dissolved in dichloromethane (1 ml) and 1-(isocyanatomethyl)-4-(2-methylpropoxy)benzene (41 mg, 200 mol) was added. After 1 hour, the mixture was concentrated and the crude was purified by silica gel chromatography, eluting with 25-100% ethyl acetate in petroleum ether. Fractions containing product were pooled and concentrated. The material was dissolved in dichloro-methane (1.5 ml) and trifluoroacetic acid (0.5 ml) was added. After 15 minutes the mixture was concentrated and redissolved in tetrahydrofuran (2 ml). Formaldehyde (37% aqueous, 29.8 μl, 400 μmol) and sodium triacetoxyborohydride (84.8 mg, 400 μl) were added. After 1 hour the mixture was diluted with sodium hydroxide (aqueous, 1M, 1 ml) and extracted with dichloromethane (3×1 ml). The organic phase was dried (phase separator) and concentrated. The crude material was purified by HPLC, eluting with 30-70% acetonitrile in water (containing 0.1% trifluoroacetic acid). Yield: 32 mg, 26%. $^1$H NMR (400 MHz, Chloroform-d) δ 12.50 (bs, 1H), 7.15 (t, 1H), 7.03 (d, 2H), 6.96-6.83 (m, 2H), 6.80 (d, 2H), 6.59 (t, 1H), 4.77 (t, 1H), 4.67 (s, 1H), 4.37 (s, 2H), 4.29 (s, 2H), 3.69 (d, 2H), 3.58 (d, 2H), 2.93-2.80 (m, 2H), 2.78 (s, 3H), 2.21 (q, 2H), 2.07 (dt, 1H), 1.90 (d, 2H), 1.02 (d, 6H); LCMS: 494.3 [M+H]$^+$.

Example 102: 1-{[4-chloro-2-(trifluoromethyl)phenyl]methyl}-1-(1-methylpiperidin-4-yl)-3-{[4-(2-methylpropoxy)phenyl]methyl}urea; trifluoroacetic acid (102)

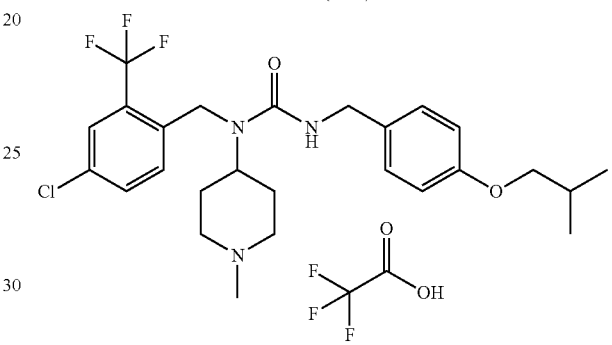

The compounds were prepared in analogy with GP B using N-{[4-chloro-2-(trifluoromethyl)phenyl]methyl}-1-methylpiperidin-4-amine (prepared in analogy with intermediate 6 (N-[(2,4-difluorophenyl)methyl]-1-methylpiperidin-4-amine) using [4-chloro-2-(trifluoromethyl)phenyl]methanamine) and 1-(isocyanatomethyl)-4-(2-methylpropoxy)benzene. Yield: 91%. $^1$H NMR (400 MHz, Chloroform-d) δ 13.09 (bs, 1H), 7.66 (s, 1H), 7.44 (d, 1H), 7.32 (d, 1H), 7.00 (d, 2H), 6.79 (d, 2H), 4.74 (t, 1H), 4.58-4.43 (m, 3H), 4.27 (d, 2H), 3.69 (d, 2H), 3.59 (d, 2H), 2.83 (t, 2H), 2.77 (s, 3H), 2.16 (q, 2H), 2.13-1.99 (m, 1H), 1.91 (d, 2H), 1.02 (d, 6H); LCMS: 512.3 [M+H]$^+$.

Example 103: 1-{[4-fluoro-2-(trifluoromethoxy)phenyl]methyl}-1-(1-methylpiperidin-4-yl)-3-{[4-(2-methylpropoxy)phenyl]methyl}urea; trifluoroacetic acid (103)

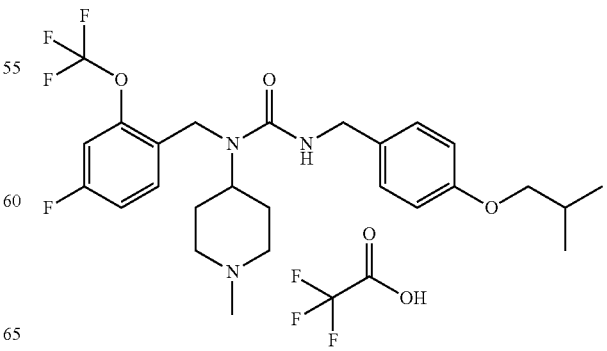

The compounds were prepared in analogy with GP B using N-{[4-fluoro-2-(trifluoromethoxy)phenyl]methyl}-1-methylpiperidin-4-amine (prepared in analogy with intermediate 6 using [4-fluoro-2-(trifluoromethoxy)phenyl]methanamine) and 1-(isocyanatomethyl)-4-(2-methylpropoxy)benzene. Yield: 85%. ¹H NMR (400 MHz, Chloroform-d) δ 13.09 (bs, 1H), 7.25-7.16 (m, 1H), 7.07-6.99 (m, 3H), 6.96 (t, 1H), 6.79 (d, 2H), 4.74 (t, 1H), 4.55 (s, 1H), 4.36 (s, 2H), 4.28 (d, 2H), 3.69 (d, 2H), 3.59 (d, 2H), 2.83 (t, 2H), 2.77 (s, 3H), 2.17 (q, 2H), 2.12-1.99 (m, 1H), 1.91 (d, 2H), 1.02 (d, 6H); LCMS: 512.3 [M+H]⁺.

Example 104: 1-[(4-fluoro-2-methylphenyl)methyl]-1-(1-methylpiperidin-4-yl)-3-{[4-(2-methylpropoxy)phenyl]methyl}urea; trifluoroacetic acid (104)

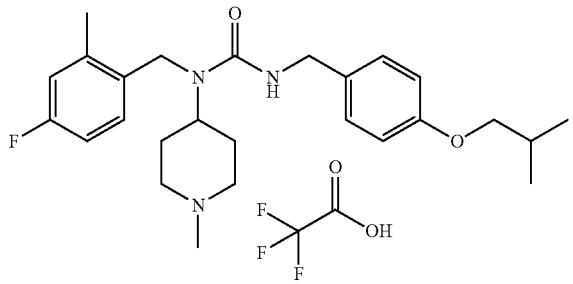

The compounds were prepared in analogy with GP B using N-[(4-fluoro-2-methylphenyl)methyl]-1-methylpiperidin-4-amine (prepared in analogy with intermediate 6 using (4-fluoro-2-methylphenyl)methanamine) and 1-(isocyanatomethyl)-4-(2-methylpropoxy)benzene. Yield: 76%. ¹H NMR (400 MHz, Chloroform-d) δ 12.59 (bs, 1H), 7.10-7.00 (m, 3H), 6.90 (d, 1H), 6.87-6.76 (m, 3H), 4.78 (t, 1H), 4.60 (s, 1H), 4.28 (d, 2H), 4.25 (s, 2H), 3.68 (d, 2H), 3.55 (d, 2H), 2.92-2.81 (m, 2H), 2.78 (s, 3H), 2.28 (s, 3H), 2.18 (q, 2H), 2.12-1.98 (m, 1H), 1.91 (d, 2H), 1.01 (d, 6H); LCMS: 442.3 [M+H]⁺.

Example 105: 1-[(2-chloro-4-methoxyphenyl)methyl]-1-(1-methylpiperidin-4-yl)-3-{[4-(2-methylpropoxy)phenyl]methyl}urea; trifluoroacetic acid (105)

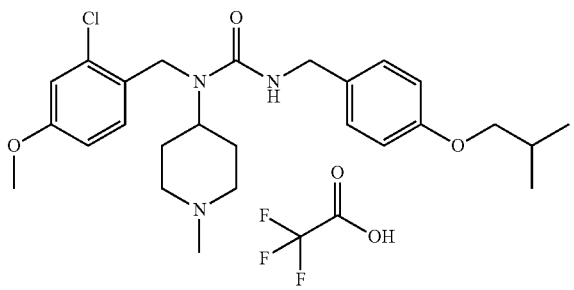

The compounds were prepared in analogy with GP B using N-[(2-chloro-4-methoxyphenyl)methyl]-1-methylpiperidin-4-amine (prepared in analogy with intermediate 6 using (2-chloro-4-methoxyphenyl)methanamine) and 1-(isocyanatomethyl)-4-(2-methylpropoxy)benzene. Yield: 78%. ¹H NMR (400 MHz, Chloroform-d) δ 13.05 (bs, 1H), 7.09-7.00 (m, 3H), 6.92 (s, 1H), 6.79 (d, 2H), 6.74 (d, 1H), 4.74 (t, 1H), 4.69-4.57 (m, 1H), 4.33 (s, 2H), 4.28 (d, 2H), 3.79 (s, 3H), 3.68 (d, 2H), 3.58 (d, 2H), 2.88-2.80 (m, 2H), 2.77 (s, 3H), 2.23-2.10 (m, 2H), 2.12-1.99 (m, 1H), 1.91 (d, 2H), 1.01 (d, 6H); LCMS: 474.3 [M+H]⁺.

Example 106: 1-[(2,4-dichlorophenyl)methyl]-1-(1-methylpiperidin-4-yl)-3-{[4-(propan-2-yloxy)phenyl]methyl}urea; trifluoroacetic acid (106)

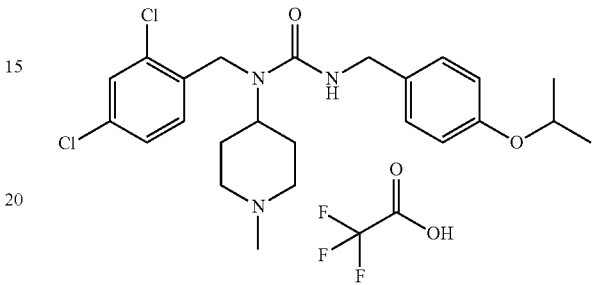

The compounds were prepared in analogy with GP B using N-[(2,4-dichlorophenyl)methyl]-1-methylpiperidin-4-amine (prepared in analogy with intermediate 6 using (2,4-dichlorophenyl)methanamine) and 1-(isocyanatomethyl)-4-(propan-2-yloxy)benzene. Yield: 78%. ¹H NMR (400 MHz, Chloroform-d) δ 12.28 (bs, 1H), 7.41 (d, 1H), 7.20 (dd, 1H), 7.10 (d, 1H), 7.02 (d, 2H), 6.79 (d, 2H), 4.77 (ddd, 1H), 4.64-4.55 (m, 1H), 4.57-4.44 (m, 1H), 4.36 (s, 2H), 4.29 (d, 2H), 3.61 (d, 2H), 2.95-2.82 (m, 2H), 2.80 (s, 3H), 2.25-2.08 (m, 2H), 1.92 (d, 2H), 1.32 (d, 6H); LCMS: 463.9 [M+H]⁺.

Example 107: 1-[(2,4-dichlorophenyl)methyl]-1-(1-methylpiperidin-4-yl)-3-{[4-(2-methylpropoxy)phenyl]methyl}urea (107)

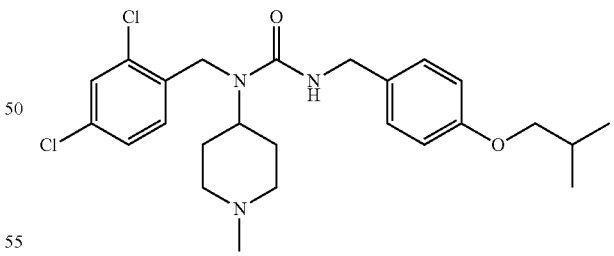

The compounds were prepared in analogy with GP B using N-[(2,4-dichlorophenyl)methyl]-1-methylpiperidin-4-amine (prepared in analogy with intermediate 6 using (2,4-dichlorophenyl)methanamine) and 1-(isocyanatomethyl)-4-(2-methylpropoxy)benzene. Yield: 68%. ¹H NMR (400 MHz, Chloroform-d) δ 7.36 (s, 1H), 7.18 (s, 2H), 7.09 (d, 2H), 6.84-6.77 (m, 2H), 4.49-4.41 (m, 1H), 4.41-4.33 (m, 3H), 4.31 (d, 2H), 3.69 (d, 2H), 2.91 (d, 2H), 2.30 (s, 3H), 2.23-1.96 (m, 3H), 1.78-1.61 (m, 4H), 1.02 (d, J=6.7 Hz, 6H); LCMS: 478.0 [M+H]⁺.

Example 108: 1-[(2,4-dichlorophenyl)methyl]-1-(piperidin-4-yl)-3-{[4-(propan-2-yloxy)phenyl]methyl}urea; trifluoroacetic acid (108)

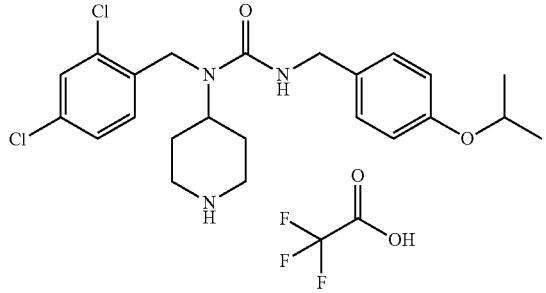

The compounds were prepared in analogy with example 4 (1-[(2,4-difluorophenyl)methyl]-3-{[4-(2-methylpropoxy)phenyl]methyl}-1-(piperidin-4-yl)urea) using N-[(2,4-dichlorophenyl)methyl]-1-methylpiperidin-4-amine (prepared in analogy with intermediate 6 using (2,4-dichlorophenyl)methanamine) and 1-(isocyanatomethyl)-4-(propan-2-yloxy)benzene. Yield: 61%. ¹H NMR (400 MHz, Chloroform-d) δ 9.48 (bs, 1H), 9.03 (bs, 1H), 7.40 (d, 1H), 7.20 (dd, 1H), 7.13 (d, 1H), 7.03 (d, 2H), 6.79 (d, 2H), 4.75-4.60 (m, 1H), 4.52 (dq, 2H), 4.36 (s, 2H), 4.28 (s, 2H), 3.41 (d, 2H), 3.06-2.87 (m, 2H), 2.04-1.87 (m, 4H), 1.32 (d, 6H); LCMS: 450.2 [M+H]⁺.

Example 109: 1-[(2-chloro-4-fluorophenyl)methyl]-3-{[4-(2-methylpropoxy)phenyl]methyl}-1-(piperidin-4-yl)urea; trifluoroacetic acid (109)

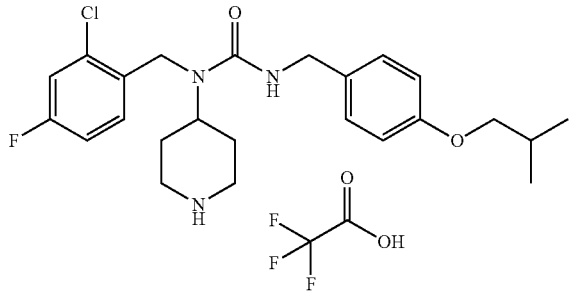

The compounds were prepared in analogy with example 4 (1-[(2,4-difluorophenyl)methyl]-3-{[4-(2-methylpropoxy)phenyl]methyl}-1-(piperidin-4-yl)urea) using N-[(2-chloro-4-fluorophenyl)methyl]-1-methylpiperidin-4-amine (prepared in analogy with intermediate 6 using (2-chloro-4-fluorophenyl)methanamine). Yield: 45%. ¹H NMR (400 MHz, Chloroform-d) δ 9.44 (bs, 1H), 9.08 (bs, 1H), 7.21-7.11 (m, 2H), 7.04 (d, 2H), 6.94 (td, 1H), 6.84-6.76 (m, 2H), 4.80-4.63 (m, 1H), 4.60-4.45 (m, 1H), 4.36 (s, 2H), 4.29 (s, 2H), 3.69 (d, 2H), 3.54-3.38 (m, 2H), 3.10-2.92 (m, 2H), 2.07 (dt, 1H), 2.04-1.73 (m, 4H), 1.02 (d, 6H); LCMS: 448.3 [M+H]⁺.

Example 110: 1-[(2-chloro-4-fluorophenyl)methyl]-1-(piperidin-4-yl)-3-{[4-(propan-2-yloxy)phenyl]methyl}urea; trifluoroacetic acid (110)

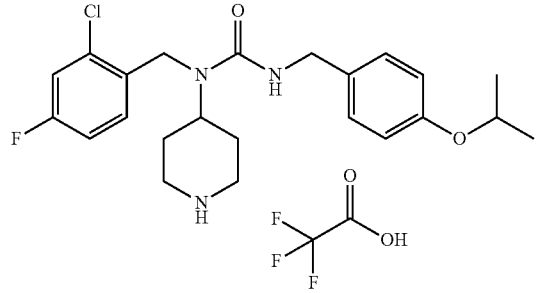

The compounds were prepared in analogy with example 4 (1-[(2,4-difluorophenyl)methyl]-3-{[4-(2-methylpropoxy)phenyl]methyl}-1-(piperidin-4-yl)urea) using N-[(2-chloro-4-fluorophenyl)methyl]-1-methylpiperidin-4-amine (prepared in analogy with intermediate 6 using (2-chloro-4-fluorophenyl)methanamine) and 1-(isocyanatomethyl)-4-(propan-2-yloxy)benzene. Yield: 60%. ¹H NMR (400 MHz, Chloroform-d) δ 9.57 (bs, 1H), 9.10 (bs, 1H), 7.22-7.10 (m, 2H), 7.03 (d, 2H), 6.94 (td, 1H), 6.79 (d, 2H), 4.76-4.61 (m, 1H), 4.59-4.44 (m, 2H), 4.36 (s, 2H), 4.28 (s, 2H), 3.42 (d, 2H), 3.02-2.85 (m, 2H), 2.07-1.84 (m, 4H), 1.32 (d, 6H); LCMS: 434.3 [M+H]⁺.

Example 111: 1-[(2,4-dichlorophenyl)methyl]-3-{[4-(2-methylpropoxy)phenyl]methyl}-1-(piperidin-4-yl)urea; trifluoroacetic acid (111)

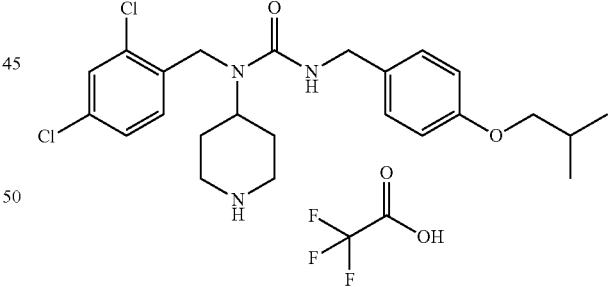

The compounds were prepared in analogy with example 4 (1-[(2,4-difluorophenyl)methyl]-3-{[4-(2-methylpropoxy)phenyl]methyl}-1-(piperidin-4-yl)urea) using N-[(2,4-dichlorophenyl)methyl]-1-methylpiperidin-4-amine (prepared in analogy with intermediate 6 using (2,4-dichlorophenyl)methanamine). Yield: 40%. ¹H NMR (400 MHz, Chloroform-d) δ 9.51 (bs, 1H), 9.11 (bs, 1H), 7.40 (d, 1H), 7.20 (dd, 1H), 7.13 (d, 1H), 7.09-7.00 (m, 2H), 6.84-6.77 (m, 2H), 4.75-4.62 (m, 1H), 4.57-4.44 (m, 1H), 4.36 (s, 2H), 4.28 (s, 2H), 3.69 (d, 2H), 3.54-3.35 (m, 2H), 3.10-2.90 (m, 2H), 2.07 (dt, 1H), 2.00-1.73 (m, 4H), 1.02 (d, 6H); LCMS: 464.2 [M+H]⁺.

Example 112 (Comparative): 1-[(2,6-difluoro-3-methylphenyl)methyl]-1-(1-methylpiperidin-4-yl)-3-{[4-(propan-2-yloxy)phenyl]methyl}urea; trifluoroacetic acid (112)

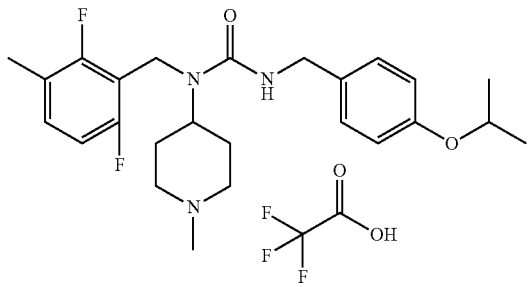

The compounds were prepared in analogy with GP B using N-[(2,6-difluoro-3-methylphenyl)methyl]-1-methylpiperidin-4-amine (prepared in analogy with intermediate 6 (N-[(2,4-difluorophenyl)methyl]-1-methylpiperidin-4-amine) using (2,6-difluoro-3-methylphenyl)methanamine) and 1-(isocyanatomethyl)-4-(propan-2-yloxy)benzene. Yield: 57%. $^1$H NMR (400 MHz, Chloroform-d) δ 12.45 (bs, 1H), 7.19-7.06 (m, 1H), 7.04 (d, 2H), 6.88-6.71 (m, 3H), 5.06 (s, 1H), 4.62-4.46 (m, 2H), 4.38 (s, 2H), 4.28 (s, 2H), 3.62 (d, 2H), 2.90-2.70 (m, 5H), 2.31 (qd, 2H), 2.16 (s, 3H), 1.94 (d, 2H), 1.32 (d, 6H); LCMS: 446.3 [M+H]$^+$.

Example 113 (comparative): 1-(1-methylpiperidin-4-yl)-3-{[4-(propan-2-yloxy)phenyl]methyl}-1-[(2,3,6-trifluorophenyl)methyl]urea; trifluoroacetic acid (113)

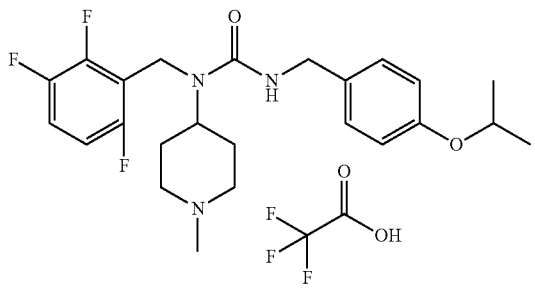

The compounds were prepared in analogy with GP B using 1-methyl-N-[(2,3,6-trifluorophenyl)methyl]piperidin-4-amine (prepared in analogy with intermediate 6 (N-[(2,4-difluorophenyl)methyl]-1-methylpiperidin-4-amine) using (2,3,6-trifluorophenyl)methanamine) and 1-(isocyanatomethyl)-4-(propan-2-yloxy)benzene. Yield: 58%. $^1$H NMR (400 MHz, Chloroform-d) δ 12.69 (bs, 1H), 7.23-7.09 (m, 1H), 7.06 (d, 2H), 6.89-6.76 (m, 3H), 4.91 (s, 1H), 4.65-4.48 (m, 2H), 4.45 (s, 2H), 4.30 (s, 2H), 3.62 (d, 2H), 2.90-2.75 (m, 5H), 2.47-2.27 (m, 2H), 1.96 (d, 2H), 1.33 (d, 6H); LCMS: 450.3 [M+H]$^+$.

Example 114: 1-[(2,4-difluoro-3-methylphenyl)methyl]-1-(1-methylpiperidin-4-yl)-3-{[4-(propan-2-yloxy)phenyl]methyl}urea; trifluoroacetic acid (114)

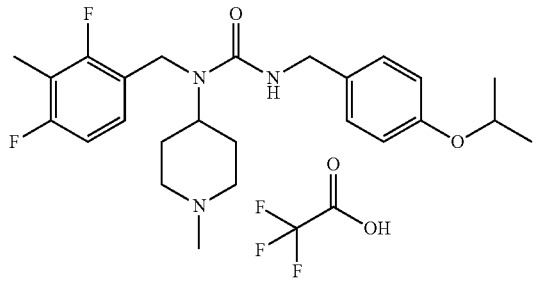

The compounds were prepared in analogy with GP B using N-[(2,4-difluoro-3-methylphenyl)methyl]-1-methylpiperidin-4-amine (prepared in analogy with intermediate 6 using (2,4-difluoro-3-methylphenyl)methanamine) and 1-(isocyanatomethyl)-4-(propan-2-yloxy)benzene. Yield: 55%. $^1$H NMR (400 MHz, Chloroform-d) δ 12.39 (bs, 1H), 7.01 (d, 2H), 6.93 (q, 1H), 6.84-6.74 (m, 3H), 4.83-4.69 (m, 1H), 4.70-4.62 (m, 1H), 4.51 (hept, 1H), 4.35 (s, 2H), 4.28 (d, 2H), 3.61 (d, 2H), 2.95-2.75 (m, 5H), 2.28-2.11 (m, 5H), 1.92 (d, 2H), 1.32 (d, 6H); LCMS: 446.3 [M+H]$^+$.

Example 115: 1-[(2-fluoro-4-methylphenyl)methyl]-1-(1-methylpiperidin-4-yl)-3-{[4-(propan-2-yloxy)phenyl]methyl}urea; trifluoroacetic acid (115)

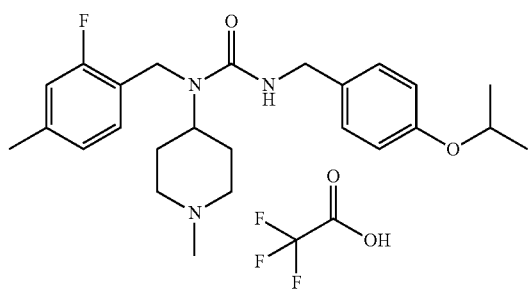

The compounds were prepared in analogy with GP B using N-[(2-fluoro-4-methylphenyl)methyl]-1-methylpiperidin-4-amine (prepared in analogy with intermediate 6 using (2-fluoro-4-methylphenyl)methanamine) and 1-(isocyanatomethyl)-4-(propan-2-yloxy)benzene. Yield: 59%. $^1$H NMR (400 MHz, Chloroform-d) δ 12.15 (bs, 1H), 7.06-6.97 (m, 3H), 6.92-6.83 (m, 2H), 6.82-6.74 (m, 2H), 4.85-4.70 (m, 2H), 4.53-4.47 (m, 1H), 4.36 (s, 2H), 4.28 (s, 2H), 3.62 (d, 2H), 2.95-2.76 (m, 5H), 2.33 (s, 3H), 2.27-2.10 (m, 2H), 1.94 (d, 2H), 1.32 (d, 6H); LCMS: 428.3 [M+H]$^+$.

Example 116: 1-[(2,4-difluorophenyl)methyl]-3-{[2-methyl-4-(propan-2-yloxy)phenyl]methyl}-1-(1-methylpiperidin-4-yl)urea; hemitartrate (116)

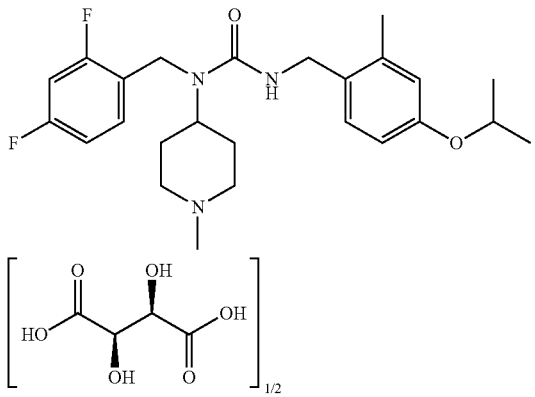

4-hydroxy-2-methyl-benzonitrile (1011 mg, 7.2 mmol), potassium carbonate (18.0 mmol, 2.49 g), tetrabutylammonium iodide (0.5 mmol, 190 mg), 2-iodopropane (18 mmol, 1.82 ml) and DMF (5.0 ml) were stirred at 70° C. for 3 hours and then partitioned between 0.5M NaOH and diethyl ether. The organic phase was washed with water several times, then dried and evaporated to afford the intermediate nitrile (1.34 g). This was reduced using lithium aluminiumhydride (14.4 mmol, 552 mg) in refluxing tetrahydrofuran (6 ml) for 1 hour, worked up and gave the intermediate benzyl amine (1.29 g, 7.2 mmol, 100% yield). This material was dissolved in dichloromethane (10 ml), pyridine (14.4 mmol, 1.20 ml) was added followed by phenyl chloroformate (9.4 mmol, 1.22 ml), dissolved in dichloromethane (4.0 ml) dropwise on an ice-bath and the mixture was stirred 30 min, then partitioned between dichloromethane and 1M HCl, the organic phase was separated, dried and evaporated to give phenyl N-{[2-methyl-4-(propan-2-yloxy)phenyl]methyl}carbamate (2.39 g, 100% yield) as an oil that slowly crystallizes.

N-[(2,4-difluorophenyl)methyl]-1-methylpiperidin-4-amine (2.24 mmol, 539 mg), phenyl N-{[2-methyl-4-(propan-2-yloxy)phenyl]methyl}carbamate (750 mg, 2.51 mmol) and potassium carbonate (4.5 mmol, 625 mg) were suspended in toluene (5.0 ml). The mixture was stirred at 70° C. for 20 hours, then partitioned between toluene and 0.5 M NaOH, the organic phase was separated, concentrated and the crude was purified by column chromatography using silicon dioxide gel, eluting with 5-50% methanol in ethyl acetate to afford pure fractions. These fractions were collected and evaporated and the residue was stirred 20 min in diethyl ether (10.0 ml) to precipitate any silica, the suspension was filtered, and the clear filtrate was evaporated to give the title compound as the free base (703 mg, 1.57 mmol, 70% yield). This material (667 mg, 1.497 mmol) and L-(+)-tartaric acid (0.7485 mmol, 113 mg) were dissolved in methanol (4 ml), the solvents were removed by evaporation and the residue was stirred in 2-propanol (4 ml) and treated in an ultrasonication bath. The solvent was removed, and the residue was treated in vacuum (0.5-1.0 mbar) for 20 hours and gave the title compound (840 mg, 100% yield): $^1$H NMR (400 MHz, Chloroform-d) δ 7.05 (m, 2H), 6.77 (m, 1H), 6.71 (m, 1H), 6.66 (d, 1H), 6.57 (s, 1H), 5.02 (t, 1H), 4.58 (m, 1H), 4.44-4.33 (m, 3H), 4.31 (s, 1H), 4.28 (d, 2H), 3.40 (t, 2H), 2.69-2.57 (m, 5H), 2.30 (s, 3H), 2.11 (m, 2H), 1.76 (d, 2H), 1.10 (d, 6H); LC-MS: 446.3 [M+H]$^+$.

Example 117: 1-[(4-cyclopropoxyphenyl)methyl]-3-[(2,4-difluorophenyl)methyl]-3-[(3S,4R)-3-fluoro-1-methylpiperidin-4-yl]urea and 1-[(4-cyclopropoxyphenyl)methyl]-3-[(2,4-difluorophenyl)methyl]-3-[(3R,4S)-3-fluoro-1-methylpiperidin-4-yl]urea (117)

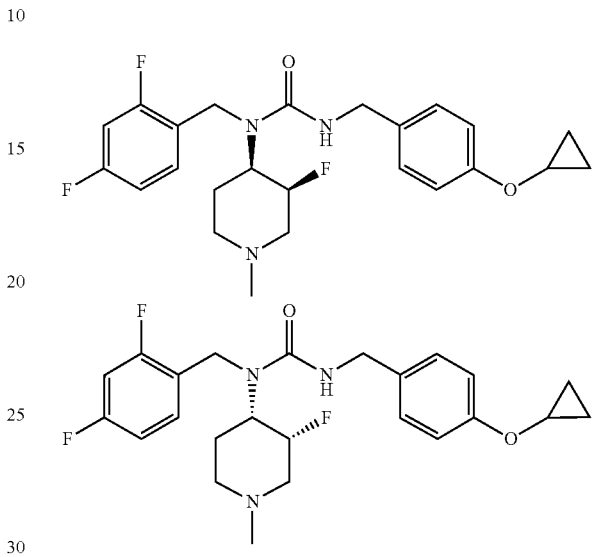

tert-Butyl 3-fluoro-4-oxopiperidine-1-carboxylate (3.0 g, 13.12 mmol), dichloromethane (15 ml), 2,4-difluorobenzyl amine (13.8 mmol, 2.04 g) and acetic acid (300 µl) were stirred for 10 min and sodium triacetoxyborohydride (22.3 mmol, 4.87 g) was added. The mixture was stirred for 1 hour, then partitioned between 0.5 M NaOH and dichloromethane. The organic phase was separated, dried, and the solvents were removed. The crude was purified by column chromatography using silicon dioxide gel, eluting with 30-50% ethyl acetate in petroleum ether to afford pure fractions of the desired compound. These fractions were collected, evaporated, and the residue was recrystallized from EtOAc/petroleum ether to afford tert-butyl 4-{[(2,4-difluorophenyl)methyl]amino}-3-fluoropiperidine-1-carboxylate (a racemic cis compound, 2.394 g, 53% yield). This cis compound (183 mg, 0.53 mmol), phenyl N-[(4-cyclopropoxyphenyl)methyl]carbamate (150 mg, 0.53 mmol) and potassium carbonate (1.0 mmol, 138 mg) were suspended in toluene (1.0 ml). The mixture was stirred at 70° C. for 14 hours, then partitioned between toluene and 0.5 M NaOH, the organic phase was separated, washed with water, dried and then concentrated. The crude was purified by column chromatography using silicon dioxide gel, eluting with 30-50% ethyl acetate in petroleum ether to afford the desired protected urea intermediate. The solvents were removed, the residue was stirred in dichloromethane (2.0 ml) and trifluoroacetic acid (2.0 ml) for 30 min, it was then evaporated and free based by partition between dichloromethane and 1 M NaOH. The residue after evaporation of the organic phase was purified by column chromatography using silicon dioxide gel, eluting with 10-100% methanol in ethyl acetate to give the intermediate (156 mg, 0.36 mmol, 68% yield). This material (149 mg, 0.34 mmol), formaldehyde (1.08 mmol, 81 µl) and sodium triacetoxyborohydride (1.1 mmol, 241 mg) were stirred in tetrahydrofuran (3.0 ml) for 2 hours, then partitioned between ether and 1 M NaOH. The organic phase was separated, dried, evaporated and the residue was purified by column chromatography using silicon dioxide gel, eluting with 10-50% methanol in ethyl acetate to afford the title compound (110 mg, 0.246 mmol, 72%): $^1$H NMR (400 MHz, Chloroform-d) δ 7.19 (q, 1H), 7.04 (d, 2H), 6.94 (d, 2H), 6.86-6.74 (m, 2H), 4.93 (d, 1H), 4.73-4.44 (m, 4H), 4.30 (d, 2H), 3.70 (m, 1H), 3.24 (t, 1H), 3.05 (d, 1H), 2.59-2.14 (m, 3H), 2.40 (s, 3H), 1.63 (d, 1H), 0.81-0.69 (m, 4H); LC-MS: 448.3 [M+H]$^+$.

Example 118: 1-[(2,4-difluorophenyl)methyl]-3-[(3-fluoro-4-methoxyphenyl)methyl]-1-(1-methylpiperidin-4-yl)urea (118)

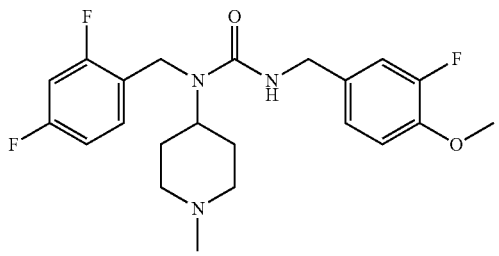 [SMILES: COc1ccc(CNC(=O)N(Cc2ccc(F)cc2F)C2CCN(C)CC2)cc1F]

3-Fluoro-4-methoxybenzoic acid (975 mg, 5.73 mmol), dichloromethane (5.0 ml), DMF (20 µl), and oxalyl chloride (17 mmol, 1.45 ml) were refluxed 1 hour, the volatiles were removed and the residue was stirred in ammonium hydroxide (28% solution, 4 ml) and ethanol (4 ml) until the solids dissolved. The solution was concentrated and a solid precipitated, the solid was collected by filtration and gave the intermediate carboxamide (713 mg, 4.21 mmol, 74% yield). This material (705 mg, 4.16 mmol) was reduced using lithium aluminiumhydride (2 equiv., 8.3 mmol, 323 mg) in refluxing tetrahydrofuran (5 ml) for 1 hour, the reaction was then quenched with 2 M NaOH and extracted with diethyl ether, the organic phase was collected and extracted with 1 M HCl, the aqueous phase was separated and made basic with 5 M NaOH, then extracted with diethyl ether and the organic phase was collected, dried and evaporated to give crude 3-fluoro-4-methoxy-benzylamine (495 mg, 3.19 mmol, 77% yield). This material was dissolved in dichloromethane (2 ml), pyridine (4.5 mmol, 360 µl) was added followed by phenyl chloroformate (3.5 mmol, 455 µl) dissolved in dichloromethane (2.0 ml) dropwise on an ice-bath and the mixture was stirred 30 min, then partitioned between dichloromethane and 0.5 M HCl, the organic phase was separated, dried, and evaporated and the residue was crystallized from ethanol/water to give phenyl N-[(3-fluoro-4-methoxyphenyl)methyl]carbamate (357 mg, 1.3 mmol, 41% yield).

N-[(2,4-difluorophenyl)methyl]-1-methylpiperidin-4-amine (0.5 mmol, 95%, 127 mg), phenyl N-[(3-fluoro-4-methoxyphenyl)methyl]carbamate (152 mg, 0.55 mmol) and potassium carbonate (1.0 mmol, 139 mg) were suspended in toluene (2.0 ml). The mixture was stirred at 70° C. for 16 hours, then partitioned between toluene and 0.5 M NaOH, the organic phase was separated, concentrated and the product purified by column chromatography using silicon dioxide gel, eluting with 5-100% methanol in ethyl acetate in petroleum ether to afford fractions that were collected, evaporated and the residue was stirred 20 min in ether (5.0 ml) to precipitate any silica, the suspension was filtered, the clear filtrate was evaporated to afford the title compound (123 mg, 0.292 mmol, 58% yield): $^1$H NMR (400 MHz, Chloroform-d) δ 7.21 (q, 1H), 6.94-6.74 (m, 5H), 4.61 (t, 1H), 4.41 (s, 2H), 4.34-4.22 (m, 1H), 4.31 (d, 2H), 3.86 (s, 3H), 2.91 (d, 2H), 2.29 (s, 3H), 2.24-1.86 (m, 2H), 1.80-1.65 (m, 4H); LC-MS: 422.2 [M+H]$^+$.

Example 119: 1-[(2,4-difluorophenyl)methyl]-3-[(2-fluoro-4-hydroxyphenyl)methyl]-1-(1-methylpiperidin-4-yl)urea (119)

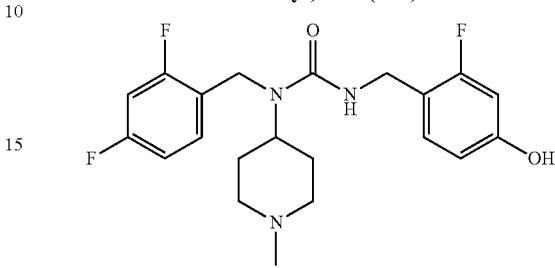

N-[(2,4-difluorophenyl)methyl]-1-methylpiperidin-4-amine (0.42 mmol, 108 mg), phenyl N-({4-[(tert-butyldimethylsilyl)oxy]-2-fluorophenyl}methyl)carbamate (0.42 mmol, 160 mg) and potassium carbonate (0.7 mmol, 100 mg) were stirred in toluene (1.5 ml) at 60° C. for 20 hours, then partitioned between toluene and water, the organic phase was separated, concentrated, and the residue was purified by column chromatography using silicon dioxide gel, eluting with 5-100% methanol in ethyl acetate to afford fractions that were collected and evaporated and the residue was stirred 20 min in ether to precipitate any silica, the suspension was filtered, and the clear filtrate was evaporated to give the intermediate silylated compound (91 mg, 0.174 mmol, 41% yield). This material was dissolved in tetrahydrofuran (1 ml), tetrabutylammonium fluoride (1 M solution in tetrahydrofuran, 1.0 mmol, 1.0 ml) was added, the mixture was stirred for 4 hours and then concentrated and partitioned between saturated potassium carbonate, water and diethyl ether at pH 10-11. The organic phase was collected, dried and evaporated to give a crude was purified by column chromatography using silicon dioxide gel, eluting with 5-100% methanol in ethyl acetate to afford fractions that were evaporated and the residue was stirred 20 min in diethyl ether/EtOAc to precipitate any silica, the suspension was filtered, and the clear filtrate was evaporated to afford the title compound (40 mg, 0.098 mmol, 56% yield): $^1$H NMR (400 MHz, Chloroform-d) δ 7.13 (q, 1H), 7.02 (t, 1H), 6.84-6.73 (m, 2H), 6.46-6.37 (m, 2H), 4.74 (t, 1H), 4.36 (s, 2H), 4.30 (d, 2H), 4.29-4.18 (m, 1H) 2.92 (d, 2H), 2.30 (s, 3H), 2.14 (m, 2H), 1.81-1.63 (m, 4H); LC-MS: 408.2 [M+H]$^+$.

Example 120: 3-[(2,4-difluorophenyl)methyl]-3-(1-methylpiperidin-4-yl)-1-[(4-phenoxyphenyl)methyl]urea (120)

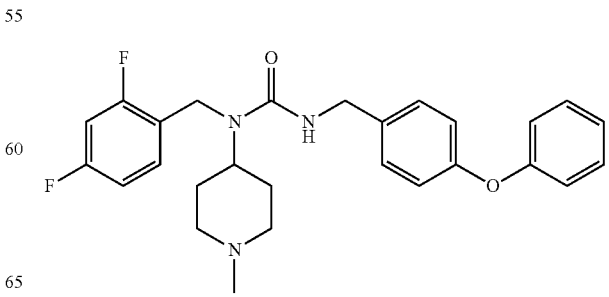

p-(Phenoxy)-benzylamine (2.88 mmol, 575 mg) and pyridine (8.3 mmol, 670 µl) was dissolved in dichloromethane (5 ml) and added dropwise to an ice-cooled solution of triphosgene (1.152 mmol, 342 mg) in dichloromethane (3 ml). The mixture was stirred for 1 hour, then partitioned between dichloromethane and 1 M sulfuric acid, the organic phase was separated, dried and evaporated to give crude 1-(isocyanatomethyl)-4-phenoxybenzene (0.5 g) that was used in the next step. N-[(2,4-difluorophenyl)methyl]-1-methylpiperidin-4-amine (0.66 mmol, 167 mg) was dissolved in dichloromethane (2 ml) and 1-(isocyanatomethyl)-4-phenoxybenzene (300 mg, 1.3 mmol) was added. The mixture was stirred for 18 hours, then purified by column chromatography using silicon dioxide gel, eluting with 0-30% methanol in ethyl acetate to afford a residue. To the residue was added diethyl ether and the solution was filtered to remove any solids. The clear solution was evaporated and gave 182 mg. This material was triturated in hexanes and gave the title compound (152 mg, 49% yield): $^1$H NMR (400 MHz, Chloroform-d) δ 7.33 (t, 2H), 7.22 (q, 1H), 7.16-7.07 (m, 3H), 6.98 (d, 2H), 6.92 (d, 2H), 6.86-6.76 (m, 2H), 4.64 (t, 1H), 4.46-4.31 (m, 5H), 3.03 (d, 2H), 2.37 (s, 3H), 2.33-2.17 (m, 2H), 1.87 (d, 2H), 1.75 (m, 2H), LC-MS: 466.3 [M+H]$^+$.

Example 121: 3-{[4-methoxy-2-(trifluoromethyl)phenyl]methyl}-3-(1-methylpiperidin-4-yl)-1-{[4-(2-methylpropoxy)phenyl]methyl}urea (121)

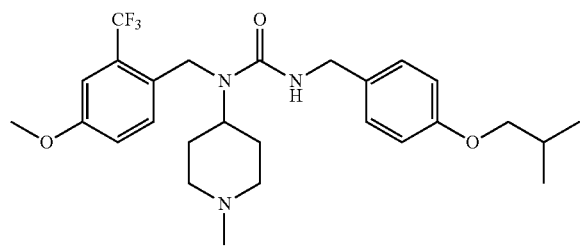 [SMILES: COc1ccc(CN(C(=O)NCc2ccc(OCC(C)C)cc2)C2CCN(C)CC2)c(C(F)(F)F)c1]

N-methyl-4-piperidone (5.0 mmol, 583 mg) was dissolved in ethanol (5.0 ml) and [4-methoxy-2-(trifluoromethyl)phenyl]methanamine (5.0 mmol, 1026 mg) followed by sodium triacetoxyborohydride (2.0 equiv., 10.0 mmol, 2.2 g) were added. The mixture was stirred at 20° C. for 3 hours, then concentrated and partitioned between diethyl ether and aqueous 0.5 M NaOH, the organic phase was collected and extracted with aqueous 2 M HCl, the aqueous phase was separated and made basic with 5 M NaOH, then extracted with diethyl ether. The organic phase was collected and concentrated and gave N-{[4-methoxy-2-(trifluoromethyl)phenyl]methyl}-1-methylpiperidin-4-amine (1.466 g, 96% yield). This material (150 mg, 0.496 mmol) was dissolved in dichloromethane (2 ml) and 1-(isocyanatomethyl)-4-(2-methylpropoxy)benzene (0.595 mmol, 123 mg) was added. The mixture was stirred for 1 hour, then concentrated and the residue was purified by column chromatography using silicon dioxide gel, eluting with 0-30% methanol in ethyl acetate in petroleum ether to afford the title compound (164 mg, 65% yield): $^1$H NMR (400 MHz, Chloroform-d) δ 7.36 (d, 1H), 7.16 (s, 1H), 7.04 (d, 2H), 6.97 (d, 1H), 6.78 (d, 2H), 4.48 (s, 2H), 4.47-4.33 (m, 2H), 4.29 (d, 2H), 3.83 (s, 3H), 3.68 (d, 2H), 2.89 (d, 2H), 2.28 (s, 3H), 2.16-1.94 (m, 3H), 1.79-1.59 (m, 4H), 1.01 (d, 6H); LC-MS: 508.4 [M+H]$^+$.

Example 122: 1-[(2-fluoro-4-methoxyphenyl)methyl]-1-(1-methylpiperidin-4-yl)-3-{[4-(propan-2-yloxy)phenyl]methyl}urea; trifluoroacetic acid (122)

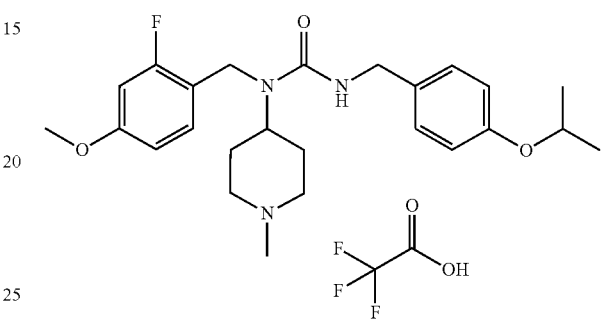

(2-fluoro-4-methoxyphenyl)methanamine hydrochloride (1.0 g, 5.2 mmol) was partitioned between diethyl ether and 0.5 M NaOH. The organic phase was separated, dried, and evaporated to give (2-fluoro-4-methoxyphenyl)methanamine as the free base (699 mg, 4.50 mmol). To this material was added N-methyl-4-piperidone (5.0 mmol, 583 mg), ethanol (5.0 ml) and sodium triacetoxyborohydride (9.0 mmol, 1.97 g) and the mixture was stirred at 20° C. for 18 hours, then partitioned between diethyl ether and aqueous 0.5 M NaOH, the organic phase was separated and extracted with aqueous 2 M HCl, the aqueous phase was separated and made basic with 5 M NaOH and then extracted with diethyl ether. The organic phase was separated, concentrated and gave N-[(2-fluoro-4-methoxyphenyl)methyl]-1-methylpiperidin-4-amine (1.059 g, 93% yield). This compound (132 mg, 0.497 mmol) was dissolved in dichloromethane (2 ml) and 1-(isocyanatomethyl)-4-(propan-2-yloxy)benzene (0.596 mmol, 114 mg) was added. The mixture was stirred for 1 hour, then purified by column chromatography using silicon dioxide gel, eluting with 0-30% methanol in ethyl acetate to afford fractions. These fractions were combined and evaporated. To the residue was added diethyl ether and the solution was filtered to remove the solids. The clear solution was evaporated and gave the desired compound as the free base (135.7 mg, 61% yield). This material (41 mg, 0.0924 mmol) was dissolved in dioxane (1.0 ml), trifluoroacetic acid (1 M solution in dioxane, 1.1 equiv., 0.102 mmol, 102 µl) was added and the mixture was freeze dried to give the title compound (49 mg): $^1$H NMR (400 MHz, DMSO-d6) δ 9.19 (s, 1H), 7.12 (d, 2H), 7.08 (t, 1H), 7.01 (t, 1H), 6.85-6.77 (m, 3H), 6.74 (dd, 1H), 4.56 (m, 1H), 4.37 (s, 2H), 4.25-4.13 (m, 3H), 3.75 (s, 3H), 3.38 (m, 2H), 2.97 (d, 2H), 2.71 (d, 3H), 1.82 (m, 2H), 1.71 (d, 2H), 1.24 (d, 6H); LC-MS: 444.3 [M+H]$^+$.

Example 123: 3-[(4-butoxyphenyl)methyl]-1-[(2,4-difluorophenyl)methyl]-1-(piperidin-4-yl)urea; hemitartrate (123)

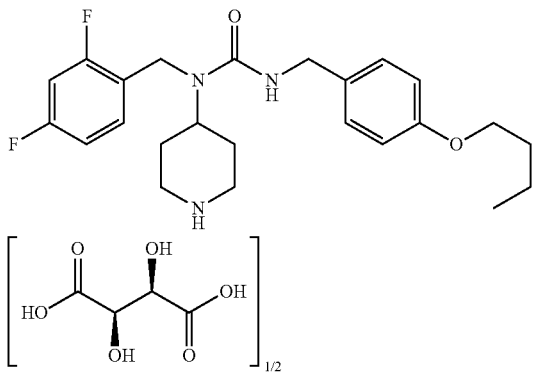

tert-Butyl 4-{[(2,4-difluorophenyl)methyl]amino}piperidine-1-carboxylate (1.00 g, 3.06 mmol) was dissolved in dichloromethane (10 ml) and 1-butoxy-4-(isocyanatomethyl)benzene (735 mg, 3.4 mmol) dissolved in dichloromethane (2 ml) was added. The mixture was stirred for 18 hours, then evaporated and the residue was purified by column chromatography using silicon dioxide gel, eluting with 30-50% ethyl acetate in petroleum ether to afford an intermediate (1.63 g). This material was stirred in dichloromethane (6 ml) and trifluoroacetic acid (4 ml) for 20 min, then evaporated and partitioned between EtOAc and 0.5 M NaOH. The organic phase was collected, evaporated, and the residue was crystallized from hexanes/EtOAc, the solids were isolated and triturated in ether and gave 3-[(4-butoxyphenyl)methyl]-1-[(2,4-difluorophenyl)methyl]-1-(piperidin-4-yl)urea (765 mg, 58% yield). This material (71.8 mg, 0.166 mmol) was dissolved in 2-propanol (1 ml) and L-(+)-tartaric acid (2 M solution in ethanol, 1.1 equiv., 0.0915 mmol, 229 µl) was added. A precipitate was formed after 1 min, the suspension was stirred 20 min and then filtered and dried to afford the title compound (62.9 mg, 0.124 mmol, 75% yield): $^1$H NMR (400 MHz, Methanol-d4) δ 7.21 (q, 1H), 7.14 (d, 2H), 6.98-6.85 (m, 2H), 6.82 (d, 2H), 4.53 (s, 2H), 4.31 (s, 1H), 4.36-4.21 (m, 1H), 4.28 (s, 2H), 3.95 (t, 2H), 3.39 (d, 2H), 2.99 (m, 2H), 1.97-1.79 (m, 4H), 1.74 (p, 2H), 1.50 (sext, 2H), 0.98 (t, 3H); LC-MS: 432.3 [M+H]$^+$.

Example 124: 3-[(4-butoxyphenyl)methyl]-1-[(2,4-difluorophenyl)methyl]-1-(1-methylpiperidin-4-yl)urea (124)

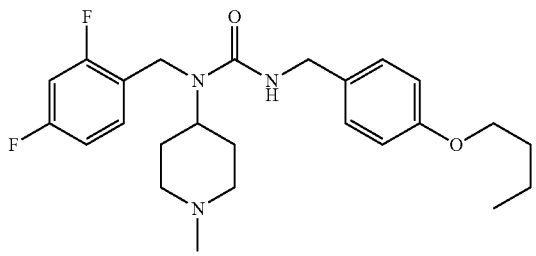 [SMILES: CCCCOc1ccc(CNC(=O)N(Cc2ccc(F)cc2F)C2CCN(C)CC2)cc1]

3-[(4-butoxyphenyl)methyl]-1-[(2,4-difluorophenyl)methyl]-1-(piperidin-4-yl)urea (200 mg, 0.463 mmol) was dissolved in tetrahydrofuran (3.0 ml) and formaldehyde (1.16 mmol, 87 µl) followed by sodium triacetoxyborohydride (1.16 mmol, 254 mg) were added. The mixture was stirred for 2 hours, partitioned between diethyl ether and 0.5 M NaOH, the organic phase was evaporated, and the residue was suspended in diethyl ether. Filtration gave 166 mg that was crystallized from ethanol/water and gave the title compound (108 mg, 52% yield). $^1$H NMR (400 MHz, Chloroform-d) δ 7.21 (q, 1H), 7.09 (d, 2H), 6.85-6.73 (m, 4H), 4.53 (t, 1H), 4.40 (s, 2H), 4.32 (d, 2H), 4.32-4.20 (m, 1H), 3.93 (t, 2H), 2.88 (d, 2H), 2.27 (s, 3H), 2.08 (m, 2H), 1.80-1.60 (m, 6H), 1.48 (h, 2H), 0.97 (t, 3H); LC-MS: 446.3 [M+H]$^+$.

Example 125: 3-[(2,4-difluorophenyl)methyl]-1-[(4-methoxyphenyl)methyl]-3-(1-methylpiperidin-4-yl)urea (125)

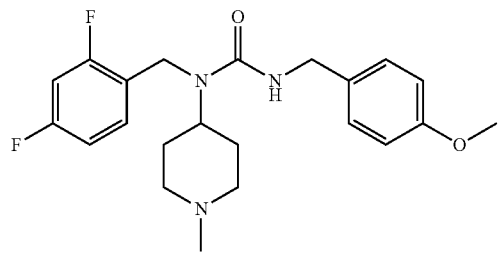 [SMILES: COc1ccc(CNC(=O)N(Cc2ccc(F)cc2F)C2CCN(C)CC2)cc1]

A solution of 1-methoxy-4-(isocyanatomethyl)benzene (172 mg 1.03 mmol) in dichloromethane (1 ml) was added to N-[(2,4-difluorophenyl)methyl]-1-methylpiperidin-4-amine (intermediate 2, 200 mg, 0.79 mmol) in dichloromethane (2 ml). The mixture was stirred for 1 hour, then evaporated and the residue was purified by column chromatography using silicon dioxide gel, eluting with 0-25% methanol in ethyl acetate to afford the title compound (192 mg, 60% yield): $^1$H NMR (400 MHz, Chloroform-d) δ 7.25-7.16 (m, 1H), 7.11 (d, 2H), 6.85-6.73 (m, 4H), 4.55 (t, 1H), 4.40 (s, 2H), 4.32 (d, 2H), 4.32-4.21 (m, 1H), 3.78 (s, 3H), 2.89 (d, 2H), 2.27 (s, 3H), 2.13-2.03 (m, 2H), 1.74-1.61 (m, 4H); LC-MS: 403.9 [M+H]$^+$.

Example 126: 1-[(2,4-difluorophenyl)methyl]-3-[(4-methoxyphenyl)methyl]-1-(piperidin-4-yl)urea; hemitartrate (126)

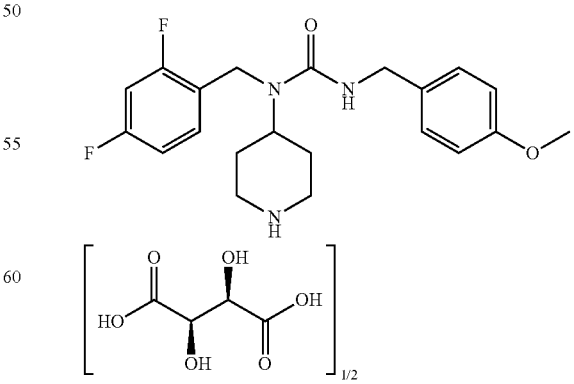

tert-Butyl 4-{[(2,4-difluorophenyl)methyl]amino}piperidine-1-carboxylate (300 mg, 0.873 mmol) was dissolved in dichloromethane (2 ml) and 1-methoxy-4-(isocyanatomethyl)benzene (190 mg, 1.14 mmol) dissolved in dichloromethane (1 ml) was added. The mixture was evaporated and purified by column chromatography using silicon dioxide gel, eluting with 50% ethyl acetate in petroleum ether to afford an intermediate (387 mg). This material was stirred in dichloromethane (2 ml) and trifluoroacetic acid (1 ml) for 1 hour, then evaporated and partitioned between diethyl ether/EtOAc and 0.5 M NaOH. The organic phase was collected, evaporated, and the residue was crystallized from diethyl ether/hexanes and gave the title compound as the free base (195 mg, 0.46 mmol, 53% yield). This material (163 mg, 0.418 mmol) was dissolved in 2-propanol (3 ml) and L-(+)-tartaric acid (0.4 M solution in ethanol, 1.1 equiv., 0.23 mmol, 575 µl) was added dropwise which resulted in crystallization. The crystals were isolated by filtration and then recrystallized from MeOH/ethanol and gave the title compound (130 mg, 67% yield from the free base): $^1$H NMR (400 MHz, Methanol-d4) δ 7.21 (q, 1H), 7.15 (d, 2H), 6.98-6.86 (m, 2H), 6.83 (d, 2H), 4.53 (s, 2H), 4.32 (s, 1H), 4.34-4.23 (m, 1H), 4.29 (s, 2H), 3.76 (s, 3H), 3.38 (d, 2H), 2.98 (m, 2H), 1.95-1.81 (m, 4H); LC-MS: 390.2 [M+H]$^+$.

Example 127: 3-[(2,4-difluorophenyl)methyl]-1-[(4-ethoxyphenyl)methyl]-3-(piperidin-4-yl)urea; hemi-tartrate (127)

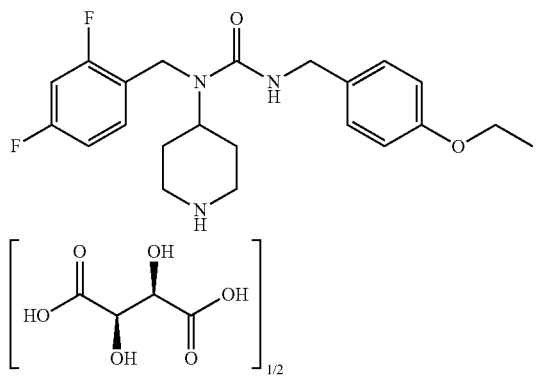

tert-butyl 4-{[(2,4-difluorophenyl)methyl]amino}piperidine-1-carboxylate (intermediate 1, 331 mg, 1.01 mmol) was dissolved in dichloromethane (2 ml) and 1-ethoxy-4-(isocyanatomethyl)benzene (265 mg, 1.30 mmol) dissolved in dichloromethane (1 ml) was added. The mixture was stirred 20 min, then partitioned between 0.5 M NaOH and dichloromethane. The organic phase was evaporated, and the residue was purified by column chromatography using silicon dioxide gel, eluting with 30-50% ethyl acetate in petroleum ether to afford an intermediate (365 mg, 0.90 mmol, 89% yield). This material was stirred in dichloromethane (2 ml) and trifluoroacetic acid (1 ml) for 20 min, the solvents were evaporated, and the residue was partitioned between ether and 0.5 M NaOH. The organic phase was collected, dried and evaporated and the residue was crystallized from EtOAc/hexanes and then from MeOH/water and gave 107 mg (0.26 mmol, 29% yield). This material was dissolved in 2-propanol (1.0 ml) and a solution of L-(+)-tartaric acid in ethanol (0.4 M, 1.1 equiv., 0.146 mmol, 365 µl) was added. The crystals were isolated by filtration, dried, and gave the title compound (119 mg, 0.248 mmol, 96% yield, total yield from starting material is 25%): $^1$H NMR (400 MHz, Methanol-d4) δ 7.21 (q, 1H), 7.14 (d, 2H), 6.98-6.86 (m, 2H), 6.82 (d, 2H), 4.53 (s, 2H), 4.32 (s, 1H), 4.34-4.23 (m, 1H), 4.28 (s, 2H), 4.00 (q, 2H), 3.38 (d, 2H), 2.98 (m, 2H), 1.95-1.81 (m, 4H), 1.37 (t, 3H); LC-MS: 404.2 [M+H]$^+$.

Example 128: 3-[(2H-1,3-benzodioxol-5-yl)methyl]-1-[(2,4-difluorophenyl)methyl]-1-(1-methylpiperidin-4-yl)urea (128)

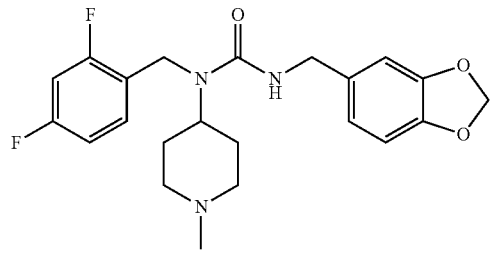 [SMILES: CN1CCC(N(Cc2ccc(F)cc2F)C(=O)NCc2ccc3c(c2)OCO3)CC1]

2H-1,3-benzodioxole-5-carbonitrile (1.73 g, 11.75 mmol) in diethyl ether (15 ml) was added portion wise to a mixture of lithium aluminiumhydride (55.2 mmol hydride, 13.8 mmol, 525 mg) in diethyl ether (15 ml). The mixture was refluxed for 2 hours, then cooled and worked up (H$_2$O, 15% NaOH, 3×H$_2$O) and gave crude benzyl amine (1.77 g, quant.). This amine (1.0 g, 6.6 mmol) and pyridine (1.1 equiv., 17.6 mmol, 1.43 ml) was dissolved in dichloromethane (5.0 ml) and added dropwise to an ice cooled mixture of triphosgene (2.7 mmol, 801 mg) in dichloromethane (5.0 ml). The mixture was stirred for 1 hour, then partitioned between cold 0.5 M sulfuric acid and dichloromethane. The organic phase was separated, dried and evaporated to give crude 5-(isocyanatomethyl)-2H-1,3-benzodioxole (1.08 g, 92% yield).

N-[(2,4-difluorophenyl)methyl]-1-methylpiperidin-4-amine (250 mg, 1.01 mmol) was dissolved in dichloromethane (1 ml) and 5-(isocyanatomethyl)-2H-1,3-benzodioxole (215 mg, 1.21 mmol) in dichloromethane (1 ml) was added in one portion. The mixture was stirred at room temperature for 1 hour and then purified by column chromatography using silicon dioxide gel, eluting with methanol to afford the title compound (275 mg, 66% yield): $^1$H NMR (400 MHz, Chloroform-d) δ 7.21 (q, 1H), 6.87-6.73 (m, 2H), 6.73-6.59 (m, 3H), 5.92 (s, 2H), 4.57 (t, 1H), 4.40 (s, 2H), 4.29 (d, 2H), 4.26 (m, 1H), 2.88 (d, 2H), 2.27 (s, 3H), 2.07 (m, 2H), 1.75-1.60 (m, 4H); LC-MS: 418.2 [M+H]$^+$.

Example 129 (Comparative): 1-[(2,3-difluorophenyl)methyl]-1-(1-methylpiperidin-4-yl)-3-{[4-(2-methylpropoxy)phenyl]methyl}urea; trifluoroacetic acid (129)

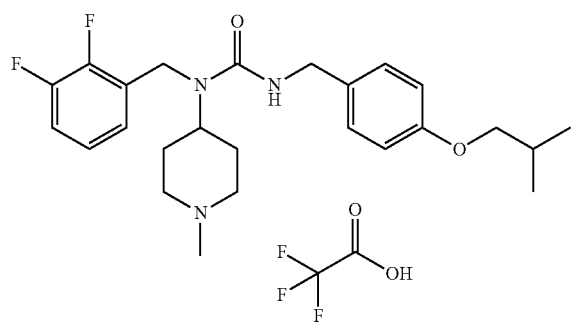 [SMILES: CC(C)COc1ccc(CNC(=O)N(Cc2cccc(F)c2F)C2CCN(C)CC2)cc1 ; O=C(O)C(F)(F)F]

The compound was prepared in analogy with GP B using N-[(2,3-difluorophenyl)methyl]-1-methylpiperidin-4-amine (prepared in analogy with intermediate 6 using (2,3-difluorophenyl)methanamine and 1-(isocyanatomethyl)-4-(2-methylpropoxy)benzene. Yield: 87%. $^1$H NMR (400 MHz, Chloroform-d) δ 7.10-6.97 (m, 4H), 6.91 (t, 1H), 6.76 (d, 2H), 5.02 (s, 1H), 4.61 (dt, 1H), 4.43 (s, 2H), 4.23 (s, 2H), 3.66 (d, 2H), 3.49 (d, 2H), 2.92-2.77 (m, 2H), 2.72 (s, 3H), 2.20-1.96 (m, 3H), 1.87 (d, 2H), 0.99 (d, 6H); LCMS: 446.3 [M+H]$^+$.

Example 130: 1-[(3,4-difluorophenyl)methyl]-1-(1-methylpiperidin-4-yl)-3-{[4-(propan-2-yloxy)phenyl]methyl}urea; trifluoroacetic acid(130)

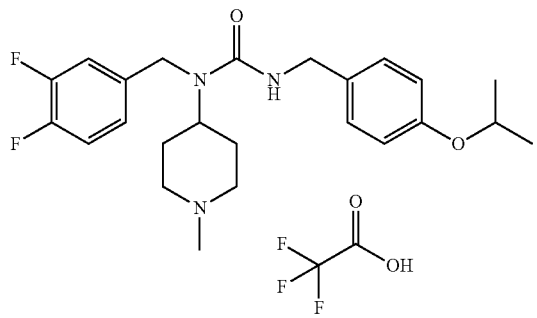 [SMILES: CC(C)Oc1ccc(CNC(=O)N(Cc2ccc(F)c(F)c2)C2CCN(C)CC2)cc1 ; O=C(O)C(F)(F)F]

The compound was prepared in analogy with GP B using N-[(3,4-difluorophenyl)methyl]-1-methylpiperidin-4-amine (prepared in analogy with intermediate 6 using (3,4-difluorophenyl)methanamine and 1-(isocyanatomethyl)-4-(propan-2-yloxy)benzene. Yield: 82%. $^1$H NMR (400 MHz, Chloroform-d) δ 7.15-7.05 (m, 1H), 7.05-6.97 (m, 3H), 6.95-6.89 (m, 1H), 6.81-6.75 (m, 2H), 4.72 (ddt, 2H), 4.50 (p, 1H), 4.34 (s, 2H), 4.27 (s, 2H), 3.56 (d, 2H), 2.86 (t, 2H), 2.77 (s, 3H), 2.18 (qd, 2H), 1.89 (d, 2H), 1.31 (d, 6H); LCMS: 432.3 [M+H]$^+$.

Example 131: 1-[(2,4-difluorophenyl)methyl]-1-[1-($^2$H$_3$)methylpiperidin-4-yl]-3-{[4-(propan-2-yloxy)phenyl]methyl}urea; trifluoroacetic acid (131)

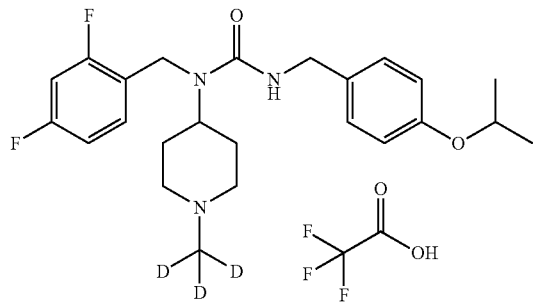

1-[(2,4-difluorophenyl)methyl]-1-(piperidin-4-yl)-3-{[4-(propan-2-yloxy)phenyl]methyl}urea (50 mg, 0.12 mmol) was dissolved in acetone (1 ml). Potassium carbonate (33 mg, 240 µmol) was added. A solution of iodo($^2$H$_3$)methane (15.6 mg, 108 µmol) in acetone (170 µl) was added. After 60 minutes of stirring at room temperature the mixture was filtered and concentrated and re-dissolved in dichloromethane (1.5 ml). Di-tert-butyl dicarbonate (31 mg, 144 µmol) was added. The reaction was stirred at room temperature overnight. To the reaction was added dichloromethane (2 ml). The mixture was washed with sodium hydroxide (7×2 ml, 0.1 M). The organic phase was concentrated. The crude material was purified by HPLC, eluting with 25-50% acetonitrile in water (containing 0.1% trifluoroacetic acid) to afford the title compound (11 mg, 17%): $^1$H NMR (400 MHz, Chloroform-d) δ 11.83 (s, 1H), 7.12 (q, 1H), 7.01 (d, 2H), 6.87-6.75 (m, 4H), 4.75 (t, 2H), 4.51 (hept, 1H), 4.37 (s, 2H), 4.28 (s, 2H), 3.62 (d, 2H), 2.88 (t, 2H), 2.26-2.11 (m, 2H), 1.92 (d, 2H), 1.32 (d, 6H); LCMS: 435.3 [M+H]$^+$.

Example 132: 1-(piperidin-4-yl)-3-{[4-(propan-2-yloxy)phenyl]methyl}-1-[(2,3,4-trifluorophenyl)methyl]urea; trifluoroacetic acid (132)

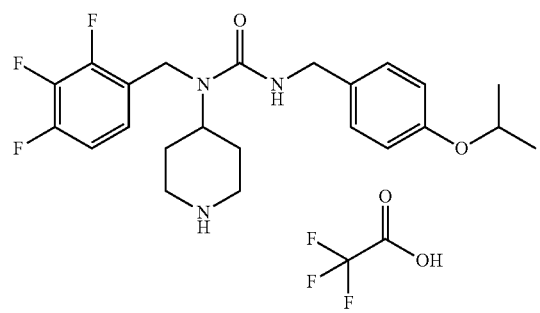

tert-butyl 4-{[(2,3,4-trifluorophenyl)methyl]amino}piperidine-1-carboxylate

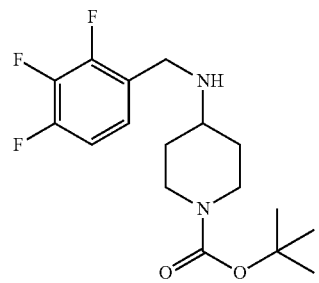 [SMILES: CC(C)(C)OC(=O)N1CCC(NCc2ccc(F)c(F)c2F)CC1]

tert-butyl 4-oxopiperidine-1-carboxylate (200 mg, 1.0 mmol) and (2,3,4-trifluorophenyl)methanamine (178 mg, 1.1 mmol) was dissolved in ethanol (2.5 ml). The reaction was stirred for 20 minutes. Sodium triacetoxyborohydride (319 mg, 1.51 mmol) was added. The reaction was stirred at room temperature overnight. The mixture was concentrated. The residue was dissolved in dichloromethane and sodium hydroxide, (0.5 M in water) was added. The phases were separated. The water phase was extracted two more times with dichloromethane. The combined organic phases were dried over sodium sulfate. The organic phase was concentrated and the crude material was used without further purification in the next step.

tert-Butyl 4-[({[4-(propan-2-yloxy)phenyl]methyl}carbamoyl)[(2,3,4-trifluorophenyl)methyl]amino]piperidine-1-carboxylate To a solution of tert-butyl 4-{[(2,3,4-trifluorophenyl)methyl]amino}piperidine-1-carboxylate (79.2 mg, 0.23 mmol) in dichloromethane (1.0 ml) was added drop-wise a solution of 1-(isocyanatomethyl)-4-(propan-2-yloxy)benzene (44.0 mg, 0.23 mmol) in dichloromethane (0.5 ml). The reaction was stirred at room-temperature overnight. The organic phase was concentrated and the crude material was purified by HPLC, eluting with 40-90% acetonitrile in water (containing 0.1% trifluoroacetic acid) to afford the desired intermediate (84 mg).

1-(piperidin-4-yl)-3-{[4-(propan-2-yloxy)phenyl]methyl}-1-[(2,3,4-trifluorophenyl)methyl]urea; trifluoroacetic acid tert-butyl 4-[({[4-(propan-2-yloxy)phenyl]methyl}carbamoyl)[(2,3,4-trifluorophenyl)methyl]amino]piperidine-1-carboxylate (82 mg, 0.15 mmol) dissolved in dichloromethane (1.5 ml) was cooled to 0° C. in an ice-bath. Trifluoroacetic acid (0.76 ml) was added drop-wise with stirring. The cooling bath was removed and the reaction was stirred at room temperature for one hour. The mixture was concentrated. The crude material was purified by HPLC, eluting with 20-60% acetonitrile in water (containing 0.1% trifluoroacetic acid) to afford the title compound (31 mg, 37%): ¹H NMR (400 MHz, Chloroform-d) δ 9.50 (s, 1H), 9.03 (s, 1H), 7.04 (d, 2H), 6.94-6.87 (m, 2H), 6.79 (d, 2H), 4.71 (s, 1H), 4.60-4.45 (m, 2H), 4.40 (s, 2H), 4.28 (s, 2H), 3.40 (d, 2H), 3.01-2.85 (m, 2H), 1.98 (q, 2H), 1.92-1.82 (m, 2H), 1.32 (d, 6H); LCMS: 436.3 [M+H]⁺.

Example 133: 3-[(4-chloro-2-fluorophenyl)methyl]-3-(piperidin-4-yl)-1-{[4-(propan-2-yloxy)phenyl]methyl}urea; trifluoroacetic acid (133)

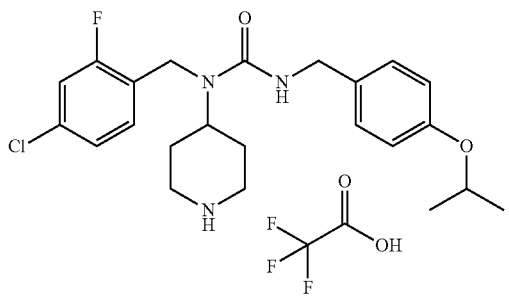

The compound was prepared in analogy with example 132 using (4-chloro-2-fluorophenyl)methanamine. The crude material was purified by HPLC, eluting with 20-55% acetonitrile in water (containing 0.1% trifluoroacetic acid) to afford the title compound (53 mg, 42%): ¹H NMR (400 MHz, Chloroform-d) δ 9.56 (s, 1H), 9.07 (s, 1H), 7.16-7.06 (m, 3H), 7.03 (d, 2H), 6.79 (d, 2H), 4.73-4.56 (m, 2H), 4.51 (hept, 1H), 4.37 (s, 2H), 4.28 (s, 2H), 3.40 (d, 2H), 3.02-2.85 (m, 2H), 2.04-1.94 (m, 2H), 1.92-1.82 (m, 2H), 1.32 (d, 6H); LCMS: 434.3 [M+H]⁺.

Example 134: 3-[(4-chloro-2-fluorophenyl)methyl]-1-{[4-(2-methylpropoxy)phenyl]methyl}-3-(piperidin-4-yl)urea; trifluoroacetic acid (134)

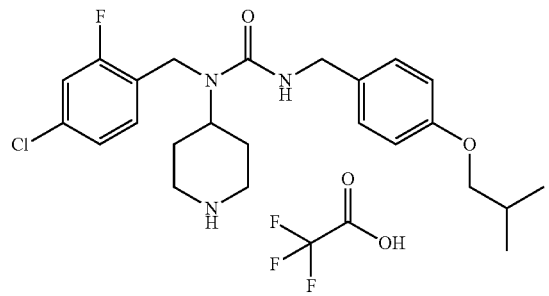

The compound was prepared in analogy with example 132 using (4-chloro-2-fluorophenyl)methanamine and 1-(isocyanatomethyl)-4-(2-methylpropoxy)benzene. The crude material was purified by HPLC, eluting with 20-60% acetonitrile in water (containing 0.1% trifluoroacetic acid) to afford the title compound (71 mg, 68%): ¹H NMR (400 MHz, Chloroform-d) δ 9.57 (s, 1H), 9.09 (s, 1H), 7.15-7.06 (m, 3H), 7.04 (d, 2H), 6.80 (d, 2H), 4.67-4.57 (m, 2H), 4.37 (s, 2H), 4.28 (s, 2H), 3.69 (d, 2H), 3.41 (d, 2H), 3.04-2.88 (m, 2H), 2.07 (tt, 1H), 2.01-1.85 (m, 4H), 1.02 (d, 6H); LCMS: 448.3 [M+H]⁺.

Example 135: 1-(1-methylpiperidin-4-yl)-3-{[4-(propan-2-yloxy)phenyl]methyl})-1-[(2,3,4-trifluorophenyl)methyl]urea; trifluoroacetic acid (135)

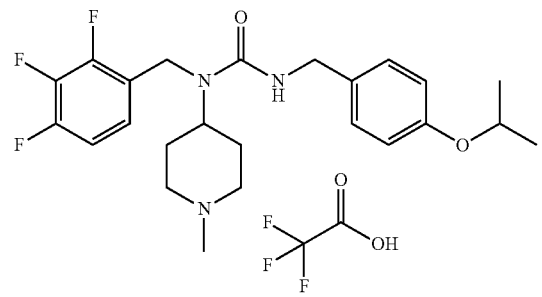

1-methyl-N-[(2,3,4-trifluorophenyl)methyl]piperidin-4-amine

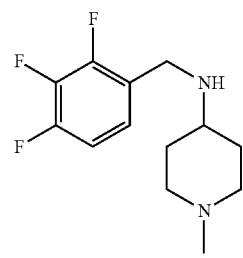 [SMILES: CN1CCC(NCc2ccc(F)c(F)c2F)CC1]

1-methylpiperidin-4-one (211 mg, 1.86 mmol) and (2,3,4-trifluorophenyl)methanamine (300 mg, 1.86 mmol) were dissolved in ethanol (7.5 ml). The reaction was stirred for 20 minutes. Sodium triacetoxyborohydride (592 mg, 2.79 mmol) was added. The reaction was stirred at room temperature overnight. The mixture was concentrated. The residue was dissolved in dichloromethane and sodium hydroxide, (0.5 M in water). The phases were separated. The water phase was extracted two more times with dichloromethane. The combined organic phases were dried over sodium sulfate. The organic phase was concentrated and the crude material was used without further purification in the next step.

1-(1-methylpiperidin-4-yl)-3-{[4-(propan-2-yloxy)phenyl]methyl}-1-[(2,3,4-trifluorophenyl)methyl]urea; trifluoroacetic acid To a solution of 1-methyl-N-[(2,3,4-trifluorophenyl)methyl]piperidin-4-amine (40.0 mg, 0.15 mmol) in dichloromethane (0.65 ml) was added drop-wise a solution of 1-(isocyanatomethyl)-4-(propan-2-yloxy)benzene (52.3 mg, 0.23 mmol) in dichloromethane (0.65 ml). The reaction was stirred at room-temperature overnight. The organic phase was concentrated and the crude material was purified by HPLC, eluting with 40-70% acetonitrile in water (containing 0.1% trifluoroacetic acid) to afford the title compound (61 mg, 70%): $^1$H NMR (400 MHz, Chloroform-d) δ 12.93 (s, 1H), 7.04 (d, 2H), 6.94-6.86 (m, 2H), 6.79 (d, 2H), 4.71 (ddd, 1H), 4.63 (s, 1H), 4.50 (dq, 1H), 4.41 (s, 2H), 4.29 (d, 2H), 3.58 (d, 2H), 2.93-2.81 (m, 2H), 2.78 (s, 3H), 2.34-2.20 (m, 2H), 1.91 (d, 2H), 1.32 (d, 6H); LCMS: 450.3 [M+H]$^+$.

Example 136: 1-[(2,6-difluoro-4-methoxyphenyl)methyl]-1-(1-methylpiperidin-4-yl)-3-{[4-(propan-2-yloxy)phenyl]methyl}urea; trifluoroacetic acid (136)

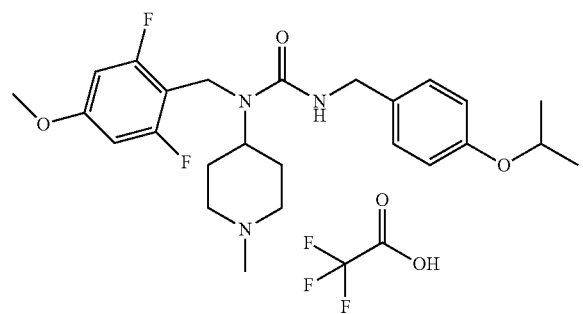

The compound was prepared in analogy with example 135 (1-(1-methylpiperidin-4-yl)-3-{[4-(propan-2-yloxy)phenyl]methyl}-1-[(2,3,4-trifluorophenyl)methyl]urea) using (2,6-difluoro-4-methoxyphenyl)methanamine. The crude material was purified by HPLC, eluting with 30-60% acetonitrile in water (containing 0.1% trifluoroacetic acid) to afford the title compound (39 mg, 44%): $^1$H NMR (400 MHz, Chloroform-d) δ 12.00 (s, 1H), 7.06 (d, 2H), 6.80 (d, 2H), 6.41 (d, 2H), 5.06 (s, 1H), 4.62 (t, 1H), 4.52 (p, 1H), 4.32 (s, 2H), 4.30 (s, 2H), 3.78 (s, 3H), 3.64 (d, 2H), 2.92-2.81 (m, 2H), 2.80 (s, 3H), 2.46-2.30 (m, 2H), 1.94 (d, 2H), 1.33 (d, 6H); LCMS: 462.3 [M+H]$^+$.

Example 137: 1-[(4-chloro-2-fluorophenyl)methyl]-1-(1-methylpiperidin-4-yl)-3-{[4-(propan-2-yloxy)phenyl]methyl}urea; trifluoroacetic acid (137)

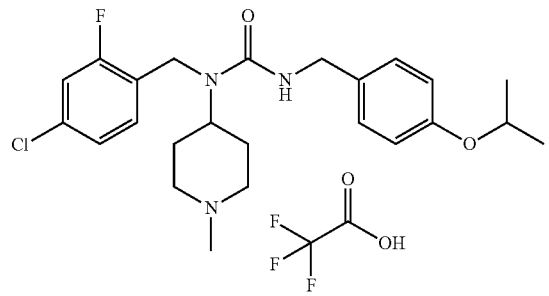

The compound was prepared in analogy with example 135 using (4-chloro-2-fluorophenyl)methanamine. The crude material was purified by HPLC, eluting with 35-65% acetonitrile in water (containing 0.1% trifluoroacetic acid) to afford the title compound (61 mg, 60%): $^1$H NMR (400 MHz, Chloroform-d) δ 12.64 (s, 1H), 7.10 (d, 3H), 7.02 (d, 2H), 6.82-6.76 (m, 2H), 4.75 (t, 1H), 4.65 (s, 1H), 4.51 (dt, 1H), 4.38 (s, 2H), 4.29 (d, 2H), 3.59 (d, 2H), 2.94-2.81 (m, 2H), 2.79 (s, 3H), 2.34-2.19 (m, 2H), 1.91 (d, 2H), 1.33 (d, 6H); LCMS: 448.3 [M+H]$^+$.

Example 138: 1-[(4,5-difluoro-2-methoxyphenyl)methyl]-1-(1-methylpiperidin-4-yl)-3-{[4-(propan-2-yloxy)phenyl]methyl}urea; trifluoroacetic acid (138)

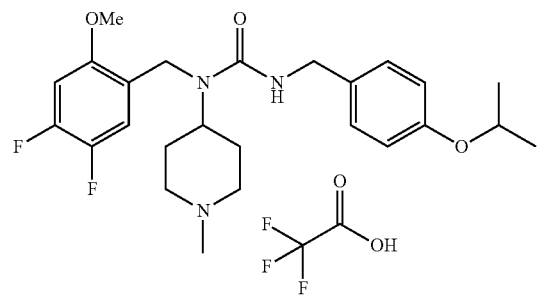

The compound was prepared in analogy with example 135 using (4,5-difluoro-2-methoxyphenyl)methanamine. The crude material was purified by HPLC, eluting with 35-65% acetonitrile in water (containing 0.1% trifluoroacetic acid) to afford the title compound (53 mg, 59%): $^1$H NMR (400 MHz, Chloroform-d) δ 12.63 (s, 1H), 7.04 (d, 2H), 6.98-6.88 (m, 1H), 6.80 (d, 2H), 6.66 (dd, 1H), 4.82-4.72 (m, 2H), 4.51 (dq, 1H), 4.29 (d, 2H), 4.25 (s, 2H), 3.73 (s, 3H), 3.58 (d, 2H), 2.87 (t, 2H), 2.79 (s, 3H), 2.29-2.15 (m, 2H), 1.91 (d, 2H), 1.36-1.29 (m, 6H); LCMS: 462.3 [M+H]$^+$.

Example 139: 1-[(4-chloro-2-fluorophenyl)methyl]-1-(1-methylpiperidin-4-yl)-3-{[4-(2-methylpropoxy)phenyl]methyl}urea; trifluoroacetic acid (139)

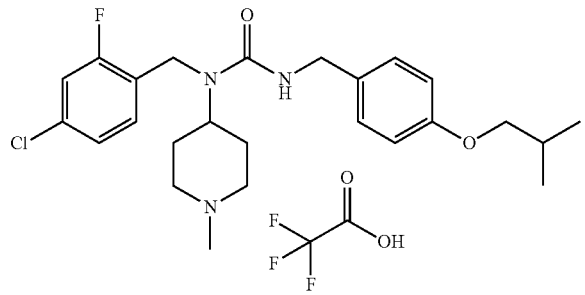

The compound was prepared in analogy with example 135 using (4-chloro-2-fluorophenyl)methanamine and 1-(isocyanatomethyl)-4-(2-methylpropoxy)benzene. The crude material was purified by HPLC, eluting with 20-60% acetonitrile in water (containing 0.1% trifluoroacetic acid) to afford the title compound (79 mg, 68%): $^1$H NMR (400 MHz, Chloroform-d) δ 12.28 (s, 1H), 7.13-7.06 (m, 3H), 7.02 (d, 2H), 6.80 (d, 2H), 4.81-4.71 (m, 1H), 4.67 (s, 1H), 4.38 (s, 2H), 4.28 (s, 2H), 3.70 (d, 2H), 3.60 (d, 2H), 2.94-2.83 (m, 2H), 2.80 (s, 3H), 2.33-2.19 (m, 2H), 2.07 (hept, 1H), 1.92 (d, 2H), 1.02 (d, 6H); LCMS: 462.3 [M+H]$^+$.

Example 140: 1-[(2,4-difluorophenyl)methyl]-1-(1-methylpiperidin-4-yl)-3-[(4-propoxyphenyl)methyl]urea

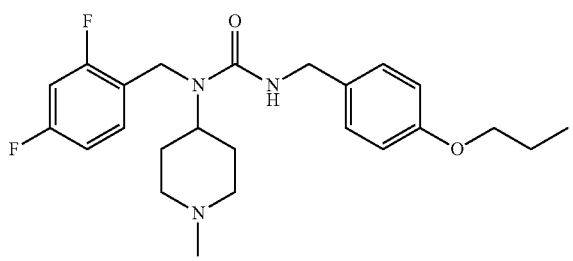 [SMILES: CCCOc1ccc(CNC(=O)N(Cc2ccc(F)cc2F)C2CCN(C)CC2)cc1]

4-propoxybenzonitrile

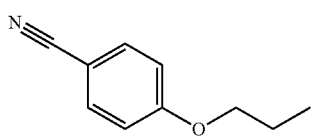

4-hydroxybenzonitrile (6.00 g, 50.4 mmol), potassium carbonate (17.4 g, 126 mmol) and n-propyl iodide (21.4 g, 126 mmol) were heated in DMF (70 ml) at 70° C. for 12 h. After cooling, water (150 ml) was added and the reaction mixture was extracted with diethyl ether (2×250 ml). The combined organic phase was washed with water (200 ml), dried (sodium sulfate) and evaporated to give the desired intermediate (8.00 g, 98%).

1-(4-propoxyphenyl)methanamine

4-propoxybenzonitrile (8.00 g, 49.6 mmol) was dissolved in tetrahydrofuran (50 ml). Lithium aluminiumhydride (2.82 g, 74.4 mmol) was added and the suspension was refluxed for 3 h. After cooling, the reaction mixture was quenched with water (3 ml), aqueous sodium hydroxide solution (15%, 3 ml) and water (9 ml). The precipitate was filtered, the filtrate dried (sodium sulfate) and evaporated to give the desired intermediate (7.00 g, 85%).

phenyl N-[(4-propoxyphenyl)methyl]carbamate

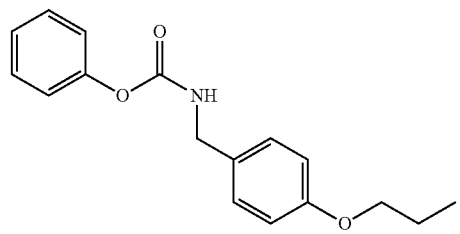 [SMILES: CCCOc1ccc(CNC(=O)Oc2ccccc2)cc1]

1-(4-propoxyphenyl)methanamine (1.66 g, 10.0 mmol) was dissolved in dichloromethane (10 ml). Pyridine (1.22 ml, 15.1 mmol) was added and the solution was cooled to 0° C. Phenyl chloroformate (2.04 g, 13.1 mmol), dissolved in dichloromethane (10 ml), was added dropwise. After addition, HCl (2M, 20 ml) was added. The organic phase was washed with water (20 ml), dried (phase separator) and evaporated. The crude product was crystallized from ethylacetate/heptane to give the desired intermediate (1.8 g, 63%).

1-[(2,4-difluorophenyl)methyl]-1-(1-methylpiperidin-4-yl)-3-[(4-propoxyphenyl)methyl]urea N-[(2,4-difluorophenyl)methyl]-1-methylpiperidin-4-amine (480 mg, 2.0 mmol), phenyl N-[(4-propoxyphenyl)methyl]carbamate (741 mg, 2.6 mmol) and potassium carbonate (414 mg, 3.0 mmol) were heated in toluene (6 ml) at 75° C. for 12 h. The solvent was evaporated and the residue treated with sodium hydroxide solution (1M, 5 ml) and diethyl ether (70 ml). The organic phase was separated, washed with water (10 ml), dried (sodium sulfate) and evaporated. The crude product was purified by chromatography using silicon dioxide gel, eluting with 10% methanol in dichloromethane with 1% ammonia to give the title compound (390 mg, 45%). $^1$H NMR (400 MHz, DMSO-d6) δ 7.24-7.14 (m, 2H), 7.12 (d, 2H), 7.05-6.95 (m, 2H), 6.84 (d, 2H), 4.39 (s, 2H), 4.18 (d, 2H), 3.97-3.91 (m, 1H), 3.88 (d, 2H), 2.70 (t, 2H), 2.09 (s, 3H), 1.88 (t, 2H), 1.70 (h, 2H), 1.56-1.41 (m, 4H), 0.96 (t, 3H); LCMS: 432.3 [M+H]$^+$.

Example 141: 3-{[4-(cyclopropylmethoxy)phenyl]methyl}-1-[(2,4-difluorophenyl)methyl]-1-(1-methylpiperidin-4-yl)urea

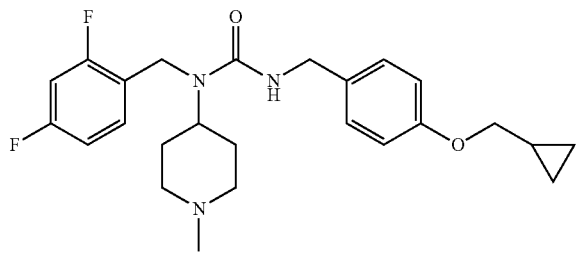 [SMILES: CN1CCC(N(Cc2ccc(F)cc2F)C(=O)NCc2ccc(OCC3CC3)cc2)CC1]

4-(cyclopropylmethoxy)benzonitrile

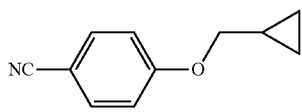

4-hydroxybenzonitrile (1.02 g, 9.9 mmol), (chloromethyl) cyclopropane (2.35 g, 25.9 mmol), tetrabutylammonium iodide (369 mg, 1.0 mmol) and potassium carbonate (4.14 g, 30 mmol) were warmed in DMF (20 ml) at 50° C. for 1 day. After cooling to room temperature, water (50 ml) was added and the aqueous layer was extracted with diethyl ether (2×200 ml). The combined organic phase was washed with water (4×100 ml), dried (sodium sulfate) and evaporated to give the desired intermediate as a yellow oil (1.68 g, 98%).

1-[4-(cyclopropylmethoxy)phenyl]methanamine

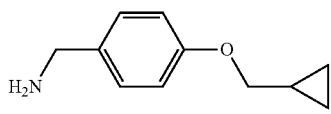

4-(cyclopropylmethoxy)benzonitrile (1.68 g, 9.7 mmol) was dissolved in tetrahydrofuran (10 ml) and added dropwise to a suspension of lithium aluminium hydride (626 mg, 16.5 mmol) in tetrahydrofuran (6 ml). The reaction mixture was refluxed for 3 hours and then quenched with water (0.62 ml), NaOH (aqueous solution 15%, 0.62 ml) and water (1.86 ml). The suspension was filtered, dried (sodium sulfate) and evaporated to give the desired intermediate (1.32 g, 77%).

Phenyl N-{[4-(cyclopropylmethoxy)phenyl]methyl}carbamate

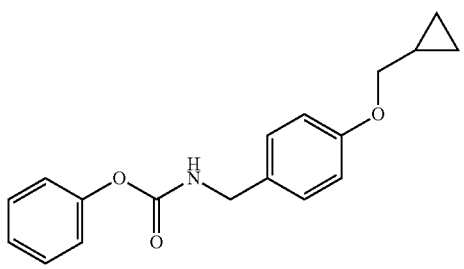 [SMILES: O=C(NCc1ccc(OCC2CC2)cc1)Oc1ccccc1]

1-[4-(cyclopropylmethoxy)phenyl]methanamine (1.32 g, 7.4 mmol) was dissolved in dichloromethane (10 ml). The solution was cooled to 0° C. and pyridine (0.9 ml) was added. Phenyl chloroformate (1.2 ml, 9.7 mmol), dissolved in dichloromethane (10 ml), was added dropwise. The reaction was stirred for 5 min and then hydrochloric acid (1 M, 20 ml) was added, the organic phase was separated and washed with water (30 ml), dried (sodium sulfate) and evaporated. The crude material was purified by chromatography using silicon dioxide gel, eluting with 20% ethyl acetate in petroleum ether to afford the desired intermediate (2.2 g, 89%).

3-{[4-(cyclopropylmethoxy)phenyl]methyl}-1-[(2,4-difluorophenyl)methyl]-1-(1-methylpiperidin-4-yl)urea N-[(2,4-difluorophenyl)methyl]-1-methylpiperidin-4-amine (685 mg, 2.85 mmol), phenyl N-{[4-(cyclopropylmethoxy)phenyl]methyl}carbamate (975 mg, 3.28 mmol) and potassium carbonate (563 mg, 4.08 mmol) were mixed in toluene (10 ml) and warmed at 75° C. for 12 hours. The solvent was evaporated and the residue partitioned between diethyl ether (200 ml) and aqueous sodium hydroxide solution (1 M, 20 ml). The organic phase was washed with water (50 ml), dried (sodium sulfate) and evaporated. The crude material was purified by column chromatography using silicon dioxide gel, eluting with 10% methanol in dichloromethane with 1% ammonia to afford the title compound (525 mg, 42%). $^1$H NMR (400 MHz, DMSO-d6) δ 7.24-7.14 (m, 2H), 7.11 (d, 2H), 7.05-6.96 (m, 2H), 6.83 (d, 2H), 4.39 (s, 2H), 4.17 (d, 2H), 3.94 (s, 1H), 3.77 (d, 2H), 2.78 (s, 2H), 2.17 (s, 3H), 2.00 (d, 2H), 1.61-1.45 (m, 4H), 1.27-1.14 (m, 1H), 0.58-0.51 (m, 2H), 0.32-0.26 (m, 2H); LCMS: 444.3[M+H]$^+$.

Example 142: 1-[(2,4-difluorophenyl)methyl]-1-(piperidin-4-yl)-3-{[4-(propan-2-yloxy)phenyl]methyl}urea (142)

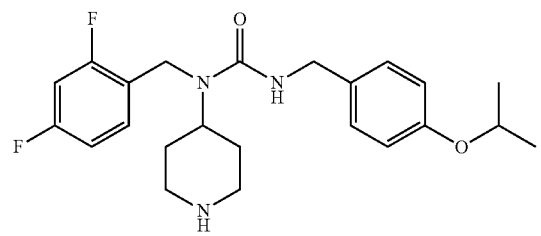 [SMILES: CC(C)Oc1ccc(CNC(=O)N(Cc2ccc(F)cc2F)C2CCNCC2)cc1]

TFA (4 ml) was added to tert-butyl 4-{[(2,4-difluorophenyl)methyl]({[4-(propan-2-yloxy)phenyl]methyl}carbamoyl)amino}piperidine-1-carboxylate (1.20 g, 2.32 mmol prepared in example 75) in CH$_2$Cl$_2$ (10 ml) at room temperature. After 20 minutes of stirring at room temperature the mixture concentrated under reduced pressure, NaHCO$_3$ (10 ml, sat. aq.) and diethyl ether (150 ml) was added. The organic phase dried with Na$_2$SO$_4$, filtered, and concentrated under reduced pressure to afford the desired intermediate (0.80 g) that was used without further purification, or to obtained concentrate purified by preparative HPLC, eluting with 20-40% acetonitrile in water (containing 0.1% trifluoroacetic acid) to afford 1-[(2,4-difluorophenyl)methyl]-1-(piperidin-4-yl)-3-{[4-(propan-2-yloxy)phenyl]methyl}urea.

Example 143: 1-[(2,4-difluorophenyl)methyl]-3-{[3-fluoro-4-(propan-2-yloxy)phenyl]methyl}-1-(1-methylpiperidin-4-yl)urea; trifluoroacetic acid

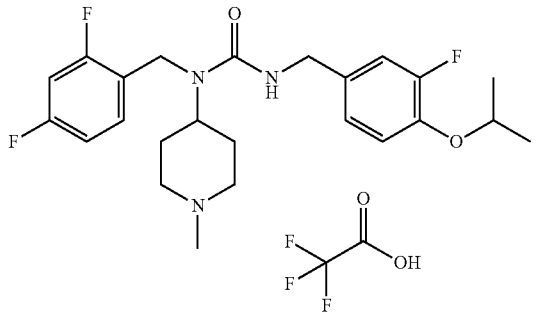 [SMILES: CC(C)Oc1ccc(CNC(=O)N(Cc2ccc(F)cc2F)C2CCN(C)CC2)cc1F ; O=C(O)C(F)(F)F]

The compound was prepared in analogy with 1-[(2,4-difluorophenyl)methyl]-1-(1-methylpiperidin-4-yl)-3-{[4-(2-methylpropoxy)phenyl]methyl}urea using N-[(2,4-difluorophenyl)methyl]-1-methylpiperidin-4-amine and 2-fluoro-4-(isocyanatomethyl)-1-(propan-2-yloxy)benzene (1.2:1). Yield: 60%. $^1$H NMR (400 MHz, Chloroform-d) δ 12.71 (bs, 1H), 7.19-7.09 (m, 1H), 6.90-6.76 (m, 5H), 4.85-4.64 (m, 2H), 4.58-4.44 (m, 1H), 4.38 (s, 2H), 4.28 (d, 2H), 3.60 (d, 2H), 2.93-2.70 (m, 5H), 2.28-2.10 (m, 2H), 1.91 (d, 2H), 1.34 (d, 6H); LCMS: 450.3 [M+H]$^+$.

Example 144: 1-[(2,4-difluorophenyl)methyl]-3-{[2-fluoro-4-(propan-2-yloxy)phenyl]methyl}-1-(1-methylpiperidin-4-yl)urea; trifluoroacetic acid

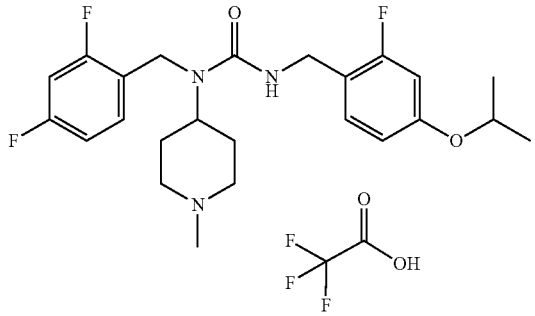 [SMILES: CC(C)Oc1ccc(CNC(=O)N(Cc2ccc(F)cc2F)C2CCN(C)CC2)c(F)c1 ; O=C(O)C(F)(F)F]

The compound was prepared in analogy with 1-[(2,4-difluorophenyl)methyl]-1-(1-methylpiperidin-4-yl)-3-{[4-(2-methylpropoxy)phenyl]methyl}urea using N-[(2,4-difluorophenyl)methyl]-1-methylpiperidin-4-amine and 2-fluoro-1-(isocyanatomethyl)-4-(propan-2-yloxy)benzene (1.2:1). Yield: 58%. $^1$H NMR (400 MHz, Chloroform-d) δ 12.89 (bs, 1H), 7.13-7.02 (m, 2H), 6.88-6.73 (m, 2H), 6.58 (dd, 1H), 6.51 (dd, 1H), 4.80-4.63 (m, 2H), 4.48 (hept, 1H), 4.35 (s, 2H), 4.30 (d, 2H), 3.59 (d, 2H), 2.88-2.72 (m, 5H), 2.17 (qd, 2H), 1.88 (d, 2H), 1.32 (d, 6H); LCMS: 450.3 [M+H]$^+$.

Example 145: 1-[(2,4-difluorophenyl)methyl]-3-{[3-methyl-4-(propan-2-yloxy)phenyl]methyl}-1-(1-methylpiperidin-4-yl)urea; trifluoroacetic acid

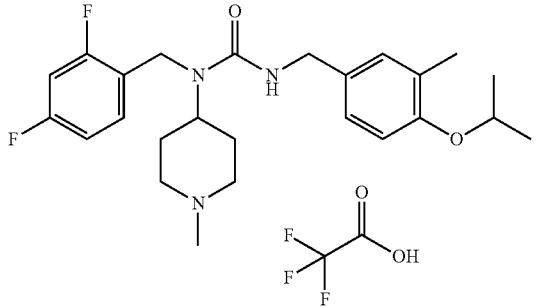

The compound was prepared in analogy with 1-[(2,4-difluorophenyl)methyl]-1-(1-methylpiperidin-4-yl)-3-{[4-(2-methylpropoxy)phenyl]methyl}urea using N-[(2,4-difluoro-phenyl)methyl]-1-methylpiperidin-4-amine and 4-(isocyanatomethyl)-2-methyl-1-(propan-2-yloxy)benzene (1.2:1). Yield: 74%. $^1$H NMR (400 MHz, Chloroform-d) δ 11.76 (bs, 1H), 7.15 (q, 1H), 6.88-6.77 (m, 4H), 6.71 (d, 1H), 4.91-4.67 (m, 2H), 4.53-4.35 (m, 3H), 4.24 (s, 2H), 3.56 (d, 2H), 2.93 (q, 2H), 2.79 (d, 3H), 2.42 (q, 2H), 2.13 (s, 3H), 1.92 (d, 2H), 1.32 (d, 6H); LCMS: 446.3 [M+H]$^+$.

Example 146: 1-[(2,4-difluorophenyl)methyl]-3-[(4-fluoro-3-methoxyphenyl)methyl]-1-(1-methylpiperidin-4-yl)urea; trifluoroacetic acid

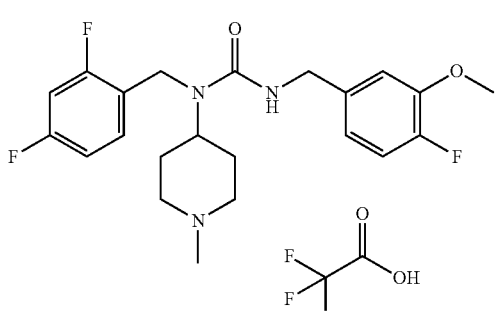

The compound was prepared in analogy with 3-[(1-benzofuran-5-yl)methyl]-1-[(2,4-difluorophenyl)methyl]-1-(1-methylpiperidin-4-yl)urea using N-[(2,4-difluorophenyl)methyl]-1-methylpiperidin-4-amine and (4-fluoro-3-methoxyphenyl)methanamine (1:1). Diisoproylethylamine was used instead of triethylamine. Yield: 62%. $^1$H NMR (400 MHz, Chloroform-d) δ 12.41 (bs, 1H), 7.16 (q, 1H), 6.97 (dd, 1H), 6.84 (t, 2H), 6.76 (dd, 1H), 6.68-6.59 (m, 1H), 4.82 (s, 1H), 4.78-4.64 (m, 1H), 4.42 (s, 2H), 4.31 (d, 2H), 3.83 (s, 3H), 3.60 (d, 2H), 2.95-2.83 (m, 2H), 2.80 (s, 3H), 2.42-2.25 (m, 2H), 1.92 (d, 2H); LCMS: 422.3 [M+H]$^+$.

Example 147: 1-[(2,4-difluorophenyl)methyl]-3-({4-[(2-ethylhexyl)oxy]phenyl}methyl)-1-(1-methylpiperidin-4-yl)urea; trifluoroacetic acid

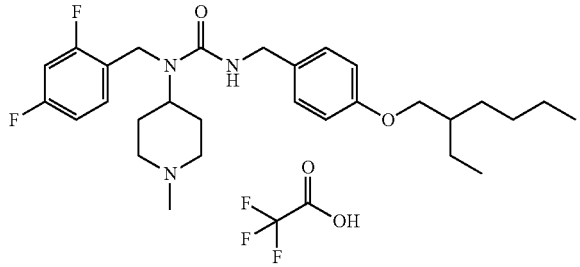 [SMILES: CCCCC(CC)COc1ccc(CNC(=O)N(Cc2ccc(F)cc2F)C2CCN(C)CC2)cc1 ; O=C(O)C(F)(F)F]

The compound was prepared in analogy with 1-[(2,4-difluorophenyl)methyl]-3-{[4-(2-fluoroethoxy)phenyl]methyl}-1-(1-methylpiperidin-4-yl)urea using 2-ethylhexan-1-ol. Sodium hydride in dimethylformamide was used instead of potassium tert-butoxide in tetrahydrofuran. Yield: 53%. $^1$H NMR (400 MHz, Chloroform-d) δ 12.44 (bs, 1H), 7.12 (q, 1H), 7.03 (d, 2H), 6.86-6.79 (m, 4H), 4.80-4.63 (m, 2H), 4.36 (s, 2H), 4.29 (s, 2H), 3.81 (dd, 2H), 3.61 (d, 2H), 2.94-2.81 (m, 2H), 2.79 (s, 3H), 2.17 (qd, 2H), 1.91 (d, 2H), 1.70 (h, 1H), 1.57-1.28 (m, 8H), 0.97-0.88 (m, 6H); LCMS: 502.4 [M+H]$^+$.

Example 148: 1-[(2,4-difluorophenyl)methyl]-1-(1-methylpiperidin-4-yl)-3-{[4-(prop-2-yn-1-yloxy)phenyl]methyl}urea; trifluoroacetic acid

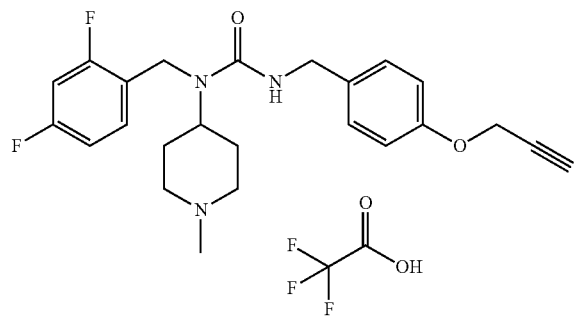 [SMILES: C#CCOc1ccc(CNC(=O)N(Cc2ccc(F)cc2F)C2CCN(C)CC2)cc1 ; O=C(O)C(F)(F)F]

The compound was prepared in analogy with 1-[(2,4-difluorophenyl)methyl]-3-{[4-(2-fluoroethoxy)phenyl]methyl}-1-(1-methylpiperidin-4-yl)urea using prop-2-yn-1-ol. Sodium hydride in dimethylformamide was used instead of potassium tert-butoxide in tetrahydrofuran and the intermediate nitrile was reduced with lithium aluminum hydride instead of borane. Yield: 26%. $^1$H NMR (400 MHz, Chloroform-d) δ 13.10 (bs, 1H), 7.17-7.10 (m, 1H), 7.07 (d, 2H), 6.92-6.86 (m, 2H), 6.82 (t, 2H), 4.78-4.62 (m, 4H), 4.37 (s, 2H), 4.30 (d, 2H), 3.59 (d, 2H), 2.85-2.75 (m, 5H), 2.52 (t, 1H), 2.26-2.10 (m, 2H), 1.90 (d, 2H); LCMS: 428.3 [M+H]$^+$.

Example 149: 3-{[4-(tert-butoxy)phenyl]methyl}-1-[(2,4-difluorophenyl)methyl]-1-(piperidin-4-yl)urea; trifluoroacetic acid

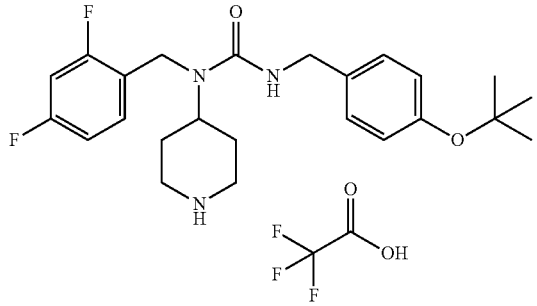

[4-(tert-butoxy)phenyl]methanamine (27.7 mg, 154 µmol) and diisopropylethylamine (53.8 µl, 309 µmol) in dichloromethane (1 ml) were added to tert-butyl 4-[(chlorocarbonyl)[(2,4-difluorophenyl)methyl]amino]piperidine-1-carboxylate (40 mg, 103 mol). After 5 hours of stirring at room temperature the mixture was washed with hydrochloric acid (aqueous, 1M, 1 ml) and dried using a phase-separator. Trifluoroacetic acid (100 µl) was added and the mixture was stirred for 30 minutes before it was concentrated. The crude material was purified by HPLC, eluting with 20-50% acetonitrile in water (containing 0.1% trifluoroacetic acid) to afford the title compound (4.7 mg, 8%): $^1$H NMR 9.36 (bs, 1H), 9.02 (bs, 1H), 7.23-7.09 (m, 1H), 7.01 (d, 2H), 6.89 (d, 2H), 6.87-6.74 (m, 2H), 4.81-4.53 (m, 2H), 4.39 (s, 2H), 4.32 (s, 2H), 3.43 (d, 2H), 3.05-2.80 (m, 2H), 2.12-1.96 (m, 2H), 1.91 (d, 2H), 1.33 (s, 9H); LCMS: 432.3 [M+H]$^+$.

Example 150: 1-[(2,6-difluoro-4-methoxyphenyl)methyl]-3-[(2,4-difluorophenyl)methyl]-3-(1-methylpiperidin-4-yl)urea; trifluoroacetic acid Pyridine (137 mg, 1.73 mmol) was added to triphosgene (174 mg, 586 µmol) in dichloromethane (2 ml) at room temperature, followed by addition of (2,6-difluoro-4-methoxyphenyl)methanamine (111 mg, 640 µmol). After 20 minutes of stirring at room temperature HCl (1 ml, 1 M aqueous) was added to the mixture. The organic phase was separated and dried using a phase separator. N-[(2,4-difluorophenyl)methyl]-1-methylpiperidin-4-amine (118 mg, 492 µmol) was added to this solution. After 19 hours of stirring at room temperature the mixture was concentrated and the crude material was purified by HPLC, eluting with 30-70% acetonitrile in water (containing 0.1% trifluoroacetic acid) to afford the title compound (137.7 mg, 51%): ¹H NMR (400 MHz, Chloroform-d) δ 12.34 (bs, 1H), 7.05 (q, 1H), 6.90-6.68 (m, 2H), 6.38 (d, 2H), 4.87-4.62 (m, 2H), 4.41-4.25 (m, 4H), 3.76 (s, 3H), 3.58 (d, 2H), 2.90-2.66 (m, 5H), 2.31-2.06 (m, 2H), 1.88 (d, 2H); LCMS: 440.2 [M+H]⁺.

Example 151: 3-[(2,4-difluorophenyl)methyl]-1-{[4-(3-fluoropropoxy)phenyl]methyl}-3-(1-methylpiperidin-4-yl)urea; trifluoroacetic acid

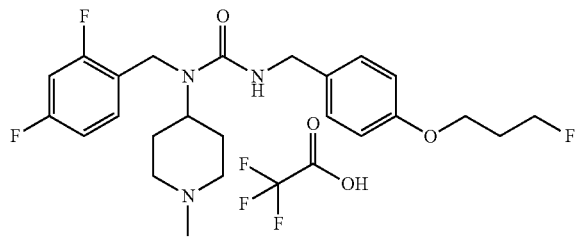

4-(3-fluoropropoxy)benzonitrile

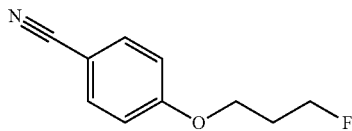 [SMILES: N#Cc1ccc(OCCCF)cc1]

Potassium carbonate (670 mg, 4.85 mmol) was added to a solution of 1-bromo-3-fluoropropane (275 mg, 1.95 mmol) and 4-hydroxybenzonitrile (202 mg, 1.70 mmol) in N,N-dimethylformamide (2 ml). After 18 hours of stirring at room temperature the mixture was added to ethylacetate (10 ml) and washed with NaOH (3×10 ml, 1 M aqueous). The organic phase was dried using a phase separator and concentrated to oil (303 mg).

[4-(3-fluoropropoxy)phenyl]methanamine

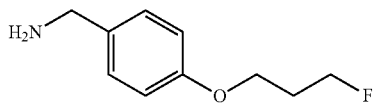 [SMILES: NCc1ccc(OCCCF)cc1]

A borane solution (5 ml, 1 M in tetrahydrofuran) at 4° C. was added to 4-(3-fluoropropoxy)benzonitrile (303 mg, 1.69 mmol). After 3 hours of stirring at room temperature additional borane solution (2 ml, 1 M in tetrahydrofuran) was added. After 18 hours of stirring at 50° C., methanol was added dropwise and the solution heated to reflux for 30 minutes. The solution was concentrated, redissolved in dichloromethane (5 ml) and washed with NaOH (5 ml, 1 M aqueous). The organic phase was dried using a phase separator and concentrated to solids (540 mg).

3-[(2,4-difluorophenyl)methyl]-1-{[4-(3-fluoropropoxy)phenyl]methyl}-3-(1-methylpiperidin-4-yl)urea; trifluoroacetic acid

[4-(3-fluoropropoxy)phenyl]methanamine (36.8 mg, 201 µmol) in dichloromethane (0.5 ml) was added to diphosgene (26.7 µl, 221 µmol) in dichloromethane (0.5 ml), followed by addition of pyridine (65 µl, 803 µmol). After 20 minutes of stirring at room temperature N-[(2,4-difluorophenyl)methyl]-1-methylpiperidin-4-amine (72.0 mg, 300 µmol) in dichloromethane (0.5 ml) was added. After 100 minutes of stirring at room temperature the mixture was washed with sodium hydroxide (2 ml, 1 M aqueous), the aqueous phase was extracted with dichloromethane (1 ml), the combined organic phases were dried using a phase separator and concentrated. The crude material was purified by HPLC, eluting with 20-50% acetonitrile in water (containing 0.1% trifluoroacetic acid) to afford the title compound (33 mg, 50% over 3 steps): ¹H NMR (400 MHz, Chloroform-d) δ 12.89 (bs, 1H), 7.12 (q, 1H), 7.04 (d, 2H), 6.89-6.76 (m, 4H), 4.78-4.64 (m, 3H), 4.58 (t, 1H), 4.36 (s, 2H), 4.28 (d, 2H), 4.06 (t, 2H), 3.58 (d, 2H), 2.88-2.74 (m, 5H), 2.28-2.06 (m, 4H), 1.90 (d, 2H); LCMS: 450.3 [M+H]⁺.

Example 152: 1-{[4-(1,1-difluoroethyl)phenyl]methyl}-3-[(2,4-difluorophenyl)methyl]-3-(1-methylpiperidin-4-yl)urea; trifluoroacetic acid

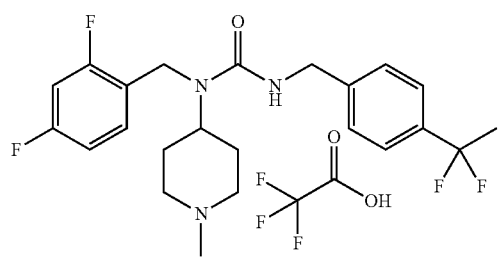

4-(1,1-difluoroethyl)benzonitrile

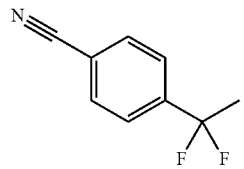

Diethylaminosulfur trifluoride (2 ml, 15.1 mmol) was added to 4-acetylbenzonitrile (300 mg, 2.07 mmol) in dichloromethane (4 ml) at room temperature. The mixture was heated gradually to 50° C. over 2 hours. After 18 hours of stirring at this temperature the mixture was added dropwise onto ice over 10 minutes, water was added and the mixture extracted with dichloromethane (3×3 ml). The combined organic phases were dried using a phase separator and concentrated to oil. The crude material was purified by column chromatography using silicon dioxide gel, eluting with 3-50% ethyl acetate in petroleum ether to afford the title compound as oil (355 mg, quantitative).

173

[4-(1,1-difluoroethyl)phenyl]methanamine

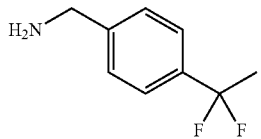

A solution of 4-(1,1-difluoroethyl)benzonitrile (149 mg, 891 µmol) in diethyl ether (1 ml) was added dropwise over 2 minutes to a suspension of LiAlH$_4$ (67.7 mg, 1.78 mmol) in diethyl ether (1 ml) at 0° C. After 10 minutes of stirring at 0° C. the mixture was brought to room temperature. After 1 hour at this temperature the mixture was heated to reflux. After an additional 30 minutes Na$_2$SO$_4$ (decahydrate) was added in portions until gas evolution ceased. The resulting slurry was filtered with using diethyl ether over a plug of celite. The solution was concentrated to afford the desired intermediate as clear oil (119 mg, 78%).

1-{[4-(1,1-difluoroethyl)phenyl]methyl}-3-[(2,4-difluorophenyl)methyl]-3-(1-methylpiperidin-4-yl) urea; trifluoroacetic acid

[4-(1,1-difluoroethyl)phenyl]methanamine (54.6 mg, 319 µmol) in dichloromethane (0.5 ml) was added to diphosgene (19.5 µl, 162 µmol) in dichloromethane (0.5 ml), followed by pyridine (51.6 µl, 638 µmol). After 10 minutes of stirring at room temperature N-[(2,4-difluorophenyl)methyl]-1-methylpiperidin-4-amine (93.4 mg, 389 µmol) in dichloromethane (0.5 ml) was added. After 170 minutes of stirring at room temperature the mixture was washed with sodium hydroxide (2 ml, 1 M aqueous), the aqueous phase was extracted with dichloromethane (3×0.5 ml), the combined organic phases were dried using a phase separator and concentrated to oil (173 mg). The crude material was purified by HPLC, eluting with 20-50% acetonitrile in water (containing 0.1% trifluoroacetic acid) to afford the title compound (78 mg, 44%): $^1$H NMR (400 MHz, Chloroform-d) δ 12.73 (bs, 1H), 7.41 (d, 2H), 7.21-7.09 (m, 3H), 6.82 (t, 2H), 4.88 (s, 1H), 4.74-4.59 (m, 1H), 4.44-4.35 (m, 4H), 3.58 (d, 2H), 2.88-2.71 (m, 5H), 2.29-2.11 (m, 2H), 1.96-1.83 (m, 5H); LCMS: 438.3 [M+H]$^+$.

Example 153: 3-[(2,4-difluorophenyl)methyl]-1-({4-[(1,3-difluoropropan-2-yl)oxy]phenyl}methyl)-3-(1-methylpiperidin-4-yl)urea; trifluoroacetic acid

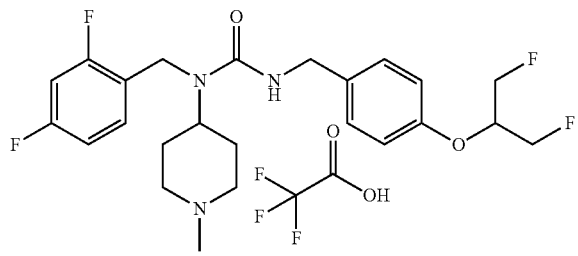

174

4-[(1,3-difluoropropan-2-yl)oxy]benzonitrile

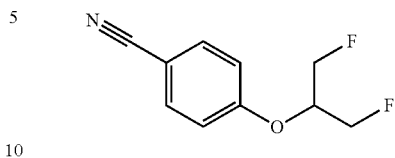

1,3-difluoropropan-2-ol (192 µl, 2.48 mmol) was added to potassium tert-butoxide (280 mg, 2.5 mmol) in dioxane (2 ml). After 7 minutes of stirring at room temperature a solution of 4-fluorobenzonitrile (209 mg, 1.73 mmol) in dioxane (2 ml) was added. After 17 hours of stirring at room temperature the reaction mixture was added to a layer of diethyl ether (5 ml) on water (5 ml). The aqueous phase was extracted with diethyl ether (3×5 ml) and the combined organic phases were dried using a phase separator and concentrated to white solids (190 mg, 56%).

{4-[(1,3-difluoropropan-2-yl)oxy]phenyl}methanamine

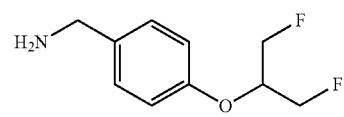 [SMILES: NCc1ccc(OC(CF)CF)cc1]

A borane solution (2 ml, 1 M in tetrahydrofuran) at 4° C. was added to 4-[(1,3-difluoropropan-2-yl)oxy]benzonitrile (89.2 mg, 452 µmol). After 1 hours of stirring at room temperature the solution was heated to 40° C. for 1 hour. The solution was concentrated, re-dissolved in methanol (2 ml), heated to reflux for 1 hour and concentrated. NaOH (1 ml, 1 M aqueous) was added and the aqueous solution extracted with ethyl acetate (2×1 ml). The combined organic phases were dried using a phase separator and concentrated to oil (81.5 mg, 90%).

3-[(2,4-difluorophenyl)methyl]-1-({4-[(1,3-difluoropropan-2-yl)oxy]phenyl}methyl)-3-(1-methylpiperidin-4-yl)urea; trifluoroacetic acid {4-[(1,3-difluoropropan-2-yl)oxy]phenyl}methanamine (40.7 mg, 202 µmol) in dichloromethane (0.5 ml) was added to diphosgene (12.2 µl, 101 µmol) in dichloromethane (0.5 ml), followed by diisopropylethylamine (70.5 µl, 405 µmol). After 15 minutes of stirring at room temperature N-[(2,4-difluorophenyl)methyl]-1-methylpiperidin-4-amine (58.3 mg, 243 µmol) in dichloromethane (0.5 ml) was added. After 2 hours of stirring at room temperature the mixture was concentrated to oil. The crude material was purified by HPLC, eluting with 15-50% acetonitrile in water (containing 0.1% trifluoroacetic acid) to afford the title compound (21 mg, 18%). $^1$H NMR (400 MHz, Chloroform-d) δ 13.09 (bs, 1H), 7.12 (q, 1H), 7.06 (d, 2H), 6.88 (d, 2H), 6.81 (t, 2H), 4.80-4.53 (m, 7H), 4.37 (s, 2H), 4.29 (d, 2H), 3.57 (d, 2H), 2.89-2.72 (m, 5H), 2.19 (q, 2H), 1.89 (d, 2H); LCMS: 468.3 [M+H]$^+$.

Example 154: 3-{[4-(2,2-difluoroethoxy)phenyl]methyl}-1-[(2,4-difluorophenyl)methyl]-1-(1-methylpiperidin-4-yl)urea; trifluoroacetic acid

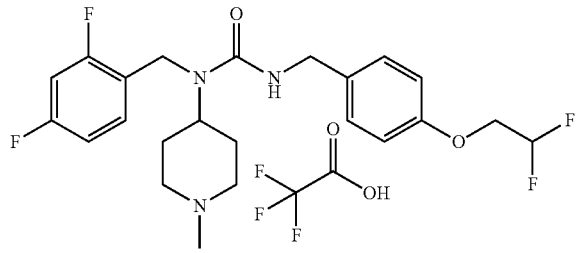

4-(2,2-difluoroethoxy)benzonitrile

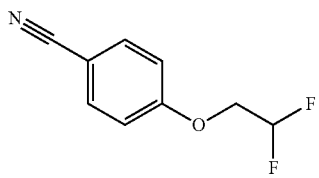 [SMILES: N#Cc1ccc(OCC(F)F)cc1]

2,2-difluoroethan-1-ol (125 µl, 1.98 mmol) was added to potassium tert-butoxide (202 mg, 1.8 mmol) in tetrahydrofuran (1.5 ml). After 5 minutes of stirring at room temperature a solution of 4-fluorobenzonitrile (200 mg, 1.65 mmol) in tetrahydrofuran (1.5 ml) was added. After 45 minutes of stirring at room temperature the reaction mixture was added to a layer of ethyl acetate (5 ml) on NaOH (3 ml, 1 M aqueous). The organic phase was washed with NaOH (3×3 ml, 1 M aqueous), the organic phase was separated, dried using a phase separator and concentrated to white solids (256 mg, 85%).

[4-(2,2-difluoroethoxy)phenyl]methanamine

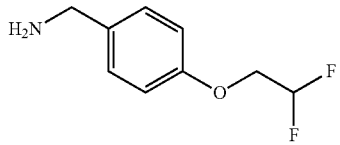 [SMILES: NCc1ccc(OCC(F)F)cc1]

A borane solution (4 ml, 1 M in tetrahydrofuran) at 4° C. was added to 4-(2,2-difluoroethoxy)benzonitrile (200 mg, 1.09 mmol). After 17 hours of stirring at room temperature the solution was concentrated, re-dissolved in methanol (2 ml), heated to reflux for 1 hour and concentrated. The residues were dissolved in dichloromethane (5 ml) and washed with NaOH (5 ml, 1 M aqueous), the organic phase was separated, dried using a phase separator and concentrated to oil (219 mg, quant).

3-{[4-(2,2-difluoroethoxy)phenyl]methyl}-1-[(2,4-difluorophenyl)methyl]-1-(1-methylpiperidin-4-yl) urea; trifluoroacetic acid Diphosgene (33 µl, 275 µmol) in dichloromethane (0.5 ml) was added to [4-(2,2-difluoroethoxy)phenyl]methanamine (103 mg, 550 µmol) in dichloromethane (0.5 ml), followed by diisopropylethylamine (192 µl, 1.10 mmol). After 20 minutes of stirring at room temperature N-[(2,4-difluorophenyl)methyl]-1-methylpiperidin-4-amine (145 mg, 605 µmol) in dichloromethane (1 ml) was added. After 30 minutes of stirring at room temperature NaOH (2 ml, 1 M aqueous) was added, the organic phase was separated, dried (phase separator) and concentrated to oil (303 mg). The crude material was purified by HPLC, eluting with 20-50% acetonitrile in water (containing 0.1% trifluoroacetic acid) to afford the title compound (102 mg, 33%). $^1$H NMR (400 MHz, Chloroform-d) δ 12.60 (bs, 1H), 7.12 (q, 1H), 7.06 (d, 2H), 6.87-6.76 (m, 4H), 6.06 (tt, 1H), 4.82-4.62 (m, 2H), 4.37 (s, 2H), 4.29 (s, 2H), 4.14 (td, 2H), 3.58 (d, 2H), 2.84 (t, 2H), 2.77 (s, 3H), 2.30-2.11 (m, 2H), 1.89 (d, 2H); LCMS: 454.2 [M+H]$^+$.

Example 155: 1-[(2,4-difluorophenyl)methyl]-3-[(2,2-dimethyl-2H-chromen-6-yl)methyl]-1-(1-methylpiperidin-4-yl)urea; trifluoroacetic acid

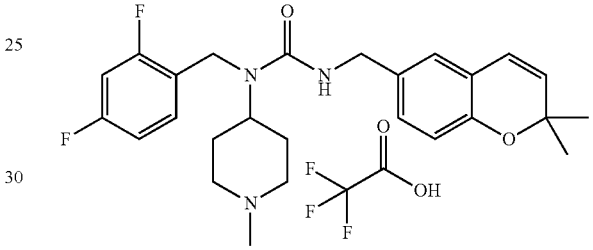

(2,2-dimethyl-2H-chromen-6-yl)methanamine

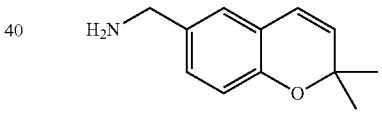

A solution of 2,2-dimethyl-2H-chromene-6-carbonitrile (300 mg, 1.62 mmol) in diethyl ether (2 ml) was added dropwise to a suspension of lithium aluminum hydride (135 mg, 3.56 mmol) in diethyl ether (3 ml) at 0° C. After 30 minutes of stirring at 0° C. the mixture was brought to room temperature. After 1 hour of stirring at room temperature, sodium sulfate decahydrate was added in small portions until gas evolution ceased. The mixture was filtered and the organic solution was concentrated to oil (269 mg, 88%).

1-[(2,4-difluorophenyl)methyl]-3-[(2,2-dimethyl-2H-chromen-6-yl)methyl]-1-(1-methylpiperidin-4-yl) urea; trifluoroacetic acid (2,2-dimethyl-2H-chromen-6-yl)methanamine (68.7 mg, 363 µmol) in dichloromethane (0.5 ml) was added to diphosgene (22 µl, 183 µmol) in dichloromethane (0.5 ml), followed by diisopropylethylamine (190 µl, 1.09 mmol). After 10 minutes of stirring at room temperature N-[(2,4-difluorophenyl)methyl]-1-methylpiperidin-4-amine (110 mg, 456 mol) in dichloromethane (0.5 ml) was added. After 2 hours of stirring at room temperature the solution was concentrated to oil. The crude material was purified by HPLC, eluting with 20-40% acetonitrile in water (containing 0.1% trifluoroacetic acid) to afford the title compound (164 mg, 79%). ¹H NMR (400 MHz, Chloroform-d) δ 12.62 (bs, 1H), 7.12 (q, 1H), 6.86-6.78 (m, 3H), 6.71-6.61 (m, 2H), 6.21 (d, 1H), 5.60 (d, 1H), 4.78-4.63 (m, 2H), 4.36 (s, 2H), 4.23 (s, 2H), 3.58 (d, 2H), 2.84 (t, 2H), 2.77 (s, 3H), 2.18 (qd, 2H), 1.90 (d, 2H), 1.40 (s, 6H); LCMS: 456.3 [M+H]⁺.

Example 156: 3-[(2,4-difluorophenyl)methyl]-1-[(4-methoxyphenyl)methyl]-3-(1-methylpiperidin-4-yl) urea

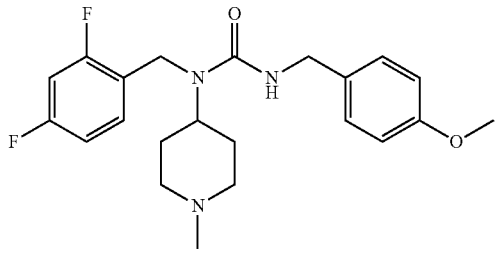 [SMILES: COc1ccc(CNC(=O)N(Cc2ccc(F)cc2F)C2CCN(C)CC2)cc1]

A solution of 1-methoxy-4-(isocyanatomethyl)benzene (172 mg 1.03 mmol) in dichloromethane (1 ml) was added to N-[(2,4-difluorophenyl)methyl]-1-methylpiperidin-4-amine (200 mg, 0.79 mmol) in dichloromethane (2 ml). The mixture was stirred 1 h, then evaporated and the residue was purified by column chromatography using silicon dioxide gel, eluting with 0-25% methanol in ethyl acetate to afford the title compound (192 mg, 60%): ¹H NMR (400 MHz, Chloroform-d) δ 7.25-7.16 (m, 1H), 7.11 (d, 2H), 6.85-6.73 (m, 4H), 4.55 (t, 1H), 4.40 (s, 2H), 4.32 (d, 2H), 4.32-4.21 (m, 2H), 3.78 (s, 3H), 2.89 (d, 2H), 2.27 (s, 3H), 2.13-2.03 (m, 2H), 1.74-1.61 (m, 4H); LC-MS: 403.9 [M+H]⁺.

Example 157: 1-[(4-cyclopropoxyphenyl)methyl]-3-[(2,4-difluorophenyl)methyl]-3-(piperidin-4-yl)urea; trifluoroacetic acid

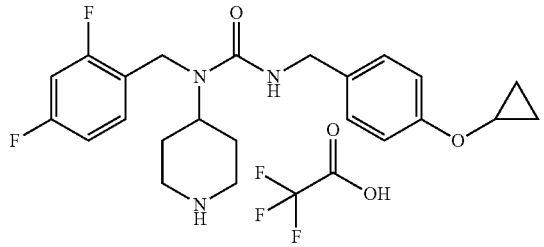

tert-butyl 4-({[(4-cyclopropoxyphenyl)methyl]carbamoyl}) [(2,4-difluorophenyl)methyl]amino)piperidine-1-carboxylate

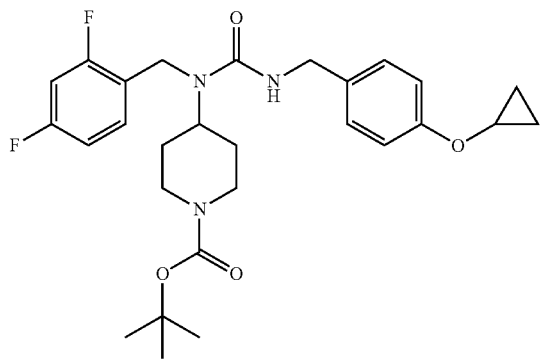 [SMILES: CC(C)(C)OC(=O)N1CCC(N(Cc2ccc(F)cc2F)C(=O)NCc2ccc(OC3CC3)cc2)CC1]

tert-butyl 4-{[(2,4-difluorophenyl)methyl] amino}piperidine-1-carboxylate (0.45 mmol, 147 mg), phenyl N-[(4-cyclopropoxyphenyl)methyl]carbamate (130 mg, 0.45 mmol) and Cs₂CO₃ (0.8 mmol, 261 mg) were suspended in toluene (2.0 ml). The mixture was stirred at 70° C. for 2 h, then partitioned between diethyl ether and NaOH (0.1 M, aqueous), a solid was removed by filtration, the organic phase was separated, concentrated, and the residue was purified by column chromatography using silicon dioxide gel, eluting with 20-100% ethyl acetate in hexanes to afford the desired intermediate (115 mg, 50%).

1-[(4-cyclopropoxyphenyl)methyl]-3-[(2,4-difluorophenyl)methyl]-3-(piperidin-4-yl)urea; trifluoroacetic acid tert-butyl 4-({[(4-cyclopropoxyphenyl)methyl]carbamoyl}[(2,4-difluorophenyl)methyl]amino)piperidine-1-carboxylate (115 mg, 0.223 mmol) was dissolved in dichloromethane (1 ml) on an ice bath and trifluoroacetic acid (1 ml) was added. The mixture was stirred for 30 min at 0° C., then concentrated from isopropyl acetate two times. The residue was dissolved in water and freeze dried to afford the title compound (107.4 mg, 91%): ¹H NMR (400 MHz, Chloroform-d) δ 9.46 (bs, 1H), 9.00 (bs, 1H), 7.15 (q, 1H), 7.05 (d, 2H), 6.95 (d, 2H), 6.87-6.77 (m, 2H), 4.70 (bs, 1H), 4.60 (m, 1H), 4.37 (s, 2H), 4.29 (s, 2H), 3.70 (m, 1H), 3.42 (d, 2H), 2.96 (m, 2H), 2.09-1.80 (m, 4H), 0.75 (m, 4H); LC-MS: 416.3 [M+H]⁺.

Example 158: 1-[(2,4-difluorophenyl)methyl]-3-[(2,2-dimethyl-2,3-dihydro-1-benzofuran-5-yl)methyl]-1-(piperidin-4-yl)urea; trifluoroacetic acid

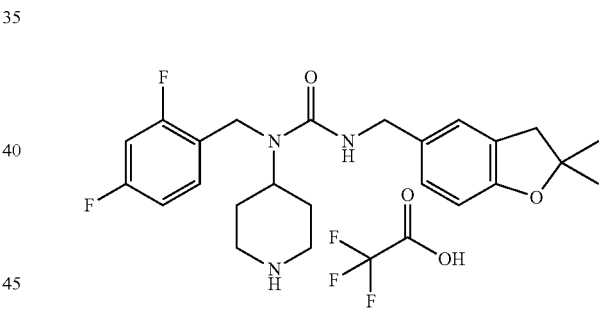

tert-butyl 4-{[(2,4-difluorophenyl)methyl]({[(2,2-dimethyl-2,3-dihydro-1-benzofuran-5-yl)methyl]carbamoyl})amino}piperidine-1-carboxylate

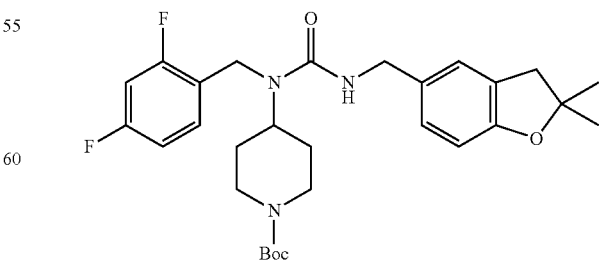

(2,2-dimethyl-2,3-dihydro-1-benzofuran-5-yl)methanamine; hydrochloride (25 mg, 0.141 mmol) and triethylamine (39.3 μl, 0.28 mmol) were dissolved in dichloromethane (0.5 ml) and was slowly added to a solution of diphosgene (14.6 mg, 74 μmol) in dichloromethane (0.5 ml). The reaction was stirred at room temperature for 30 min. tert-butyl 4-{[(2,4-difluorophenyl)methyl]amino}piperidine-1-carboxylate (48 mg, 0.15 mmol) was dissolved in dichloromethane (0.5 ml) and the solution was added to the reaction and stirred overnight. The mixture was concentrated and purified by column chromatography using silicon dioxide gel, eluting with 30-70% ethyl acetate in petroleum ether to afford the desired intermediate (57 mg, 76%).

1-[(2,4-difluorophenyl)methyl]-3-[(2,2-dimethyl-2,3-dihydro-1-benzofuran-5-yl)methyl]-1-(piperidin-4-yl)urea; trifluoroacetic acid tert-butyl 4-{[(2,4-difluorophenyl)methyl]({[(2,2-dimethyl-2,3-dihydro-1-benzofuran-5-yl)methyl]carbamoyl})amino}piperidine-1-carboxylate (57 mg, 0.11 mmol) was dissolved in dichloromethane (1.1 ml). The solution was cooled to 0° C. and trifluoroacetic acid (0.16 ml) was added and stirred at 0° C. for 30 min. The solution was concentrated. The crude material was purified by HPLC, eluting with 20-55% acetonitrile in water (containing 0.1% trifluoroacetic acid) to afford the title compound (23 mg, 39%): $^1$H NMR (400 MHz, Chloroform-d) δ 9.36 (s, 1H), 8.93 (s, 1H), 7.19-7.10 (m, 1H), 6.91-6.76 (m, 4H), 6.61 (d, 1H), 4.69 (s, 1H), 4.60 (t, 1H), 4.37 (s, 2H), 4.26 (s, 2H), 3.43 (d, 2H), 3.05-2.88 (m, 4H), 2.10-1.83 (m, 4H), 1.46 (s, 6H); LCMS: 430.3 [M+H]$^+$.

Example 159: 1-[(2,4-difluorophenyl)methyl]-3-{[2,3-dihydro(2,2,3,3-$^2$H$_4$)-1-benzofuran-5-yl]methyl}-1-(1-methylpiperidin-4-yl)urea; trifluoroacetic acid (160)

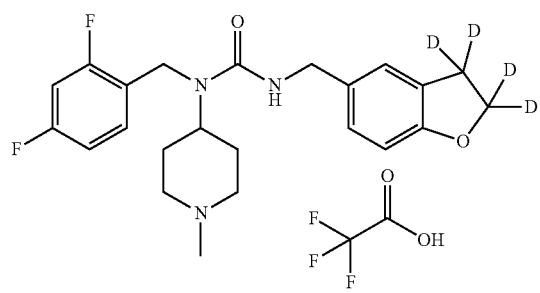

4-(2-methoxy-2-oxoethyl)phenyl 2-chloroacetate

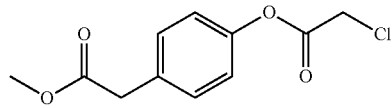 [SMILES: COC(=O)Cc1ccc(OC(=O)CCl)cc1]

Chloroacetyl chloride (877 μl, 11 mmol) was added to methyl 2-(4-hydroxyphenyl)acetate (1.66 g, 10 mmol) and triethylamine (2.09 ml, 15 mmol) in dichloromethane (10 ml). After 1 hour of stirring at room temperature the mixture was concentrated. The crude material was purified by column chromatography using silicon dioxide gel, eluting with 10-25% ethyl acetate in petroleum ether to afford the desired intermediate (2.23 g, 92%).

methyl 2-(3-oxo-2,3-dihydro-1-benzofuran-5-yl)acetate

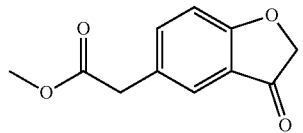

Aluminum trichloride (3.85 g, 28.8 mmol) was added to 4-(2-methoxy-2-oxoethyl)phenyl 2-chloroacetate (1.75 mg, 7.21 mmol) and the mixture was heated to 180° C. After 30 minutes, the solid crude was cooled to ambient temperature and added to hydrochloric acid (aqueous, 1M, 100 ml). The resulting mixture was stirred for 1 hour before it was extracted with ethyl acetate (3×100 ml). The organic phase was dried (sodium sulfate), filtered and concentrated. The crude material was purified by column chromatography using silicon dioxide gel, eluting with 25-100% ethyl acetate in petroleum ether to afford the desired intermediate (486 mg, 35%).

methyl 2-[2,3-dihydro(2,2,3,3-$^2$H$_4$)-1-benzofuran-5-yl]acetate

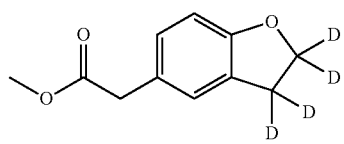 [SMILES: [2H]C1([2H])Oc2ccc(CC(=O)OC)cc2C1([2H])[2H]]

Methyl 2-(3-oxo-2,3-dihydro-1-benzofuran-5-yl)acetate (380 mg, 1.84 mmol) was dissolved in acetic acid-dl (3.8 ml) and the mixture was heated to 100° C. After 30 minutes, the mixture was concentrated, redissolved in acetic acid-dl (3.8 ml) and stirred for additionally 30 minutes at 100° C. before it was cooled to ambient temperature and concentrated. The crude was dissolved in acetic acid-dl (3.8 ml) and zinc (361 mg, 5.53 mmol) was added. The mixture was heated to 100° C. and stirred for 30 minutes before it was cooled to ambient temperature, filtered and concentrated. The crude material was purified by column chromatography using silicon dioxide gel, eluting with 5-20% ethyl acetate in petroleum ether to afford the desired intermediate (76 mg, 21%).

1-[(2,4-difluorophenyl)methyl]-3-{[2,3-dihydro(2,2,3,3-$^2$H$_4$)-1-benzofuran-5-yl]methyl}-1-(1-methylpiperidin-4-yl)urea; trifluoroacetic acid The compound was prepared in analogy with example 8 (1-[(2,4-difluorophenyl)methyl]-3-[(2,2-dimethyl-2,3-dihydro-1-benzofuran-5-yl)methyl]-1-(1-methylpiperidin-4-yl)urea; trifluoroacetic acid) using N-[(2,4-difluorophenyl)methyl]-1-methylpiperidin-4-amine and methyl 2-[2,3-dihydro(2,2,3,3-$^2$H$_4$)-1-benzofuran-5-yl]acetate. Yield: 34%. $^1$H NMR (400 MHz, Chloroform-d) δ 12.31 (bs, 1H), 7.18-7.11 (m, 1H), 6.91 (s, 1H), 6.87-6.78 (m, 3H), 6.67 (d, 1H), 4.77 (t, 1H), 4.69 (s, 1H), 4.40 (s, 2H), 4.26 (s, 2H), 3.58 (d, 2H), 2.84-2.76 (m, 5H), 2.38 (q, 2H), 1.92 (d, 2H); LCMS: 420.0 [M+H]$^+$.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

Assays

In Vitro Determination of Receptor Activity

Receptor Selection and Amplification (R-SAT) Assays. The functional receptor assay, Receptor Selection and Amplification Technology (R-SAT®), was used (with minor modifications from the procedure described previously (Brann, M. R. U.S. Pat. No. 5,707,798, 1998; Chem. Abstr. 1998, 128, 111548) to screen compounds for activity at the 5-HT2A receptor. Briefly, NIH3T3 cells were grown in 96 well tissue culture plates to 70-80% confluence. Cells were transfected for 12-16 h with plasmid DNAs using superfect (Qiagen Inc.) as per manufacturer's protocols. R-SAT's were generally performed with 50 ng/well of receptor and 20 ng/well of β-galactosidase plasmid DNA. All receptor constructs used were in the pSI mammalian expression vector (Promega Inc) as described previously. The 5-HT2A receptor gene was amplified by nested PCR (polymerase chain reaction) from brain cDNA using the oligodeoxynucleotides based on the published sequence (Saltzman et. Al, Biochem. Biophys. Res. Comm. 1991, 181, 1469). For large-scale transfections, cells were transfected for 12-16 h, then trypsinized and frozen in DMSO. Frozen cells were later thawed, plated at 10,000-40,000 cells per well of a 96 well plate that contained a compound according to Formula (I). To run functional antagonist assays, cells and compounds were additionally combined with a fixed concentration (approximately 3× the previously determined EC50) of an agonist (usually 5-CT) at 5-HT2A or other appropriate agonists for other receptors. With both methods, cells were then grown in a humidified atmosphere with 5% ambient $CO_2$ for five days. Media was then removed from the plates and marker gene activity was measured by the addition of the b-galactosidase substrate o-nitrophenyl b-D-galactopyranoside (ONPG, in PBS with 5% NP-40). The resulting colorimetric reaction was measured in a spectrophotometric plate reader (Titertek Inc.) at 420 nM. All data were analyzed using the computer program XLFit (IDBSm). Efficacy is the percent maximal repression compared to repression by a control compound (ritanserin in the case of 5-HT2A). $IC_{50}$ is the calculated concentration in molar that produces 50% maximal repression. The $IC_{50}$ determined in the RSAT assay was converted into a Ki value using the method of Cheng and Prussoff, Biochem Pharmacol., 1973 Dec. 1; 22(23): 3099-108. pKi is the negative of the log(Ki).

hERG Assay: Drugs belonging to different classes have been shown to be associated with QT prolongation and in some cases serious ventricular arrhythmias. The most common mechanism for these adverse events is the inhibition of one or more cardiac potassium channels, in particular hERG. This current is important for cardiac myocyte repolarization and is a common target for drugs that prolong the QT interval. Test articles in this study were therefore characterized to determine their ability to inhibit the hERG channel. Ion channel activity was measured at AVIVA Biosciences Corporation (San Diego, Calif.), using a stably transfected Chinese Hamster Ovary (CHO) cell line expressing the hERG mRNA. The pharmacology of this cloned channel expressed in the CHO cell line is very similar to that observed in native tissue.

Cells: AVIVA's CHO cell line, which stably expresses hERG channels, was used for the study. Cells were cultured in DMEM/F12 containing 10% FBS, 1% penicillin/streptomycin and 500 μg/ml G418. Before testing, cells were harvested using Accumax (Innovative Cell Technologies).

Solutions: For electrophysiological recordings, the following solutions were used: External Solution: 2 mM $CaCl_2$; 2 mM $MgCl_2$; 4 mM KCl; 150 mM NaCl; 10 mM Glucose; 10 mM HEPES; 305-315 mOsm; pH 7.4 (adjusted with 5M NaOH); Internal Solution: 140 mM KCl; 10 mM $MgCl_2$; 6 mM EGTA; 5 mM HEPES-Na; 5 mM ATP-Mg; 295-305 mOsm; pH 7.25 (adjusted with 1M KOH).

Electrophysiology: Whole cell recordings were performed using PX 7000A (Axon Instruments) with AVIVA's SealChip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally, a step back to −50 mV for 5 s removed activation and the deactivating tail current was recorded.

Test Article Handling and Dilutions: All test articles were prepared from 10 mM DMSO stock solutions provided by Sponsor. Solutions were mixed by sonication for 20 min, followed by vigorous vortexing. Prior to testing, compounds were diluted to test concentrations in glass vials using External Solution. Dilutions were prepared no longer than 20 min prior to use.

Electrophysiology Procedures: After achieving whole cell configuration, cells were monitored for 90 s to assess stability and then washed with External Solution for 66 s. The voltage protocol previously described was then applied to the cells every 12 s throughout the procedure. Only stable cells with recording parameters above threshold (see Quality Control section) were allowed to enter the drug addition procedure. External solution containing 0.1% DMSO (vehicle) was applied to the cells to establish a baseline. After allowing the current to stabilize for 3 to 10 min, test articles were applied. Test article solutions were added to cells in 4 separate additions. Cells were kept in test solution until effect of the test article reached steady state, to a maximum of 12 min. Next, 1 μM cisapride (positive control) was added. Finally, washout with External Solution was performed until the recovery current reached steady state.

Data Analysis: Data analysis was performed using DataXpress (Axon Instruments), Clampfit (Axon Instruments) and Origin (OriginLab Corporation) software.

Quality Control: Data included in the report originated from experiments that satisfied all of the following criteria: Recording Parameters: membrane resistance (Rm): >200 MΩ; Access resistance (Ra): <10 MΩ; Ttail current amplitude: >150 pA; Pharmacological Parameters: 1 μM cisapride: >95% inhibition.

Beta-Arrestin Recruitment Assay:

Detecting GPCR Signaling Using the Tango Technology

GPCR signaling through beta-arrestin was detected by the Tango Technology at Thermofisher. This technology is based upon the interaction of intracellular beta-arrestin proteins and the target receptor. Upon ligand binding to the target receptor, the protease tagged arrestin is stimulated and recruited to the engineered protease site on the C-terminus of the GPCR, which triggers release of the tethered transcription factor. The free transcription factor then enters the nucleus and stimulates the beta-lactamase (bla) activity.

Test compounds are received at 1000× (or greater) of the desired starting concentration in 100% DMSO. The 1000× test compounds are serially diluted (10 point/2-log increments) in 100% DMSO.

Substrate Loading Solution:

The Substrate Loading Solution consists of three reagents: Solution A (1 mM LiveBLAzer™-FRET B/G Substrate); Solution B, and Solution C.

Agonist Assay Protocol:

Plate type utilized and the addition of cells (Step 1) or compound (Step 2) first to the plate is dictated by each cell line and described in the Cell Line-Specific Assay Conditions.

Barcoded Corning 384 well Flat Clear Bottom Black Polystyrene TC-Treated Microplates (Corning Cat. #3712); Barcoded Corning 384 well Flat Clear Bottom Black Polystyrene Poly-D-Lysine Coated Microplates (Corning Cat. #3664)

1. 32 µL of cells diluted in Assay Media to appropriate cell density are added to the assay plate. If needed, cells are incubated at 37° C./5% CO2 for 6 or 16-24 hours (depending upon cell line specifics) before compound is added.

2. 40 nL of 1000× compound or known activator titration plus 4 µL of assay media is added to the cells in the assay plate.

3. 4 µL of Assay Media is added to all wells to bring the final assay volume to 40 L.

4. The assay plate is incubated for 5 or 16 hours (depending upon cell line specifics) at 37° C./5% CO2 in a humidified incubator.

5. 8 µL of the Substrate Loading Solution is added to the assay plate.

6. The assay plate is incubated for 2 hours at room temperature, in the dark.

7. The assay plate is read on a fluorescence plate reader (Tecan Safire2) and the data is analyzed.

Antagonist Assay Protocol:

An Agonist assay screen (see above) is run to obtain the EC80 concentration of the known activator to add in step 3.

1. 32 µL of cells diluted in Assay Media to appropriate cell density are added to the assay plate. If needed, cells are incubated at 37° C./5% CO2 for 6 or 16-24 hours (depending upon cell line specifics) before compound is added.

2. 40 nL of 1000× compound or known antagonist titration plus 4 µL of Assay Media is added to the cells in the assay plate and incubated for 30 minutes at 37° C./5% CO2 in a humidified incubator.

3. 4 µL of the 10×EC80 concentration of agonist, as determined in an Agonist assay, is added to all wells containing test compound and known inhibitor to bring the final assay volume to 40 µL.

4. 4 µL of Assay Media is added to remaining control wells to bring the volume up to 40 µL.

5. The assay plate is incubated for 5 or 16 hours (depending upon cell line specifics) at 37° C./5% CO2 in a humidified incubator.

6. 8 µL of the Substrate Loading Solution is added to the assay plate.

7. The assay plate is incubated for 2 hours at room temperature, in the dark.

8. The assay plate is read on a fluorescence plate reader (Tecan Safire2) and the data is analyzed.

The following controls are run on each plate for each individual cell-line:

Full Agonist control

The full agonist control contains 0.1% DMSO, cells and a maximum concentration of the known agonist (stim). In agonist mode, the full agonist control is used to determine the upper end of the assay or 100% activation. In antagonist mode, the full agonist control is used to determine the actual EC80 used in the assay with the EC80 concentration chosen from previous agonist experiments.

No Agonist Control

The no agonist control contains 0.1% DMSO, cells and assay media in place of the agonist (stim). In agonist mode, it is used to determine the lower end of the assay or 0% activation. In antagonist mode, it is used to determine maximal inhibition or 100% inhibition.

Cell-Free Control

The cell-free control contains 0.1% DMSO and assay media. It is used to determine the background fluorescence for both coumarin and fluorescein wavelengths. This value is used for background subtraction.

EC80 Control (Antagonist Mode Only)

The EC80 control is a concentration of the known agonist in assay media that has been determined through an agonist experiment. In antagonist mode, the EC80 control is used to determine the actual baseline of activation or 0% inhibition.

Known Agonist (Agonist Mode) or Antagonist (Antagonist Mode) Titration

A known agonist or antagonist titration is run on every plate for each cell-line to ensure the cell line is either activated or inhibited within an expected EC50/IC50 range as previously determined.

Graphing Software

SelectScreen Cell-Based GPCR Profiling Service uses XLfit from IDBS. The dose response curve is curve fit to model number 205 (sigmoidal dose-response model). Custom logic was built in-house for the data analysis tool to address the different compound characteristics that can be observed with functional assays. Using this logic the relative EC50/IC50 value for each given compound is provided.

The following equations were used for each set of data points:

Equation:

Background-Subtracted Fluorescence ($Fl$=Fluorescence Intensity):$Fl$ Sample–$Fl$ Cell-Free Ctrl Emission Ratio (using values corrected for background fluorescence):

Coumarin Emission (460 nm)/Fluorescein Emission (530 nm)

Response Ratio:

Emission Ratio Compound/Emission Ratio No Agonist Ctrl

% Activation–Agonist Assays:

{(Response Ratio Compound–Response Ratio No Agonist Ctrl)/Response Ratio Full Agonist Ctrl–Response Ratio No Agonist Ctrl}*100

% Inhibition–Antagonist Assays:

{1–(Response Ratio Compound–Response Ratio No Agonist Ctrl/Response Ratio EC80 Ctrl–Response Ratio No Agonist Ctrl)}*100

$pIC_{50}$: negative logarithm of the concentration which causes 50% inhibition

The compounds as provided herein were assayed as described hereinabove. This data below indicates that compounds as provide herein may be useful as pharmaceutical agents. The data in table one may for example be interpreted using the following guidance

| | |
|---|---|
| High affinity | pKi ≥ 8.4 |
| Moderate affinity | pKi ≥ 7.7. |

TABLE 2 pKi values of exemplified compounds

| Compound | 5-HT2a (pKi) (R-SAT) | 5HT2A (pIC50) Beta-arrestin | hERG (% inhibition (1 μM)) |
|---|---|---|---|
| 1a/1b | 7.6 | | |
| 2 | 5.5 | | |
| 3 | 8.9 | | 33 |
| 4 | 8.6 | | 11 |
| 5 | 9.0 | | 29 |
| 6 | 8.7 | | 70 |
| 7 | 8.7 | | 87 |
| 8 | 9.1 | | 22 |
| 9 | 8.1 | | 63 |
| 10 | 9.0 | | 10 |
| 11 | 1.0 | | |
| 12 | 1.0 | | |
| 13 | 10.1 | | 34 |
| 13b | 7.2 | | |
| 14 | 8.8 | | 77 |
| 15 | 8.5 | | 19 |
| 16 | 8.7 | | 29 |
| 17 | 9.4 | | 32 |
| 18 | 9.5 | | 17 |
| 19 | 8.8 | | 33 |
| 20 | 8.8 | | 30 |
| 21 | | 6.7 | |
| 22 | | 1.0 | 10 |
| 23 | | 7.8 | 13 |
| 24 | | 6.9 | 10 |
| 25 | | 7.0 | |
| 26 | 1.0 | | |
| 27 | | 7.1 | |
| 28 | 8.4 | | 32 |
| 29 | 8.0 | | |
| 30 | 7.2 | | |
| 31 | 8.2 | | |
| 32 | 8.1 | | |
| 33 | 1.0 | | |
| 34 | | 6.5 | |
| 35 | | 6.7 | |
| 36 | | 7.6 | 29 |
| 37 | | 6.2 | 8 |
| 38 | | 8.4 | |
| 39 | | 7.8 | 21 |
| 40 | | 1.0 | 9 |
| 41 | | 1.0 | 23 |
| 42 | | 6.6 | |
| 43 | | 6.9 | 42 |
| 44 | | 6.8 | 70 |
| 46 | 9.1 | | |
| 47 | 6.9 | | |
| 48 | 7.0 | | |
| 49 | 8.2 | | |
| 50 | 7.0 | | |
| 51 | 7.6 | | |
| 52 | 7.4 | | 8 |
| 53 | 7.6 | | |
| 54 | 8.1 | | |
| 55 | | 1.0 | 10 |
| 56 | | 1.0 | |
| 57 | 1.0 | | |
| 58 | 6.8 | | |
| 59 | 7.8 | | |
| 60 | 1.0 | | |
| 61 | 7.8 | | 23 |
| 62 | 7.1 | | 32 |
| 63 | 7.1 | | |
| 64 | 1.0 | | |
| 65 | 1.0 | | |
| 66 | 1.0 | | |
| 67 | 7.1 | | |
| 68 | 7.7 | | |
| 69 | 6.2 | | |
| 70 | 7.3 | | |
| 71 | 7.9 | | |
| 72 | 7.8 | | |
| 73 | 8.2 | | |
| 74 | 7.4 | | |
| 75 | | 8.4 | |
| 76 | 8.4 | | 12 |
| 77 | 7.1 | | |
| 78 | 8.2 | | |
| 80 | 8.6 | | |
| 81 | | 1.0 | |
| 82 | | 1.0 | |
| 83 | 6.8 | | |
| 84 | 7.3 | | |
| 85 | 8.4 | | |
| 85 | 8.8 | | |
| 86 | 1.0 | | |
| 87 | 8.0 | | |
| 88 | 7.2 | | |
| 89 | 1.0 | | |
| 90 | 7.9 | | |
| 91 | 7.8 | | |
| 92 | 9.5 | | 45 |
| 93 | 7.4 | | |
| 94 | 7.0 | | |
| 95 | 7.3 | | 8 |
| 96 | 8.0 | | |
| 97 | 7.4 | | |
| 98 | 8.5 | | 62 |
| 99 | 7.1 | | |
| 100 | 7.7 | | |
| 101 | 7.1 | | |
| 102 | 1.0 | | |
| 103 | 6.6 | | |
| 104 | 7.4 | | |
| 105 | 7.0 | | |
| 106 | 7.3 | | |
| 107 | 6.9 | | 43 |
| 108 | 7.1 | | |
| 109 | 7.6 | | |
| 110 | 7.6 | | |
| 111 | 7.1 | | |
| 112 | 7.4 | | |
| 113 | 6.9 | | |
| 114 | 8.2 | | |
| 115 | 9.5 | | 49 |
| 116 | 7.2 | | |
| 117 | 9.4 | | |
| 118 | 8.0 | | |
| 119 | 7.2 | | |
| 120 | 8.1 | | |
| 121 | 6.9 | | |
| 122 | 8.1 | | |
| 123 | 7.8 | | |
| 124 | 8.0 | | |
| 125 | 8.4 | | 17 |
| 126 | 8.1 | | 15 |
| 127 | 8.2 | | 9 |
| 128 | 8.1 | | |
| 129 | 7.3 | | |
| 130 | 7.1 | | |
| 131 | 9.2 | | |
| 132 | 7.1 | | |
| 133 | 8.3 | | |
| 134 | 8.4 | | |

TABLE 2-continued pKi values of exemplified compounds

| Compound | 5-HT2a (pKi) (R-SAT) | 5HT2A (pIC50) Beta-arrestin | hERG (% inhibition (1 μM)) |
|---|---|---|---|
| 135 | 7.8 | | |
| 136 | 8.1 | | |
| 137 | 8.4 | | 37 |
| 138 | 2.8 | | 13 |
| 139 | 8.4 | | 35 |
| 140 | 8.5 | | |
| 141 | 9.2 | | 42 |
| 142 | 9.0 | | 8 |
| 143 | 9.3 | | 41 |
| 144 | 9.0 | | 37 |
| 145 | 8.8 | | 39 |
| 146 | 8.3 | | |
| 147 | 8.5 | | |
| 148 | 8.7 | | 33 |
| 149 | 9.0 | | 40 |
| 150 | 8.3 | | |
| 151 | 8.7 | | 16 |
| 152 | 8.6 | | 38 |
| 153 | 8.8 | | 29 |
| 154 | 8.9 | | 23 |
| 155 | 9.8 | | 47 |
| 156 | 8.4 | | 17 |
| 157 | 9.2 | | 20 |
| 158 | 9.1 | | 8 |
| 159 | 8.1 | | |

Assays on Three Ion Channels Expressed in Cardiac Tissue

Methods: Except where noted, all experiments carried out at Charles River Laboratories Cleveland, Inc. (CR-CLE), 14656 Neo Parkway, Cleveland, Ohio 44128.

HERG Assay:

Test System: Cells were maintained in tissue culture incubators per CR-CLE SOP. Stocks were maintained in cryogenic storage. Cells used for electrophysiology were plated in plastic culture dishes. Each culture dish was identified by a notation of clone identity number, passage number and date.

Rationale for Selection of Ion Channel and Expression System: The cardiac potassium channel, hERG, is responsible for a rapid delayed rectifier current ($I_{Kr}$) in human ventricle and inhibition of $I_{Kr}$ is the most common cause of cardiac action potential prolongation by non-cardiac drugs (Brown and Rampe, *Pharmaceutical News* 7:15-20 (2000); Weirich and Antoni, *Basic Res. Cardiol.* 93 (Suppl. 1):125-132 (1998); Yap and Camm, *Clin. Exp. Allergy* 29 (Suppl. 3):174-181 (1999)). Increased action potential duration causes prolongation of the QT interval that has been associated with a dangerous ventricular arrhythmia, torsade de pointes. In the present study, hERG potassium channels are expressed in a human embryonic kidney (HEK293) cell line that lacks endogenous ($I_{Kr}$).

HEK/hERG:
Organism: *Homo sapiens*
Designation: 293
Tissue: Kidney; transformed with adenovirus 5 DNA; Transfected with human-ether-a-go-go cDNA
Morphology: Epithelial
Age/Stage: Embryo
Source Strain: ATCC, Manassas, Va.
Source Substrain: CR-CLE, Cleveland, Ohio
Cell Culture Procedures: HEK293 cells were transfected with hERG cDNA. Stable transfectants were selected by coexpression of the G418-resistance gene incorporated into the expression plasmid. Selection pressure was maintained by including G418 in the culture medium. Cells were cultured in Dulbecco's Modified Eagle Medium/Nutrient Mixture F-12 (D-MEM/F-12) supplemented with 10% fetal bovine serum, 100 U/mL penicillin G sodium, 100 μg/mL streptomycin sulfate and 500 μg/mL G418.

Test Method:

Treatment Groups: All experiments were performed at near-physiological temperature (33-35° C.). Each cell acted as its own control.

Concentration-Response Test Groups: Concentrations ranging between 0.03 and M were selected to evaluate the concentration-response relationship on hERG current. Each concentration was tested in three cells (n=3).

Positive Control Groups: The positive control, 90 nM cisapride (Sigma-Aldrich), was tested in two cells (n=2). Previous results have shown that 90 nM cisapride inhibits hERG potassium current by approximately 80%.

Vehicle Control: The vehicle control solution for both current recording consisted of a HEPES-buffered physiological saline (HB-PS) solution (composition in mM): NaCl, 137; KCl, 4.0; $CaCl_2$, 1.8; $MgCl_2$, 1; HEPES, 10; glucose, 10; pH adjusted to 7.4 with NaOH, refrigerated until use and supplemented with 0.3% DMSO. Chemicals used in HB-PS preparation were purchased from Sigma-Aldrich (St. Louis, Mo.) unless otherwise noted and were of ACS reagent grade purity or higher.

Name: HB-PS+0.3% DMSO
Source: CR-CLE
Batch Number: To be documented in the study file
Storage Conditions: Refrigerated
Rationale for Selection: HB-PS provides the appropriate ionic composition for in vitro hERG current recording.

Formulations: Test article concentrations were prepared fresh daily by diluting the DMSO (dimethyl sulfoxide, Sigma-Aldrich) stock solutions in the appropriate vehicle solution (final DMSO concentration, 0.3% v/v). Previous results have shown that 0.3% DMSO does not affect hERG current.

Electrophysiology: Cells were transferred to the recording chamber and superfused with the appropriate vehicle control solution. The recording was performed at a temperature of 33 to 35° C. using a combination of in-line solution pre-heater, chamber heater, and feedback temperature controller. Temperature was measured using a thermistor probe in the recording chamber. Micropipettes for patch clamp recording were made from glass capillary tubing using a P-97 micropipette puller (Sutter Instruments, Novato, Calif.). A commercial patch clamp amplifier (Axopatch 200B from Molecular Devices) was used for whole cell recordings. Before digitization, current records were low-pass filtered.

Pipette solution for hERG: Pipette (intracellular) solution for hERG whole-cell recording consisted of (composition in mM): potassium aspartate, 130; $MgCl_2$, 5; EGTA, 5; ATP, 4; HEPES, 10; pH adjusted to 7.2 with KOH. The pipette solution was prepared in batches, stored frozen, and freshly thawed on the day of use.

Electrophysiology for hERG: Cells stably expressing hERG were held at −80 mV. Onset and steady state inhibition of hERG potassium current due to the test article was measured using a pulse pattern with fixed amplitudes (conditioning prepulse: +20 mV for 1 s; repolarizing test ramp to −80 mV (−0.5 V/s) repeated at 5 s intervals). Each recording ended with a final application of a supramaximal concentration of the reference substance (E-4031, 500 nM), to assess the contribution of endogenous currents. The remaining uninhibited current was subtracted off-line digitally from the data to determine the potency of the test substance for hERG inhibition.

Data Analysis: Data were stored on the CR-CLE computer network for off-line analysis. Data acquisition and analyses were performed using the suite of pCLAMP (version 8.2) programs (Molecular Devices, Sunnyvale, Calif.) and were reviewed by the Study Director.

Steady state was defined by the limiting constant rate of change with time (linear time dependence). The steady state before and after test article application was used to calculate the percentage of current inhibited at each concentration. Concentration-response data was fit to an equation of the following form:

$$\% \text{ Inhibition} = \{1 - 1/[1 + ([\text{Test}]/IC_{50})^N]\} * 100$$

Where [Test] is the concentration of test article, $IC_{50}$ is the concentration of the test article producing half-maximal inhibition, N is the Hill coefficient, and % Inhibition is the percentage of hERG potassium current inhibited at each test article concentration. Nonlinear least squares fits will be solved with the Solver add-in for Excel 2000, or later (Microsoft, Redmond, Wash.).

CaV 1.2:

Test System: Cells were maintained in tissue culture incubators per testing facility SOP. Stocks were maintained in cryogenic storage. Cells used for electrophysiology were plated in plastic culture dishes. Each culture dish was identified by a notation of channel name, passage number, and date.

Rationale for Selection of Ion Channel and Expression Systems: Reduction of $I_{Ca,L}$ is associated with action potential shortening in atrial fibrillation (Van Wagoner, et al., Circ Res 85:428-436 (1999)) while augmentation of $I_{Ca,L}$ current may produce action potential prolongation (Ahmmed, et al., Circ Res 86:558-570 (2000)) and early after depolarizations (January, et al., Circ Res 62:563-571 (1988)). $I_{Ca,L}$ is produced by the combination of calcium channel subunits encoded by CACNA1C (α1-subunit), CACNB2 (β2-subunit) and CACNA2D1 (α2δ-subunit) cDNAs. In this assay, the hCav1.2/β2/α2δ channels were expressed in a Chinese hamster ovary (CHO) cell line, which is a sensitive mammalian expression system that does not display $I_{Ca,L}$ before transfection with the genes which encode hCav1.2/β2/α2δ and induced expression.

CHO/hCav1.2:
Organism: Cricetulus griseus
Tissue: Ovary; transfected with human CACNA1C (α1-subunit), CACNB2 (β2-subunit), and CACNA2D1 (α2δ-subunit) cDNAs
Morphology: Epithelial
Age/Stage: Adult
Source Strain: ATCC, Manassas, Va.
Source Substrain: CR-CLE CHO Cell Culture Procedures: CHO cells were stably co-transfected with human CACNA1C (α1-subunit), CACNB2 (β2-subunit), and CACNA2D1 (α2δ-subunit) cDNAs. Stable transfectants were selected by coexpression of the cDNAs with antibiotic resistance genes for blasticidin, hygromycin, G418, and zeocin. Selection pressure was maintained by including these antibiotics in the culture medium. Cells were cultured in Ham's F12 Medium supplemented with 10% fetal bovine serum, penicillin-streptomycin (100 units/mL), blasticidin (10 µg/mL), zeocin (400 µg/mL), G418 (250 µg/mL) and hygromycin (250 µg/mL). To avoid $Ca^{2+}$-induced toxicity, verapamil (3 µmol/L) was added to the cultured cells.

hCav1.2/β2/α2δ-CHO is a tetracycline-inducible cell line. To induce expression, tetracycline at a final concentration of 1 µg/mL was added to media lacking the selection antibiotics. Currents were recorded greater than 16 hours post-induction.

Test Method

Treatment Groups: All experiments were performed at room temperature. Each cell acted as its own control.

Concentration-Response Test Group: Concentrations ranging between 0.1 and 30 µM were selected to evaluate the concentration-response relationship on CaV1.2 current. Each concentration was tested in at least three cells (n≥3).

Positive Control Group: The positive control article nifedipine (Sigma-Aldrich) was tested in two cells (n=2) at 0.1 µM. Previous results have shown that nifedipine at 0.1 µM inhibits hCav1.2 current by approximately 90%.

Vehicle Control: The vehicle control solution for both current recording consisted of a HEPES-buffered physiological saline (HB-PS) solution (composition in mM): NaCl, 137; KCl, 4.0; $CaCl_2$, 1.8; $MgCl_2$, 1; HEPES, 10; glucose, 10; pH adjusted to 7.4 with NaOH, refrigerated until use and supplemented with 0.3% DMSO. Chemicals used in HB-PS preparation were purchased from Sigma-Aldrich (St. Louis, Mo.) unless otherwise noted and were of ACS reagent grade purity or higher.

Name: HB-PS+0.3% DMSO
Source: CR-CLE
Batch Number: To be documented
Storage Conditions: Refrigerated
Rationale for Selection: HB-PS provides the appropriate ionic composition for in vitro hCav1.2 current recording.

Formulations: Test article concentrations were prepared fresh daily by diluting the DMSO (dimethyl sulfoxide, Sigma-Aldrich) stock solutions in the appropriate vehicle solution (final DMSO concentration, 0.3% v/v). Previous results have shown that 0.3% DMSO does not affect CaV1.2 current.

Electrophysiological Procedures: Cells were superfused with vehicle control solution. Micropipette solution for whole cell patch clamp recordings was composed of (mM): Cs-methanesulfonate (MES), 130; TEA-Cl, 20, $MgCl_2$, 1; EGTA, 10; Mg-ATP, 4; Tris-GTP, 0.3, phosphocreatine di-(Tris) salt, 14, creatine phosphokinase, 50 U/mL, and HEPES, 10; pH adjusted to 7.2 with N-methyl-D-glucamine or CsOH. Micropipette solution was prepared in batches, aliquoted, stored frozen, and a fresh aliquot thawed each day. Micropipettes for patch clamp recording were made from glass capillary tubing using a P-97 (Sutter Instruments, Novato, Calif.) or PC-10 (Narishige, Amityville, N.Y.) micropipette puller. A commercial patch clamp amplifier (Axopatch 200B from Molecular Devices, Sunnyvale, Calif.) was used for whole cell recordings. Before digitization, current records were low-pass filtered at one-fifth of the sampling frequency.

Experimental Procedures: Onset and steady inhibition was evaluated at a test potential of 0 mV (150 ms duration), repeated at ten-second intervals from a holding potential of −40 mV. Peak current was measured during the step to 0 mV. Peak current was monitored until a new steady state was achieved. hCav1.2 current was monitored until a new steady state was achieved and a steady state was maintained for at least 20 s before applying test article or positive control article formulations. The minimum test article application was 5 minutes.

Data Analysis: Data were stored on the CR-CLE computer network for off-line analysis. Data acquisition and analyses were performed using the suite of pCLAMP (version 8.2) programs (Molecular Devices, Sunnyvale, Calif.) and were reviewed by the Study Director.

Steady state was defined by the limiting constant rate of change with time (linear time dependence). The steady state before and after test article application was used to calculate the percentage of current inhibited at each concentration. Concentration-response data were fit to an equation of the form:

$$\% \text{ Inhibition} = \{1 - 1/[1 + ([\text{Test}]/IC_{50})^N]\} * 100$$

Where [Test] is the test article concentration, $IC_{50}$ is the test article concentration at half-maximal inhibition, N is the Hill coefficient, and % Inhibition is the percentage of current inhibited at each test article concentration. Nonlinear least squares fits were solved with the Solver add-in for Excel 2003 or later (Microsoft, Redmond, Wash.) and the $IC_{50}$ was calculated.

NaV1.5 (for pimavanserin):
Carrier for Test Article and Positive Control Article
Name: Dimethyl sulfoxide (DMSO)
Source: Sigma-Aldrich
Formula Weight (g/mol): 78.13
Storage Conditions: Room temperature
Rationale for Selection: Previous results have shown that 0.3% DMSO does not affect late sodium channel current.

Vehicle Control and Carrier for End Blocker: The vehicle control solution and carrier for the end blocker (2 mM lidocaine) consisted of a HEPES-buffered physiological saline (HB-PS) solution (composition in mM): NaCl, 137; KCl, 4.0; $CaCl_2$, 1.8; $MgCl_2$, 1; HEPES, 10; glucose, 10; pH adjusted to 7.4 with NaOH (refrigerated until use), supplemented with 0.3% DMSO and 0.1 µM ATX-II. 0.1 µM ATX-II was omitted from the vehicle control solution used during initial gigaohm seal formation, transition to whole-cell patch clamp configuration and preliminary baseline recording before activation of late Nav1.5 current with 0.1 µM ATX-II. Chemicals used in vehicle preparation were purchased from Sigma-Aldrich (St. Louis, Mo.) unless otherwise noted and were of ACS reagent grade purity or higher.

Name: HB-PS+0.3% DMSO+0.1 M ATX-II
Source: CR-CLE
Storage Conditions: Refrigerated (set to maintain 2 to 8° C.)
Rationale for Selection: HB-PS provides the appropriate ionic composition for in vitro recording.
Positive Control Article:
Name: Ranolazine dihydrochloride
Source: Tocris
Batch Number: 2A/215231
Molecular Weight: 509.47 g/mol
Purity: 98.7%
Storage Conditions: Room temperature
Rationale for Selection: Previous results have shown that 100 µM ranolazine dihydrochloride inhibits $I_{Na,L}$ by approximately 85%
End Blocker
Name: Lidocaine
Source: Sigma-Aldrich
Lot Number: MKBX2132V
Molecular Weight 234.34 (g/mol):
Storage Conditions: Room temperature
Rationale for Selection: Lidocaine is an inhibitor of peak hNav1.5 and late hNav1.5 currents. Each recording will end with application of 2 mM lidocaine to determine the amplitude of endogenous currents.

Late hNav1.5 Current Agonist
Name: ATX-II
Source: Alomone Labs
Lot Number: STA700TX2005
Molecular Weight 4935 (g/mol):
Storage Conditions (bulk): Frozen
Rationale for Selection: ATX-II increases $I_{Na,L}$ (Oliveira, et al., *J. Biol. Chem.* 279: 33323-33335 (2004)) with an $EC_{50}$ of approximately 4 nM.

Late hNav1.5 Current Agonist Carrier
Name: Sterile water for injection (SWI), USP
Source: Pfizer/Hospira
Storage Conditions: Room temperature
Rationale for Selection: ATX-II is water-soluble.

Formulations: A stock solution of the positive control article was prepared in SWI (see assessment of protocol deviation in Electrophysiological Procedures section), stored frozen and used within one month. A stock solution of the agonist was prepared in SWI and stored frozen. Positive control article and end blocker formulations were prepared fresh daily by direct dissolution in vehicle control solution. Stock solutions of the test articles were prepared in DMSO at ~33 and 0.3 mM (see assessment of protocol deviation in Electrophysiological Procedures section) and stored frozen, protected from light in amber vials.

Test article concentrations were prepared fresh daily by diluting stock solutions in vehicle (final DMSO concentration, 0.3% v/v). Test article formulations were prepared at room temperature (15-30° C.) and stored at room temperature (15-30° C.), protected from light until use.

Preparation of Vehicle and Formulation Samples: Vehicle control samples (blank, 4 samples, 1 mL each, accurately measured directly into amber HPLC vials) were taken from the vehicle reservoir at the beginning of testing.

Representative test article formulation samples for concentration verification were collected on the first day of testing. Samples of each test concentration (4 samples, 1 mL each, accurately measured directly into amber HPLC vials) were aliquoted from the outflow of the perfusion apparatus.

The above formulation samples were stored frozen (−10 to −30° C.) and protected from light.

Test System: Cells were maintained in tissue culture incubators per testing facility SOP. Stocks were maintained in cryogenic storage. Cells used for electrophysiology were plated in plastic culture dishes. Each culture dish was identified by a notation of channel name, passage number, and date.

Rationale for Selection of Ion Channel and Expression Systems: The late hNav1.5 channel current was selected because inhibition of this current causes action potential shortening in cardiac tissue and disruption of normal channel function can lead to diastolic dysfunction and arrhythmia (Makielski, et al., *J Cardiovasc Pharmacol* 54:279-286 (2009)). Excitation of the late hNav1.5 channel current causes action potential prolongation in cardiac tissue.

The hNav1.5 channels were expressed in a human embryonic kidney (HEK-293) cell line, which is a sensitive mammalian expression system that does not display $I_{Na,L}$ before transfection with the genes which encode hNav1.5.

HEK-293/hNav1.5 Cell Line:
Organism: *Homo sapiens*
Designation: 293
Tissue: Kidney; transformed with Adenovirus 5 DNA; transfected with SCN5A (hHNa) cDNA Morphology: Epithelial
Age Stage: Embryo
Strain Source: ATCC, Manassas, Va.
Sub-Strain Source: CR-CLE, Cleveland, Ohio Cell Culture Procedures: HEK293 cells were transfected with SCN5A (hHNa) cDNA. Stable transfectants were selected by coexpression of the hHNa cDNA and G418-resistance gene incorporated into the expression plasmid. Selection pressure was maintained with G418 in the culture medium. Cells were cultured in a 50:50 mix of Dulbecco's Modified Eagle's Medium/Ham's Nutrient Mixture F-12 (DMEM/F-12) supplemented with 10% fetal bovine serum, 100 U/mL penicillin G sodium, 100 µg/mL streptomycin sulfate and 500 µg/mL G418.

Test Method

Treatment Groups: All experiments were performed at room temperature. Each cell acted as its own control.

Concentration-Response Test Group: For each test article, five (5) concentrations were selected based on the results from initial testing at 10 µM to evaluate the concentration-response relationship. Each concentration was tested in at least three cells (n≥3).

Positive Control Group: The positive control article ranolazine was tested in two cells (n=2) at 100 µM.

Electrophysiological Procedures: Cells were superfused with vehicle control solution without ATX-II (HB-PS+0.3% DMSO) until after whole-cell configuration was achieved and a stable baseline current was recorded. Then vehicle control solution containing ATX-II (HB-PS+0.3% DMSO+ 0.1 µM ATX-II) was applied to activate late hNav1.5 current. Micropipette solution for whole cell patch clamp recordings was composed of (in mM): L-aspartic acid, 130; CsOH, 130; $MgCl_2$, 5; EGTA, 5; HEPES, 10; $Na_2ATP$, 4; Tris-GTP, 0.1; pH adjusted to 7.2 with CsOH or NMDG, stored frozen until use, and used within six months. Micropipette solution was prepared in batches, aliquoted, stored frozen, and a fresh aliquot thawed each day. Micropipettes for patch clamp recording were made from glass capillary tubing using a P-97 (Sutter Instruments, Novato, Calif.) micropipette puller. A commercial patch clamp amplifier (Axopatch 200B from Molecular Devices, Sunnyvale, Calif.) was used for whole cell recordings. Before digitization, current records were low-pass filtered at one-fifth of the sampling frequency.

Experimental Procedures: From a holding potential of −80 mV, onset and steady-state excitation was evaluated by a voltage stimulus consisting of a hyperpolarizing pre-pulse to −120 mV (200 ms duration) followed immediately by a depolarizing test pulse to −20 mV (500 ms duration) applied every 5 seconds. Late hNav1.5 current was measured during the step to −20 mV (450-500 ms). Each recording ended with a final application of the end blocker (lidocaine, 2 mM) to determine the contribution of endogenous currents. The remaining uninhibited current was subtracted off-line digitally from the data to determine the potency of the test substance for late hNav1.5 current inhibition. Late hNav1.5 current was monitored until a new steady state is achieved and a steady state will be maintained for at least 20 s before applying test article, agonist or positive control article formulations. The minimum test article application was 5 minutes.

Data Analysis: Data were stored on the CR-CLE computer network for off-line analysis. Data acquisition and analyses were performed using the suite of pCLAMP (version 8.2) programs (Molecular Devices, Sunnyvale, Calif.).

Steady state was defined by the limiting constant rate of change with time (linear time dependence). The steady state before and after test article application was used to calculate the percentage of current inhibited at each concentration. Concentration-response data were fit to an equation of the form:

% Inhibition=$\{1-1/[1+([Test]/IC_{50})^N]\}*100$

Where [Test] is the test article concentration, $IC_{50}$ is the test article concentration at half-maximal inhibition, N is the Hill coefficient, and % Inhibition is the percentage of current inhibited at each test article concentration. Nonlinear least squares fits were solved with the Solver add-in for Excel 2003 or later (Microsoft, Redmond, Wash.) and the $IC_{50}$ was calculated.

NaV1.5 methods (for ACP-201, ACP-203 and ACP-204): These experiments were carried out at AVIVA Biosciences Corporation, 6330 Nancy Ridge Drive, Suite 103, San Diego, Calif. 92121.

Experimental Methods

Cells: HEK293 cells transfected with Nav1.5 sodium ion channel (alpha subunit) were selected for this study. Cells were cultured in DMEM/F12 containing 10% FBS, 500 g/mL G418 and 1% penicillin/streptomycin. Trypsin (0.05%) was utilized for cell harvesting.

Solutions: For electrophysiological recordings the following solutions were used:

External Solution: 90 mM NaCl; 50 mM TEA; 10 mM HEPES; 10 mM glucose; 4 mM KCl; 2 mM $CaCl_2$; 305-315 mOsm; pH 7.4 (adjusted with 5M NaOH).

Internal Solution: 140 mM CsF; 10 mM NaCl; 1 mM $MgCl_2$; 10 mM HEPES; 5 mM EGTA; 295-305 mOsm; pH 7.4 (adjusted with 1M NaOH).

Electrophysiology: All whole cell recordings were performed using PX 7000A (Axon Instruments) with AVIVA's SEALCHIP technology. To achieve stable recordings, cells were voltage clamped at a holding potential 20 mV more negative than steady state half inactivation potential (Vh=$V_{1/2}$−20 mV). Nav1.5 current was activated by a depolarizing step to 0 mV for 20 ms at 3 s intervals. $V_{1/2}$ was determined by a pre-step from −130 mV to −40 MV for 1000 ms followed by a −10 mV step. $V_{1/2}$ was determined independently for each cell to correct for both electrode potential and liquid junction potential offsets.

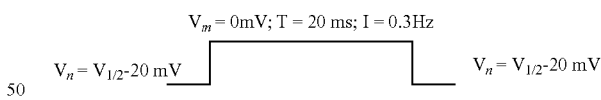

Test Article Handling and Dilutions: All test articles were prepare from 10 mM DMSO stock solutions. Solutions were mixed by sonication for 20 min, followed by vigorous vortexing. Prior to testing, compounds were diluted to test concentrations in glass vials using External Solution. Dilutions were prepared no longer than 20 min prior to use.

Electrophysiology Procedures: After achieving whole cell configuration, cells were monitored for 90 s to assess stability and then washed with External Solution for 66 s. for each cell achieving whole-cell access, an IV curve and steady state inactivation curve was measured. After determining steady state half-inactivation potential (V½), the previously described voltage protocol was applied every 3 s. Whole cell parameters were monitored throughout the recoding procedure and corrected for any possible access resistance or input capacitance change (whole-cell compensation). Only cells with recording parameters above threshold (see Quality Control section) were allowed to enter the drug addition procedure.

External Solution containing 0.1% DMSO (vehicle) was applied to the cells to establish the baseline. After allowing the current to stabilize for 3 to 5 min, test articles were applied. Test article solutions were added to cells in 4 separate additions. Cells were kept in test solution until effect of the test article reached steady state, to a maximum of 10 mins. Next, 30 LM tetracaine (positive control) was added. Finally, washout with External Solution was performed until the recovery current reached steady state.

Data Analysis

Data analysis was performed using DataXpress2 (Axon Instruments), Clampfit (Axon Instruments) and Origin (Originlab Corporation) software.

Quality Control

Data included in the report originated from experiments that satisfied all of the following:

Criteria: Recording Parameters: membrane resistance (Rm): >200 MΩ
access resistance ($R_a$): <10 MΩ
tail current amplitude: >200 pA

TABLE 3

Effects of pimavanserin and three Examples disclosed herein at three ion channels expressed in cardiac tissue.

| | Pimavanserin | Example 5 | Example 3 | Example 17 |
|---|---|---|---|---|
| hERG $IC_{50}$ (μM) | 0.2 | 1.8 | 0.5 | 1.8 |
| CaV 1.2 $IC_{50}$ (μM) | 1.2 | 11.3 | 1.4 | 3.5 |
| NaV 1.5 $IC_{50}$ (μM) | 1.2 | >10 | 4.2 | >10 |

$IC_{50}$ = concentration that produces 50% inhibition. Values provided in micromolar. Data are from manual patch clamp studies.
hERG = human ether-a-go-go voltage-gated potassium channel;
CaV1.2 = human L-type voltage-gated calcium channel comprised of a complex of three subunits including CACNA1C (α1-subunit), CACNB2 (β2-subunit), and CACNA2D1 (α2δ-subunit).
Nav1.5 = human voltage-gated sodium channel Pimavanserin (1-[4-fluorophenyl]methyl)-1-(1-methylpiperidin-4-yl)-3-{[4-(2-methylpropoxy)phenyl]methyl}urea)

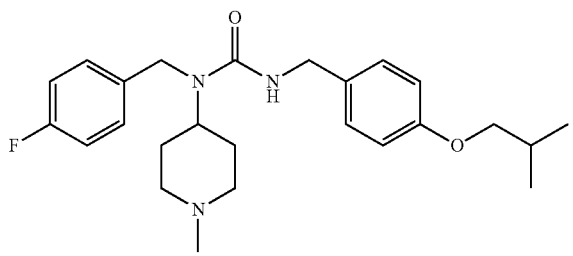 [SMILES: CC(C)COc1ccc(CNC(=O)N(Cc2ccc(F)cc2)C2CCN(C)CC2)cc1]

Table 3 shows the inhibition potency of three compounds compared to pimavanserin at three voltage-gated ion channels known to adversely affect heart rhythm. At hERG, the three examples ranged from 2.5 to 9 fold less potent than pimavanserin. At CaV 1.2, the three examples ranged from 1.2 to 9 fold less potent than pimavanserin. At NaV 1.5, the three examples ranged from 3.5 to over 8 fold less potent than pimavanserin.

The cardiac potassium channel, hERG, is responsible for a rapid delayed rectifier current (IKr) in human ventricle and inhibition of IKr is the most common cause of cardiac action potential prolongation by non-cardiac drugs (Brown and Rampe, 2000; Weirich and Antoni, 1998; Yap and Camm, 1999). Increased action potential duration causes prolongation of the QT interval that has been associated with a dangerous ventricular arrhythmia, torsade de pointes (Brown and Rampe, 2000). The drug label for pimavanserin states that it prolongs the QT interval. The drug label also states that pimavanserin should be avoided in patients with known QT prolongation or in combination with drugs known to prolong the QT interval. The drug label also states that pimavanserin should be avoided in patients with a history of cardiac arrhythmias, and in other circumstances that may increase the risk of occurrence of torsade de pointes and/or sudden death, including symptomatic bradycardia, hypokalemia or hypomagnesia, and the presence of congenital prolongation of QT interval. The results provided herewith unexpectedly indicate that these three examples will have properties different than pimavanserin, e.g. low potency at hERG, CaV1.2 and NaV1.2 compared to pimavanserin, which indicate less risk of prolonging the QT interval.

What is claimed is:

1. A compound according to Formula (I):

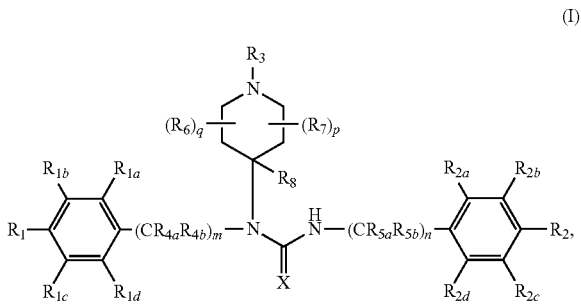

or a pharmaceutically acceptable salt, hydrate, solvate, stereoisomer, or deuterated analogue thereof, wherein:
m and n are 1;
p and q are independently an integer selected from the group consisting of 0, 1, 2, 3, and 4;
$R_1$ and $R_{1d}$ are fluoro;
$R_{1a}$, $R_{1b}$, and $R_c$ are hydrogen;
$R_2$, $R_{2a}$, $R_{2b}$, $R_{2c}$ and $R_{2d}$ are independently selected from the group consisting of hydrogen, deuterium, amino, hydroxyl, —OD, halogen, cyano, nitro, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{2-6}$ alkenyloxy, unsubstituted or substituted $C_{2-6}$ alkynyl, unsubstituted or substituted $C_{2-6}$ alkynyloxy, unsubstituted or substituted $C_{1-8}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl, wherein $R_2$ is not hydrogen, hydroxy or benzyloxy; or $R_2$ and $R_{2b}$ or $R_{2c}$, taken together with the atoms to which they are attached form a ring system; or $R_{2a}$ and $R_{2b}$, or $R_{2c}$ and $R_{2d}$, taken together with the atoms to which they are attached form a ring system;

R₃ is selected from hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

$R_{4a}$, $R_{4b}$, $R_{5a}$, and $R_{5b}$, are independently selected from the group consisting of hydrogen, deuterium, and unsubstituted or substituted $C_{1-6}$ alkyl; wherein when m and n are 1 then $R_{4a}$, $R_{4b}$, $R_{5a}$, $R_{5b}$ are hydrogen;

R₆ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl; or R₆ and R₃, taken together with the atoms to which they are attached form a ring system;

R₇ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;

R₈ is selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy;

X is O.

2. The compound, or pharmaceutically acceptable salt, hydrate, solvate, stereoisomer, or deuterated analogue thereof of claim 1, wherein R₂ is selected from the group consisting of hydrogen, deuterium, amino, hydroxyl, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;

$R_{2d}$ is selected from the group consisting of hydrogen, deuterium, amino, hydroxyl, —OD, halogen, cyano, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{1-6}$ alkoxy, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl; and $R_{2a}$, $R_{2b}$, and $R_{2c}$ are hydrogen; or $R_{2a}$, $R_{2c}$ and $R_{2d}$ are hydrogen and R₂ and $R_{2b}$, taken together with the atoms to which they are attached form a heteroalicyclic or heteroaryl ring system.

3. The compound, or pharmaceutically acceptable salt, hydrate, solvate, stereoisomer, or deuterated analogue thereof of claim 1, wherein R₂, $R_{2a}$, $R_{2b}$, $R_{2c}$ and $R_{2d}$ independently are selected from the group consisting of hydrogen, halogen, hydroxyl, cyano, $C_{1-6}$ alkyl, $C_{1-6}$ haloalkyl, $C_{1-6}$ alkoxy, $C_{2-6}$ alkenyloxy, $C_{1-6}$ alkynyloxy $C_{1-6}$ haloalkoxy, $C_{3-4}$ cycloalkyl, $C_{3-4}$ cycloalkyl-$C_{1-3}$ alkyl, and deuterated analogues thereof; or R₂ and $R_{2b}$, taken together with the phenyl ring they attach to and the atoms to which they are attached, form a bicyclic fused ring system that has the following formulae:

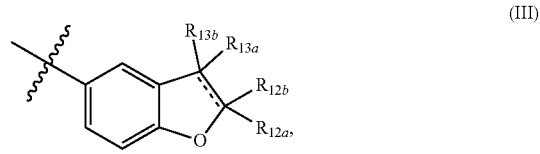

(III)

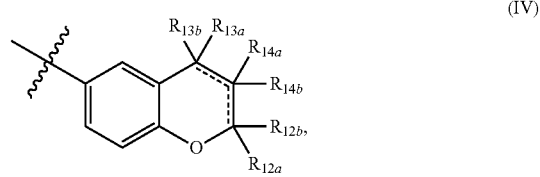

(IV)

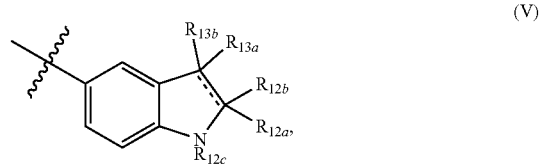

(V)

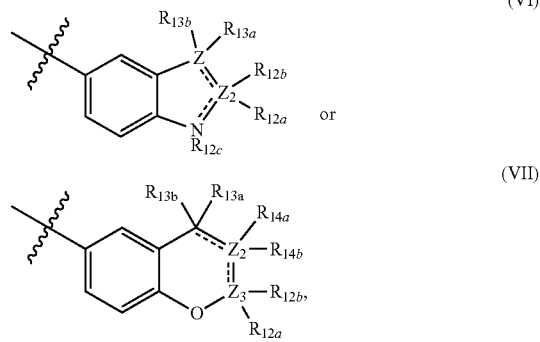

(VI)

(VII)

wherein $R_{12a}$, $R_{12b}$, $R_{12c}$, $R_{13a}$, $R_{13b}$, $R_{14a}$, and $R_{14b}$ independently are absent or selected from the group consisting of hydrogen, halogen, hydroxyl, cyano, $C_{1-4}$ alkyl, and $C_{1-4}$ alkoxy, and wherein $Z_1$, $Z_2$ and $Z_3$ independently are selected from the group consisting of C, N, O, and S; and the dashed bond, ⸺, represents an unsaturated or saturated bond.

4. The compound, or pharmaceutically acceptable salt, hydrate, solvate, stereoisomer, or deuterated analogue thereof of claim 1, wherein $R_{2a}$, $R_{2c}$, $R_{2d}$, and $R_{2b}$, provided $R_{2b}$ is not forming a ring system with R₂, independently are selected from the group consisting of hydrogen, deuterium, halogen, hydroxyl, methyl, —CD₃, methoxy, —OCD₃, —OCF₃, and —CF₃.

5. The compound, or pharmaceutically acceptable salt, hydrate, solvate, stereoisomer, or deuterated analogue thereof of claim 1, wherein R₂, provided R₂ is not forming a ring system with $R_{2b}$, is selected from the group consisting of halogen, cyano, methyl, —CD₃, ethyl, —CD₂CD₃, optionally deuterated n-propyl, optionally deuterated iso-propyl, optionally deuterated n-butyl, optionally deuterated iso-butyl, optionally deuterated n-pentyl, optionally deuterated 2-methyl-butyl, optionally deuterated n-hexyl, optionally deuterated 2-methyl-pentyl, optionally deuterated methoxy, optionally deuterated ethoxy, optionally deuterated n-propoxy, optionally deuterated isopropoxy, optionally deuterated allyloxy, optionally deuterated prop-2-yn-1-yloxy, optionally deuterated n-butoxy, optionally deuterated iso-butoxy, optionally deuterated tert-butoxy, optionally deuterated pentyl-oxy, optionally deuterated 4-methyl-butoxy, optionally deuterated hexyl-oxy, optionally deuterated 4-methylpentoxy, optionally deuterated cyclopropyloxy, optionally deuterated cyclopropylmethoxy, optionally deuterated cyclopropylethoxy, optionally deuterated cyclobutyloxy, optionally deuterated cyclobutyloxy, optionally deuterated cyclobutylmethoxy, optionally deuterated cyclobutylethoxy, optionally deuterated $C_{1-6}$ haloalkoxy, —$OCF_3$, —$OCF_2CF_3$, —$OCHF_2$, —$OCDF_2$, —$CF_3$, —$CF_2CF_3$, —$CHF_2$, $CDF_2$, —$CH_2CF_3$, —$CD_2CF_3$, —$CH_2F$, —$CF_2CH_3$ 1,1,2,2-tetrafluorobutyl, and 1,1,1,2,2-pentafluorobutyl; or $R_2$ and $R_{2b}$, taken together with the phenyl ring they attach to and the atoms to which they are attached form a bicyclic fused ring system, that has the following general formula:

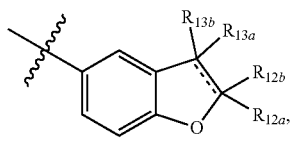

(III)

wherein $R_{12a}$ and $R_{12b}$ are hydrogen or methyl, and both $R_{13a}$ and $R_{13b}$ are hydrogen or methyl, and $R_{2a}$, $R_{2c}$, and $R_{2d}$ are hydrogen; and the dashed bond, ═, represents an unsaturated or saturated bond.

6. The compound, or pharmaceutically acceptable salt, hydrate, solvate, stereoisomer, or deuterated analogue thereof of claim 1, wherein $R_2$ is selected from the group consisting of ethoxy, n-propoxy, isopropoxy, allyloxy, iso-butoxy, tert-butoxy, cyclopropyloxy, cyclopropylmethoxy, 2-fluoroethoxy, 3-fluoropropoxy, 2,2-difluoroethoxy; or $R_2$ and $R_{2b}$, taken together with the phenyl ring they attach to and the atoms to which they are attached form unsubstituted 2,3-dihydrobenzofuran-5-yl, unsubstituted benzofuran-5-yl, and unsubstituted 2,2-dimethyl-2,3-dihydrobenzofuran-5-yl.

7. The compound, or pharmaceutically acceptable salt, hydrate, solvate, stereoisomer, or deuterated analogue thereof of claim 1, wherein halogen is fluoro.

8. The compound, or pharmaceutically acceptable salt, hydrate, solvate, stereoisomer, or deuterated analogue thereof of claim 1, wherein $R_3$ is selected from the group consisting of hydrogen, deuterium, hydroxyl, —OD, substituted or unsubstituted $C_{1-6}$ alkyl, substituted or unsubstituted $C_{1-6}$ alkoxy, substituted or unsubstituted —$(CH_2)_s$—$C_{3-6}$ cycloalkyl, substituted or unsubstituted —$(CH_2)_s$—$C_{2-5}$ heteroalicyclyl, substituted or unsubstituted —$(CH_2)_s$—$C_{2-5}$ heteroaryl, and substituted or unsubstituted —$(CH_2)_s$—$C_{5-6}$ aryl, wherein each s is selected from the group consisting of 0, 1, 2, and 3.

9. The compound, or pharmaceutically acceptable salt, hydrate, solvate, stereoisomer, or deuterated analogue thereof of claim 1, wherein $R_3$ is hydrogen or methyl.

10. The compound, or pharmaceutically acceptable salt, hydrate, solvate, stereoisomer, or deuterated analogue thereof of claim 1, wherein $R_{4a}$, $R_{4b}$, $R_{5a}$ and $R_{5b}$ are independently hydrogen or methyl.

11. The compound, or pharmaceutically acceptable salt, hydrate, solvate, stereoisomer, or deuterated analogue thereof of claim 1, wherein $R_{4a}$, $R_{4b}$, $R_{5a}$, and $R_{5b}$ are hydrogen.

12. The compound, or pharmaceutically acceptable salt, hydrate, solvate, stereoisomer, or deuterated analogue thereof of claim 1, wherein q is 0, or $R_6$ is selected from halogen and $C_{1-4}$ alkyl.

13. The compound, or pharmaceutically acceptable salt, hydrate, solvate, stereoisomer, or deuterated analogue thereof of claim 1, wherein q is 1 and $R_6$ is fluoro.

14. The compound, or pharmaceutically acceptable salt, hydrate, solvate, stereoisomer, or deuterated analogue thereof of claim 1, wherein p is 0.

15. The compound, or pharmaceutically acceptable salt, hydrate, solvate, stereoisomer, or deuterated analogue thereof of claim 1, wherein $R_8$ is selected from the group consisting of hydrogen, halogen, methyl, ethyl, propyl, methoxy, ethoxy, $C_{1-2}$-haloalkyl, and $C_{1-2}$-haloalkoxy.

16. The compound, or pharmaceutically acceptable salt, hydrate, solvate, stereoisomer, or deuterated analogue thereof of claim 1, wherein $R_8$ is hydrogen.

17. The compound, or pharmaceutically acceptable salt, hydrate, solvate, stereoisomer, or deuterated analogue thereof of claim 1, wherein:

$R_{4a}$, $R_{4b}$, $R_{5a}$, $R_{5b}$, $R_6$, $R_7$, $R_8$ are each hydrogen;
p and q are 0 or 1; and
$R_3$ is selected from the group consisting of hydrogen, methyl, —$CD_3$, ethyl, —$CD_2CD_3$, n-propyl, —$CD_2CD_2CD_3$, iso-propyl, cyclopropyl, —$CDCD_3CD_3$, —$(CR_{9a}R_{9b})_tC(═O)OR_{9c}$, and —$(CH_2)_tC(═O)NR_{9a}R_{9b}$, wherein $R_{9a}$, $R_{9b}$, and $R_{9c}$ independently are hydrogen or $C_{1-4}$-alkyl, wherein each t is selected from the group consisting of 0, 1, 2, and 3.

18. The compound, or pharmaceutically acceptable salt, hydrate, solvate, stereoisomer, or deuterated analogue thereof of claim 1, wherein:

$R_{4a}$, $R_{4b}$, $R_{5a}$, $R_{5b}$, $R_6$, $R_7$, $R_8$ are each hydrogen;
p and q are 0; and
$R_3$ is selected from the group consisting of hydrogen, methyl, —$CD_3$, ethyl, —$CD_2CD_3$, n-propyl, —$CD_2CD_2CD_3$, iso-propyl, cyclopropyl, —$CDCD_3CD_3$, —$(CR_{9a}R_{9b})_tC(═O)OR_{9c}$, and —$(CH_2)_tC(═O)NR_{9a}R_{9b}$, wherein $R_{9a}$, $R_{9b}$, and $R_{9c}$ independently are hydrogen or $C_{1-4}$-alkyl, wherein each t is selected from the group consisting of 0, 1, 2, and 3.

19. The compound, or pharmaceutically acceptable salt, hydrate, solvate, stereoisomer, or deuterated analogue thereof of claim 17, wherein $R_3$ is methyl or hydrogen; and
$R_2$ is selected from the group consisting of ethoxy, n-propoxy, isopropoxy, allyloxy, iso-butoxy, tert-butoxy, cyclopropyloxy, cyclopropylmethoxy, 2-fluoroethoxy, 3-fluoropropoxy and 2,2-difluoroethoxy; or $R_2$ and $R_{2b}$, taken together with the phenyl ring they attach to and the atoms to which they are attached form unsubstituted 2,3-dihydrobenzofuran-5-yl, unsubstituted benzofuran-5-yl, and unsubstituted 2,2-dimethyl-2,3-dihydrobenzofuran-5-yl.

20. A compound, or pharmaceutically acceptable salt, hydrate, solvate, stereoisomer, or deuterated analogue thereof, selected from the group consisting of:

1-[(2,4-dimethoxyphenyl)methyl]-3-[(3R,4S)-3-fluoro-1-methylpiperidin-4-yl]-3-[(4-fluorophenyl)methyl]urea;

1-[(2,4-dimethoxyphenyl)methyl]-3-[(3S,4R)-3-fluoro-1-methylpiperidin-4-yl]-3-[(4-fluorophenyl)methyl]urea;

3-[(2,4-dimethoxyphenyl)methyl]-3-(1-methylpiperidin-4-yl)-1-{[4-(2-methylpropoxy)-phenyl]methyl}urea;

1-[(2,4-difluorophenyl)methyl]-1-(1-methylpiperidin-4-yl)-3-{[4-(2-methylpropoxy)-phenyl]methyl}urea;

1-[(2,4-difluorophenyl)methyl]-3-{[4-(2-methylpropoxy)phenyl]methyl}-1-(piperidin-4-yl)urea; 1-[(2,4-difluorophenyl)methyl]-1-(1-methylpiperidin-4-yl)-3-{[4-(propan-2-yloxy)phenyl]-methyl}urea;

3-{[3-fluoro-4-(2-methylpropoxy)phenyl]methyl}-1-[(4-fluorophenyl)methyl]-1-(1-methylpiperidin-4-yl)urea;

3-{[2-fluoro-4-(2-methylpropoxy)phenyl]methyl}-1-[(4-fluorophenyl)methyl]-1-(1-methylpiperidin-4-yl)urea;

1-[(2,4-difluorophenyl)methyl]-3-[(2,2-dimethyl-2,3-dihydro-1-benzofuran-5-yl)methyl]-1-(1-methylpiperidin-4-yl)urea;

1-[(2,4-difluorophenyl)methyl]-3-[(3,3-dimethyl-2,3-dihydro-1-benzofuran-5-yl)methyl]-1-(1-methylpiperidin-4-yl)urea;

1-[(2,4-difluorophenyl)methyl]-3-[(2,3-dihydro-1-benzofuran-5-yl)methyl]-1-(1-methylpiperidin-4-yl)urea;

1-[(4-fluoro-2-hydroxyphenyl)methyl]-1-(1-methylpiperidin-4-yl)-3-{[4-(2-methylpropoxy)-phenyl]methyl}urea;

1-[(4-fluorophenyl)methyl]-3-{[2-hydroxy-4-(2-methylpropoxy)phenyl]methyl}-1-(1-methylpiperidin-4-yl)urea;

1-[(2,4-difluorophenyl)methyl]-3-{[4-(2-fluoroethoxy)phenyl]methyl}-1-(1-methylpiperidin-4-yl)urea;

1-[(2,4-difluorophenyl)methyl]-3-[(4-ethoxyphenyl)methyl]-1-(1-methylpiperidin-4-yl)urea;

3-[(4-cyclopropoxyphenyl)methyl]-1-[(2,4-difluorophenyl)methyl]-1-(1-methylpiperidin-4-yl)urea;

3-{[4-(tert-butoxy)phenyl]methyl}-1-[(2,4-difluorophenyl)methyl]-1-(1-methylpiperidin-4-yl)urea;

3-(4-(allyloxy)benzyl)-1-(2,4-difluorobenzyl)-1-(1-methylpiperidin-4-yl)urea;

3-[(1-benzofuran-5-yl)methyl]-1-[(2,4-difluorophenyl)methyl]-1-(1-methylpiperidin-4-yl)urea;

1-[(2,4-difluorophenyl)methyl]-3-[(3-methyl-1H-indol-5-yl)methyl]-1-(1-methylpiperidin-4-yl)urea;

1-[(2,4-difluorophenyl)methyl]-3-[(2-methyl-1,3-benzoxazol-5-yl)methyl]-1-(1-methylpiperidin-4-yl)urea;

1-[(2,4-difluorophenyl)methyl]-3-[(1-methyl-2,3-dihydro-1H-indol-5-yl)methyl]-1-(1-methylpiperidin-4-yl)urea;

1-[(2,4-difluorophenyl)methyl]-3-[(3-methyl-1,2-benzoxazol-6-yl)methyl]-1-(1-methylpiperidin-4-yl)urea;

1-[(2,4-difluorophenyl)methyl]-3-[(1,2-dimethyl-1H-indol-5-yl)methyl]-1-(1-methylpiperidin-4-yl)urea;

3-[(4-cyclopropoxyphenyl)methyl]-1-[1-(2,4-difluorophenyl)ethyl]-1-(1-methylpiperidin-4-yl)urea;

3-[(2,4-difluorophenyl)methyl]-3-(1-methylpiperidin-4-yl)-1-[(quinolin-6-yl)methyl]urea;

1-[(2,4-difluorophenyl)methyl]-3-[(3-methyl-1,2-benzoxazol-5-yl)methyl]-1-(1-methylpiperidin-4-yl)urea;

3-[(1,3-benzoxazol-6-yl)methyl]-1-[(2,4-difluorophenyl)methyl]-1-(1-methylpiperidin-4-yl)urea;

3-[(1,3-benzoxazol-5-yl)methyl]-1-[(2,4-difluorophenyl)methyl]-1-(1-methylpiperidin-4-yl)urea;

1-[(2,4-difluorophenyl)methyl]-3-[(1-methyl-1H-indol-5-yl)methyl]-1-(1-methylpiperidin-4-yl)urea;

3-[(2,4-difluorophenyl)methyl]-1-[(4-methyl-3,4-dihydro-2H-1,4-benzoxazin-6-yl)methyl]-3-(1-methylpiperidin-4-yl)urea;

3-[(2,4-difluorophenyl)methyl]-1-[(4-hydroxy-2,2-dimethyl-3,4-dihydro-2H-1-benzopyran-7-yl)methyl]-3-(1-methylpiperidin-4-yl)urea;

3-[(2,4-difluorophenyl)methyl]-1-[(2,2-dimethyl-2H-chromen-7-yl)methyl]-3-(1-methylpiperidin-4-yl)urea;

1-[(2,4-difluorophenyl)methyl]-3-[(1-methyl-1H-indazol-6-yl)methyl]-1-(1-methylpiperidin-4-yl)urea;

1-[(2,4-difluorophenyl)methyl]-3-[(2-methyl-1H-indol-5-yl)methyl]-1-(1-methylpiperidin-4-yl)urea;

1-[(2,4-difluorophenyl)methyl]-3-[(1,1-dioxo-2,3-dihydro-1λ$^6$-benzothiophen-5-yl)methyl]-1-(1-methylpiperidin-4-yl)urea;

1-[(2,4-difluorophenyl)methyl]-3-[(2,3-dihydro-1H-inden-5-yl)methyl]-1-(1-methylpiperidin-4-yl)urea;

3-[(1,3-benzothiazol-6-yl)methyl]-1-[(2,4-difluorophenyl)methyl]-1-(1-methylpiperidin-4-yl)urea;

1-[(2,4-difluorophenyl)methyl]-3-[(1,3-dimethyl-2-oxo-2,3-dihydro-1H-1,3-benzodiazol-5-yl)methyl]-1-(1-methylpiperidin-4-yl)urea;

1-[(2,4-difluorophenyl)methyl]-3-[(2H-indazol-6-yl)methyl]-1-(1-methylpiperidin-4-yl)urea;

1-[(2,4-difluorophenyl)methyl]-3-[(3-methyl-2H-indazol-5-yl)methyl]-1-(1-methylpiperidin-4-yl)urea;

1-[(4-cyano-2-fluorophenyl)methyl]-1-(1-methylpiperidin-4-yl)-3-{[4-(propan-2-yloxy)phenyl]methyl}urea;

1-[(2-fluoro-4-nitrophenyl)methyl]-1-(1-methylpiperidin-4-yl)-3-{[4-(propan-2-yloxy)phenyl]methyl}urea;

1-[(2,4-difluorophenyl)methyl]-3-[(4-{[2-($^2$H$_3$)methyl(1,1,1,3,3,3-$^2$H$_6$)propan-2-yl]oxy}phenyl)methyl]-1-(1-methylpiperidin-4-yl)urea;

3-[(4-cyclopropoxyphenyl)methyl]-1-[(1R)-1-(2,4-difluorophenyl)ethyl]-1-(1-methylpiperidin-4-yl)urea;

3-[(3-cyano-4-methoxyphenyl)methyl]-1-[(2,4-difluorophenyl)methyl]-1-(1-methylpiperidin-4-yl)urea;

3-[(2,4-difluorophenyl)methyl]-1-[(4-fluorophenyl)methyl]-3-(1-methylpiperidin-4-yl)urea;

3-[(2-chloro-4-methoxyphenyl)methyl]-1-[(2,4-difluorophenyl)methyl]-1-(1-methylpiperidin-4-yl)urea;

1-[(2,4-difluorophenyl)methyl]-3-[(2,2-dimethyl-2,3-dihydro-1-benzofuran-5-yl)methyl]-1-(1-methylpiperidin-4-yl)urea;

1-[(2,4-difluorophenyl)methyl]-3-{[4-methoxy-2-(trifluoromethyl)phenyl]methyl}-1-(1-methylpiperidin-4-yl)urea;

3-[(2,4-difluorophenyl)methyl]-1-[(2-fluoro-4-nitrophenyl)methyl]-3-(1-methylpiperidin-4-yl)urea;

N-(5-fluoro-2-{[1-(1-methylpiperidin-4-yl)({[4-(propan-2-yloxy)phenyl]methyl}carbamoyl)amino]methyl}phenyl)acetamide 1-[(2,4-difluorophenyl)methyl]-3-[(1-methyl-1H-1,3-benzodiazol-5-yl)methyl]-1-(1-methylpiperidin-4-yl)urea;

1-[(2,4-difluorophenyl)methyl]-3-[(1-methyl-1H-indazol-5-yl)methyl]-1-(1-methylpiperidin-4-yl)urea;

1-[(2,4-dichlorophenyl)methyl]-3-{[4-(2-methylpropoxy)phenyl]methyl}-1-(piperidin-4-yl)urea;

1-[(2,4-difluorophenyl)methyl]-3-[(2,2-dimethyl-2,3-dihydro-1-benzofuran-4-yl)methyl]-1-(1-methylpiperidin-4-yl)urea;

1-[(2,4-difluorophenyl)methyl]-3-[(2,2-dimethyl-2,3-dihydro-1-benzofuran-6-yl)methyl]-1-(1-methylpiperidin-4-yl)urea;

1-[(4-chloro-2-fluorophenyl)methyl]-1-(1-methylpiperidin-4-yl)-3-{[4-(propan-2-yloxy)phenyl]methyl}urea;

1-[(2,4-difluorophenyl)methyl]-3-[(4-methoxyphenyl)methyl]-1-(piperidin-4-yl)urea;

1-[(2-chloro-4-fluorophenyl)methyl]-1-(1-methylpiperidin-4-yl)-3-{[4-(propan-2-yloxy)phenyl]methyl}urea;

1-(1-methylpiperidin-4-yl)-3-{[4-(propan-2-yloxy)phenyl]methyl}-1-[(2,3,6-trifluorophenyl)methyl]urea;

3-[(4-chloro-2-methoxyphenyl)methyl]-3-(1-methylpiperidin-4-yl)-1-{[4-(2-methylpropoxy)phenyl]methyl}urea;

3-{[4-methoxy-2-(trifluoromethyl)phenyl]methyl}-3-(1-methylpiperidin-4-yl)-1-{[4-(2-methylpropoxy)phenyl]methyl}urea;

1-{[2-chloro-4-(trifluoromethyl)phenyl]methyl}-1-(1-methylpiperidin-4-yl)-3-{[4-(2-methylpropoxy)phenyl]methyl}urea;

1-{[2-fluoro-4-(trifluoromethyl)phenyl]methyl}-1-(1-methylpiperidin-4-yl)-3-{[4-(2-methylpropoxy)phenyl]methyl}urea;

1-{[4-chloro-2-(trifluoromethyl)phenyl]methyl}-1-(1-methylpiperidin-4-yl)-3-{[4-(2-methylpropoxy)phenyl]methyl}urea;

1-[(2-chloro-4-fluorophenyl)methyl]-1-(1-methylpiperidin-4-yl)-3-{[4-(2-methylpropoxy)phenyl]methyl}urea;

1-[(4-chloro-2,6-difluorophenyl)methyl]-1-(1-methylpiperidin-4-yl)-3-{[4-(2-methylpropoxy)phenyl]methyl}urea;

1-[(2,4-dichlorophenyl)methyl]-1-(piperidin-4-yl)-3-{[4-(propan-2-yloxy)phenyl]methyl}urea;

1-[(2,6-difluoro-3-methylphenyl)methyl]-1-(1-methylpiperidin-4-yl)-3-{[4-(propan-2-yloxy)phenyl]methyl}urea;

1-[(2,4-difluorophenyl)methyl]-3-{[4-($^2$H$_3$)methoxyphenyl]methyl}-1-(1-methylpiperidin-4-yl)urea;

1-[(2,4-difluorophenyl)methyl]-3-{[2-methoxy-4-(propan-2-yloxy)phenyl]methyl}-1-(1-methylpiperidin-4-yl)urea;

1-[(2,4-difluorophenyl)methyl]-1-{1-[(1,1,1,3,3,3-$^2$H$_6$)propan-2-yl]piperidin-4-yl}-3-{[4-(propan-2-yloxy)phenyl]methyl}urea;

1-[(2,4-difluorophenyl)methyl]-1-(piperidin-4-yl)-3-{[4-(propan-2-yloxy)phenyl]methyl}urea;

1-[(2,4-difluorophenyl)methyl]-1-(piperidin-4-yl)-3-[(4-propoxyphenyl)methyl]urea;

3-[(1H-1,3-benzodiazol-5-yl)methyl]-1-[(2,4-difluorophenyl)methyl]-1-(1-methylpiperidin-4-yl)urea;

1-[(7R,8aS)-octahydroindolizin-7-yl]-3-[(4-cyclopropoxyphenyl)methyl]-1-[(2,4-difluorophenyl)methyl]urea;

1-[(7R,8aS)-octahydroindolizin-7-yl]-1-[(2,4-difluorophenyl)methyl]-3-{[4-(propan-2-yloxy)phenyl]methyl}urea;

1-[(2,4-difluorophenyl)methyl]-1-(piperidin-4-yl)-3-[(quinoxalin-6-yl)methyl]urea;

1-[(2,4-difluorophenyl)methyl]-1-(1-methylpiperidin-4-yl)-3-[(quinoxalin-6-yl)methyl]urea 3-[(4,5-difluoro-2-methoxyphenyl)methyl]-3-(piperidin-4-yl)-1-{[4-(propan-2-yloxy)phenyl]methyl}urea;

3-[(2,4-difluorophenyl)methyl]-3-[(1R,3R,5S)-8-methyl-8-azabicyclo[3.2.1]octan-3-yl]-1-{[4-(propan-2-yloxy)phenyl]methyl}urea;

1-[(2,4-difluorophenyl)methyl]-1-[(3R,4S)-1,3-dimethylpiperidin-4-yl]-3-{[4-(propan-2-yloxy)phenyl]methyl}urea;

1-[(2,4-difluorophenyl)methyl]-1-[(3S,4R)-1,3-dimethylpiperidin-4-yl]-3-{[4-(propan-2-yloxy)phenyl]methyl}urea;

1-[(2,4-difluorophenyl)methyl]-1-(1,4-dimethylpiperidin-4-yl)-3-{[4-(propan-2-yloxy)phenyl]methyl}urea;

1-[(2,4-difluorophenyl)methyl]-3-{[4-(2-hydroxy-2,3-dimethylbutoxy)phenyl]methyl}-1-(1-methylpiperidin-4-yl)urea;

1-[(2,4-difluorophenyl)methyl]-3-({3-fluoro-4-[(2-hydroxyethoxy)methyl]phenyl}methyl)-1-(1-methylpiperidin-4-yl)urea;

N-(5-fluoro-2-{[1-(1-methylpiperidin-4-yl)({[4-(propan-2-yloxy)phenyl]methyl}carbamoyl)-amino]methyl}phenyl)acetamide;

1-{[2-hydroxy-4-(trifluoromethyl)phenyl]methyl}-1-(1-methylpiperidin-4-yl)-3-{[4-(2-methylpropoxy)phenyl]methyl}urea;

1-[(4-fluoro-2-methoxyphenyl)methyl]-1-(1-methylpiperidin-4-yl)-3-{[4-(2-methylpropoxy)phenyl]methyl}urea;

5-fluoro-2-{[1-(1-methylpiperidin-4-yl)({[4-(2-methylpropoxy)phenyl]methyl}-carbamoyl)amino]methyl}phenyl acetate;

1-[(2,4-difluorophenyl)methyl]-3-[(1H-indazol-5-yl)methyl]-1-(1-methylpiperidin-4-yl)urea;

1-[(2,4-difluorophenyl)methyl]-3-({4-[(1R)-1,2-dihydroxyethyl]phenyl}methyl)-1-(1-methylpiperidin-4-yl)urea;

1-[(2,4-difluorophenyl)methyl]-3-({4-[(1S)-1,2-dihydroxyethyl]phenyl}methyl)-1-(1-methylpiperidin-4-yl)urea;

1-[(2,4-difluorophenyl)methyl]-3-[(1,3-dihydro-2-benzofuran-5-yl)methyl]-1-(1-methylpiperidin-4-yl)urea;

1-[(2,4-difluorophenyl)methyl]-3-{[4-(3-methoxypropoxy)phenyl]methyl}-1-(1-methylpiperidin-4-yl)urea;

1-[(2,4-difluorophenyl)methyl]-3-[(2-fluoro-4-nitrophenyl)methyl]-1-(1-methylpiperidin-4-yl)urea;

3-[(4-chloro-3-methoxyphenyl)methyl]-1-[(2,4-difluorophenyl)methyl]-1-(1-methylpiperidin-4-yl)urea;

1-[(2,4-difluorophenyl)methyl]-3-{[4-fluoro-2-(trifluoromethoxy)phenyl]methyl}-1-(1-methylpiperidin-4-yl)urea;

3-[(2,4-difluorophenyl)methyl]-1-[(4-fluorophenyl)methyl]-1-(1-methylpiperidin-4-yl)urea;

1-{[2-(difluoromethoxy)-4-fluorophenyl]methyl}-1-(1-methylpiperidin-4-yl)-3-{[4-(2-methylpropoxy)phenyl]methyl}urea;

1-{[4-chloro-2-(trifluoromethyl)phenyl]methyl}-1-(1-methylpiperidin-4-yl)-3-{[4-(2-methylpropoxy)phenyl]methyl}urea;

1-{[4-fluoro-2-(trifluoromethoxy)phenyl]methyl}-1-(1-methylpiperidin-4-yl)-3-{[4-(2-methylpropoxy)phenyl]methyl}urea;

1-[(4-fluoro-2-methylphenyl)methyl]-1-(1-methylpiperidin-4-yl)-3-{[4-(2-methylpropoxy)phenyl]methyl}urea;

1-[(2-chloro-4-methoxyphenyl)methyl]-1-(1-methylpiperidin-4-yl)-3-{[4-(2-methylpropoxy)phenyl]methyl}urea;

1-[(2,4-dichlorophenyl)methyl]-1-(1-methylpiperidin-4-yl)-3-{[4-(propan-2-yloxy)phenyl]methyl}urea;

1-[(2,4-dichlorophenyl)methyl]-1-(1-methylpiperidin-4-yl)-3-{[4-(2-methylpropoxy)phenyl]methyl}urea;

1-[(2,4-dichlorophenyl)methyl]-1-(piperidin-4-yl)-3-{[4-(propan-2-yloxy)phenyl]methyl}urea;

1-[(2-chloro-4-fluorophenyl)methyl]-3-{[4-(2-methylpropoxy)phenyl]methyl}-1-(piperidin-4-yl)urea;
1-[(2-chloro-4-fluorophenyl)methyl]-1-(piperidin-4-yl)-3-{[4-(propan-2-yloxy)phenyl]methyl}urea;
1-[(2,4-dichlorophenyl)methyl]-3-{[4-(2-methylpropoxy)phenyl]methyl}-1-(piperidin-4-yl)urea;
1-[(2,4-difluoro-3-methylphenyl)methyl]-1-(1-methylpiperidin-4-yl)-3-{[4-(propan-2-yloxy)-phenyl]methyl}urea;
1-[(2-fluoro-4-methylphenyl)methyl]-1-(1-methylpiperidin-4-yl)-3-{[4-(propan-2-yloxy)phenyl]methyl}urea;
1-[(2,4-difluorophenyl)methyl]-3-{[2-methyl-4-(propan-2-yloxy)phenyl]methyl}-1-(1-methylpiperidin-4-yl)urea;
1-[(4-cyclopropoxyphenyl)methyl]-3-[(2,4-difluorophenyl)methyl]-3-[(3S,4R)-3-fluoro-1-methylpiperidin-4-yl]urea;
1-[(4-cyclopropoxyphenyl)methyl]-3-[(2,4-difluorophenyl)methyl]-3-[(3R,4S)-3-fluoro-1-methylpiperidin-4-yl]urea;
1-[(2,4-difluorophenyl)methyl]-3-[(3-fluoro-4-methoxyphenyl)methyl]-1-(1-methylpiperidin-4-yl)urea;
1-[(2,4-difluorophenyl)methyl]-3-[(2-fluoro-4-hydroxyphenyl)methyl]-1-(1-methylpiperidin-4-yl)urea;
3-[(2,4-difluorophenyl)methyl]-3-(1-methylpiperidin-4-yl)-1-[(4-phenoxyphenyl)methyl]urea;
3-{[4-methoxy-2-(trifluoromethyl)phenyl]methyl}-3-(1-methylpiperidin-4-yl)-1-{[4-(2-methylpropoxy)phenyl]methyl}urea;
1-[(2-fluoro-4-methoxyphenyl)methyl]-1-(1-methylpiperidin-4-yl)-3-{[4-(propan-2-yloxy)phenyl]methyl}urea;
3-[(4-butoxyphenyl)methyl]-1-[(2,4-difluorophenyl)methyl]-1-(piperidin-4-yl)urea;
3-[(4-butoxyphenyl)methyl]-1-[(2,4-difluorophenyl)methyl]-1-(1-methylpiperidin-4-yl)urea;
3-[(2,4-difluorophenyl)methyl]-1-[(4-methoxyphenyl)methyl]-3-(1-methylpiperidin-4-yl)urea;
1-[(2,4-difluorophenyl)methyl]-3-[(4-methoxyphenyl)methyl]-1-(piperidin-4-yl)urea;
3-[(2,4-difluorophenyl)methyl]-1-[(4-ethoxyphenyl)methyl]-3-(piperidin-4-yl)urea;
3-[(2H-1,3-benzodioxol-5-yl)methyl]-1-[(2,4-difluorophenyl)methyl]-1-(1-methylpiperidin-4-yl)urea;
1-[(3,4-difluorophenyl)methyl]-1-(1-methylpiperidin-4-yl)-3-{[4-(propan-2-yloxy)phenyl]-methyl}urea;
1-[(2,4-difluorophenyl)methyl]-1-[1-($^{2}H_{3}$)methylpiperidin-4-yl]-3-{[4-(propan-2-yloxy)phenyl]methyl}urea;
1-(piperidin-4-yl)-3-{[4-(propan-2-yloxy)phenyl]methyl}-1-[(2,3,4-trifluorophenyl)methyl]urea;
3-[(4-chloro-2-fluorophenyl)methyl]-3-(piperidin-4-yl)-1-{[4-(propan-2-yloxy)phenyl]methyl}urea;
3-[(4-chloro-2-fluorophenyl)methyl]-1-{[4-(2-methylpropoxy)phenyl]methyl}-3-(piperidin-4-yl)urea;
1-(1-methylpiperidin-4-yl)-3-{[4-(propan-2-yloxy)phenyl]methyl}-1-[(2,3,4-trifluorophenyl)methyl]urea;
1-[(2,6-difluoro-4-methoxyphenyl)methyl]-1-(1-methylpiperidin-4-yl)-3-{[4-(propan-2-yloxy)phenyl]methyl}urea;
1-[(4-chloro-2-fluorophenyl)methyl]-1-(1-methylpiperidin-4-yl)-3-{[4-(propan-2-yloxy)phenyl]methyl}urea;
1-[(4,5-difluoro-2-methoxyphenyl)methyl]-1-(1-methylpiperidin-4-yl)-3-{[4-(propan-2-yloxy)phenyl]methyl}urea;
1-[(4-chloro-2-fluorophenyl)methyl]-1-(1-methylpiperidin-4-yl)-3-{[4-(2-methylpropoxy)phenyl]methyl}urea;
1-[(2,4-difluorophenyl)methyl]-1-(1-methylpiperidin-4-yl)-3-[(4-propoxyphenyl)methyl]urea;
3-{[4-(cyclopropylmethoxy)phenyl]methyl}-1-[(2,4-difluorophenyl)methyl]-1-(1-methylpiperidin-4-yl)urea;
1-[(2,4-difluorophenyl)methyl]-3-{[3-fluoro-4-(propan-2-yloxy)phenyl]methyl}-1-(1-methylpiperidin-4-yl)urea;
1-[(2,4-difluorophenyl)methyl]-3-{[2-fluoro-4-(propan-2-yloxy)phenyl]methyl}-1-(1-methylpiperidin-4-yl)urea;
1-[(2,4-difluorophenyl)methyl]-3-{[3-methyl-4-(propan-2-yloxy)phenyl]methyl}-1-(1-methylpiperidin-4-yl)urea;
1-[(2,4-difluorophenyl)methyl]-3-[(4-fluoro-3-methoxyphenyl)methyl]-1-(1-methylpiperidin-4-yl)urea;
1-[(2,4-difluorophenyl)methyl]-3-({4-[(2-ethylhexyl)oxy]phenyl}methyl)-1-(1-methylpiperidin-4-yl)urea;
1-[(2,4-difluorophenyl)methyl]-1-(1-methylpiperidin-4-yl)-3-{[4-(prop-2-yn-1-yloxy)phenyl]methyl}urea;
3-{[4-(tert-butoxy)phenyl]methyl}-1-[(2,4-difluorophenyl)methyl]-1-(piperidin-4-yl)urea;
1-[(2,6-difluoro-4-methoxyphenyl)methyl]-3-[(2,4-difluorophenyl)methyl]-3-(1-methylpiperidin-4-yl)urea;
3-[(2,4-difluorophenyl)methyl]-1-{[4-(3-fluoropropoxy)phenyl]methyl}-3-(1-methylpiperidin-4-yl)urea;
1-{[4-(1,1-difluoroethyl)phenyl]methyl}-3-[(2,4-difluorophenyl)methyl]-3-(1-methylpiperidin-4-yl)urea;
3-[(2,4-difluorophenyl)methyl]-1-({4-[(1,3-difluoropropan-2-yl)oxy]phenyl}methyl)-3-(1-methylpiperidin-4-yl)urea;
3-{[4-(2,2-difluoroethoxy)phenyl]methyl}-1-[(2,4-difluorophenyl)methyl]-1-(1-methylpiperidin-4-yl)urea;
1-[(2,4-difluorophenyl)methyl]-3-[(2,2-dimethyl-2H-chromen-6-yl)methyl]-1-(1-methylpiperidin-4-yl)urea;
3-[(2,4-difluorophenyl)methyl]-1-[(4-methoxyphenyl)methyl]-3-(1-methylpiperidin-4-yl)urea;
1-[(4-cyclopropoxyphenyl)methyl]-3-[(2,4-difluorophenyl)methyl]-3-(piperidin-4-yl)urea;
1-[(2,4-difluorophenyl)methyl]-3-[(2,2-dimethyl-2,3-dihydro-1-benzofuran-5-yl)methyl]-1-(piperidin-4-yl)urea; and
1-[(2,4-difluorophenyl)methyl]-3-{[2,3-dihydro(2,2,3,3-$^{2}H_{4}$)-1-benzofuran-5-yl]methyl}-1-(1-methylpiperidin-4-yl)urea.

21. A compound, or pharmaceutically acceptable salt, hydrate, solvate, stereoisomer, or deuterated analogue thereof, selected from the group consisting of:
1-[(2,4-difluorophenyl)methyl]-1-(piperidin-4-yl)-3-[(4-propoxyphenyl)methyl]urea;
1-[(2,4-difluorophenyl)methyl]-1-(1-methylpiperidin-4-yl)-3-[(4-propoxyphenyl)methyl]urea;
3-{[4-(cyclopropylmethoxy)phenyl]methyl}-1-[(2,4-difluorophenyl)methyl]-1-(1-methylpiperidin-4-yl)urea;
1-[(4-cyclopropoxyphenyl)methyl]-3-[(2,4-difluorophenyl)methyl]-3-(piperidin-4-yl)urea;
3-{[4-(2,2-difluoroethoxy)phenyl]methyl}-1-[(2,4-difluorophenyl)methyl]-1-(1-methylpiperidin-4-yl)urea;
3-{[4-(tert-butoxy)phenyl]methyl}-1-[(2,4-difluorophenyl)methyl]-1-(piperidin-4-yl)urea;
3-(4-(allyloxy)benzyl)-1-(2,4-difluorobenzyl)-1-(1-methylpiperidin-4-yl)urea;
3-[(4-cyclopropoxyphenyl)methyl]-1-[(2,4-difluorophenyl)methyl]-1-(1-methylpiperidin-4-yl)urea;
1-[(2,4-difluorophenyl)methyl]-3-{[4-(2-fluoroethoxy)phenyl]methyl}-1-(1-methylpiperidin-4-yl)urea;
3-[(2,4-difluorophenyl)methyl]-1-{[4-(3-fluoropropoxy)phenyl]methyl}-3-(1-methylpiperidin-4-yl)urea;

3-{[4-(tert-butoxy)phenyl]methyl}-1-[(2,4-difluorophenyl)methyl]-1-(1-methylpiperidin-4-yl)urea;
1-[(2,4-difluorophenyl)methyl]-1-(piperidin-4-yl)-3-{[4-(propan-2-yloxy)phenyl]methyl}urea;
1-[(2,4-difluorophenyl)methyl]-3-[(4-ethoxyphenyl)methyl]-1-(1-methylpiperidin-4-yl)urea;
1-[(2,4-difluorophenyl)methyl]-1-(1-methylpiperidin-4-yl)-3-{[4-(propan-2-yloxy)phenyl]methyl}urea; and
1-[(2,4-difluorophenyl)methyl]-1-(1-methylpiperidin-4-yl)-3-{[4-(2-methylpropoxy)phenyl]methyl}urea.

22. A compound according to Formula (I):

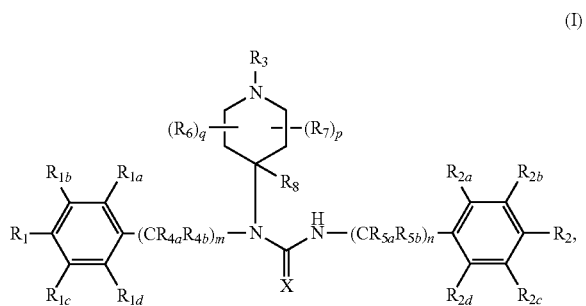

(I)

or a pharmaceutically acceptable salt, hydrate, solvate, stereoisomer, or deuterated analogue thereof, wherein:
m and n are 1;
p and q are independently an integer selected from the group consisting of 0, 1, 2, 3, and 4;
$R_1$ and $R_{1d}$ are fluoro;
$R_{1a}$, $R_{1b}$, and $R_c$ are hydrogen;
$R_2$ is selected from the group consisting of methoxy, ethoxy, n-propoxy, isopropoxy, allyloxy, prop-2-yn-1-yloxy, n-butoxy, iso-butoxy, tert-butoxy, pentyloxy, 4-methyl-butoxy, hexyl-oxy, 4-methylpentoxy, cyclopropyloxy, cyclopropylmethoxy, cyclopropylethoxy, cyclobutyloxy, cyclobutylmethoxy, cyclobutylethoxy, 2-fluoroethoxy, 3-fluoropropoxy, 4-fluorobutoxy, 2-fluoroethoxy, 3-fluoropropoxy, 2,2-difluoroethoxy, 4-methoxybutoxy, 2-hydroxyethoxy, 1,2-dihydroxyethyl, 2-hydroxy-2,3-dimethylbutoxy, —$OCF_3$, and (1,3-difluoropropan-2-yl)oxy;
$R_{2a}$, $R_{2b}$, $R_{2c}$, and $R_{2d}$ are hydrogen;
$R_3$ is selected from hydrogen, deuterium, hydroxyl, —OD, unsubstituted or substituted $C_{1-6}$ alkyl, unsubstituted or substituted $C_{1-6}$ haloalkyl, unsubstituted or substituted $C_{1-6}$ hydroxyalkyl, unsubstituted or substituted $C_{2-6}$ alkenyl, unsubstituted or substituted $C_{3-6}$ cycloalkyl, unsubstituted or substituted $C_{3-6}$ heteroalicyclyl, substituted or unsubstituted aryl, and substituted or unsubstituted heteroaryl;
$R_{4a}$, $R_{4b}$, $R_{5a}$, and $R_{5b}$, are independently selected from the group consisting of hydrogen, deuterium, and unsubstituted or substituted $C_{1-6}$ alkyl; wherein when m and n are 1 then $R_{4a}$, $R_{4b}$, $R_{5a}$, $R_{5b}$ are hydrogen;
$R_6$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy, substituted or unsubstituted aryl; or $R_6$ and $R_3$, taken together with the atoms to which they are attached form a ring system;
$R_7$ is selected from the group consisting of hydrogen, deuterium, halogen, hydroxyl, oxo, —OD, cyano, substituted or unsubstituted $C_{1-4}$ alkyl, and substituted or unsubstituted $C_{1-4}$ alkoxy;
$R_8$ is absent, or selected from the group consisting of hydrogen, deuterium, cyano, hydroxyl, —OD, substituted or unsubstituted $C_{1-4}$ alkyl, substituted or unsubstituted $C_{2-4}$ alkenyl, substituted or unsubstituted $C_{3-6}$ cycloalkyl, and substituted or unsubstituted $C_{1-4}$ alkoxy; and
X is O.

23. The compound, or pharmaceutically acceptable salt, hydrate, solvate, stereoisomer, or deuterated analogue thereof of claim 22, wherein $R_2$ is selected from the group consisting of ethoxy, n-propoxy, isopropoxy, allyloxy, isobutoxy, tert-butoxy, cyclopropyloxy, and cyclopropylmethoxy.

24. The compound of claim 22 that is 1-[(2,4-difluorophenyl)methyl]-1-(piperidin-4-yl)-3-[(4-propoxyphenyl)methyl]urea, or a pharmaceutically acceptable salt, hydrate, solvate, or deuterated analogue thereof.

25. The compound of claim 22 that is 1-[(2,4-difluorophenyl)methyl]-1-(1-methylpiperidin-4-yl)-3-[(4-propoxyphenyl)methyl]urea, or a pharmaceutically acceptable salt, hydrate, solvate, or deuterated analogue thereof.

26. The compound of claim 22 that is 3-{[4-(cyclopropylmethoxy)phenyl]methyl}-1-[(2,4-difluorophenyl)methyl]-1-(1-methylpiperidin-4-yl)urea, or a pharmaceutically acceptable salt, hydrate, solvate, or deuterated analogue thereof.

27. The compound of claim 22 that is 1-[(4-cyclopropoxyphenyl)methyl]-3-[(2,4-difluorophenyl)methyl]-3-(piperidin-4-yl)urea, or a pharmaceutically acceptable salt, hydrate, solvate, or deuterated analogue thereof.

28. The compound of claim 22 that is 3-{[4-(2,2-difluoroethoxy)phenyl]methyl}-1-[(2,4-difluorophenyl)methyl]-1-(1-methylpiperidin-4-yl)urea, or a pharmaceutically acceptable salt, hydrate, solvate, or deuterated analogue thereof.

29. The compound of claim 22 that is 3-{[4-(tert-butoxy)phenyl]methyl}-1-[(2,4-difluorophenyl)methyl]-1-(piperidin-4-yl)urea, or a pharmaceutically acceptable salt, hydrate, solvate, or deuterated analogue thereof.

30. The compound of claim 22 that is 3-(4-(allyloxy)benzyl)-1-(2,4-difluorobenzyl)-1-(1-methylpiperidin-4-yl)urea, or a pharmaceutically acceptable salt, hydrate, solvate, or deuterated analogue thereof.

31. The compound of claim 22 that is 3-[(4-cyclopropoxyphenyl)methyl]-1-[(2,4-difluorophenyl)methyl]-1-(1-methylpiperidin-4-yl)urea, or a pharmaceutically acceptable salt, hydrate, solvate, or deuterated analogue thereof.

32. The compound of claim 22 that is 1-[(2,4-difluorophenyl)methyl]-3-{[4-(2-fluoroethoxy)phenyl]methyl}-1-(1-methylpiperidin-4-yl)urea, or a pharmaceutically acceptable salt, hydrate, solvate, or deuterated analogue thereof.

33. The compound of claim 22 that is 3-[(2,4-difluorophenyl)methyl]-1-{[4-(3-fluoropropoxy)phenyl]methyl}-3-(1-methylpiperidin-4-yl)urea, or a pharmaceutically acceptable salt, hydrate, solvate, or deuterated analogue thereof.

34. The compound of claim 22 that is 3-{[4-(tert-butoxy)phenyl]methyl}-1-[(2,4-difluorophenyl)methyl]-1-(1-methylpiperidin-4-yl)urea, or a pharmaceutically acceptable salt, hydrate, solvate, or deuterated analogue thereof.

35. The compound of claim 22 that is 1-[(2,4-difluorophenyl)methyl]-1-(piperidin-4-yl)-3-{[4-(propan-2-yloxy)phenyl]methyl}urea, or a pharmaceutically acceptable salt, hydrate, solvate, or deuterated analogue thereof.

36. The compound of claim 22 that is 1-[(2,4-difluorophenyl)methyl]-3-[(4-ethoxyphenyl)methyl]-1-(1-methylpiperidin-4-yl)urea, or a pharmaceutically acceptable salt, hydrate, solvate, or deuterated analogue thereof.

37. The compound of claim 22 that is 1-[(2,4-difluorophenyl)methyl]-1-(1-methylpiperidin-4-yl)-3-{[4-(propan-2-yloxy)phenyl]methyl}urea, or a pharmaceutically acceptable salt, hydrate, solvate, or deuterated analogue thereof.

38. The compound of claim 22 that is 1-[(2,4-difluorophenyl)methyl]-1-(1-methylpiperidin-4-yl)-3-{[4-(2-methylpropoxy)phenyl]methyl}urea, or a pharmaceutically acceptable salt, hydrate, solvate, or deuterated analogue thereof.

* * * * *

UNITED STATES PATENT AND TRADEMARK OFFICE
CERTIFICATE OF CORRECTION

| | |
|---|---|
| PATENT NO. | : 11,345,693 B2 |
| APPLICATION NO. | : 16/797611 |
| DATED | : May 31, 2022 |
| INVENTOR(S) | : Burstein et al. |

It is certified that error appears in the above-identified patent and that said Letters Patent is hereby corrected as shown below:

On the Title Page

Item (74) replace Sterne, Kessler, Goidstesn & Fox P.L.L.C. with -- Sterne, Kessler, Goldstein & Fox P.L.L.C. --

Signed and Sealed this
Sixth Day of September, 2022

*Katherine Kelly Vidal*

Katherine Kelly Vidal
*Director of the United States Patent and Trademark Office*